United States Patent
Geneste et al.

(10) Patent No.: US 9,862,704 B2
(45) Date of Patent: Jan. 9, 2018

(54) OXINDOLE DERIVATIVES CARRYING AN AMINE-SUBSTITUTED PIPERIDYL-ACETIDINYL SUBSTITUENT AND USE THEREOF FOR TREATING VASOPRESSINE-RELATED DISEASES

(71) Applicants: AbbVie Deutschland GmbH & Co. KG, Wiesbaden (DE); AbbVie Inc., North Chicago, IL (US)

(72) Inventors: Hervé Geneste, Ludwigshafen (DE); Wilfried Hornberger, Ludwigshafen (DE); Charles W. Hutchins, Green Oaks, IL (US); Katja Jantos, Ludwigshafen (DE); Andreas Kling, Ludwigshafen (DE); Loic Laplanche, Ludwigshafen (DE); Marcel Van Gaalen, Ludwigshafen (DE)

(73) Assignees: ABBVIE DEUTSCHLAND GMBH & CO. KG, Wiesbaden (DE); ABBVIE INC., North Chicago, IL (US)

( * ) Notice: Subject to any disclaimer, the term of this patent is extended or adjusted under 35 U.S.C. 154(b) by 0 days.

(21) Appl. No.: 15/106,662

(22) PCT Filed: Dec. 19, 2014

(86) PCT No.: PCT/EP2014/078702
§ 371 (c)(1),
(2) Date: Jun. 20, 2016

(87) PCT Pub. No.: WO2015/091934
PCT Pub. Date: Jun. 25, 2015

(65) Prior Publication Data
US 2017/0001982 A1    Jan. 5, 2017

Related U.S. Application Data

(60) Provisional application No. 61/919,256, filed on Dec. 20, 2013.

(51) Int. Cl.
*C07D 401/14*    (2006.01)
(52) U.S. Cl.
CPC .................. *C07D 401/14* (2013.01)
(58) Field of Classification Search
CPC .................................................. C07D 401/14
See application file for complete search history.

(56) References Cited

U.S. PATENT DOCUMENTS

| | | | |
|---|---|---|---|
| 7,799,782 B2 * | 9/2010 | Munson ............... | C07D 231/56 514/234.5 |
| 9,527,856 B2 * | 12/2016 | Braje ................... | C07D 487/10 |
| 2008/0318923 A1 | 12/2008 | Sekiguchi et al. | |
| 2011/0065720 A1 | 3/2011 | Netz et al. | |
| 2011/0092513 A1 | 4/2011 | Hager-Wernet | |
| 2011/0092516 A1 | 4/2011 | Hager-Wernet | |
| 2011/0257194 A1 | 10/2011 | Hager-Wernet | |
| 2014/0275110 A1 | 9/2014 | Oost et al. | |
| 2014/0303138 A1 | 10/2014 | Braje et al. | |
| 2017/0008875 A1 | 1/2017 | Geneste et al. | |

FOREIGN PATENT DOCUMENTS

| | | |
|---|---|---|
| WO | 2005030755 | 4/2005 |
| WO | 2006005609 | 1/2006 |
| WO | 2006080574 | 8/2006 |
| WO | 2008080970 | 7/2008 |
| WO | 2008080971 | 7/2008 |
| WO | 2008080972 | 7/2008 |
| WO | 2008080973 | 7/2008 |

(Continued)

OTHER PUBLICATIONS

Thibonnier, M., "Development and therapeutic indications of orally-active non-peptide vasopressin receptor antagonists." Expert Opinion on Investigational Drugs, 1998, 7(5), 729-740.
Ryckmans, T."Modulation of the vasopressin system for the treatment of CNS diseases" Current Opinion in Drug Discovery & Development, 2010, 13 (5), 538-547.
Decaux, G. et al., "Non-peptide arginine-vasopressin antagonists: the vaptans," Lancet, 2010, 371, 1624-1632.
Lemmens-Gruber, R. et al. "Vasopressin antagonists," Cellular and Molecular Life Sciences, 2006, 63, 1766-1779.
Diaz, G. J. et al., "The [3H]dofetilide binding assay is a predictive screening tool for hERG blockade and proarrhythmia: Comparison of intact cell and membrane preparations and effects of altering [K+]o," Journal of Pharmacological and Toxicological Methods, 2004, 50, 187-199.

(Continued)

*Primary Examiner* — Rei-Tsang Shiao
(74) *Attorney, Agent, or Firm* — Neal, Gerber & Eisenberg LLP

(57) ABSTRACT

The present invention relates to novel substituted oxindole derivatives of formula (I) wherein the variables are as defined in the claims and description; to pharmaceutical compositions comprising them, and to their use for the treatment of vasopressin-related disorders.

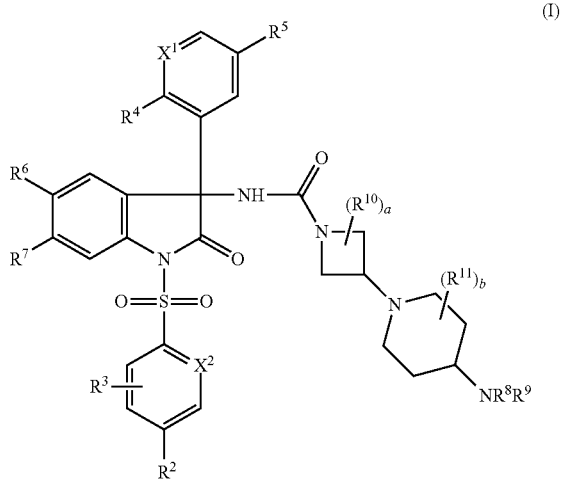

30 Claims, No Drawings

(56) References Cited

FOREIGN PATENT DOCUMENTS

| WO | 2009071687 | 6/2009 |
| WO | 2009071689 | 6/2009 |
| WO | 2009071690 | 6/2009 |
| WO | 2009071691 | 6/2009 |
| WO | 2009083559 | 7/2009 |
| WO | 2010009775 | 1/2010 |
| WO | 2010142739 | 12/2010 |

OTHER PUBLICATIONS

International Preliminary Report on Patentability for PCT Application PCT/EP2014/078702 dated Jun. 21, 2016.

* cited by examiner

OXINDOLE DERIVATIVES CARRYING AN AMINE-SUBSTITUTED PIPERIDYL-ACETIDINYL SUBSTITUENT AND USE THEREOF FOR TREATING VASOPRESSINE-RELATED DISEASES

CROSS-REFERENCE TO RELATED APPLICATIONS

This is a National Stage of International Patent Application No. PCT/EP2014/078702 filed on Dec. 19, 2014, which claims priority to U.S. Patent Application No. 61/919,256, filed on Dec. 20, 2013, the entire contents of which are incorporated herein by reference.

The present invention relates to novel substituted oxindole derivatives, pharmaceutical compositions comprising them, and their use for the treatment of vasopressin-related disorders.

Vasopressin is an endogenous hormone which exerts various effects on organs and tissues. It is suspected that the vasopressin system is involved in various pathological states such as, for example, heart failure and high blood pressure. At present, three receptors (V1a, V1b or V3 and V2) via which vasopressin mediates its numerous effects are known. Antagonists of these receptors are therefore being investigated as possible new therapeutic approaches for the treatment of diseases (M. Thibonnier, Exp. Opin. Invest. Drugs 1998, 7(5), 729-740; T. Ryckmans, Current Opinion in Drug Discovery & Development 13 (2010), 538-547; G. Decaux et al., Lancet 371 (2008), 1624-1632; R. Lemmens-Gruber, M. Kamyar, Cell. Mol. Life Sci. 63 (2006), 1766-1779).

1-(Het)Arylsulfonyl-1,3-dihydro-2H-indol-2-ones have previously been described as ligands of vasopressin receptors, for example in WO 2005/030755, WO 2006/005609, WO 2006/080574, WO 2008/080970, WO 2008/080971, WO 2008/080972, WO 2008/080973, WO 2009/071687, WO 2009/071689, WO 2009/071690, WO2009/071691, WO 2009/083559, WO 2010/009775 or WO 2010/142739.

Besides the binding affinity for the vasopressin V1b receptor, further properties may be advantageous for the treatment and/or prophylaxis of vasopressin-related disorders, such as, for example:

1.) a selectivity for the vasopressin V1b receptor compared with the vasopressin V1a receptor, i.e. the quotient of the binding affinity for the V1a receptor (Ki(V1a) (determined in the unit "nanomolar (nM)") and the binding affinity for the V1b receptor (Ki(V1b)) (determined in the unit "nanomolar (nM)"). A larger quotient Ki(V1a)/Ki(V1b) means a greater V1b selectivity;

2.) a selectivity for the vasopressin V1b receptor compared with the vasopressin V2 receptor, i.e. the quotient of the binding affinity for the V2 receptor (Ki(V2) (determined in the unit "nanomolar (nM)") and the binding affinity for the V1b receptor (Ki(V1b)) (determined in the unit "nanomolar (nM)"). A larger quotient Ki(V2)/Ki(V1b) means a greater V1b selectivity;

3.) a selectivity for the vasopressin V1b receptor compared with the oxytocin OT receptor, i.e. the quotient of the binding affinity for the OT receptor (Ki(OT) (determined in the unit "nanomolar (nM)") and the binding affinity for the V1b receptor (Ki(V1b)) (determined in the unit "nanomolar (nM)"). A larger quotient Ki(OT)/Ki(V1b) means a greater V1b selectivity.

4.) the metabolic stability, for example determined from the half-lives, measured in vitro, in liver microsomes from various species (e.g. rat or human);

5.) no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

6.) a suitable solubility in water (in mg/ml);

7.) suitable pharmacokinetics (time course of the concentration of the compound of the invention in plasma or in tissue, for example brain). The pharmacokinetics can be described by the following parameters: half-life (in h), volume of distribution (in l·kg−1), plasma clearance (in l·h−1·kg−1), AUC (area under the curve, area under the concentration-time curve, in ng·h·l−1), oral bioavailability (the dose-normalized ratio of AUC after oral administration and AUC after intravenous administration), the so-called brain-plasma ratio (the ratio of AUC in brain tissue and AUC in plasma);

8.) no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187 199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

It was therefore an object of the present invention to provide compounds for the treatment or prophylaxis of various vasopressin-related diseases. The compounds were intended to have a high activity and selectivity, especially a high affinity and selectivity for the vasopressin V1b receptor. In addition, the substance of the invention was intended to have one or more of the aforementioned advantages 1.) to 8.).

The object is achieved by compounds of the formula I

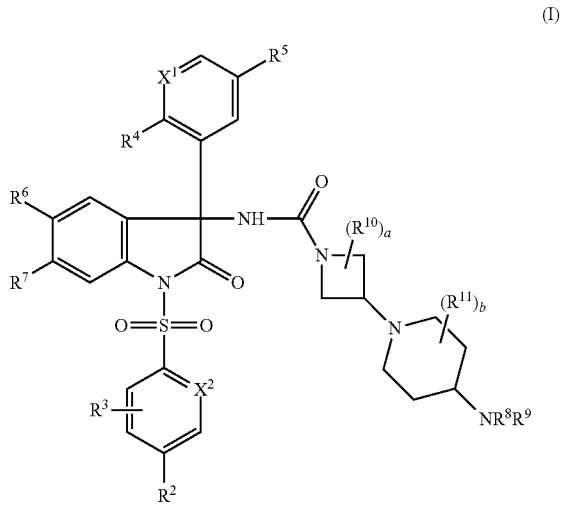

wherein
X$^1$ is N or CH;
X$^2$ is C—R$^1$ or N;
R$^1$ and R$^2$, independently of each other, are selected from hydrogen, halogen, cyano, C$_1$-C$_3$-alkyl, fluorinated C$_1$-C$_3$-alkyl, C$_1$-C$_3$-hydroxyalkyl, C$_1$-C$_3$-alkoxy and fluorinated C$_1$-C$_3$-alkoxy;
R$^3$ is selected from hydrogen, halogen, cyano, hydroxyl, C$_1$-C$_3$-alkyl, fluorinated C$_1$-C$_3$-alkyl, C$_1$-C$_3$-hydroxyalkyl, C$_1$-C$_3$-alkoxy and fluorinated C$_1$-C$_3$-alkoxy;
R$^4$ is selected from C$_1$-C$_3$-alkoxy;
R$^5$ is selected from hydrogen and C$_1$-C$_3$-alkoxy;
R$^6$ is selected from cyano and halogen;
R$^7$ is selected from hydrogen, halogen and cyano;
R$^8$ and R$^9$, independently of each other, are selected from hydrogen, cyano, C$_1$-C$_6$-alkyl, C$_1$-C$_6$-haloalkyl, C$_2$-C$_6$-alkenyl, C$_2$-C$_6$-haloalkenyl, C$_2$-C$_6$-alkynyl, C$_2$-C$_6$-haloalkynyl, C$_3$-C$_7$-cycloalkyl, C$_3$-C$_7$-halocycloalkyl and phenyl which may carry 1, 2 or 3 substituents selected from halogen, hydroxyl, cyano, C$_1$-C$_4$-alkyl, C$_1$-C$_4$-haloalkyl, C$_1$-C$_4$-alkoxy and C$_1$-C$_4$-haloalkoxy; or
R$^8$ and R$^9$, together with the nitrogen atom they are bound to, form a 3-, 4-, 5-, 6- or 7-membered saturated, partially unsaturated or maximally unsaturated heterocyclic ring as ring member, via which the ring is bound to the remainder of the molecule, where the heterocyclic ring may carry 1 or 2 substituents selected from cyano, C$_1$-C$_4$-alkyl and C$_1$-C$_4$-haloalkyl [the heterocyclic ring formed by R$^8$ and R$^9$ together with the nitrogen atom they are bound to thus having only this nitrogen atom as heteroatom ring member via which the ring is bound to the remainder of the molecule (the remaining ring members being carbon atoms)];
R$^{10}$ and R$^{11}$, independently of each other and independently of each occurrence, are selected from halogen, C$_1$-C$_4$-alkyl, C$_1$-C$_4$-haloalkyl, C$_1$-C$_4$-alkoxy and C$_1$-C$_4$-haloalkoxy, with the proviso that R$^{10}$ and R$^{11}$ are not halogen, C$_1$-C$_4$-alkoxy or C$_1$-C$_4$-haloalkoxy if they are bound to a carbon atom in α-position to a nitrogen ring atom; or
two non-geminal radicals R$^{10}$ form together a group —(CH$_2$)$_n$—, where n is 1, 2, 3 or 4, where 1 or 2 hydrogen atoms in this group may be replaced a methyl group; or
two non-geminal radicals R$^{11}$ form together a group —(CH$_2$)$_n$—, where n is 1, 2, 3 or 4, where 1 or 2 hydrogen atoms in this group may be replaced a methyl group;
a is 0, 1 or 2; and
b is 0, 1, 2, 3 or 4;
and the N-oxides, stereoisomers and pharmaceutically acceptable salts thereof, and the compound of the formula I, wherein at least one of the atoms has been replaced by its stable, non-radioactive isotope.

Accordingly, the present invention relates to compounds of the formula I (also "compounds I" hereinafter) and the N-oxides, stereoisomers and the pharmaceutically acceptable salts of the compounds I of the compounds I.

In another aspect, the invention relates to a pharmaceutical composition comprising a therapeutically effective amount of at least one compound of formula I or an N-oxide, a stereoisomer or a pharmaceutically acceptable salt thereof, or comprising at least one compound as defined above or below wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance.

In yet another aspect, the invention relates to a compound of formula I or an N-oxide, a stereoisomer or a pharmaceutically acceptable salt thereof for use as a medicament.

In yet another aspect, the invention relates to a compound of formula I or an N-oxide, a stereoisomer or a pharmaceutically acceptable salt thereof for the treatment and/or prophylaxis of vasopressin-related diseases, especially of disorders which respond to the modulation of the vasopressin receptor, in particular of the V1b receptor.

In yet another aspect, the invention relates to the use of a compound of formula I or of an N-oxide, a stereoisomer or a pharmaceutically acceptable salt thereof for the manufacture of a medicament for the treatment and/or prophylaxis of vasopressin-related diseases; especially of disorders which respond to the modulation of the vasopressin receptor, in particular of the V1b receptor.

The pharmaceutically acceptable salts of compounds of the formula I, which are also referred to as physiologically tolerated salts, are ordinarily obtainable by reacting the free base of the compounds I of the invention (i.e. of the compounds I according to structural formula I) with suitable acids. Examples of suitable acids are listed in "Fortschritte der Arzneimittelforschung", 1966, Birkhauser Verlag, vol. 10, pp. 224-285. These include for example hydrochloric acid, citric acid, tartaric acid, lactic acid, phosphoric acid, methanesulfonic acid, acetic acid, trifluoroacetic acid, formic acid, maleic acid and fumaric acid.

Halogen in the terms of the present invention is fluorine, chlorine, bromine or iodine, preferably fluorine, chlorine or bromine and especially fluorine or chlorine.

C$_1$-C$_3$-Alkyl is a linear or branched alkyl radical having 1 to 3 carbon atoms, such as methyl, ethyl, n-propyl or isopropyl. C$_1$-C$_4$-Alkyl is a linear or branched alkyl radical having 1 to 4 carbon atoms, such as methyl, ethyl, n-propyl, isopropyl, n-butyl, sec-butyl, isobutyl or tert-butyl.

Fluorinated alkyl is a straight-chain or branched alkyl group having usually from 1 to 4 (=fluorinated C$_1$-C$_4$-alkyl), in particular 1 to 3 carbon atoms (=fluorinated C$_1$-C$_3$-alkyl), more preferably 1 or 2 carbon atoms (=fluorinated C$_1$-C$_2$-alkyl), wherein at least one, e.g. 1, 2, 3, 4 or all of the hydrogen atoms are replaced by fluorine atoms. Examples for fluorinated C$_1$-C$_2$-alkyl are fluoromethyl, difluoromethyl, trifluoromethyl, 1-fluoroethyl, (R)-1-fluoroethyl, (S)-1-fluoroethyl, 2-fluoroethyl, 1,1-difluoroethyl, 2,2-difluoroethyl, 2,2,2-trifluoroethyl, pentafluoroethyl and the like. Examples for fluorinated C$_1$-C$_3$-alkyl are, apart those mentioned above for fluorinated C$_1$-C$_2$-alkyl, 1-fluoropropyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, 2-fluoropropyl, 2-fluoro-1-methylethyl, (R)-2-fluoro-1-methylethyl, (S)-2-fluoro-1-methylethyl, 2,2-difluoro-1-methylethyl, (R)-2,2-difluoro-1-methylethyl, (S)-2,2-difluoro-1-methylethyl, 1,2-difluoro-1-methylethyl, (R)-1,2-difluoro-1-methylethyl, (S)-1,2-difluoro-1-methylethyl, 2,2,2-trifluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl and the like. Examples for fluorinated C$_1$-C$_4$-alkyl are, apart those mentioned above for fluorinated C$_1$-C$_3$-alkyl, 1-fluorobutyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, and the like.

C$_1$-C$_4$-Haloalkyl is C$_1$-C$_4$-alkyl as defined above wherein at least one, e.g. 1, 2, 3, 4 or all of the hydrogen atoms are replaced by a halogen atom. Examples are, apart those mentioned above for fluorinated C$_1$-C$_4$-alkyl, chloromethyl, bromomethyl, dichloromethyl, trichloromethyl, chlorofluoromethyl, dichlorofluoromethyl, chlorodifluoromethyl, 1-chloroethyl, 1-bromoethyl, 2-chloro-2-fluoroethyl, 2-chloro-2,2-difluoroethyl, 2,2-dichloro-2-fluoroethyl, 2,2,2-trichloroethyl, 3-chloropropyl, 4-chlorobutyl and the like.

$C_1$-$C_3$-Hydroxyalkyl is $C_1$-$C_3$-alkyl as defined above wherein one of the hydrogen atoms is replaced by a hydroxyl group. Examples are hydroxymethyl, 1- and 2-hydroxyethyl, 1-, 2- and 3-hydroxy-n-propyl, 1-(hydroxymethyl)-ethyl and the like.

$C_3$-$C_7$-Cycloalkyl is a monocyclic saturated hydrocarbon radical having 3 to 7, in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of $C_3$-$C_4$-cycloalkyl comprise cyclopropyl and cyclobutyl. Examples of $C_3$-$C_5$-cycloalkyl comprise cyclopropyl, cyclobutyl and cyclopentyl. Examples of $C_3$-$C_6$-cycloalkyl comprise cyclopropyl, cyclobutyl, cyclopentyl and cyclohexyl. Examples of $C_3$-$C_7$-cycloalkyl comprise cyclopropyl, cyclobutyl, cyclopentyl, cyclohexyl and cycloheptyl.

$C_3$-$C_7$-Halocycloalkyl is a monocyclic saturated hydrocarbon radical having 3 to 7, in particular 3 to 6 ("$C_3$-$C_6$-halocycloalkyl") or 3 to 5 ("$C_3$-$C_5$-halocycloalkyl") or 3 to 4 ("$C_3$-$C_4$-halocycloalkyl") carbon ring members (as mentioned above) in which some or all of the hydrogen atoms are replaced by halogen atoms as mentioned above, in particular fluorine, chlorine and bromine.

$C_1$-$C_3$-Alkoxy is a linear or branched alkyl radical linked via an oxygen atom and having 1 to 3 carbon atoms. Examples are methoxy, ethoxy, n-propoxy and isopropoxy. $C_1$-$C_4$-Alkoxy is a linear or branched alkyl radical linked via an oxygen atom and having 1 to 4 carbon atoms. Examples are methoxy, ethoxy, n-propoxy, isopropoxy, n-butoxy, sec-butoxy, isobutoxy and tert-butoxy.

$C_1$-$C_4$-Haloalkoxy is $C_1$-$C_4$-alkoxy as defined above wherein at least one, e.g. 1, 2, 3, 4 or all of the hydrogen atoms are replaced by a halogen atom. Preferably, $C_1$-$C_4$-haloalkoxy is fluorinated $C_1$-$C_4$-alkoxy. This is a straight-chain or branched alkoxy group having from 1 to 4, in particular 1 to 3 carbon atoms (=fluorinated $C_1$-$C_3$-alkoxy), more preferably 1 or 2 carbon atoms (=fluorinated $C_1$-$C_2$-alkoxy), wherein at least one, e.g. 1, 2, 3, 4 or all of the hydrogen atoms are replaced by fluorine atoms, such as in fluoromethoxy, difluoromethoxy, trifluoromethoxy, 1-fluoroethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1-fluoropropoxy, (R)-1-fluoropropoxy, (S)-1-fluoropropoxy, 2-fluoropropoxy, 3-fluoropropoxy, 1,1-difluoropropoxy, 2,2-difluoropropoxy, 3,3-difluoropropoxy, 3,3,3-trifluoropropoxy, 2-fluoro-1-methylethoxy, (R)-2-fluoro-1-methylethoxy, (S)-2-fluoro-1-methylethoxy, 2,2-difluoro-1-methylethoxy, (R)-2,2-difluoro-1-methylethoxy, (S)-2,2-difluoro-1-methylethoxy, 1,2-difluoro-1-methylethoxy, (R)-1,2-difluoro-1-methylethoxy, (S)-1,2-difluoro-1-methylethoxy, 2,2,2-trifluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, etc The term "$R^8$ and $R^9$, together with the nitrogen atom they are bound to, form a 3-, 4-, 5-, 6- or 7-membered saturated, partially unsaturated or maximally unsaturated heterocyclic ring" denotes a 3-, 4-, 5-, 6- or 7-membered saturated, partially unsaturated or maximum unsaturated heteromonocyclic ring containing one nitrogen atom (as only heteroatom) as ring member besides carbon atoms as ring members which is bound via its nitrogen ring atom to the remainder of the molecule (i.e. to the piperidyl ring). Unsaturated rings contain at least one C—C bond(s). Maximally unsaturated rings contain as many conjugated C—C bonds as allowed by the ring size. A maximally unsaturated 5-membered heterocyclic ring is aromatic. Examples of a 3-, 4-, 5-, 6- or 7-membered saturated heterocyclic ring include: aziridin-1-yl, azetidin-1-yl, pyrrolidin-1-yl, piperidin-1-yl and azepan-1-yl. Examples of a 3-, 4-, 5-, 6- or 7-membered partially unsaturated heterocyclic ring include: 2,3-dihydropyrrol-1-yl, 2,5-dihydropyrrol-1-yl, 3,4-dihydro-2H-pyridin-1-yl, 3,6-dihydro-2H-pyridin-1-yl, 2,3,4,5-tetrahydroazepin-1-yl, 2,3,4,7-tetrahydroazepin-1-yl, 2,3,6,7-tetrahydroazepin-1-yl, 2,3-dihydroazepin-1-yl, 2,7-dihydroazepin-1-yl, 4,5-dihydroazepin-1-yl and the like.

Examples for a 3-, 4-, 5-, 6- or 7-membered maximally unsaturated (including aromatic) heterocyclic ring are 1-pyrrolyl, 2H-pyridin-1-yl, and also a homoaromatic radical, such as 1H-azepine.

The compounds of the invention of the formula I and their N-oxides, stereoisomers and pharmacologically acceptable salts may also be present in the form of solvates or hydrates. Solvates mean in the context of the present invention crystalline forms of the compounds I or of their pharmaceutically acceptable salts which comprise solvent molecules incorporated in the crystal lattice. The solvent molecules are preferably incorporated in stoichiometric ratios. Hydrates are a specific form of solvates; the solvent in this case being water.

The statements made hereinafter concerning suitable and preferred features of the invention, especially concerning the radicals $R^1$, $R^2$, $R^3$, $R^4$, $R^5$, $R^6$, $R^7$, $R^8$, $R^9$, $R^{10}$, $R^{11}$, $X^1$, $X^2$, a and b in the compound I, but also concerning the features of the process of the invention and of the use according to the invention apply both taken on their own as well as preferably in any possible combination with one another.

The compounds I are preferably provided in the form of the free base (i.e. according to structural formula I) or in the form of their acid addition salts.

In a preferred embodiment, $X^2$ is C—$R^1$ and $R^1$, $R^2$ and $R^3$, independently of each other, are selected from hydrogen, halogen, $C_1$-$C_3$-alkyl, fluorinated $C_1$-$C_3$-alkyl, $C_1$-$C_3$-alkoxy and fluorinated $C_1$-$C_3$-alkoxy. More preferably, $R^1$, $R^2$ and $R^3$, independently of each other, are selected from hydrogen, fluorine and methoxy.

In particular, $R^1$ is selected from hydrogen, fluorine and methoxy. Specifically, $R^1$ is methoxy.

In particular, $R^2$ is selected from hydrogen, fluorine and methoxy. Specifically, $R^2$ is methoxy.

In a specific embodiment, $R^1$ and $R^2$ are both methoxy.

In particular, $R^3$ is selected from hydrogen and fluorine. Specifically, $R^3$ is hydrogen.

$R^3$ is preferably bound in 3- or 5-position, in particular in 5-position, relative to the 2- and 4-positions of $R^1$ and $R^2$.

In another preferred embodiment, $X^2$ is N and $R^2$ and $R^3$, independently of each other, are selected from hydrogen, halogen, $C_1$-$C_3$-alkyl, fluorinated $C_1$-$C_3$-alkyl, $C_1$-$C_3$-alkoxy and fluorinated $C_1$-$C_3$-alkoxy. More preferably, $R^1$, $R^2$ and $R^3$, independently of each other, are selected from hydrogen, fluorine and methoxy.

In this case, $R^2$ is preferably selected from hydrogen, fluorine and methoxy, and is in particular methoxy.

In this case, $R^3$ is preferably selected from hydrogen, fluorine and methoxy, and is in particular hydrogen.

Preferably, $R^4$ is selected from methoxy and ethoxy.

Preferably, $R^5$ is hydrogen or methoxy, and in particular hydrogen.

Preferably, $R^6$ is selected from cyano, fluorine and chlorine. In particular, $R^6$ is selected from cyano and chlorine.

Preferably, $R^7$ is selected from hydrogen and fluorine. In particular, $R^7$ is hydrogen.

In a preferred embodiment, $R^8$ is selected from hydrogen, $C_1$-$C_4$-alkyl, $C_1$-$C_4$-haloalkyl, $C_3$-$C_6$-cycloalkyl and $C_3$-$C_6$-halocycloalkyl;

$R^9$ is selected from hydrogen, $C_1$-$C_4$-alkyl, $C_1$-$C_4$-haloalkyl, $C_3$-$C_6$-cycloalkyl and $C_3$-$C_6$-halocycloalkyl; or $R^8$ and $R^9$, together with the nitrogen atom they are bound to, form a 3-, 4-, 5- or 6-membered saturated, partially unsaturated or maximally unsaturated heterocyclic ring, where the heterocyclic ring may carry 1 or 2 substituents selected from cyano, $C_1$-$C_4$-alkyl and $C_1$-$C_4$-haloalkyl.

The 3-, 4-, 5- or 6-membered saturated, partially unsaturated or maximally unsaturated heterocyclic ring which $R^8$ and $R^9$, together with the nitrogen atom they are bound to, form, has besides carbon atoms as ring members one nitrogen atom (as only heteroatom) as ring member, via which the ring is bound to the remainder of the molecule. Examples include aziridin-1-yl, azetidin-1-yl, pyrrolidin-1-yl, piperidin-1-yl, 2,3-dihydropyrrol-1-yl, 2,5-dihydropyrrol-1-yl, 3,4-dihydro-2H-pyridin-1-yl, 3,6-dihydro-2H-pyridin-1-yl, 2H-pyridin-1-yl and 1-pyrrolyl.

More preferably, $R^8$ is selected from $C_1$-$C_4$-alkyl, fluorinated $C_1$-$C_4$-alkyl, $C_3$-$C_6$-cycloalkyl and fluorinated $C_3$-$C_6$-cycloalkyl;

$R^9$ is selected from $C_1$-$C_4$-alkyl, fluorinated $C_1$-$C_4$-alkyl, $C_3$-$C_6$-cycloalkyl and fluorinated $C_3$-$C_6$-cycloalkyl; or $R^8$ and $R^9$, together with the nitrogen atom they are bound to, form a 3-, 4-, 5- or 6-membered saturated heterocyclic ring, where the heterocyclic ring may carry 1 or 2 substituents selected from cyano, $C_1$-$C_4$-alkyl and $C_1$-$C_4$-haloalkyl.

In particular, $R^8$ is selected from $C_1$-$C_4$-alkyl; and $R^9$ is selected from $C_1$-$C_4$-alkyl; or $R^8$ and $R^9$, together form a group —$(CH_2)_n$—, where n is 2, 3, 4, or 5, thus forming together with the nitrogen atom they are bound to a 3-, 4-, 5- or 6-membered saturated heterocyclic ring.

The saturated heterocyclic ring formed by $R^8$ and $R^9$ together with the nitrogen atom they are bound to is preferably selected from aziridin-1-yl, azetidin-1-yl, pyrrolidin-1-yl and piperidin-1-yl, where the 4 last mentioned rings are unsubstituted or substituted by 1 or 2 substituents selected from cyano, $C_1$-$C_4$-alkyl and $C_1$-$C_4$-haloalkyl, and are preferably unsubstituted.

Preferably, each $R^{10}$ is independently selected from halogen and $C_1$-$C_4$-alkyl, preferably from F, Cl and $CH_3$, with the proviso that $R^{10}$ is not halogen if it is bound to a carbon atom in α-position to a nitrogen ring atom; and is in particular $CH_3$.

Preferably, each $R^{11}$ is independently selected from halogen and $C_1$-$C_4$-alkyl, preferably from F, Cl and $CH_3$, with the proviso that $R^{11}$ is not halogen if it is bound to a carbon atom in α-position to a nitrogen ring atom; and is in particular $CH_3$;

or two non-geminal radicals $R^{11}$ form together a group —$CH_2$—.

In one embodiment, $X^1$ is N.

In another embodiment, $X^1$ is CH.

In one embodiment, $X^2$ is C—$R^1$.

In another embodiment, $X^2$ is N.

a is preferably 0 or 1, in particular 0.

b is preferably 0, 1 or 2, in particular 0.

The invention preferably relates to compounds of the formula I in which $R^1$ (if present), $R^2$ and $R^3$, independently of each other, are selected from hydrogen, halogen, $C_1$-$C_3$-alkyl, fluorinated $C_1$-$C_3$-alkyl, $C_1$-$C_3$-alkoxy and fluorinated $C_1$-$C_3$-alkoxy;

$R^4$ is selected from methoxy and ethoxy;

$R^5$ is hydrogen or methoxy;

$R^6$ is selected from cyano, fluorine and chlorine;

$R^7$ is hydrogen or fluorine;

$R^8$ is selected from hydrogen, $C_1$-$C_4$-alkyl, $C_1$-$C_4$-haloalkyl, $C_3$-$C_6$-cycloalkyl and $C_3$-$C_6$-halocycloalkyl;

$R^9$ is selected from hydrogen, $C_1$-$C_4$-alkyl, $C_1$-$C_4$-haloalkyl, $C_3$-$C_6$-cycloalkyl and $C_3$-$C_6$-halocycloalkyl; or $R^8$ and $R^9$, together with the nitrogen atom they are bound to, form a 3-, 4-, 5- or 6-membered saturated, partially unsaturated or maximally unsaturated heterocyclic ring, where the heterocyclic ring may carry 1 or 2 substituents selected from cyano, $C_1$-$C_4$-alkyl and $C_1$-$C_4$-haloalkyl each $R^{10}$ is independently selected from halogen and $C_1$-$C_4$-alkyl or two non-geminal radicals $R^{10}$ form together a group —$CH_2$— or —$CH_2CH_2$—;

each $R^{11}$ is independently selected from halogen and $C_1$-$C_4$-alkyl or two non-geminal radicals $R^{11}$ form together a group —$CH_2$— or —$CH_2CH_2$—;

a is 0, 1 or 2;

b is 0, 1 or 2;

and the pharmaceutically acceptable salts thereof.

The invention more preferably relates to compounds of the formula I in which $R^1$ (if present), $R^2$ and $R^3$, independently of each other, are selected from hydrogen, halogen, $C_1$-$C_3$-alkyl, fluorinated $C_1$-$C_3$-alkyl, $C_1$-$C_3$-alkoxy and fluorinated $C_1$-$C_3$-alkoxy;

$R^4$ is selected from methoxy and ethoxy;

$R^5$ is hydrogen or methoxy;

$R^6$ is selected from cyano, fluorine and chlorine;

$R^7$ is hydrogen or fluorine;

$R^8$ is selected from $C_1$-$C_4$-alkyl, fluorinated $C_1$-$C_4$-alkyl, $C_3$-$C_6$-cycloalkyl and fluorinated $C_3$-$C_6$-cycloalkyl;

$R^9$ is selected from $C_1$-$C_4$-alkyl, fluorinated $C_1$-$C_4$-alkyl, $C_3$-$C_6$-cycloalkyl and fluorinated $C_3$-$C_6$-cycloalkyl; or $R^8$ and $R^9$, together with the nitrogen atom they are bound to, form a 3-, 4-, 5- or 6-membered saturated heterocyclic ring, where the heterocyclic ring may carry 1 or 2 substituents selected from cyano, $C_1$-$C_4$-alkyl and $C_1$-$C_4$-haloalkyl;

each $R^{10}$ is independently selected from halogen and $C_1$-$C_4$-alkyl or two non-geminal radicals $R^{10}$ form together a group —$CH_2$— or —$CH_2CH_2$—;

each $R^{11}$ is independently selected from halogen and $C_1$-$C_4$-alkyl or two non-geminal radicals $R^{11}$ form together a group —$CH_2$— or —$CH_2CH_2$—;

a is 0, 1, or 2;

b is 0, 1 or 2;

and the pharmaceutically acceptable salts thereof.

The invention more preferably relates to compounds of the formula I in which $R^1$ (if present), $R^2$ and $R^3$, independently of each other, are selected from hydrogen, fluorine and methoxy;

$R^4$ is selected from methoxy and ethoxy;

$R^5$ is hydrogen or methoxy;

$R^6$ is selected from cyano, fluorine and chlorine;

$R^7$ is hydrogen or fluorine;

$R^8$ is $C_1$-$C_4$-alkyl;

$R^9$ is $C_1$-$C_4$-alkyl; or $R^8$ and $R^9$, form together a group —$(CH_2)_n$—, where n is 2, 3, 4, or 5, thus forming together with the nitrogen atom they are bound to a 3-, 4-, 5- or 6-membered saturated heterocyclic ring, wherein the heterocyclic ring is unsubstituted or substituted by 1 or 2 substituents selected from cyano, $C_1$-$C_4$-alkyl and $C_1$-$C_4$-haloalkyl;

each $R^{10}$ is independently selected from F, Cl and methyl or two non-geminal radicals $R^{10}$ form together a group —$CH_2$—;

each $R^{11}$ is independently selected from F, Cl and methyl or two non-geminal radicals $R^{11}$ form together a group —$CH_2$—;

$X^1$ is N or CH;
$X^2$ is C—$R^1$ or N;
a is 0, 1 or 2, preferably 0 or 1;
b is 0, 1 or 2, preferably 0 or 2;
and the pharmaceutically acceptable salts thereof.

The invention even more preferably relates to compounds of the formula I in which
$R^1$ (if present) is selected from hydrogen, fluorine and methoxy;
$R^2$ is selected from hydrogen, fluorine and methoxy;
$R^3$ is selected from hydrogen and fluorine;
$R^4$ is selected from methoxy and ethoxy;
$R^5$ is hydrogen or methoxy;
$R^6$ is selected from cyano, fluorine and chlorine;
$R^7$ is hydrogen or fluorine;
$R^8$ is $C_1$-$C_4$-alkyl;
$R^9$ is $C_1$-$C_4$-alkyl; or
$R^8$ and $R^9$, form together a group —$(CH_2)_n$—, where n is 2, 3, 4, or 5, thus forming together with the nitrogen atom they are bound to a 3-, 4-, 5- or 6-membered saturated heterocyclic ring;
$X^1$ is N or CH;
$X^2$ is C—$R^1$ or N;
a is 0;
b is 0;
and the pharmaceutically acceptable salts thereof.

The invention even in particular relates to compounds of the formula I in which
$R^1$ (if present) is methoxy;
$R^2$ is methoxy;
$R^3$ is hydrogen;
$R^4$ is selected from methoxy and ethoxy;
$R^5$ is hydrogen;
$R^6$ is selected from cyano, and chlorine;
$R^7$ is hydrogen;
$R^8$ is $C_1$-$C_4$-alkyl;
$R^9$ is $C_1$-$C_4$-alkyl; or
$R^8$ and $R^9$, form together a group —$(CH_2)_n$—, where n is 2, 3, 4, or 5, thus forming together with the nitrogen atom they are bound to a 3-, 4-, 5- or 6-membered saturated heterocyclic ring;
$X^1$ is N or CH;
$X^2$ is C—$R^1$ or N;
a is 0;
b is 0;
and the pharmaceutically acceptable salts thereof.

Examples of preferred embodiment of the present invention are compounds of the formulae I.1 to I.40 and the N-oxides, stereoisomers and the pharmaceutically acceptable salts thereof, in which the radicals $R^1$, $R^2$, $R^3$, $R^6$, $R^7$, $R^8$ and $R^9$ have one of the above general or preferred meanings. In particular, preferred compounds are the individual compounds compiled in the tables 1 to 7160 below. Moreover, the meanings mentioned below for the individual variables in the tables are per se, independently of the combination in which they are mentioned, a particularly preferred embodiment of the substituents in question.

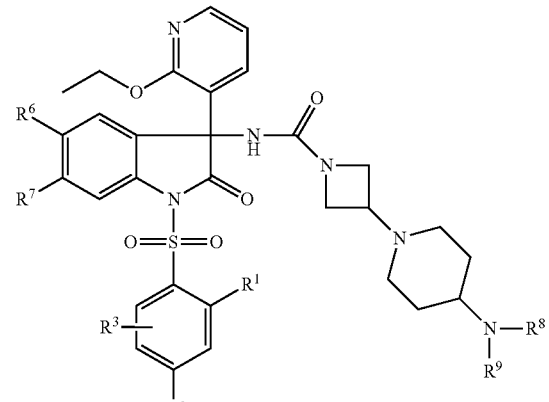

I.1

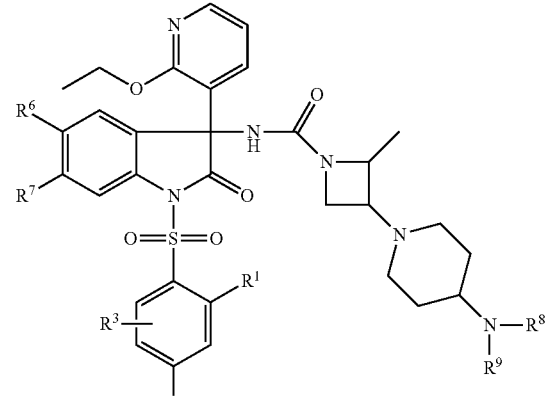

I.2

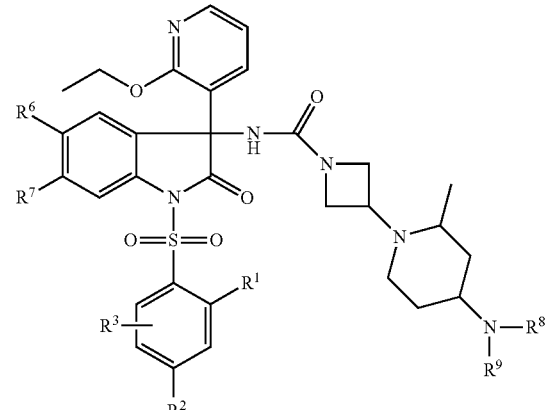

I.3

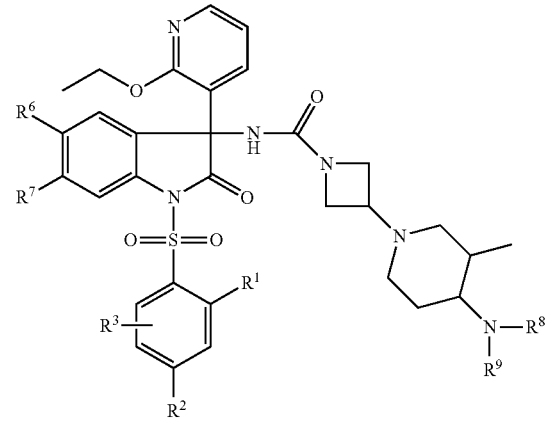

I.4

I.5
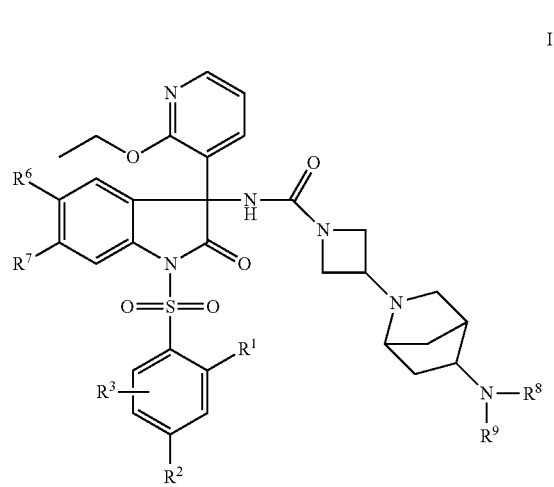
I.6
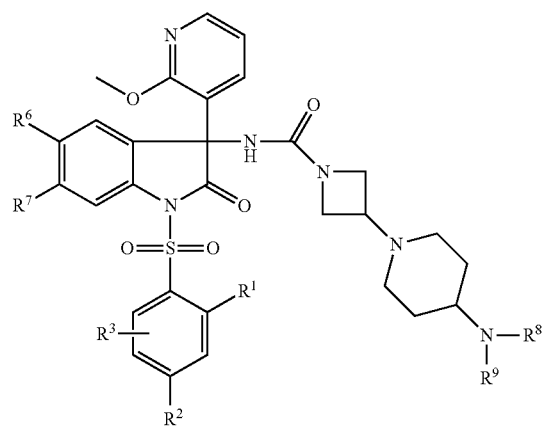
I.7
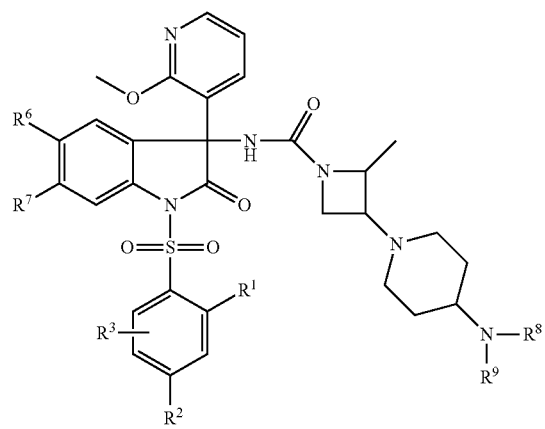
I.8
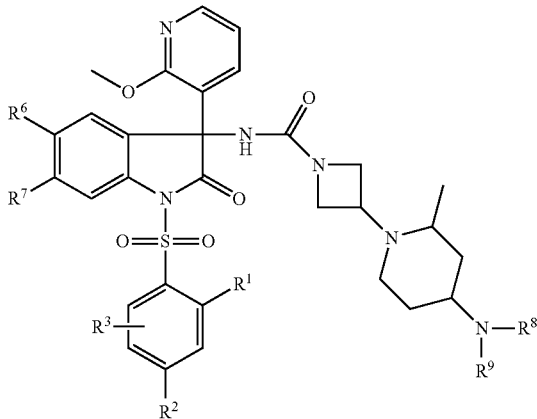
I.9
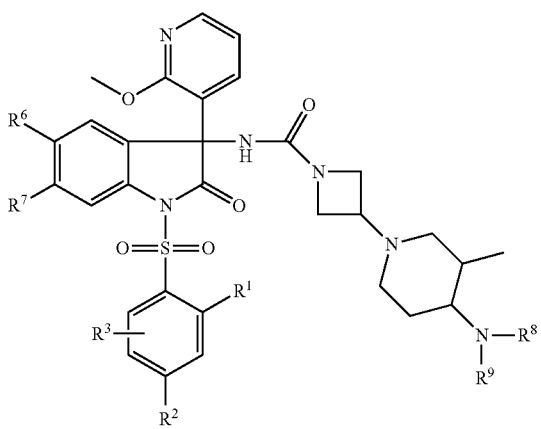
I.10
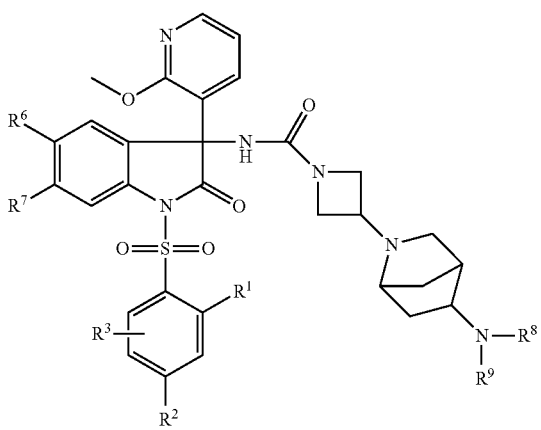

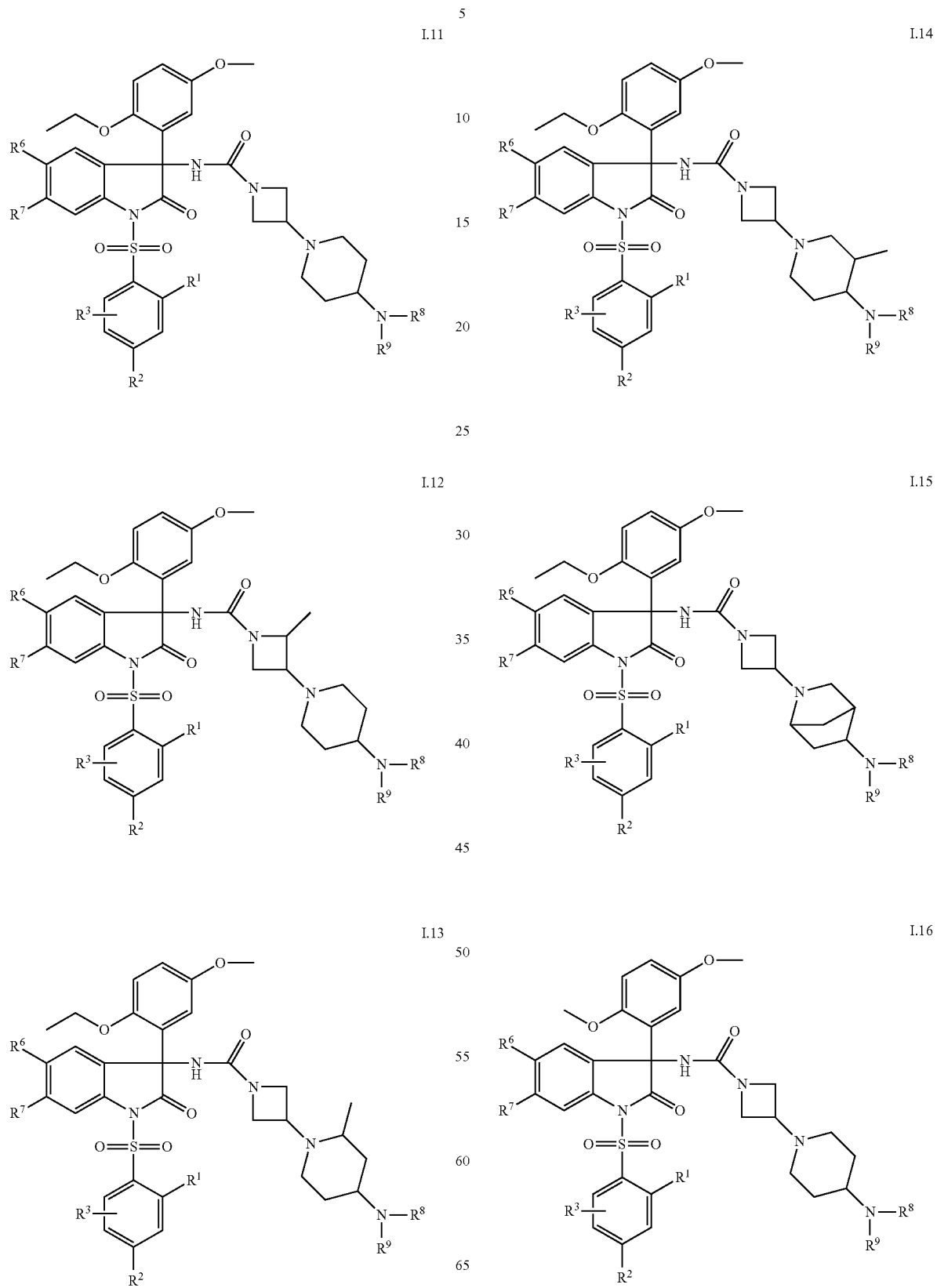

I.17
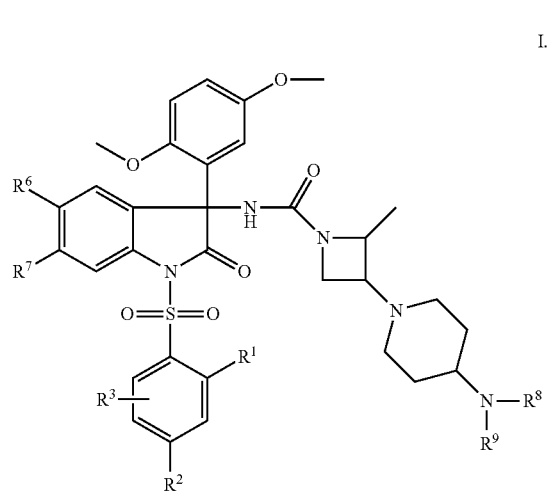
I.18
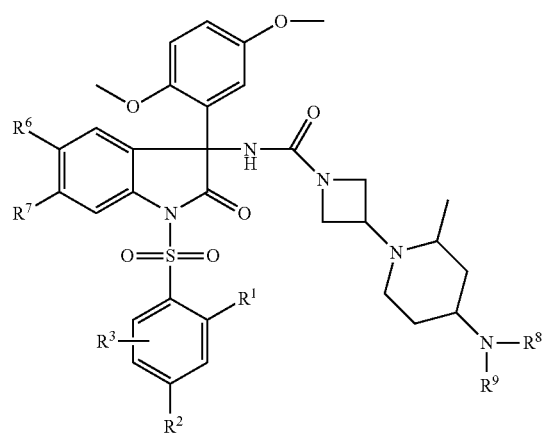
I.19
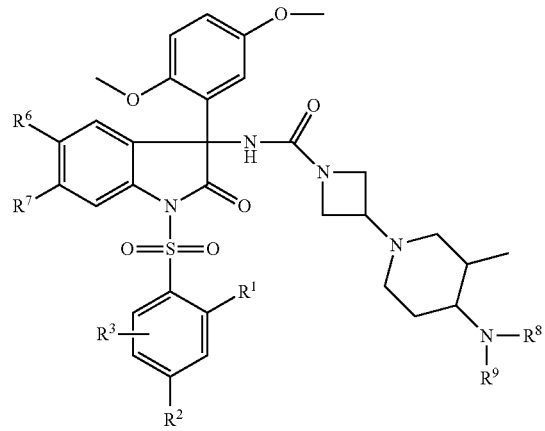
I.20
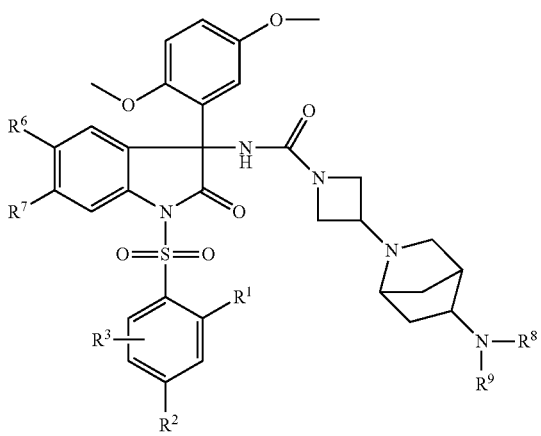
I.21
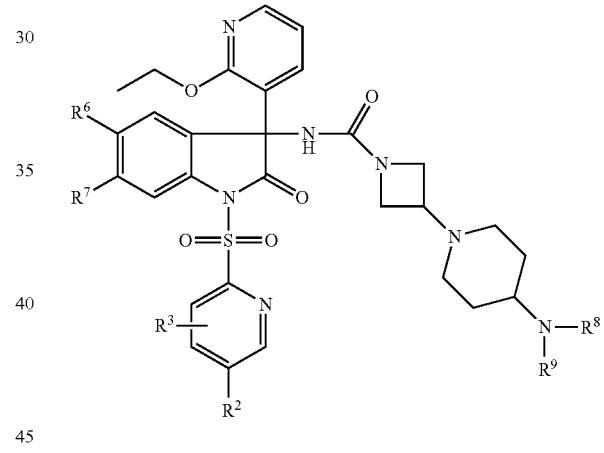
I.22
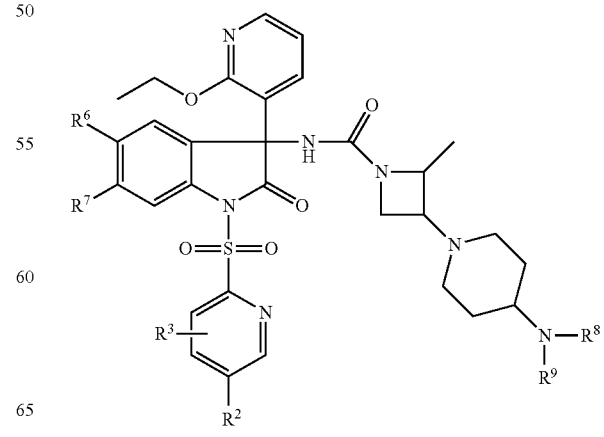

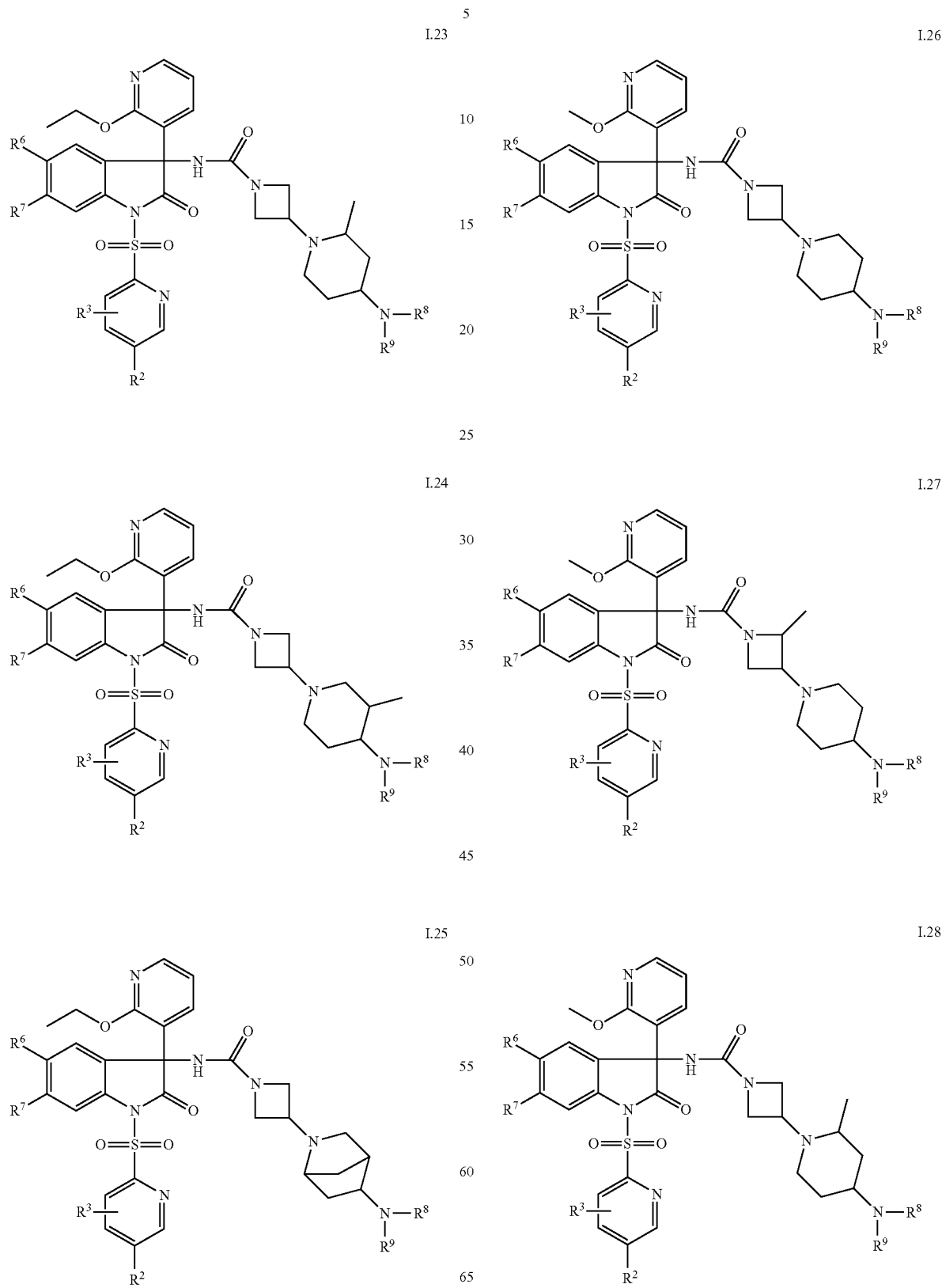

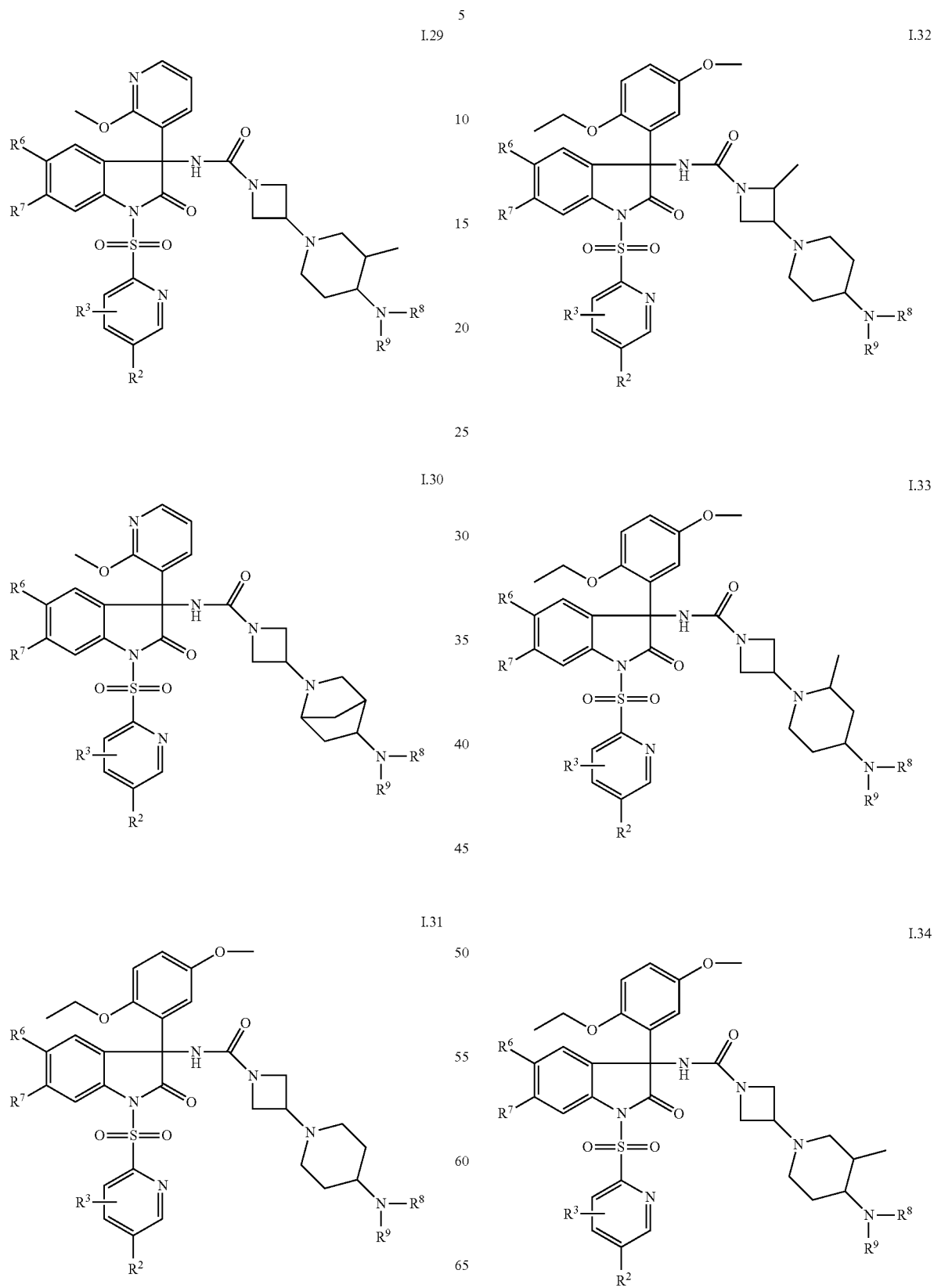

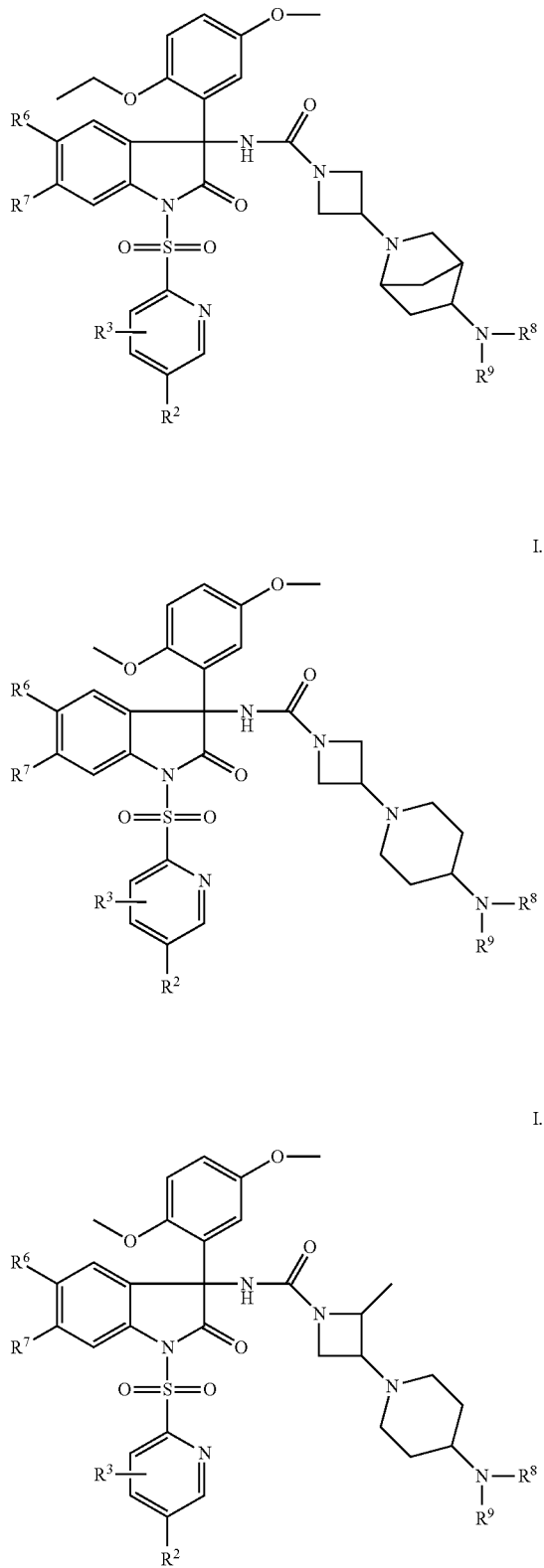
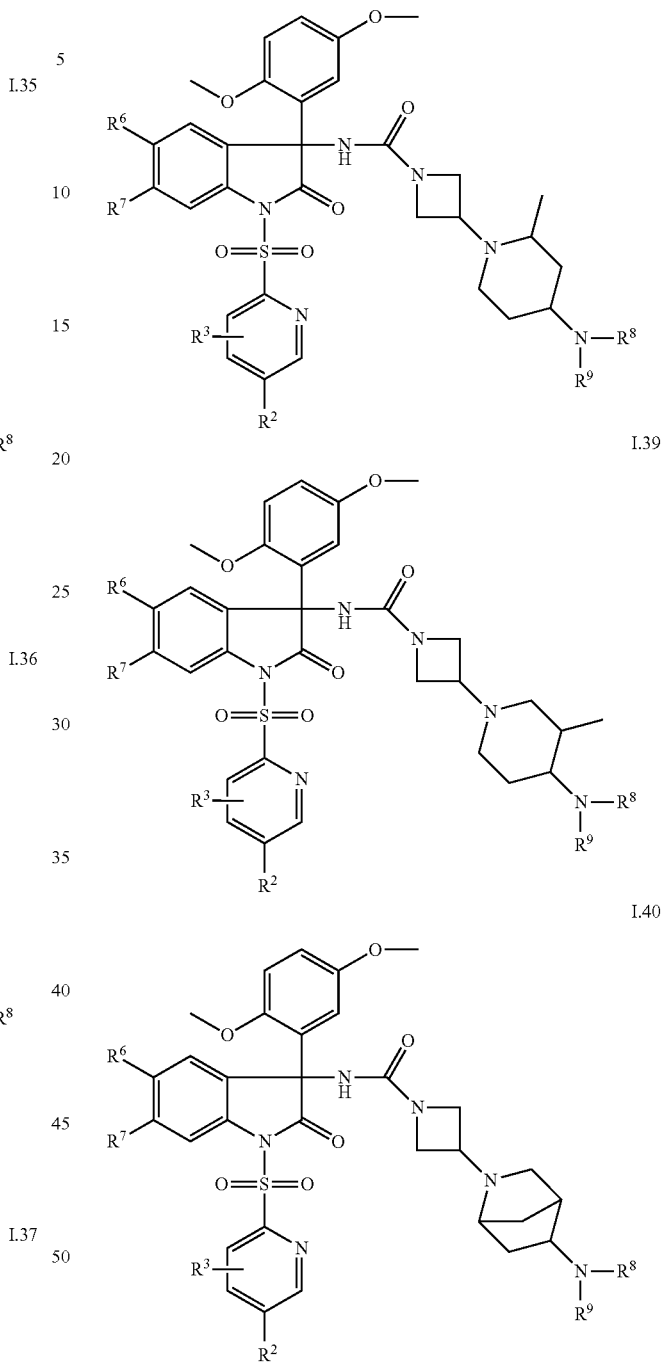

Table 1

Compounds of the formula I.1 in which $R^8$ is hydrogen, $R^9$ is hydrogen, and $R^1$, $R^2$, $R^3$, $R^6$ and $R^7$ for a compound corresponds in each case to one row of Table A.

Table 2

Compounds of the formula I.1 in which $R^8$ is hydrogen, $R^9$ is methyl, and $R^1$, and $R^7$ for a compound corresponds in each case to one row of Table A.

Table 3

Compounds of the formula I.1 in which $R^8$ is hydrogen, $R^9$ is ethyl, and $R^1$, $R^2$, $R^3$, $R^6$ and $R^7$ for a compound corresponds in each case to one row of Table A.

Table 4
Compounds of the formula I.1 in which $R^8$ is hydrogen, $R^9$ is n-propyl, and $R^1$, $R^2$, $R^3$, $R^6$ and $R^7$ for a compound corresponds in each case to one row of Table A.

Table 5
Compounds of the formula I.1 in which $R^8$ is hydrogen, $R^9$ is propan-2-yl, and $R^1$, $R^2$, $R^3$, $R^6$ and $R^7$ for a compound corresponds in each case to one row of Table A.

Table 6
Compounds of the formula I.1 in which $R^8$ is hydrogen, $R^9$ is n-butyl, and $R^1$, $R^2$, $R^3$, $R^6$ and $R^7$ for a compound corresponds in each case to one row of Table A.

Table 7
Compounds of the formula I.1 in which $R^8$ is hydrogen, $R^9$ is 1-methylpropyl, and $R^1$, $R^2$, $R^3$, $R^6$ and $R^7$ for a compound corresponds in each case to one row of Table A.

Table 8
Compounds of the formula I.1 in which $R^8$ is hydrogen, $R^9$ is 2-methylpropyl, and $R^1$, $R^2$, $R^3$, $R^6$ and $R^7$ for a compound corresponds in each case to one row of Table A.

Table 9
Compounds of the formula I.1 in which $R^8$ is hydrogen, $R^9$ is 1,1-dimethylethyl, and $R^1$, $R^2$, $R^3$, $R^6$ and $R^7$ for a compound corresponds in each case to one row of Table A.

Table 10
Compounds of the formula I.1 in which $R^8$ is hydrogen, $R^9$ is difluoromethyl, and $R^1$, $R^2$, $R^3$, $R^6$ and $R^7$ for a compound corresponds in each case to one row of Table A.

Table 11
Compounds of the formula I.1 in which $R^8$ is hydrogen, $R^9$ is trifluoromethyl, and $R^1$, $R^2$, $R^3$, $R^6$ and $R^7$ for a compound corresponds in each case to one row of Table A.

Table 12
Compounds of the formula I.1 in which $R^8$ is hydrogen, $R^9$ is 2,2,2-trifluoroethyl, and $R^1$, $R^2$, $R^3$, $R^6$ and $R^7$ for a compound corresponds in each case to one row of Table A.

Table 13
Compounds of the formula I.1 in which $R^8$ is hydrogen, $R^9$ is pentafluoroethyl, and $R^1$, $R^2$, $R^3$, $R^6$ and $R^7$ for a compound corresponds in each case to one row of Table A.

Table 14
Compounds of the formula I.1 in which $R^8$ is hydrogen, $R^9$ is cyclopropyl, and $R^1$, $R^2$, $R^3$, $R^6$ and $R^7$ for a compound corresponds in each case to one row of Table A.

Table 15
Compounds of the formula I.1 in which $R^8$ is hydrogen, $R^9$ is cyclobutyl, and $R^1$, $R^2$, $R^3$, $R^6$ and $R^7$ for a compound corresponds in each case to one row of Table A.

Table 16
Compounds of the formula I.1 in which $R^8$ is hydrogen, $R^9$ is cyclopentyl, and $R^1$, $R^2$, $R^3$, $R^6$ and $R^7$ for a compound corresponds in each case to one row of Table A.

Table 17
Compounds of the formula I.1 in which $R^8$ is hydrogen, $R^9$ is cyclohexyl, and $R^1$, $R^2$, $R^3$, $R^6$ and $R^7$ for a compound corresponds in each case to one row of Table A.

Table 18
Compounds of the formula I.1 in which $R^8$ is hydrogen, $R^9$ is phenyl, and $R^1$, $R^2$, $R^3$, $R^6$ and $R^7$ for a compound corresponds in each case to one row of Table A.

Table 19
Compounds of the formula I.1 in which $R^8$ is methyl, $R^9$ is methyl, and $R^1$, $R^2$, $R^3$, $R^6$ and $R^7$ for a compound corresponds in each case to one row of Table A.

Table 20
Compounds of the formula I.1 in which $R^8$ is methyl, $R^9$ is ethyl, and $R^1$, $R^2$, $R^3$, $R^6$ and $R^7$ for a compound corresponds in each case to one row of Table A.

Table 21
Compounds of the formula I.1 in which $R^8$ is methyl, $R^9$ is n-propyl, and $R^1$, $R^2$, $R^3$, $R^6$ and $R^7$ for a compound corresponds in each case to one row of Table A.

Table 22
Compounds of the formula I.1 in which $R^8$ is methyl, $R^9$ is propan-2-yl, and $R^1$, $R^2$, $R^3$, $R^6$ and $R^7$ for a compound corresponds in each case to one row of Table A.

Table 23
Compounds of the formula I.1 in which $R^8$ is methyl, $R^9$ is n-butyl, and $R^1$, $R^2$, $R^3$, $R^6$ and $R^7$ for a compound corresponds in each case to one row of Table A.

Table 24
Compounds of the formula I.1 in which $R^8$ is methyl, $R^9$ is 1-methylpropyl, and $R^1$, $R^2$, $R^3$, $R^6$ and $R^7$ for a compound corresponds in each case to one row of Table A.

Table 25
Compounds of the formula I.1 in which $R^8$ is methyl, $R^9$ is 2-methylpropyl, and $R^1$, $R^2$, $R^3$, $R^6$ and $R^7$ for a compound corresponds in each case to one row of Table A.

Table 26
Compounds of the formula I.1 in which $R^8$ is methyl, $R^9$ is 1,1-dimethylethyl, and $R^1$, $R^2$, $R^3$, $R^6$ and $R^7$ for a compound corresponds in each case to one row of Table A.

Table 27
Compounds of the formula I.1 in which $R^8$ is methyl, $R^9$ is difluoromethyl, and $R^1$, $R^2$, $R^3$, $R^6$ and $R^7$ for a compound corresponds in each case to one row of Table A.

Table 28
Compounds of the formula I.1 in which $R^8$ is methyl, $R^9$ is trifluoromethyl, and $R^1$, $R^2$, $R^3$, $R^6$ and $R^7$ for a compound corresponds in each case to one row of Table A.

Table 29
Compounds of the formula I.1 in which $R^8$ is methyl, $R^9$ is 2,2,2-trifluoroethyl, and $R^1$, $R^2$, $R^3$, $R^6$ and $R^7$ for a compound corresponds in each case to one row of Table A.

Table 30
Compounds of the formula I.1 in which $R^8$ is methyl, $R^9$ is pentafluoroethyl, and $R^1$, $R^2$, $R^3$, $R^6$ and $R^7$ for a compound corresponds in each case to one row of Table A.

Table 31
Compounds of the formula I.1 in which $R^8$ is methyl, $R^9$ is cyclopropyl, and $R^1$, $R^2$, $R^3$, $R^6$ and $R^7$ for a compound corresponds in each case to one row of Table A.

Table 32
Compounds of the formula I.1 in which $R^8$ is methyl, $R^9$ is cyclobutyl, and $R^1$, $R^2$, $R^3$, $R^6$ and $R^7$ for a compound corresponds in each case to one row of Table A.

Table 33
Compounds of the formula I.1 in which $R^8$ is methyl, $R^9$ is cyclopentyl, and $R^1$, $R^2$, $R^3$, $R^6$ and $R^7$ for a compound corresponds in each case to one row of Table A.

Table 34
Compounds of the formula I.1 in which $R^8$ is methyl, $R^9$ is cyclohexyl, and $R^1$, $R^2$, $R^3$, $R^6$ and $R^7$ for a compound corresponds in each case to one row of Table A.

Table 35
Compounds of the formula I.1 in which $R^8$ is methyl, $R^9$ is phenyl, and $R^1$, $R^2$, $R^3$, $R^6$ and $R^7$ for a compound corresponds in each case to one row of Table A.

Table 36
Compounds of the formula I.1 in which $R^8$ is ethyl, $R^9$ is ethyl, and $R^1$, $R^2$, $R^3$, $R^6$ and $R^7$ for a compound corresponds in each case to one row of Table A.

Table 37
Compounds of the formula I.1 in which $R^8$ is ethyl, $R^9$ is n-propyl, and $R^1$, $R^2$, $R^3$, $R^6$ and $R^7$ for a compound corresponds in each case to one row of Table A.

Table 38
Compounds of the formula I.1 in which $R^8$ is ethyl, $R^9$ is propan-2-yl, and $R^1$, $R^2$, $R^3$, $R^6$ and $R^7$ for a compound corresponds in each case to one row of Table A.

Table 39
Compounds of the formula I.1 in which $R^8$ is ethyl, $R^9$ is n-butyl, and $R^1$, $R^2$, $R^3$, $R^6$ and $R^7$ for a compound corresponds in each case to one row of Table A.

Table 40
Compounds of the formula I.1 in which $R^8$ is ethyl, $R^9$ is 1-methylpropyl, and $R^1$, $R^2$, $R^3$, $R^6$ and $R^7$ for a compound corresponds in each case to one row of Table A.

Table 41
Compounds of the formula I.1 in which $R^8$ is ethyl, $R^9$ is 2-methylpropyl, and $R^1$, $R^2$, $R^3$, $R^6$ and $R^7$ for a compound corresponds in each case to one row of Table A.

Table 42
Compounds of the formula I.1 in which $R^8$ is ethyl, $R^9$ is 1,1-dimethylethyl, and $R^1$, $R^2$, $R^3$, $R^6$ and $R^7$ for a compound corresponds in each case to one row of Table A.

Table 43
Compounds of the formula I.1 in which $R^8$ is ethyl, $R^9$ is difluoromethyl, and $R^1$, $R^2$, $R^3$, $R^6$ and $R^7$ for a compound corresponds in each case to one row of Table A.

Table 44
Compounds of the formula I.1 in which $R^8$ is ethyl, $R^9$ is trifluoromethyl, and $R^1$, $R^2$, $R^3$, $R^6$ and $R^7$ for a compound corresponds in each case to one row of Table A.

Table 45
Compounds of the formula I.1 in which $R^8$ is ethyl, $R^9$ is 2,2,2-trifluoroethyl, and $R^1$, $R^2$, $R^3$, $R^6$ and $R^7$ for a compound corresponds in each case to one row of Table A.

Table 46
Compounds of the formula I.1 in which $R^8$ is ethyl, $R^9$ is pentafluoroethyl, and $R^1$, $R^2$, $R^3$, $R^6$ and $R^7$ for a compound corresponds in each case to one row of Table A.

Table 47
Compounds of the formula I.1 in which $R^8$ is ethyl, $R^9$ is cyclopropyl, and $R^1$, $R^2$, $R^3$, $R^6$ and $R^7$ for a compound corresponds in each case to one row of Table A.

Table 48
Compounds of the formula I.1 in which $R^8$ is ethyl, $R^9$ is cyclobutyl, and $R^1$, $R^2$, $R^3$, $R^6$ and $R^7$ for a compound corresponds in each case to one row of Table A.

Table 49
Compounds of the formula I.1 in which $R^8$ is ethyl, $R^9$ is cyclopentyl, and $R^1$, $R^2$, $R^3$, $R^6$ and $R^7$ for a compound corresponds in each case to one row of Table A.

Table 50
Compounds of the formula I.1 in which $R^8$ is ethyl, $R^9$ is cyclohexyl, and $R^1$, $R^2$, $R^3$, $R^6$ and $R^7$ for a compound corresponds in each case to one row of Table A.

Table 51
Compounds of the formula I.1 in which $R^8$ is ethyl, $R^9$ is phenyl, and $R^1$, $R^2$, $R^3$, $R^6$ and $R^7$ for a compound corresponds in each case to one row of Table A.

Table 52
Compounds of the formula I.1 in which $R^8$ is n-propyl, $R^9$ is n-propyl, and $R^1$, $R^2$, $R^3$, $R^6$ and $R^7$ for a compound corresponds in each case to one row of Table A.

Table 53
Compounds of the formula I.1 in which $R^8$ is n-propyl, $R^9$ is propan-2-yl, and $R^1$, $R^2$, $R^3$, $R^6$ and $R^7$ for a compound corresponds in each case to one row of Table A.

Table 54
Compounds of the formula I.1 in which $R^8$ is n-propyl, $R^9$ is n-butyl, and $R^1$, $R^2$, $R^3$, $R^6$ and $R^7$ for a compound corresponds in each case to one row of Table A.

Table 55
Compounds of the formula I.1 in which $R^8$ is n-propyl, $R^9$ is 1-methylpropyl, and $R^1$, $R^2$, $R^3$, $R^6$ and $R^7$ for a compound corresponds in each case to one row of Table A.

Table 56
Compounds of the formula I.1 in which $R^8$ is n-propyl, $R^9$ is 2-methylpropyl, and $R^1$, $R^2$, $R^3$, $R^6$ and $R^7$ for a compound corresponds in each case to one row of Table A.

Table 57
Compounds of the formula I.1 in which $R^8$ is n-propyl, $R^9$ is 1,1-dimethylethyl, and $R^1$, $R^2$, $R^3$, $R^6$ and $R^7$ for a compound corresponds in each case to one row of Table A.

Table 58
Compounds of the formula I.1 in which $R^8$ is n-propyl, $R^9$ is difluoromethyl, and $R^1$, $R^2$, $R^3$, $R^6$ and $R^7$ for a compound corresponds in each case to one row of Table A.

Table 59
Compounds of the formula I.1 in which $R^8$ is n-propyl, $R^9$ is trifluoromethyl, and $R^1$, $R^2$, $R^3$, $R^6$ and $R^7$ for a compound corresponds in each case to one row of Table A.

Table 60
Compounds of the formula I.1 in which $R^8$ is n-propyl, $R^9$ is 2,2,2-trifluoroethyl, and $R^1$, $R^2$, $R^3$, $R^6$ and $R^7$ for a compound corresponds in each case to one row of Table A.

Table 61
Compounds of the formula I.1 in which $R^8$ is n-propyl, $R^9$ is pentafluoroethyl, and $R^1$, $R^2$, $R^3$, $R^6$ and $R^7$ for a compound corresponds in each case to one row of Table A.

Table 62
Compounds of the formula I.1 in which $R^8$ is n-propyl, $R^9$ is cyclopropyl, and $R^1$, $R^2$, $R^3$, $R^6$ and $R^7$ for a compound corresponds in each case to one row of Table A.

Table 63
Compounds of the formula I.1 in which $R^8$ is n-propyl, $R^9$ is cyclobutyl, and $R^1$, $R^2$, $R^3$, $R^6$ and $R^7$ for a compound corresponds in each case to one row of Table A.

Table 64
Compounds of the formula I.1 in which $R^8$ is n-propyl, $R^9$ is cyclopentyl, and $R^1$, $R^2$, $R^3$, $R^6$ and $R^7$ for a compound corresponds in each case to one row of Table A.

Table 65
Compounds of the formula I.1 in which $R^8$ is n-propyl, $R^9$ is cyclohexyl, and $R^1$, $R^2$, $R^3$, $R^6$ and $R^7$ for a compound corresponds in each case to one row of Table A.

Table 66
Compounds of the formula I.1 in which $R^8$ is n-propyl, $R^9$ is phenyl, and $R^1$, $R^2$, $R^3$, $R^6$ and $R^7$ for a compound corresponds in each case to one row of Table A.

Table 67
Compounds of the formula I.1 in which $R^8$ is propan-2-yl, $R^9$ is propan-2-yl, and $R^1$, $R^2$, $R^3$, $R^6$ and $R^7$ for a compound corresponds in each case to one row of Table A.

Table 68
Compounds of the formula I.1 in which $R^8$ is propan-2-yl, $R^9$ is n-butyl, and $R^1$, $R^2$, $R^3$, $R^6$ and $R^7$ for a compound corresponds in each case to one row of Table A.

Table 69
Compounds of the formula I.1 in which $R^8$ is propan-2-yl, $R^9$ is 1-methylpropyl, and $R^1$, $R^2$, $R^3$, $R^6$ and $R^7$ for a compound corresponds in each case to one row of Table A.

Table 70
Compounds of the formula I.1 in which $R^8$ is propan-2-yl, $R^9$ is 2-methylpropyl, and $R^1$, $R^2$, $R^3$, $R^6$ and $R^7$ for a compound corresponds in each case to one row of Table A.

Table 71
Compounds of the formula I.1 in which $R^8$ is propan-2-yl, $R^9$ is 1,1-dimethylethyl, and $R^1$, $R^2$, $R^3$, $R^6$ and $R^7$ for a compound corresponds in each case to one row of Table A.

Table 72
Compounds of the formula I.1 in which $R^8$ is propan-2-yl, $R^9$ is difluoromethyl, and $R^1$, $R^2$, $R^3$, $R^6$ and $R^7$ for a compound corresponds in each case to one row of Table A.

Table 73
Compounds of the formula I.1 in which $R^8$ is propan-2-yl, $R^9$ is trifluoromethyl, and $R^1$, $R^2$, $R^3$, $R^6$ and $R^7$ for a compound corresponds in each case to one row of Table A.

Table 74
Compounds of the formula I.1 in which $R^8$ is propan-2-yl, $R^9$ is 2,2,2-trifluoroethyl, and $R^1$, $R^2$, $R^3$, $R^6$ and $R^7$ for a compound corresponds in each case to one row of Table A.

Table 75
Compounds of the formula I.1 in which $R^8$ is propan-2-yl, $R^9$ is pentafluoroethyl, and $R^1$, $R^2$, $R^3$, $R^6$ and $R^7$ for a compound corresponds in each case to one row of Table A.

Table 76
Compounds of the formula I.1 in which $R^8$ is propan-2-yl, $R^9$ is cyclopropyl, and $R^1$, $R^2$, $R^3$, $R^6$ and $R^7$ for a compound corresponds in each case to one row of Table A.

Table 77
Compounds of the formula I.1 in which $R^8$ is propan-2-yl, $R^9$ is cyclobutyl, and $R^1$, $R^2$, $R^3$, $R^6$ and $R^7$ for a compound corresponds in each case to one row of Table A.

Table 78
Compounds of the formula I.1 in which $R^8$ is propan-2-yl, $R^9$ is cyclopentyl, and $R^1$, $R^2$, $R^3$, $R^6$ and $R^7$ for a compound corresponds in each case to one row of Table A.

Table 79
Compounds of the formula I.1 in which $R^8$ is propan-2-yl, $R^9$ is cyclohexyl, and $R^1$, $R^2$, $R^3$, $R^6$ and $R^7$ for a compound corresponds in each case to one row of Table A.

Table 80
Compounds of the formula I.1 in which $R^8$ is propan-2-yl, $R^9$ is phenyl, and $R^1$, $R^2$, $R^3$, $R^6$ and $R^7$ for a compound corresponds in each case to one row of Table A.

Table 81
Compounds of the formula I.1 in which $R^8$ is n-butyl, $R^9$ is n-butyl, and $R^1$, $R^2$, $R^3$, $R^6$ and $R^7$ for a compound corresponds in each case to one row of Table A.

Table 82
Compounds of the formula I.1 in which $R^8$ is n-butyl $R^9$ is 1-methylpropyl, and $R^1$, $R^2$, $R^3$, $R^6$ and $R^7$ for a compound corresponds in each case to one row of Table A.

Table 83
Compounds of the formula I.1 in which $R^8$ is n-butyl, $R^9$ is 2-methylpropyl, and $R^1$, $R^2$, $R^3$, $R^6$ and $R^7$ for a compound corresponds in each case to one row of Table A.

Table 84
Compounds of the formula I.1 in which $R^8$ is n-butyl, $R^9$ is 1,1-dimethylethyl, and $R^1$, $R^2$, $R^3$, $R^6$ and $R^7$ for a compound corresponds in each case to one row of Table A.

Table 85
Compounds of the formula I.1 in which $R^8$ is n-butyl, $R^9$ is difluoromethyl, and $R^1$, $R^2$, $R^3$, $R^6$ and $R^7$ for a compound corresponds in each case to one row of Table A.

Table 86
Compounds of the formula I.1 in which $R^8$ is n-butyl, $R^9$ is trifluoromethyl, and $R^1$, $R^2$, $R^3$, $R^6$ and $R^7$ for a compound corresponds in each case to one row of Table A.

Table 87
Compounds of the formula I.1 in which $R^8$ is n-butyl, $R^9$ is 2,2,2-trifluoroethyl, and $R^1$, $R^2$, $R^3$, $R^6$ and $R^7$ for a compound corresponds in each case to one row of Table A.

Table 88
Compounds of the formula I.1 in which $R^8$ is n-butyl, $R^9$ is pentafluoroethyl, and $R^1$, $R^2$, $R^3$, $R^6$ and $R^7$ for a compound corresponds in each case to one row of Table A.

Table 89
Compounds of the formula I.1 in which $R^8$ is n-butyl, $R^9$ is cyclopropyl, and $R^1$, $R^2$, $R^3$, $R^6$ and $R^7$ for a compound corresponds in each case to one row of Table A.

Table 90
Compounds of the formula I.1 in which $R^8$ is n-butyl, $R^9$ is cyclobutyl, and $R^1$, $R^2$, $R^3$, $R^6$ and $R^7$ for a compound corresponds in each case to one row of Table A.

Table 91
Compounds of the formula I.1 in which $R^8$ is n-butyl, $R^9$ is cyclopentyl, and $R^1$, $R^2$, $R^3$, $R^6$ and $R^7$ for a compound corresponds in each case to one row of Table A.

Table 92
Compounds of the formula I.1 in which $R^8$ is n-butyl, $R^9$ is cyclohexyl, and $R^1$, $R^2$, $R^3$, $R^6$ and $R^7$ for a compound corresponds in each case to one row of Table A.

Table 93
Compounds of the formula I.1 in which $R^8$ is n-butyl, $R^9$ is phenyl, and $R^1$, $R^2$, $R^3$, $R^6$ and $R^7$ for a compound corresponds in each case to one row of Table A.

Table 94
Compounds of the formula I.1 in which $R^8$ is 1-methylpropyl, $R^9$ is 1-methylpropyl, and $R^1$, $R^2$, $R^3$, $R^6$ and $R^7$ for a compound corresponds in each case to one row of Table A.

Table 95
Compounds of the formula I.1 in which $R^8$ is 1-methylpropyl, $R^9$ is 2-methylpropyl, and $R^1$, $R^2$, $R^3$, $R^6$ and $R^7$ for a compound corresponds in each case to one row of Table A.

Table 96
Compounds of the formula I.1 in which $R^8$ is 1-methylpropyl, $R^9$ is 1,1-dimethylethyl, and $R^1$, $R^2$, $R^3$, $R^6$ and $R^7$ for a compound corresponds in each case to one row of Table A.

Table 97
Compounds of the formula I.1 in which $R^8$ is 1-methylpropyl, $R^9$ is difluoromethyl, and $R^1$, $R^2$, $R^3$, $R^6$ and $R^7$ for a compound corresponds in each case to one row of Table A.

Table 98
Compounds of the formula I.1 in which $R^8$ is 1-methylpropyl, $R^9$ is trifluoromethyl, and $R^1$, $R^2$, $R^3$, $R^6$ and $R^7$ for a compound corresponds in each case to one row of Table A.

Table 99
Compounds of the formula I.1 in which $R^8$ is 1-methylpropyl, $R^9$ is 2,2,2-trifluoroethyl, and $R^1$, $R^2$, $R^3$, $R^6$ and $R^7$ for a compound corresponds in each case to one row of Table A.

Table 100
Compounds of the formula I.1 in which $R^8$ is 1-methylpropyl, $R^9$ is pentafluoroethyl, and $R^1$, $R^2$, $R^3$, $R^6$ and $R^7$ for a compound corresponds in each case to one row of Table A.

Table 101
Compounds of the formula I.1 in which $R^8$ is 1-methylpropyl, $R^9$ is cyclopropyl, and $R^1$, $R^2$, $R^3$, $R^6$ and $R^7$ for a compound corresponds in each case to one row of Table A.

Table 102
Compounds of the formula I.1 in which $R^8$ is 1-methylpropyl, $R^9$ is cyclobutyl, and $R^1$, $R^2$, $R^3$, $R^6$ and $R^7$ for a compound corresponds in each case to one row of Table A.

Table 103
Compounds of the formula I.1 in which $R^8$ is 1-methylpropyl, $R^9$ is cyclopentyl, and $R^1$, $R^2$, $R^3$, $R^6$ and $R^7$ for a compound corresponds in each case to one row of Table A.

Table 104
Compounds of the formula I.1 in which $R^8$ is 1-methylpropyl, $R^9$ is cyclohexyl, and $R^1$, $R^2$, $R^3$, $R^6$ and $R^7$ for a compound corresponds in each case to one row of Table A.

Table 105
Compounds of the formula I.1 in which $R^8$ is 1-methylpropyl, $R^9$ is phenyl, and $R^1$, $R^2$, $R^3$, $R^6$ and $R^7$ for a compound corresponds in each case to one row of Table A.

Table 106
Compounds of the formula I.1 in which $R^8$ is 2-methylpropyl, $R^9$ is 2-methylpropyl, and $R^1$, $R^2$, $R^3$, $R^6$ and $R^7$ for a compound corresponds in each case to one row of Table A.

Table 107
Compounds of the formula I.1 in which $R^8$ is 2-methylpropyl, $R^9$ is 1,1-dimethylethyl, and $R^1$, $R^2$, $R^3$, $R^6$ and $R^7$ for a compound corresponds in each case to one row of Table A.

Table 108
Compounds of the formula I.1 in which $R^8$ is 2-methylpropyl, $R^9$ is difluoromethyl, and $R^1$, $R^2$, $R^3$, $R^6$ and $R^7$ for a compound corresponds in each case to one row of Table A.

Table 109
Compounds of the formula I.1 in which $R^8$ is 2-methylpropyl, $R^9$ is trifluoromethyl, and $R^1$, $R^2$, $R^3$, $R^6$ and $R^7$ for a compound corresponds in each case to one row of Table A.

Table 110
Compounds of the formula I.1 in which $R^8$ is 2-methylpropyl, $R^9$ is 2,2,2-trifluoroethyl, and $R^1$, $R^2$, $R^3$, $R^6$ and $R^7$ for a compound corresponds in each case to one row of Table A.

Table 111
Compounds of the formula I.1 in which $R^8$ is 2-methylpropyl, $R^9$ is pentafluoroethyl, and $R^1$, $R^2$, $R^3$, $R^6$ and $R^7$ for a compound corresponds in each case to one row of Table A.

Table 112
Compounds of the formula I.1 in which $R^8$ is 2-methylpropyl, $R^9$ is cyclopropyl, and $R^1$, $R^2$, $R^3$, $R^6$ and $R^7$ for a compound corresponds in each case to one row of Table A.

Table 113
Compounds of the formula I.1 in which $R^8$ is 2-methylpropyl, $R^9$ is cyclobutyl, and $R^1$, $R^2$, $R^3$, $R^6$ and $R^7$ for a compound corresponds in each case to one row of Table A.

Table 114
Compounds of the formula I.1 in which $R^8$ is 2-methylpropyl, $R^9$ is cyclopentyl, and $R^1$, $R^2$, $R^3$, $R^6$ and $R^7$ for a compound corresponds in each case to one row of Table A.

Table 115
Compounds of the formula I.1 in which $R^8$ is 2-methylpropyl, $R^9$ is cyclohexyl, and $R^1$, $R^2$, $R^3$, $R^6$ and $R^7$ for a compound corresponds in each case to one row of Table A.

Table 116
Compounds of the formula I.1 in which $R^8$ is 2-methylpropyl, $R^9$ is phenyl, and $R^1$, $R^2$, $R^3$, $R^6$ and $R^7$ for a compound corresponds in each case to one row of Table A.

Table 117
Compounds of the formula I.1 in which $R^8$ is 1,1-dimethylethyl, $R^9$ is 1,1-dimethylethyl, and $R^1$, $R^2$, $R^3$, $R^6$ and $R^7$ for a compound corresponds in each case to one row of Table A.

Table 118
Compounds of the formula I.1 in which $R^8$ is 1,1-dimethylethyl, $R^9$ is difluoromethyl, and $R^1$, $R^2$, $R^3$, $R^6$ and $R^7$ for a compound corresponds in each case to one row of Table A.

Table 119
Compounds of the formula I.1 in which $R^8$ is 1,1-dimethylethyl, $R^9$ is trifluoromethyl, and $R^1$, $R^2$, $R^3$, $R^6$ and $R^7$ for a compound corresponds in each case to one row of Table A.

Table 120
Compounds of the formula I.1 in which $R^8$ is 1,1-dimethylethyl, $R^9$ is 2,2,2-trifluoroethyl, and $R^1$, $R^2$, $R^3$, $R^6$ and $R^7$ for a compound corresponds in each case to one row of Table A.

Table 121
Compounds of the formula I.1 in which $R^8$ is 1,1-dimethylethyl, $R^9$ is pentafluoroethyl, and $R^1$, $R^2$, $R^3$, $R^6$ and $R^7$ for a compound corresponds in each case to one row of Table A.

Table 122
Compounds of the formula I.1 in which $R^8$ is 1,1-dimethylethyl, $R^9$ is cyclopropyl, and $R^1$, $R^2$, $R^3$, $R^6$ and $R^7$ for a compound corresponds in each case to one row of Table A.

Table 123
Compounds of the formula I.1 in which $R^8$ is 1,1-dimethylethyl, $R^9$ is cyclobutyl, and $R^1$, $R^2$, $R^3$, $R^6$ and $R^7$ for a compound corresponds in each case to one row of Table A.

Table 124
Compounds of the formula I.1 in which $R^8$ is 1,1-dimethylethyl, $R^9$ is cyclopentyl, and $R^1$, $R^2$, $R^3$, $R^6$ and $R^7$ for a compound corresponds in each case to one row of Table A.

Table 125
Compounds of the formula I.1 in which $R^8$ is 1,1-dimethylethyl, $R^9$ is cyclohexyl, and $R^1$, $R^2$, $R^3$, $R^6$ and $R^7$ for a compound corresponds in each case to one row of Table A.

Table 126
Compounds of the formula I.1 in which $R^8$ is 1,1-dimethylethyl, $R^9$ is phenyl, and $R^1$, $R^2$, $R^3$, $R^6$ and $R^7$ for a compound corresponds in each case to one row of Table A.

Table 127
Compounds of the formula I.1 in which $R^8$ is difluoromethyl, $R^9$ is difluoromethyl, and $R^1$, $R^2$, $R^3$, $R^6$ and $R^7$ for a compound corresponds in each case to one row of Table A.

Table 128
Compounds of the formula I.1 in which $R^8$ is difluoromethyl, $R^9$ is trifluoromethyl, and $R^1$, $R^2$, $R^3$, $R^6$ and $R^7$ for a compound corresponds in each case to one row of Table A.

Table 129
Compounds of the formula I.1 in which $R^8$ is difluoromethyl, $R^9$ is 2,2,2-trifluoroethyl, and $R^1$, $R^2$, $R^3$, $R^6$ and $R^7$ for a compound corresponds in each case to one row of Table A.

Table 130
Compounds of the formula I.1 in which $R^8$ is difluoromethyl, $R^9$ is pentafluoroethyl, and $R^1$, $R^2$, $R^3$, $R^6$ and $R^7$ for a compound corresponds in each case to one row of Table A.

Table 131
Compounds of the formula I.1 in which $R^8$ is difluoromethyl, $R^9$ is cyclopropyl, and $R^1$, $R^2$, $R^3$, $R^6$ and $R^7$ for a compound corresponds in each case to one row of Table A.

Table 132
Compounds of the formula I.1 in which $R^8$ is difluoromethyl, $R^9$ is cyclobutyl, and $R^1$, $R^2$, $R^3$, $R^6$ and $R^7$ for a compound corresponds in each case to one row of Table A.

Table 133
Compounds of the formula I.1 in which $R^8$ is difluoromethyl, $R^9$ is cyclopentyl, and $R^1$, $R^2$, $R^3$, $R^6$ and $R^7$ for a compound corresponds in each case to one row of Table A.

Table 134
Compounds of the formula I.1 in which $R^8$ is difluoromethyl, $R^9$ is cyclohexyl, and $R^1$, $R^2$, $R^3$, $R^6$ and $R^7$ for a compound corresponds in each case to one row of Table A.

Table 135
Compounds of the formula I.1 in which $R^8$ is difluoromethyl, $R^9$ is phenyl, and $R^1$, $R^2$, $R^3$, $R^6$ and $R^7$ for a compound corresponds in each case to one row of Table A.

Table 136
Compounds of the formula I.1 in which $R^8$ is trifluormethyl, $R^9$ is trifluormethyl, and $R^1$, $R^2$, $R^3$, $R^6$ and $R^7$ for a compound corresponds in each case to one row of Table A.

Table 137
Compounds of the formula I.1 in which $R^8$ is trifluormethyl, $R^9$ is 2,2,2-trifluoroethyl, and $R^1$, $R^2$, $R^3$, $R^6$ and $R^7$ for a compound corresponds in each case to one row of Table A.

Table 138
Compounds of the formula I.1 in which $R^8$ is trifluormethyl, $R^9$ is pentafluoroethyl, and $R^1$, $R^2$, $R^3$, $R^6$ and $R^7$ for a compound corresponds in each case to one row of Table A.

Table 139
Compounds of the formula I.1 in which $R^8$ is trifluormethyl, $R^9$ is cyclopropyl, and $R^1$, $R^2$, $R^3$, $R^6$ and $R^7$ for a compound corresponds in each case to one row of Table A.

Table 140
Compounds of the formula I.1 in which $R^8$ is trifluormethyl, $R^9$ is cyclobutyl, and $R^1$, $R^2$, $R^3$, $R^6$ and $R^7$ for a compound corresponds in each case to one row of Table A.

Table 141
Compounds of the formula I.1 in which $R^8$ is trifluormethyl, $R^9$ is cyclopentyl, and $R^1$, $R^2$, $R^3$, $R^6$ and $R^7$ for a compound corresponds in each case to one row of Table A.

Table 142
Compounds of the formula I.1 in which $R^8$ is trifluormethyl, $R^9$ is cyclohexyl, and $R^1$, $R^2$, $R^3$, $R^6$ and $R^7$ for a compound corresponds in each case to one row of Table A.

Table 143
Compounds of the formula I.1 in which $R^8$ is trifluormethyl, $R^9$ is phenyl, and $R^1$, $R^2$, $R^3$, $R^6$ and $R^7$ for a compound corresponds in each case to one row of Table A.

Table 144
Compounds of the formula I.1 in which $R^8$ is 2,2,2-trifluoroethyl, $R^9$ is 2,2,2-trifluoroethyl, and $R^1$, $R^2$, $R^3$, $R^6$ and $R^7$ for a compound corresponds in each case to one row of Table A.

Table 145
Compounds of the formula I.1 in which $R^8$ is 2,2,2-trifluoroethyl, $R^9$ is pentafluoroethyl, and $R^1$, $R^2$, $R^3$, $R^6$ and $R^7$ for a compound corresponds in each case to one row of Table A.

Table 146
Compounds of the formula I.1 in which $R^8$ is 2,2,2-trifluoroethyl, $R^9$ is cyclopropyl, and $R^1$, $R^2$, $R^3$, $R^6$ and $R^7$ for a compound corresponds in each case to one row of Table A.

Table 147
Compounds of the formula I.1 in which $R^8$ is 2,2,2-trifluoroethyl, $R^9$ is cyclobutyl, and $R^1$, $R^2$, $R^3$, $R^6$ and $R^7$ for a compound corresponds in each case to one row of Table A.

Table 148
Compounds of the formula I.1 in which $R^8$ is 2,2,2-trifluoroethyl, $R^9$ is cyclopentyl, and $R^1$, $R^2$, $R^3$, $R^6$ and $R^7$ for a compound corresponds in each case to one row of Table A.

Table 149
Compounds of the formula I.1 in which $R^8$ is 2,2,2-trifluoroethyl, $R^9$ is cyclohexyl, and $R^1$, $R^2$, $R^3$, $R^6$ and $R^7$ for a compound corresponds in each case to one row of Table A.

Table 150
Compounds of the formula I.1 in which $R^8$ is 2,2,2-trifluoroethyl, $R^9$ is phenyl, and $R^1$, $R^2$, $R^3$, $R^6$ and $R^7$ for a compound corresponds in each case to one row of Table A.

Table 151
Compounds of the formula I.1 in which $R^8$ is pentafluoroethyl, $R^9$ is pentafluoroethyl, and $R^1$, $R^2$, $R^3$, $R^6$ and $R^7$ for a compound corresponds in each case to one row of Table A.

Table 152
Compounds of the formula I.1 in which $R^8$ is pentafluoroethyl, $R^9$ is cyclopropyl, and $R^1$, $R^2$, $R^3$, $R^6$ and $R^7$ for a compound corresponds in each case to one row of Table A.

Table 153
Compounds of the formula I.1 in which $R^8$ is pentafluoroethyl, $R^9$ is cyclobutyl, and $R^1$, $R^2$, $R^3$, $R^6$ and $R^7$ for a compound corresponds in each case to one row of Table A.

Table 154
Compounds of the formula I.1 in which $R^8$ is pentafluoroethyl, $R^9$ is cyclopentyl, and $R^1$, $R^2$, $R^3$, $R^6$ and $R^7$ for a compound corresponds in each case to one row of Table A.

Table 155
Compounds of the formula I.1 in which $R^8$ is pentafluoroethyl, $R^9$ is cyclohexyl, and $R^1$, $R^2$, $R^3$, $R^6$ and $R^7$ for a compound corresponds in each case to one row of Table A.

Table 156
Compounds of the formula I.1 in which $R^8$ is pentafluoroethyl, $R^9$ is phenyl, and $R^1$, $R^2$, $R^3$, $R^6$ and $R^7$ for a compound corresponds in each case to one row of Table A.

Table 157
Compounds of the formula I.1 in which $R^8$ is phenyl, $R^9$ is phenyl, and $R^1$, $R^2$, $R^3$, $R^6$ and $R^7$ for a compound corresponds in each case to one row of Table A.

Table 158
Compounds of the formula I.1 in which $R^8$ and $R^9$ together with the nitrogen atom they are bound to form aziridin-1-yl, and $R^1$, $R^2$, $R^3$, $R^6$ and $R^7$ for a compound corresponds in each case to one row of Table A.

Table 159
Compounds of the formula I.1 in which $R^8$ and $R^9$ together with the nitrogen atom they are bound to form azetidin-1-yl, and $R^1$, $R^2$, $R^3$, $R^6$ and $R^7$ for a compound corresponds in each case to one row of Table A.

Table 160
Compounds of the formula I.1 in which $R^8$ and $R^9$ together with the nitrogen atom they are bound to form pyrrolidin-1-yl, and $R^1$, $R^2$, $R^3$, $R^6$ and $R^7$ for a compound corresponds in each case to one row of Table A.

Table 161
Compounds of the formula I.1 in which $R^8$ and $R^9$ together with the nitrogen atom they are bound to form piperidin-1-yl, and $R^1$, $R^2$, $R^3$, $R^6$ and $R^7$ for a compound corresponds in each case to one row of Table A.

Table 162
Compounds of the formula I.1 in which $R^8$ and $R^9$ together with the nitrogen atom they are bound to form azepan-1-yl, and $R^1$, $R^2$, $R^3$, $R^6$ and $R^7$ for a compound corresponds in each case to one row of Table A.

Table 163
Compounds of the formula I.1 in which $R^8$ and $R^9$ together with the nitrogen atom they are bound to form 2,3-dihydropyrrol-1-yl, and $R^1$, $R^2$, $R^3$, $R^6$ and $R^7$ for a compound corresponds in each case to one row of Table A.

Table 164
Compounds of the formula I.1 in which $R^8$ and $R^9$ together with the nitrogen atom they are bound to form 2,5-dihydropyrrol-1-yl, and $R^1$, $R^2$, $R^3$, $R^6$ and $R^7$ for a compound corresponds in each case to one row of Table A.

Table 165
Compounds of the formula I.1 in which $R^8$ and $R^9$ together with the nitrogen atom they are bound to form 3,4-dihydro-2H-pyridin-1-yl, and $R^1$, $R^2$, $R^3$, $R^6$ and $R^7$ for a compound corresponds in each case to one row of Table A.

Table 166
Compounds of the formula I.1 in which $R^8$ and $R^9$ together with the nitrogen atom they are bound to form 3,6-dihydro-2H-pyridin-1-yl, and $R^1$, $R^2$, $R^3$, $R^6$ and $R^7$ for a compound corresponds in each case to one row of Table A.

Table 167
Compounds of the formula I.1 in which $R^8$ and $R^9$ together with the nitrogen atom they are bound to form 2,3,4,5-tetrahydroazepin-1-yl, and $R^1$, $R^2$, $R^3$, $R^6$ and $R^7$ for a compound corresponds in each case to one row of Table A.

Table 168
Compounds of the formula I.1 in which $R^8$ and $R^9$ together with the nitrogen atom they are bound to form 2,3,4,7-tetrahydroazepin-1-yl, and $R^1$, $R^2$, $R^3$, $R^6$ and $R^7$ for a compound corresponds in each case to one row of Table A.

Table 169
Compounds of the formula I.1 in which $R^8$ and $R^9$ together with the nitrogen atom they are bound to form 2,3,6,7-tetrahydroazepin-1-yl, and $R^1$, $R^2$, $R^3$, $R^6$ and $R^7$ for a compound corresponds in each case to one row of Table A.

Table 170
Compounds of the formula I.1 in which $R^8$ and $R^9$ together with the nitrogen atom they are bound to form 2,3-dihydroazepin-1-yl and $R^1$, $R^2$, $R^3$, $R^6$ and $R^7$ for a compound corresponds in each case to one row of Table A.

Table 171
Compounds of the formula I.1 in which $R^8$ and $R^9$ together with the nitrogen atom they are bound to form 2,7-dihydroazepin-1-yl and $R^1$, $R^2$, $R^3$, $R^6$ and $R^7$ for a compound corresponds in each case to one row of Table A.

Table 172
Compounds of the formula I.1 in which $R^8$ and $R^9$ together with the nitrogen atom they are bound to form 4,5-dihydroazepin-1-yl, and $R^1$, $R^2$, $R^3$, $R^6$ and $R^7$ for a compound corresponds in each case to one row of Table A.

Table 173
Compounds of the formula I.1 in which $R^8$ and $R^9$ together with the nitrogen atom they are bound to form 1-pyrrolyl, and $R^1$, $R^2$, $R^3$, $R^6$ and $R^7$ for a compound corresponds in each case to one row of Table A.

Table 174
Compounds of the formula I.1 in which $R^8$ and $R^9$ together with the nitrogen atom they are bound to form 3-methylpyrrolidin-1-yl, and $R^1$, $R^2$, $R^3$, $R^6$ and $R^7$ for a compound corresponds in each case to one row of Table A.

Table 175
Compounds of the formula I.1 in which $R^8$ and $R^9$ together with the nitrogen atom they are bound to form 3,4-dimethylpyrrolidin-1-yl, and $R^1$, $R^2$, $R^3$, $R^6$ and $R^7$ for a compound corresponds in each case to one row of Table A.

Table 176
Compounds of the formula I.1 in which $R^8$ and $R^9$ together with the nitrogen atom they are bound to form 4-methylpiperidin-1-yl, and $R^1$, $R^2$, $R^3$, $R^6$ and $R^7$ for a compound corresponds in each case to one row of Table A.

Table 177
Compounds of the formula I.1 in which $R^8$ and $R^9$ together with the nitrogen atom they are bound to form 4-methylpiperidin-1-yl, and $R^1$, $R^2$, $R^3$, $R^6$ and $R^7$ for a compound corresponds in each case to one row of Table A.

Table 178
Compounds of the formula I.1 in which $R^8$ and $R^9$ together with the nitrogen atom they are bound to form 4,4-dimethylpiperidin-1-yl, and $R^1$, $R^2$, $R^3$, $R^6$ and $R^7$ for a compound corresponds in each case to one row of Table A.

Table 179
Compounds of the formula I.1 in which $R^8$ and $R^9$ together with the nitrogen atom they are bound to form 3,4-dimethylpiperidin-1-yl, and $R^1$, $R^2$, $R^3$, $R^6$ and $R^7$ for a compound corresponds in each case to one row of Table A.

Tables 180 to 358
Compounds of the formula I.2, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 359 to 537
Compounds of the formula I.3, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 538 to 716
Compounds of the formula I.4, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 717 to 895
Compounds of the formula I.5, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 896 to 1074
Compounds of the formula I.6, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 1075 to 1253
Compounds of the formula I.7, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 1254 to 1432
Compounds of the formula I.8, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 1433 to 1611
Compounds of the formula I.9, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 1612 to 1790
Compounds of the formula I.10, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 1791 to 1969
Compounds of the formula I.11, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 1970 to 2148
Compounds of the formula I.12, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 2149 to 2327
Compounds of the formula I.13, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 2328 to 2506
Compounds of the formula I.14, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 2507 to 2685
Compounds of the formula I.15, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 2686 to 2864
Compounds of the formula I.16, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 2865 to 3043
Compounds of the formula I.17, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 3044 to 3222
Compounds of the formula I.18, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 3223 to 3401
Compounds of the formula I.19, in which the combination of $R^8$ and $R^9$ is as defined in any one of Tables 1 to 179 and $R^1$, $R^2$, $R^3$, $R^6$ and $R^7$ for a compound corresponds in each case to one row of Table A.

Tables 3402 to 3580
Compounds of the formula I.20, in which the combination of $R^8$ and $R^9$ is as defined in any one of Tables 1 to 179 and $R^1$, $R^2$, $R^3$, $R^6$ and $R^7$ for a compound corresponds in each case to one row of Table A Tables 3581 to 3759
Compounds of the formula I.21, in which the combination of $R^8$ and $R^9$ is as defined in any one of Tables 1 to 179 and $R^2$, $R^3$, $R^6$ and $R^7$ for a compound corresponds in each case to one row of Table B.

Tables 3760 to 3938
Compounds of the formula I.22, in which the combination of $R^8$ and $R^9$ is as defined in any one of Tables 1 to 179 and $R^2$, $R^3$, $R^6$ and $R^7$ for a compound corresponds in each case to one row of Table B.

Tables 3939 to 4117
Compounds of the formula I.23, in which the combination of $R^8$ and $R^9$ is as defined in any one of Tables 1 to 179 and $R^2$, $R^3$, $R^6$ and $R^7$ for a compound corresponds in each case to one row of Table B.

Tables 4118 to 4296
Compounds of the formula I.24, in which the combination of $R^8$ and $R^9$ is as defined in any one of Tables 1 to 179 and $R^2$, $R^3$, $R^6$ and $R^7$ for a compound corresponds in each case to one row of Table B.

Tables 4297 to 4475
Compounds of the formula I.25, in which the combination of $R^8$ and $R^9$ is as defined in any one of Tables 1 to 179 and $R^2$, $R^3$, $R^6$ and $R^7$ for a compound corresponds in each case to one row of Table B.

Tables 4476 to 4654
Compounds of the formula I.26, in which the combination of $R^8$ and $R^9$ is as defined in any one of Tables 1 to 179 and $R^2$, $R^3$, $R^6$ and $R^7$ for a compound corresponds in each case to one row of Table B.

Tables 4655 to 4833
Compounds of the formula I.27, in which the combination of $R^8$ and $R^9$ is as defined in any one of Tables 1 to 179 and $R^2$, $R^3$, $R^6$ and $R^7$ for a compound corresponds in each case to one row of Table B.

Tables 4834 to 5012
Compounds of the formula I.28, in which the combination of $R^8$ and $R^9$ is as defined in any one of Tables 1 to 179 and $R^2$, $R^3$, $R^6$ and $R^7$ for a compound corresponds in each case to one row of Table B.

Tables 5013 to 5191
Compounds of the formula I.29, in which the combination of $R^8$ and $R^9$ is as defined in any one of Tables 1 to 179 and $R^2$, $R^3$, $R^6$ and $R^7$ for a compound corresponds in each case to one row of Table B.

Tables 5192 to 5370
Compounds of the formula I.30, in which the combination of $R^8$ and $R^9$ is as defined in any one of Tables 1 to 179 and $R^2$, $R^3$, $R^6$ and $R^7$ for a compound corresponds in each case to one row of Table B.

Tables 5371 to 5549
Compounds of the formula I.31, in which the combination of $R^8$ and $R^9$ is as defined in any one of Tables 1 to 179 and $R^2$, $R^3$, $R^6$ and $R^7$ for a compound corresponds in each case to one row of Table B.

Tables 5550 to 5728
Compounds of the formula I.32, in which the combination of $R^8$ and $R^9$ is as defined in any one of Tables 1 to 179 and $R^2$, $R^3$, $R^6$ and $R^7$ for a compound corresponds in each case to one row of Table B.

Tables 5729 to 5907
Compounds of the formula I.33, in which the combination of $R^8$ and $R^9$ is as defined in any one of Tables 1 to 179 and $R^2$, $R^3$, $R^6$ and $R^7$ for a compound corresponds in each case to one row of Table B.

Tables 5908 to 6086
Compounds of the formula I.34, in which the combination of $R^8$ and $R^9$ is as defined in any one of Tables 1 to 179 and $R^2$, $R^3$, $R^6$ and $R^7$ for a compound corresponds in each case to one row of Table B.

Tables 6087 to 6265
Compounds of the formula I.35, in which the combination of $R^8$ and $R^9$ is as defined in any one of Tables 1 to 179 and $R^2$, $R^3$, $R^6$ and $R^7$ for a compound corresponds in each case to one row of Table B.

Tables 6266 to 6444

Compounds of the formula I.36, in which the combination of $R^8$ and $R^9$ is as defined in any one of Tables 1 to 179 and $R^2$, $R^3$, $R^6$ and $R^7$ for a compound corresponds in each case to one row of Table B.

Tables 6445 to 6623

Compounds of the formula I.37, in which the combination of $R^8$ and $R^9$ is as defined in any one of Tables 1 to 179 and $R^2$, $R^3$, $R^6$ and $R^7$ for a compound corresponds in each case to one row of Table B.

Tables 6624 to 6802

Compounds of the formula I.38, in which the combination of $R^8$ and $R^9$ is as defined in any one of Tables 1 to 179 and $R^2$, $R^3$, $R^6$ and $R^7$ for a compound corresponds in each case to one row of Table B.

Tables 6803 to 6981

Compounds of the formula I.39, in which the combination of $R^8$ and $R^9$ is as defined in any one of Tables 1 to 179 and $R^2$, $R^3$, $R^6$ and $R^7$ for a compound corresponds in each case to one row of Table B.

Tables 6982 to 7160

Compounds of the formula I.40, in which the combination of $R^8$ and $R^9$ is as defined in any one of Tables 1 to 179 and $R^2$, $R^3$, $R^6$ and $R^7$ for a compound corresponds in each case to one row of Table B.

TABLE A

| Example No. | $R^1$ | $R^2$ | $R^3$ | $R^6$ | $R^7$ |
|---|---|---|---|---|---|
| A-1. | H | H | H | CN | H |
| A-2. | F | H | H | CN | H |
| A-3. | CH$_3$ | H | H | CN | H |
| A-4. | OCH$_3$ | H | H | CN | H |
| A-5. | CH$_2$F | H | H | CN | H |
| A-6. | CHF$_2$ | H | H | CN | H |
| A-7. | CF$_3$ | H | H | CN | H |
| A-8. | OCH$_2$F | H | H | CN | H |
| A-9. | OCHF$_2$ | H | H | CN | H |
| A-10. | OCF$_3$ | H | H | CN | H |
| A-11. | H | F | H | CN | H |
| A-12. | H | CH$_3$ | H | CN | H |
| A-13. | H | OCH$_3$ | H | CN | H |
| A-14. | H | CN | H | CN | H |
| A-15. | H | CH$_2$F | H | CN | H |
| A-16. | H | CHF$_2$ | H | CN | H |
| A-17. | H | CF$_3$ | H | CN | H |
| A-18. | H | OCH$_2$F | H | CN | H |
| A-19. | H | OCHF$_2$ | H | CN | H |
| A-20. | H | OCF$_3$ | H | CN | H |
| A-21. | H | H | 3-F | CN | H |
| A-22. | H | H | 3-CH$_3$ | CN | H |
| A-23. | H | H | 3-OCH$_3$ | CN | H |
| A-24. | H | H | 5-F | CN | H |
| A-25. | H | H | 5-CH$_3$ | CN | H |
| A-26. | H | H | 5-OCH$_3$ | CN | H |
| A-27. | F | F | H | CN | H |
| A-28. | F | CH$_3$ | H | CN | H |
| A-29. | F | OCH$_3$ | H | CN | H |
| A-30. | F | CN | H | CN | H |
| A-31. | F | CH$_2$F | H | CN | H |
| A-32. | F | CHF$_2$ | H | CN | H |
| A-33. | F | CF$_3$ | H | CN | H |
| A-34. | F | OCH$_2$F | H | CN | H |
| A-35. | F | OCHF$_2$ | H | CN | H |
| A-36. | F | OCF$_3$ | H | CN | H |
| A-37. | F | H | 3-F | CN | H |
| A-38. | F | H | 3-CH$_3$ | CN | H |
| A-39. | F | H | 3-OCH$_3$ | CN | H |
| A-40. | F | H | 5-F | CN | H |
| A-41. | F | H | 5-CH$_3$ | CN | H |
| A-42. | F | H | 5-OCH$_3$ | CN | H |
| A-43. | CH$_3$ | F | H | CN | H |
| A-44. | CH$_3$ | CH$_3$ | H | CN | H |
| A-45. | CH$_3$ | OCH$_3$ | H | CN | H |

TABLE A-continued

| Example No. | $R^1$ | $R^2$ | $R^3$ | $R^6$ | $R^7$ |
|---|---|---|---|---|---|
| A-46. | CH$_3$ | CN | H | CN | H |
| A-47. | CH$_3$ | CH$_2$F | H | CN | H |
| A-48. | CH$_3$ | CHF$_2$ | H | CN | H |
| A-49. | CH$_3$ | CF$_3$ | H | CN | H |
| A-50. | CH$_3$ | OCH$_2$F | H | CN | H |
| A-51. | CH$_3$ | OCHF$_2$ | H | CN | H |
| A-52. | CH$_3$ | OCF$_3$ | H | CN | H |
| A-53. | CH$_3$ | H | 3-F | CN | H |
| A-54. | CH$_3$ | H | 3-CH$_3$ | CN | H |
| A-55. | CH$_3$ | H | 3-OCH$_3$ | CN | H |
| A-56. | CH$_3$ | H | 5-F | CN | H |
| A-57. | CH$_3$ | H | 5-CH$_3$ | CN | H |
| A-58. | CH$_3$ | H | 5-OCH$_3$ | CN | H |
| A-59. | OCH$_3$ | F | H | CN | H |
| A-60. | OCH$_3$ | CH$_3$ | H | CN | H |
| A-61. | OCH$_3$ | OCH$_3$ | H | CN | H |
| A-62. | OCH$_3$ | CN | H | CN | H |
| A-63. | OCH$_3$ | CH$_2$F | H | CN | H |
| A-64. | OCH$_3$ | CHF$_2$ | H | CN | H |
| A-65. | OCH$_3$ | CF$_3$ | H | CN | H |
| A-66. | OCH$_3$ | OCH$_2$F | H | CN | H |
| A-67. | OCH$_3$ | OCHF$_2$ | H | CN | H |
| A-68. | OCH$_3$ | OCF$_3$ | H | CN | H |
| A-69. | OCH$_3$ | H | 3-F | CN | H |
| A-70. | OCH$_3$ | H | 3-CH$_3$ | CN | H |
| A-71. | OCH$_3$ | H | 3-OCH$_3$ | CN | H |
| A-72. | OCH$_3$ | H | 5-F | CN | H |
| A-73. | OCH$_3$ | H | 5-CH$_3$ | CN | H |
| A-74. | OCH$_3$ | H | 5-OCH$_3$ | CN | H |
| A-75. | H | F | 3-F | CN | H |
| A-76. | H | F | 3-CH$_3$ | CN | H |
| A-77. | H | F | 3-OCH$_3$ | CN | H |
| A-78. | H | F | 5-F | CN | H |
| A-79. | H | F | 5-CH$_3$ | CN | H |
| A-80. | H | F | 5-OCH$_3$ | CN | H |
| A-81. | H | CH$_3$ | 3-F | CN | H |
| A-82. | H | CH$_3$ | 3-CH$_3$ | CN | H |
| A-83. | H | CH$_3$ | 3-OCH$_3$ | CN | H |
| A-84. | H | CH$_3$ | 5-F | CN | H |
| A-85. | H | CH$_3$ | 5-CH$_3$ | CN | H |
| A-86. | H | CH$_3$ | 5-OCH$_3$ | CN | H |
| A-87. | H | OCH$_3$ | 3-F | CN | H |
| A-88. | H | OCH$_3$ | 3-CH$_3$ | CN | H |
| A-89. | H | OCH$_3$ | 3-OCH$_3$ | CN | H |
| A-90. | H | OCH$_3$ | 5-F | CN | H |
| A-91. | H | OCH$_3$ | 5-CH$_3$ | CN | H |
| A-92. | H | OCH$_3$ | 5-OCH$_3$ | CN | H |
| A-93. | H | CN | 3-F | CN | H |
| A-94. | H | CN | 3-CH$_3$ | CN | H |
| A-95. | H | CN | 3-OCH$_3$ | CN | H |
| A-96. | H | CN | 5-F | CN | H |
| A-97. | H | CN | 5-CH$_3$ | CN | H |
| A-98. | H | CN | 5-OCH$_3$ | CN | H |
| A-99. | H | CH$_2$F | 3-F | CN | H |
| A-100. | H | CH$_2$F | 3-CH$_3$ | CN | H |
| A-101. | H | CH$_2$F | 3-OCH$_3$ | CN | H |
| A-102. | H | CH$_2$F | 5-F | CN | H |
| A-103. | H | CH$_2$F | 5-CH$_3$ | CN | H |
| A-104. | H | CH$_2$F | 5-OCH$_3$ | CN | H |
| A-105. | H | CHF$_2$ | 3-F | CN | H |
| A-106. | H | CHF$_2$ | 3-CH$_3$ | CN | H |
| A-107. | H | CHF$_2$ | 3-OCH$_3$ | CN | H |
| A-108. | H | CHF$_2$ | 5-F | CN | H |
| A-109. | H | CHF$_2$ | 5-CH$_3$ | CN | H |
| A-110. | H | CHF$_2$ | 5-OCH$_3$ | CN | H |
| A-111. | H | CF$_3$ | 3-F | CN | H |
| A-112. | H | CF$_3$ | 3-CH$_3$ | CN | H |
| A-113. | H | CF$_3$ | 3-OCH$_3$ | CN | H |
| A-114. | H | CF$_3$ | 5-F | CN | H |
| A-115. | H | CF$_3$ | 5-CH$_3$ | CN | H |
| A-116. | H | CF$_3$ | 5-OCH$_3$ | CN | H |
| A-117. | H | OCH$_2$F | 3-F | CN | H |
| A-118. | H | OCH$_2$F | 3-CH$_3$ | CN | H |
| A-119. | H | OCH$_2$F | 3-OCH$_3$ | CN | H |
| A-120. | H | OCH$_2$F | 5-F | CN | H |
| A-121. | H | OCH$_2$F | 5-CH$_3$ | CN | H |
| A-122. | H | OCH$_2$F | 5-OCH$_3$ | CN | H |
| A-123. | H | OCHF$_2$ | 3-F | CN | H |

TABLE A-continued

| Example No. | R¹ | R² | R³ | R⁶ | R⁷ |
|---|---|---|---|---|---|
| A-124. | H | OCHF$_2$ | 3-CH$_3$ | CN | H |
| A-125. | H | OCHF$_2$ | 3-OCH$_3$ | CN | H |
| A-126. | H | OCHF$_2$ | 5-F | CN | H |
| A-127. | H | OCHF$_2$ | 5-CH$_3$ | CN | H |
| A-128. | H | OCHF$_2$ | 5-OCH$_3$ | CN | H |
| A-129. | H | OCF$_3$ | 3-F | CN | H |
| A-130. | H | OCF$_3$ | 3-CH$_3$ | CN | H |
| A-131. | H | OCF$_3$ | 3-OCH$_3$ | CN | H |
| A-132. | H | OCF$_3$ | 5-F | CN | H |
| A-133. | H | OCF$_3$ | 5-CH$_3$ | CN | H |
| A-134. | H | OCF$_3$ | 5-OCH$_3$ | CN | H |
| A-135. | F | F | 3-F | CN | H |
| A-136. | F | F | 3-CH$_3$ | CN | H |
| A-137. | F | F | 3-OCH$_3$ | CN | H |
| A-138. | F | F | 5-F | CN | H |
| A-139. | F | F | 5-CH$_3$ | CN | H |
| A-140. | F | F | 5-OCH$_3$ | CN | H |
| A-141. | F | CH$_3$ | 3-F | CN | H |
| A-142. | F | CH$_3$ | 3-CH$_3$ | CN | H |
| A-143. | F | CH$_3$ | 3-OCH$_3$ | CN | H |
| A-144. | F | CH$_3$ | 5-F | CN | H |
| A-145. | F | CH$_3$ | 5-CH$_3$ | CN | H |
| A-146. | F | CH$_3$ | 5-OCH$_3$ | CN | H |
| A-147. | F | OCH$_3$ | 3-F | CN | H |
| A-148. | F | OCH$_3$ | 3-CH$_3$ | CN | H |
| A-149. | F | OCH$_3$ | 3-OCH$_3$ | CN | H |
| A-150. | F | OCH$_3$ | 5-F | CN | H |
| A-151. | F | OCH$_3$ | 5-CH$_3$ | CN | H |
| A-152. | F | OCH$_3$ | 5-OCH$_3$ | CN | H |
| A-153. | F | CN | 3-F | CN | H |
| A-154. | F | CN | 3-CH$_3$ | CN | H |
| A-155. | F | CN | 3-OCH$_3$ | CN | H |
| A-156. | F | CN | 5-F | CN | H |
| A-157. | F | CN | 5-CH$_3$ | CN | H |
| A-158. | F | CN | 5-OCH$_3$ | CN | H |
| A-159. | F | CH$_2$F | 3-F | CN | H |
| A-160. | F | CH$_2$F | 3-CH$_3$ | CN | H |
| A-161. | F | CH$_2$F | 3-OCH$_3$ | CN | H |
| A-162. | F | CH$_2$F | 5-F | CN | H |
| A-163. | F | CH$_2$F | 5-CH$_3$ | CN | H |
| A-164. | F | CH$_2$F | 5-OCH$_3$ | CN | H |
| A-165. | F | CHF$_2$ | 3-F | CN | H |
| A-166. | F | CHF$_2$ | 3-CH$_3$ | CN | H |
| A-167. | F | CHF$_2$ | 3-OCH$_3$ | CN | H |
| A-168. | F | CHF$_2$ | 5-F | CN | H |
| A-169. | F | CHF$_2$ | 5-CH$_3$ | CN | H |
| A-170. | F | CHF$_2$ | 5-OCH$_3$ | CN | H |
| A-171. | F | CF$_3$ | 3-F | CN | H |
| A-172. | F | CF$_3$ | 3-CH$_3$ | CN | H |
| A-173. | F | CF$_3$ | 3-OCH$_3$ | CN | H |
| A-174. | F | CF$_3$ | 5-F | CN | H |
| A-175. | F | CF$_3$ | 5-CH$_3$ | CN | H |
| A-176. | F | CF$_3$ | 5-OCH$_3$ | CN | H |
| A-177. | F | OCH$_2$F | 3-F | CN | H |
| A-178. | F | OCH$_2$F | 3-CH$_3$ | CN | H |
| A-179. | F | OCH$_2$F | 3-OCH$_3$ | CN | H |
| A-180. | F | OCH$_2$F | 5-F | CN | H |
| A-181. | F | OCH$_2$F | 5-CH$_3$ | CN | H |
| A-182. | F | OCH$_2$F | 5-OCH$_3$ | CN | H |
| A-183. | F | OCHF$_2$ | 3-F | CN | H |
| A-184. | F | OCHF$_2$ | 3-CH$_3$ | CN | H |
| A-185. | F | OCHF$_2$ | 3-OCH$_3$ | CN | H |
| A-186. | F | OCHF$_2$ | 5-F | CN | H |
| A-187. | F | OCHF$_2$ | 5-CH$_3$ | CN | H |
| A-188. | F | OCHF$_2$ | 5-OCH$_3$ | CN | H |
| A-189. | F | OCF$_3$ | 3-F | CN | H |
| A-190. | F | OCF$_3$ | 3-CH$_3$ | CN | H |
| A-191. | F | OCF$_3$ | 3-OCH$_3$ | CN | H |
| A-192. | F | OCF$_3$ | 5-F | CN | H |
| A-193. | F | OCF$_3$ | 5-CH$_3$ | CN | H |
| A-194. | F | OCF$_3$ | 5-OCH$_3$ | CN | H |
| A-195. | CH$_3$ | F | 3-F | CN | H |
| A-196. | CH$_3$ | F | 3-CH$_3$ | CN | H |
| A-197. | CH$_3$ | F | 3-OCH$_3$ | CN | H |
| A-198. | CH$_3$ | F | 5-F | CN | H |
| A-199. | CH$_3$ | F | 5-CH$_3$ | CN | H |
| A-200. | CH$_3$ | F | 5-OCH$_3$ | CN | H |
| A-201. | CH$_3$ | CH$_3$ | 3-F | CN | H |
| A-202. | CH$_3$ | CH$_3$ | 3-CH$_3$ | CN | H |
| A-203. | CH$_3$ | CH$_3$ | 3-OCH$_3$ | CN | H |
| A-204. | CH$_3$ | CH$_3$ | 5-F | CN | H |
| A-205. | CH$_3$ | CH$_3$ | 5-CH$_3$ | CN | H |
| A-206. | CH$_3$ | CH$_3$ | 5-OCH$_3$ | CN | H |
| A-207. | CH$_3$ | OCH$_3$ | 3-F | CN | H |
| A-208. | CH$_3$ | OCH$_3$ | 3-CH$_3$ | CN | H |
| A-209. | CH$_3$ | OCH$_3$ | 3-OCH$_3$ | CN | H |
| A-210. | CH$_3$ | OCH$_3$ | 5-F | CN | H |
| A-211. | CH$_3$ | OCH$_3$ | 5-CH$_3$ | CN | H |
| A-212. | CH$_3$ | OCH$_3$ | 5-OCH$_3$ | CN | H |
| A-213. | CH$_3$ | CN | 3-F | CN | H |
| A-214. | CH$_3$ | CN | 3-CH$_3$ | CN | H |
| A-215. | CH$_3$ | CN | 3-OCH$_3$ | CN | H |
| A-216. | CH$_3$ | CN | 5-F | CN | H |
| A-217. | CH$_3$ | CN | 5-CH$_3$ | CN | H |
| A-218. | CH$_3$ | CN | 5-OCH$_3$ | CN | H |
| A-219. | CH$_3$ | CH$_2$F | 3-F | CN | H |
| A-220. | CH$_3$ | CH$_2$F | 3-CH$_3$ | CN | H |
| A-221. | CH$_3$ | CH$_2$F | 3-OCH$_3$ | CN | H |
| A-222. | CH$_3$ | CH$_2$F | 5-F | CN | H |
| A-223. | CH$_3$ | CH$_2$F | 5-CH$_3$ | CN | H |
| A-224. | CH$_3$ | CH$_2$F | 5-OCH$_3$ | CN | H |
| A-225. | CH$_3$ | CHF$_2$ | 3-F | CN | H |
| A-226. | CH$_3$ | CHF$_2$ | 3-CH$_3$ | CN | H |
| A-227. | CH$_3$ | CHF$_2$ | 3-OCH$_3$ | CN | H |
| A-228. | CH$_3$ | CHF$_2$ | 5-F | CN | H |
| A-229. | CH$_3$ | CHF$_2$ | 5-CH$_3$ | CN | H |
| A-230. | CH$_3$ | CHF$_2$ | 5-OCH$_3$ | CN | H |
| A-231. | CH$_3$ | CF$_3$ | 3-F | CN | H |
| A-232. | CH$_3$ | CF$_3$ | 3-CH$_3$ | CN | H |
| A-233. | CH$_3$ | CF$_3$ | 3-OCH$_3$ | CN | H |
| A-234. | CH$_3$ | CF$_3$ | 5-F | CN | H |
| A-235. | CH$_3$ | CF$_3$ | 5-CH$_3$ | CN | H |
| A-236. | CH$_3$ | CF$_3$ | 5-OCH$_3$ | CN | H |
| A-237. | CH$_3$ | OCH$_2$F | 3-F | CN | H |
| A-238. | CH$_3$ | OCH$_2$F | 3-CH$_3$ | CN | H |
| A-239. | CH$_3$ | OCH$_2$F | 3-OCH$_3$ | CN | H |
| A-240. | CH$_3$ | OCH$_2$F | 5-F | CN | H |
| A-241. | CH$_3$ | OCH$_2$F | 5-CH$_3$ | CN | H |
| A-242. | CH$_3$ | OCH$_2$F | 5-OCH$_3$ | CN | H |
| A-243. | CH$_3$ | OCHF$_2$ | 3-F | CN | H |
| A-244. | CH$_3$ | OCHF$_2$ | 3-CH$_3$ | CN | H |
| A-245. | CH$_3$ | OCHF$_2$ | 3-OCH$_3$ | CN | H |
| A-246. | CH$_3$ | OCHF$_2$ | 5-F | CN | H |
| A-247. | CH$_3$ | OCHF$_2$ | 5-CH$_3$ | CN | H |
| A-248. | CH$_3$ | OCHF$_2$ | 5-OCH$_3$ | CN | H |
| A-249. | CH$_3$ | OCF$_3$ | 3-F | CN | H |
| A-250. | CH$_3$ | OCF$_3$ | 3-CH$_3$ | CN | H |
| A-251. | CH$_3$ | OCF$_3$ | 3-OCH$_3$ | CN | H |
| A-252. | CH$_3$ | OCF$_3$ | 5-F | CN | H |
| A-253. | CH$_3$ | OCF$_3$ | 5-CH$_3$ | CN | H |
| A-254. | CH$_3$ | OCF$_3$ | 5-OCH$_3$ | CN | H |
| A-255. | OCH$_3$ | F | 3-F | CN | H |
| A-256. | OCH$_3$ | F | 3-CH$_3$ | CN | H |
| A-257. | OCH$_3$ | F | 3-OCH$_3$ | CN | H |
| A-258. | OCH$_3$ | F | 5-F | CN | H |
| A-259. | OCH$_3$ | F | 5-CH$_3$ | CN | H |
| A-260. | OCH$_3$ | F | 5-OCH$_3$ | CN | H |
| A-261. | OCH$_3$ | CH$_3$ | 3-F | CN | H |
| A-262. | OCH$_3$ | CH$_3$ | 3-CH$_3$ | CN | H |
| A-263. | OCH$_3$ | CH$_3$ | 3-OCH$_3$ | CN | H |
| A-264. | OCH$_3$ | CH$_3$ | 5-F | CN | H |
| A-265. | OCH$_3$ | CH$_3$ | 5-CH$_3$ | CN | H |
| A-266. | OCH$_3$ | CH$_3$ | 5-OCH$_3$ | CN | H |
| A-267. | OCH$_3$ | OCH$_3$ | 3-F | CN | H |
| A-268. | OCH$_3$ | OCH$_3$ | 3-CH$_3$ | CN | H |
| A-269. | OCH$_3$ | OCH$_3$ | 3-OCH$_3$ | CN | H |
| A-270. | OCH$_3$ | OCH$_3$ | 5-F | CN | H |
| A-271. | OCH$_3$ | OCH$_3$ | 5-CH$_3$ | CN | H |
| A-272. | OCH$_3$ | OCH$_3$ | 5-OCH$_3$ | CN | H |
| A-273. | OCH$_3$ | CN | 3-F | CN | H |
| A-274. | OCH$_3$ | CN | 3-CH$_3$ | CN | H |
| A-275. | OCH$_3$ | CN | 3-OCH$_3$ | CN | H |
| A-276. | OCH$_3$ | CN | 5-F | CN | H |
| A-277. | OCH$_3$ | CN | 5-CH$_3$ | CN | H |
| A-278. | OCH$_3$ | CN | 5-OCH$_3$ | CN | H |
| A-279. | OCH$_3$ | CH$_2$F | 3-F | CN | H |

TABLE A-continued

| Example No. | R¹ | R² | R³ | R⁶ | R⁷ |
|---|---|---|---|---|---|
| A-280. | $OCH_3$ | $CH_2F$ | 3-$CH_3$ | CN | H |
| A-281. | $OCH_3$ | $CH_2F$ | 3-$OCH_3$ | CN | H |
| A-282. | $OCH_3$ | $CH_2F$ | 5-F | CN | H |
| A-283. | $OCH_3$ | $CH_2F$ | 5-$CH_3$ | CN | H |
| A-284. | $OCH_3$ | $CH_2F$ | 5-$OCH_3$ | CN | H |
| A-285. | $OCH_3$ | $CHF_2$ | 3-F | CN | H |
| A-286. | $OCH_3$ | $CHF_2$ | 3-$CH_3$ | CN | H |
| A-287. | $OCH_3$ | $CHF_2$ | 3-$OCH_3$ | CN | H |
| A-288. | $OCH_3$ | $CHF_2$ | 5-F | CN | H |
| A-289. | $OCH_3$ | $CHF_2$ | 5-$CH_3$ | CN | H |
| A-290. | $OCH_3$ | $CHF_2$ | 5-$OCH_3$ | CN | H |
| A-291. | $OCH_3$ | $CF_3$ | 3-F | CN | H |
| A-292. | $OCH_3$ | $CF_3$ | 3-$CH_3$ | CN | H |
| A-293. | $OCH_3$ | $CF_3$ | 3-$OCH_3$ | CN | H |
| A-294. | $OCH_3$ | $CF_3$ | 5-F | CN | H |
| A-295. | $OCH_3$ | $CF_3$ | 5-$CH_3$ | CN | H |
| A-296. | $OCH_3$ | $CF_3$ | 5-$OCH_3$ | CN | H |
| A-297. | $OCH_3$ | $OCH_2F$ | 3-F | CN | H |
| A-298. | $OCH_3$ | $OCH_2F$ | 3-$CH_3$ | CN | H |
| A-299. | $OCH_3$ | $OCH_2F$ | 3-$OCH_3$ | CN | H |
| A-300. | $OCH_3$ | $OCH_2F$ | 5-F | CN | H |
| A-301. | $OCH_3$ | $OCH_2F$ | 5-$CH_3$ | CN | H |
| A-302. | $OCH_3$ | $OCH_2F$ | 5-$OCH_3$ | CN | H |
| A-303. | $OCH_3$ | $OCHF_2$ | 3-F | CN | H |
| A-304. | $OCH_3$ | $OCHF_2$ | 3-$CH_3$ | CN | H |
| A-305. | $OCH_3$ | $OCHF_2$ | 3-$OCH_3$ | CN | H |
| A-306. | $OCH_3$ | $OCHF_2$ | 5-F | CN | H |
| A-307. | $OCH_3$ | $OCHF_2$ | 5-$CH_3$ | CN | H |
| A-308. | $OCH_3$ | $OCHF_2$ | 5-$OCH_3$ | CN | H |
| A-309. | $OCH_3$ | $OCF_3$ | 3-F | CN | H |
| A-310. | $OCH_3$ | $OCF_3$ | 3-$CH_3$ | CN | H |
| A-311. | $OCH_3$ | $OCF_3$ | 3-$OCH_3$ | CN | H |
| A-312. | $OCH_3$ | $OCF_3$ | 5-F | CN | H |
| A-313. | $OCH_3$ | $OCF_3$ | 5-$CH_3$ | CN | H |
| A-314. | $OCH_3$ | $OCF_3$ | 5-$OCH_3$ | CN | H |
| A-315. | $CH_2F$ | F | 3-F | CN | H |
| A-316. | $CH_2F$ | F | 3-$CH_3$ | CN | H |
| A-317. | $CH_2F$ | F | 3-$OCH_3$ | CN | H |
| A-318. | $CH_2F$ | F | 5-F | CN | H |
| A-319. | $CH_2F$ | F | 5-$CH_3$ | CN | H |
| A-320. | $CH_2F$ | F | 5-$OCH_3$ | CN | H |
| A-321. | $CH_2F$ | $CH_3$ | 3-F | CN | H |
| A-322. | $CH_2F$ | $CH_3$ | 3-$CH_3$ | CN | H |
| A-323. | $CH_2F$ | $CH_3$ | 3-$OCH_3$ | CN | H |
| A-324. | $CH_2F$ | $CH_3$ | 5-F | CN | H |
| A-325. | $CH_2F$ | $CH_3$ | 5-$CH_3$ | CN | H |
| A-326. | $CH_2F$ | $CH_3$ | 5-$OCH_3$ | CN | H |
| A-327. | $CH_2F$ | $OCH_3$ | 3-F | CN | H |
| A-328. | $CH_2F$ | $OCH_3$ | 3-$CH_3$ | CN | H |
| A-329. | $CH_2F$ | $OCH_3$ | 3-$OCH_3$ | CN | H |
| A-330. | $CH_2F$ | $OCH_3$ | 5-F | CN | H |
| A-331. | $CH_2F$ | $OCH_3$ | 5-$CH_3$ | CN | H |
| A-332. | $CH_2F$ | $OCH_3$ | 5-$OCH_3$ | CN | H |
| A-333. | $CH_2F$ | CN | 3-F | CN | H |
| A-334. | $CH_2F$ | CN | 3-$CH_3$ | CN | H |
| A-335. | $CH_2F$ | CN | 3-$OCH_3$ | CN | H |
| A-336. | $CH_2F$ | CN | 5-F | CN | H |
| A-337. | $CH_2F$ | CN | 5-$CH_3$ | CN | H |
| A-338. | $CH_2F$ | CN | 5-$OCH_3$ | CN | H |
| A-339. | $CH_2F$ | $CH_2F$ | 3-F | CN | H |
| A-340. | $CH_2F$ | $CH_2F$ | 3-$CH_3$ | CN | H |
| A-341. | $CH_2F$ | $CH_2F$ | 3-$OCH_3$ | CN | H |
| A-342. | $CH_2F$ | $CH_2F$ | 5-F | CN | H |
| A-343. | $CH_2F$ | $CH_2F$ | 5-$CH_3$ | CN | H |
| A-344. | $CH_2F$ | $CH_2F$ | 5-$OCH_3$ | CN | H |
| A-345. | $CH_2F$ | $CHF_2$ | 3-F | CN | H |
| A-346. | $CH_2F$ | $CHF_2$ | 3-$CH_3$ | CN | H |
| A-347. | $CH_2F$ | $CHF_2$ | 3-$OCH_3$ | CN | H |
| A-348. | $CH_2F$ | $CHF_2$ | 5-F | CN | H |
| A-349. | $CH_2F$ | $CHF_2$ | 5-$CH_3$ | CN | H |
| A-350. | $CH_2F$ | $CHF_2$ | 5-$OCH_3$ | CN | H |
| A-351. | $CH_2F$ | $CF_3$ | 3-F | CN | H |
| A-352. | $CH_2F$ | $CF_3$ | 3-$CH_3$ | CN | H |
| A-353. | $CH_2F$ | $CF_3$ | 3-$OCH_3$ | CN | H |
| A-354. | $CH_2F$ | $CF_3$ | 5-F | CN | H |
| A-355. | $CH_2F$ | $CF_3$ | 5-$CH_3$ | CN | H |
| A-356. | $CH_2F$ | $CF_3$ | 5-$OCH_3$ | CN | H |
| A-357. | $CH_2F$ | $OCH_2F$ | 3-F | CN | H |
| A-358. | $CH_2F$ | $OCH_2F$ | 3-$CH_3$ | CN | H |
| A-359. | $CH_2F$ | $OCH_2F$ | 3-$OCH_3$ | CN | H |
| A-360. | $CH_2F$ | $OCH_2F$ | 5-F | CN | H |
| A-361. | $CH_2F$ | $OCH_2F$ | 5-$CH_3$ | CN | H |
| A-362. | $CH_2F$ | $OCH_2F$ | 5-$OCH_3$ | CN | H |
| A-363. | $CH_2F$ | $OCHF_2$ | 3-F | CN | H |
| A-364. | $CH_2F$ | $OCHF_2$ | 3-$CH_3$ | CN | H |
| A-365. | $CH_2F$ | $OCHF_2$ | 3-$OCH_3$ | CN | H |
| A-366. | $CH_2F$ | $OCHF_2$ | 5-F | CN | H |
| A-367. | $CH_2F$ | $OCHF_2$ | 5-$CH_3$ | CN | H |
| A-368. | $CH_2F$ | $OCHF_2$ | 5-$OCH_3$ | CN | H |
| A-369. | $CH_2F$ | $OCF_3$ | 3-F | CN | H |
| A-370. | $CH_2F$ | $OCF_3$ | 3-$CH_3$ | CN | H |
| A-371. | $CH_2F$ | $OCF_3$ | 3-$OCH_3$ | CN | H |
| A-372. | $CH_2F$ | $OCF_3$ | 5-F | CN | H |
| A-373. | $CH_2F$ | $OCF_3$ | 5-$CH_3$ | CN | H |
| A-374. | $CH_2F$ | $OCF_3$ | 5-$OCH_3$ | CN | H |
| A-375. | $CHF_2$ | F | 3-F | CN | H |
| A-376. | $CHF_2$ | F | 3-$CH_3$ | CN | H |
| A-377. | $CHF_2$ | F | 3-$OCH_3$ | CN | H |
| A-378. | $CHF_2$ | F | 5-F | CN | H |
| A-379. | $CHF_2$ | F | 5-$CH_3$ | CN | H |
| A-380. | $CHF_2$ | F | 5-$OCH_3$ | CN | H |
| A-381. | $CHF_2$ | $CH_3$ | 3-F | CN | H |
| A-382. | $CHF_2$ | $CH_3$ | 3-$CH_3$ | CN | H |
| A-383. | $CHF_2$ | $CH_3$ | 3-$OCH_3$ | CN | H |
| A-384. | $CHF_2$ | $CH_3$ | 5-F | CN | H |
| A-385. | $CHF_2$ | $CH_3$ | 5-$CH_3$ | CN | H |
| A-386. | $CHF_2$ | $CH_3$ | 5-$OCH_3$ | CN | H |
| A-387. | $CHF_2$ | $OCH_3$ | 3-F | CN | H |
| A-388. | $CHF_2$ | $OCH_3$ | 3-$CH_3$ | CN | H |
| A-389. | $CHF_2$ | $OCH_3$ | 3-$OCH_3$ | CN | H |
| A-390. | $CHF_2$ | $OCH_3$ | 5-F | CN | H |
| A-391. | $CHF_2$ | $OCH_3$ | 5-$CH_3$ | CN | H |
| A-392. | $CHF_2$ | $OCH_3$ | 5-$OCH_3$ | CN | H |
| A-393. | $CHF_2$ | CN | 3-F | CN | H |
| A-394. | $CHF_2$ | CN | 3-$CH_3$ | CN | H |
| A-395. | $CHF_2$ | CN | 3-$OCH_3$ | CN | H |
| A-396. | $CHF_2$ | CN | 5-F | CN | H |
| A-397. | $CHF_2$ | CN | 5-$CH_3$ | CN | H |
| A-398. | $CHF_2$ | CN | 5-$OCH_3$ | CN | H |
| A-399. | $CHF_2$ | $CH_2F$ | 3-F | CN | H |
| A-400. | $CHF_2$ | $CH_2F$ | 3-$CH_3$ | CN | H |
| A-401. | $CHF_2$ | $CH_2F$ | 3-$OCH_3$ | CN | H |
| A-402. | $CHF_2$ | $CH_2F$ | 5-F | CN | H |
| A-403. | $CHF_2$ | $CH_2F$ | 5-$CH_3$ | CN | H |
| A-404. | $CHF_2$ | $CH_2F$ | 5-$OCH_3$ | CN | H |
| A-405. | $CHF_2$ | $CHF_2$ | 3-F | CN | H |
| A-406. | $CHF_2$ | $CHF_2$ | 3-$CH_3$ | CN | H |
| A-407. | $CHF_2$ | $CHF_2$ | 3-$OCH_3$ | CN | H |
| A-408. | $CHF_2$ | $CHF_2$ | 5-F | CN | H |
| A-409. | $CHF_2$ | $CHF_2$ | 5-$CH_3$ | CN | H |
| A-410. | $CHF_2$ | $CHF_2$ | 5-$OCH_3$ | CN | H |
| A-411. | $CHF_2$ | $CF_3$ | 3-F | CN | H |
| A-412. | $CHF_2$ | $CF_3$ | 3-$CH_3$ | CN | H |
| A-413. | $CHF_2$ | $CF_3$ | 3-$OCH_3$ | CN | H |
| A-414. | $CHF_2$ | $CF_3$ | 5-F | CN | H |
| A-415. | $CHF_2$ | $CF_3$ | 5-$CH_3$ | CN | H |
| A-416. | $CHF_2$ | $CF_3$ | 5-$OCH_3$ | CN | H |
| A-417. | $CHF_2$ | $OCH_2F$ | 3-F | CN | H |
| A-418. | $CHF_2$ | $OCH_2F$ | 3-$CH_3$ | CN | H |
| A-419. | $CHF_2$ | $OCH_2F$ | 3-$OCH_3$ | CN | H |
| A-420. | $CHF_2$ | $OCH_2F$ | 5-F | CN | H |
| A-421. | $CHF_2$ | $OCH_2F$ | 5-$CH_3$ | CN | H |
| A-422. | $CHF_2$ | $OCH_2F$ | 5-$OCH_3$ | CN | H |
| A-423. | $CHF_2$ | $OCHF_2$ | 3-F | CN | H |
| A-424. | $CHF_2$ | $OCHF_2$ | 3-$CH_3$ | CN | H |
| A-425. | $CHF_2$ | $OCHF_2$ | 3-$OCH_3$ | CN | H |
| A-426. | $CHF_2$ | $OCHF_2$ | 5-F | CN | H |
| A-427. | $CHF_2$ | $OCHF_2$ | 5-$CH_3$ | CN | H |
| A-428. | $CHF_2$ | $OCHF_2$ | 5-$OCH_3$ | CN | H |
| A-429. | $CHF_2$ | $OCF_3$ | 3-F | CN | H |
| A-430. | $CHF_2$ | $OCF_3$ | 3-$CH_3$ | CN | H |
| A-431. | $CHF_2$ | $OCF_3$ | 3-$OCH_3$ | CN | H |
| A-432. | $CHF_2$ | $OCF_3$ | 5-F | CN | H |
| A-433. | $CHF_2$ | $OCF_3$ | 5-$CH_3$ | CN | H |
| A-434. | $CHF_2$ | $OCF_3$ | 5-$OCH_3$ | CN | H |
| A-435. | $CF_3$ | F | 3-F | CN | H |

TABLE A-continued

| Example No. | R$^1$ | R$^2$ | R$^3$ | R$^6$ | R$^7$ |
|---|---|---|---|---|---|
| A-436. | CF$_3$ | F | 3-CH$_3$ | CN | H |
| A-437. | CF$_3$ | F | 3-OCH$_3$ | CN | H |
| A-438. | CF$_3$ | F | 5-F | CN | H |
| A-439. | CF$_3$ | F | 5-CH$_3$ | CN | H |
| A-440. | CF$_3$ | F | 5-OCH$_3$ | CN | H |
| A-441. | CF$_3$ | CH$_3$ | 3-F | CN | H |
| A-442. | CF$_3$ | CH$_3$ | 3-CH$_3$ | CN | H |
| A-443. | CF$_3$ | CH$_3$ | 3-OCH$_3$ | CN | H |
| A-444. | CF$_3$ | CH$_3$ | 5-F | CN | H |
| A-445. | CF$_3$ | CH$_3$ | 5-CH$_3$ | CN | H |
| A-446. | CF$_3$ | CH$_3$ | 5-OCH$_3$ | CN | H |
| A-447. | CF$_3$ | OCH$_3$ | 3-F | CN | H |
| A-448. | CF$_3$ | OCH$_3$ | 3-CH$_3$ | CN | H |
| A-449. | CF$_3$ | OCH$_3$ | 3-OCH$_3$ | CN | H |
| A-450. | CF$_3$ | OCH$_3$ | 5-F | CN | H |
| A-451. | CF$_3$ | OCH$_3$ | 5-CH$_3$ | CN | H |
| A-452. | CF$_3$ | OCH$_3$ | 5-OCH$_3$ | CN | H |
| A-453. | CF$_3$ | CN | 3-F | CN | H |
| A-454. | CF$_3$ | CN | 3-CH$_3$ | CN | H |
| A-455. | CF$_3$ | CN | 3-OCH$_3$ | CN | H |
| A-456. | CF$_3$ | CN | 5-F | CN | H |
| A-457. | CF$_3$ | CN | 5-CH$_3$ | CN | H |
| A-458. | CF$_3$ | CN | 5-OCH$_3$ | CN | H |
| A-459. | CF$_3$ | CH$_2$F | 3-F | CN | H |
| A-460. | CF$_3$ | CH$_2$F | 3-CH$_3$ | CN | H |
| A-461. | CF$_3$ | CH$_2$F | 3-OCH$_3$ | CN | H |
| A-462. | CF$_3$ | CH$_2$F | 5-F | CN | H |
| A-463. | CF$_3$ | CH$_2$F | 5-CH$_3$ | CN | H |
| A-464. | CF$_3$ | CH$_2$F | 5-OCH$_3$ | CN | H |
| A-465. | CF$_3$ | CHF$_2$ | 3-F | CN | H |
| A-466. | CF$_3$ | CHF$_2$ | 3-CH$_3$ | CN | H |
| A-467. | CF$_3$ | CHF$_2$ | 3-OCH$_3$ | CN | H |
| A-468. | CF$_3$ | CHF$_2$ | 5-F | CN | H |
| A-469. | CF$_3$ | CHF$_2$ | 5-CH$_3$ | CN | H |
| A-470. | CF$_3$ | CHF$_2$ | 5-OCH$_3$ | CN | H |
| A-471. | CF$_3$ | CF$_3$ | 3-F | CN | H |
| A-472. | CF$_3$ | CF$_3$ | 3-CH$_3$ | CN | H |
| A-473. | CF$_3$ | CF$_3$ | 3-OCH$_3$ | CN | H |
| A-474. | CF$_3$ | CF$_3$ | 5-F | CN | H |
| A-475. | CF$_3$ | CF$_3$ | 5-CH$_3$ | CN | H |
| A-476. | CF$_3$ | CF$_3$ | 5-OCH$_3$ | CN | H |
| A-477. | CF$_3$ | OCH$_2$F | 3-F | CN | H |
| A-478. | CF$_3$ | OCH$_2$F | 3-CH$_3$ | CN | H |
| A-479. | CF$_3$ | OCH$_2$F | 3-OCH$_3$ | CN | H |
| A-480. | CF$_3$ | OCH$_2$F | 5-F | CN | H |
| A-481. | CF$_3$ | OCH$_2$F | 5-CH$_3$ | CN | H |
| A-482. | CF$_3$ | OCH$_2$F | 5-OCH$_3$ | CN | H |
| A-483. | CF$_3$ | OCHF$_2$ | 3-F | CN | H |
| A-484. | CF$_3$ | OCHF$_2$ | 3-CH$_3$ | CN | H |
| A-485. | CF$_3$ | OCHF$_2$ | 3-OCH$_3$ | CN | H |
| A-486. | CF$_3$ | OCHF$_2$ | 5-F | CN | H |
| A-487. | CF$_3$ | OCHF$_2$ | 5-CH$_3$ | CN | H |
| A-488. | CF$_3$ | OCHF$_2$ | 5-OCH$_3$ | CN | H |
| A-489. | CF$_3$ | OCF$_3$ | 3-F | CN | H |
| A-490. | CF$_3$ | OCF$_3$ | 3-CH$_3$ | CN | H |
| A-491. | CF$_3$ | OCF$_3$ | 3-OCH$_3$ | CN | H |
| A-492. | CF$_3$ | OCF$_3$ | 5-F | CN | H |
| A-493. | CF$_3$ | OCF$_3$ | 5-CH$_3$ | CN | H |
| A-494. | CF$_3$ | OCF$_3$ | 5-OCH$_3$ | CN | H |
| A-495. | OCH$_2$F | F | 3-F | CN | H |
| A-496. | OCH$_2$F | F | 3-CH$_3$ | CN | H |
| A-497. | OCH$_2$F | F | 3-OCH$_3$ | CN | H |
| A-498. | OCH$_2$F | F | 5-F | CN | H |
| A-499. | OCH$_2$F | F | 5-CH$_3$ | CN | H |
| A-500. | OCH$_2$F | F | 5-OCH$_3$ | CN | H |
| A-501. | OCH$_2$F | CH$_3$ | 3-F | CN | H |
| A-502. | OCH$_2$F | CH$_3$ | 3-CH$_3$ | CN | H |
| A-503. | OCH$_2$F | CH$_3$ | 3-OCH$_3$ | CN | H |
| A-504. | OCH$_2$F | CH$_3$ | 5-F | CN | H |
| A-505. | OCH$_2$F | CH$_3$ | 5-CH$_3$ | CN | H |
| A-506. | OCH$_2$F | CH$_3$ | 5-OCH$_3$ | CN | H |
| A-507. | OCH$_2$F | OCH$_3$ | 3-F | CN | H |
| A-508. | OCH$_2$F | OCH$_3$ | 3-CH$_3$ | CN | H |
| A-509. | OCH$_2$F | OCH$_3$ | 3-OCH$_3$ | CN | H |
| A-510. | OCH$_2$F | OCH$_3$ | 5-F | CN | H |
| A-511. | OCH$_2$F | OCH$_3$ | 5-CH$_3$ | CN | H |
| A-512. | OCH$_2$F | OCH$_3$ | 5-OCH$_3$ | CN | H |
| A-513. | OCH$_2$F | CN | 3-F | CN | H |
| A-514. | OCH$_2$F | CN | 3-CH$_3$ | CN | H |
| A-515. | OCH$_2$F | CN | 3-OCH$_3$ | CN | H |
| A-516. | OCH$_2$F | CN | 5-F | CN | H |
| A-517. | OCH$_2$F | CN | 5-CH$_3$ | CN | H |
| A-518. | OCH$_2$F | CN | 5-OCH$_3$ | CN | H |
| A-519. | OCH$_2$F | CH$_2$F | 3-F | CN | H |
| A-520. | OCH$_2$F | CH$_2$F | 3-CH$_3$ | CN | H |
| A-521. | OCH$_2$F | CH$_2$F | 3-OCH$_3$ | CN | H |
| A-522. | OCH$_2$F | CH$_2$F | 5-F | CN | H |
| A-523. | OCH$_2$F | CH$_2$F | 5-CH$_3$ | CN | H |
| A-524. | OCH$_2$F | CH$_2$F | 5-OCH$_3$ | CN | H |
| A-525. | OCH$_2$F | CHF$_2$ | 3-F | CN | H |
| A-526. | OCH$_2$F | CHF$_2$ | 3-CH$_3$ | CN | H |
| A-527. | OCH$_2$F | CHF$_2$ | 3-OCH$_3$ | CN | H |
| A-528. | OCH$_2$F | CHF$_2$ | 5-F | CN | H |
| A-529. | OCH$_2$F | CHF$_2$ | 5-CH$_3$ | CN | H |
| A-530. | OCH$_2$F | CHF$_2$ | 5-OCH$_3$ | CN | H |
| A-531. | OCH$_2$F | CF$_3$ | 3-F | CN | H |
| A-532. | OCH$_2$F | CF$_3$ | 3-CH$_3$ | CN | H |
| A-533. | OCH$_2$F | CF$_3$ | 3-OCH$_3$ | CN | H |
| A-534. | OCH$_2$F | CF$_3$ | 5-F | CN | H |
| A-535. | OCH$_2$F | CF$_3$ | 5-CH$_3$ | CN | H |
| A-536. | OCH$_2$F | CF$_3$ | 5-OCH$_3$ | CN | H |
| A-537. | OCH$_2$F | OCH$_2$F | 3-F | CN | H |
| A-538. | OCH$_2$F | OCH$_2$F | 3-CH$_3$ | CN | H |
| A-539. | OCH$_2$F | OCH$_2$F | 3-OCH$_3$ | CN | H |
| A-540. | OCH$_2$F | OCH$_2$F | 5-F | CN | H |
| A-541. | OCH$_2$F | OCH$_2$F | 5-CH$_3$ | CN | H |
| A-542. | OCH$_2$F | OCH$_2$F | 5-OCH$_3$ | CN | H |
| A-543. | OCH$_2$F | OCHF$_2$ | 3-F | CN | H |
| A-544. | OCH$_2$F | OCHF$_2$ | 3-CH$_3$ | CN | H |
| A-545. | OCH$_2$F | OCHF$_2$ | 3-OCH$_3$ | CN | H |
| A-546. | OCH$_2$F | OCHF$_2$ | 5-F | CN | H |
| A-547. | OCH$_2$F | OCHF$_2$ | 5-CH$_3$ | CN | H |
| A-548. | OCH$_2$F | OCHF$_2$ | 5-OCH$_3$ | CN | H |
| A-549. | OCH$_2$F | OCF$_3$ | 3-F | CN | H |
| A-550. | OCH$_2$F | OCF$_3$ | 3-CH$_3$ | CN | H |
| A-551. | OCH$_2$F | OCF$_3$ | 3-OCH$_3$ | CN | H |
| A-552. | OCH$_2$F | OCF$_3$ | 5-F | CN | H |
| A-553. | OCH$_2$F | OCF$_3$ | 5-CH$_3$ | CN | H |
| A-554. | OCH$_2$F | OCF$_3$ | 5-OCH$_3$ | CN | H |
| A-555. | OCHF$_2$ | F | 3-F | CN | H |
| A-556. | OCHF$_2$ | F | 3-CH$_3$ | CN | H |
| A-557. | OCHF$_2$ | F | 3-OCH$_3$ | CN | H |
| A-558. | OCHF$_2$ | F | 5-F | CN | H |
| A-559. | OCHF$_2$ | F | 5-CH$_3$ | CN | H |
| A-560. | OCHF$_2$ | F | 5-OCH$_3$ | CN | H |
| A-561. | OCHF$_2$ | CH$_3$ | 3-F | CN | H |
| A-562. | OCHF$_2$ | CH$_3$ | 3-CH$_3$ | CN | H |
| A-563. | OCHF$_2$ | CH$_3$ | 3-OCH$_3$ | CN | H |
| A-564. | OCHF$_2$ | CH$_3$ | 5-F | CN | H |
| A-565. | OCHF$_2$ | CH$_3$ | 5-CH$_3$ | CN | H |
| A-566. | OCHF$_2$ | CH$_3$ | 5-OCH$_3$ | CN | H |
| A-567. | OCHF$_2$ | OCH$_3$ | 3-F | CN | H |
| A-568. | OCHF$_2$ | OCH$_3$ | 3-CH$_3$ | CN | H |
| A-569. | OCHF$_2$ | OCH$_3$ | 3-OCH$_3$ | CN | H |
| A-570. | OCHF$_2$ | OCH$_3$ | 5-F | CN | H |
| A-571. | OCHF$_2$ | OCH$_3$ | 5-CH$_3$ | CN | H |
| A-572. | OCHF$_2$ | OCH$_3$ | 5-OCH$_3$ | CN | H |
| A-573. | OCHF$_2$ | CN | 3-F | CN | H |
| A-574. | OCHF$_2$ | CN | 3-CH$_3$ | CN | H |
| A-575. | OCHF$_2$ | CN | 3-OCH$_3$ | CN | H |
| A-576. | OCHF$_2$ | CN | 5-F | CN | H |
| A-577. | OCHF$_2$ | CN | 5-CH$_3$ | CN | H |
| A-578. | OCHF$_2$ | CN | 5-OCH$_3$ | CN | H |
| A-579. | OCHF$_2$ | CH$_2$F | 3-F | CN | H |
| A-580. | OCHF$_2$ | CH$_2$F | 3-CH$_3$ | CN | H |
| A-581. | OCHF$_2$ | CH$_2$F | 3-OCH$_3$ | CN | H |
| A-582. | OCHF$_2$ | CH$_2$F | 5-F | CN | H |
| A-583. | OCHF$_2$ | CH$_2$F | 5-CH$_3$ | CN | H |
| A-584. | OCHF$_2$ | CH$_2$F | 5-OCH$_3$ | CN | H |
| A-585. | OCHF$_2$ | CHF$_2$ | 3-F | CN | H |
| A-586. | OCHF$_2$ | CHF$_2$ | 3-CH$_3$ | CN | H |
| A-587. | OCHF$_2$ | CHF$_2$ | 3-OCH$_3$ | CN | H |
| A-588. | OCHF$_2$ | CHF$_2$ | 5-F | CN | H |
| A-589. | OCHF$_2$ | CHF$_2$ | 5-CH$_3$ | CN | H |
| A-590. | OCHF$_2$ | CHF$_2$ | 5-OCH$_3$ | CN | H |
| A-591. | OCHF$_2$ | CF$_3$ | 3-F | CN | H |

TABLE A-continued

| Example No. | R¹ | R² | R³ | R⁶ | R⁷ |
|---|---|---|---|---|---|
| A-592. | OCHF$_2$ | CF$_3$ | 3-CH$_3$ | CN | H |
| A-593. | OCHF$_2$ | CF$_3$ | 3-OCH$_3$ | CN | H |
| A-594. | OCHF$_2$ | CF$_3$ | 5-F | CN | H |
| A-595. | OCHF$_2$ | CF$_3$ | 5-CH$_3$ | CN | H |
| A-596. | OCHF$_2$ | CF$_3$ | 5-OCH$_3$ | CN | H |
| A-597. | OCHF$_2$ | OCH$_2$F | 3-F | CN | H |
| A-598. | OCHF$_2$ | OCH$_2$F | 3-CH$_3$ | CN | H |
| A-599. | OCHF$_2$ | OCH$_2$F | 3-OCH$_3$ | CN | H |
| A-600. | OCHF$_2$ | OCH$_2$F | 5-F | CN | H |
| A-601. | OCHF$_2$ | OCH$_2$F | 5-CH$_3$ | CN | H |
| A-602. | OCHF$_2$ | OCH$_2$F | 5-OCH$_3$ | CN | H |
| A-603. | OCHF$_2$ | OCHF$_2$ | 3-F | CN | H |
| A-604. | OCHF$_2$ | OCHF$_2$ | 3-CH$_3$ | CN | H |
| A-605. | OCHF$_2$ | OCHF$_2$ | 3-OCH$_3$ | CN | H |
| A-606. | OCHF$_2$ | OCHF$_2$ | 5-F | CN | H |
| A-607. | OCHF$_2$ | OCHF$_2$ | 5-CH$_3$ | CN | H |
| A-608. | OCHF$_2$ | OCHF$_2$ | 5-OCH$_3$ | CN | H |
| A-609. | OCHF$_2$ | OCF$_3$ | 3-F | CN | H |
| A-610. | OCHF$_2$ | OCF$_3$ | 3-CH$_3$ | CN | H |
| A-611. | OCHF$_2$ | OCF$_3$ | 3-OCH$_3$ | CN | H |
| A-612. | OCHF$_2$ | OCF$_3$ | 5-F | CN | H |
| A-613. | OCHF$_2$ | OCF$_3$ | 5-CH$_3$ | CN | H |
| A-614. | OCHF$_2$ | OCF$_3$ | 5-OCH$_3$ | CN | H |
| A-615. | OCF$_3$ | F | 3-F | CN | H |
| A-616. | OCF$_3$ | F | 3-CH$_3$ | CN | H |
| A-617. | OCF$_3$ | F | 3-OCH$_3$ | CN | H |
| A-618. | OCF$_3$ | F | 5-F | CN | H |
| A-619. | OCF$_3$ | F | 5-CH$_3$ | CN | H |
| A-620. | OCF$_3$ | F | 5-OCH$_3$ | CN | H |
| A-621. | OCF$_3$ | CH$_3$ | 3-F | CN | H |
| A-622. | OCF$_3$ | CH$_3$ | 3-CH$_3$ | CN | H |
| A-623. | OCF$_3$ | CH$_3$ | 3-OCH$_3$ | CN | H |
| A-624. | OCF$_3$ | CH$_3$ | 5-F | CN | H |
| A-625. | OCF$_3$ | CH$_3$ | 5-CH$_3$ | CN | H |
| A-626. | OCF$_3$ | CH$_3$ | 5-OCH$_3$ | CN | H |
| A-627. | OCF$_3$ | OCH$_3$ | 3-F | CN | H |
| A-628. | OCF$_3$ | OCH$_3$ | 3-CH$_3$ | CN | H |
| A-629. | OCF$_3$ | OCH$_3$ | 3-OCH$_3$ | CN | H |
| A-630. | OCF$_3$ | OCH$_3$ | 5-F | CN | H |
| A-631. | OCF$_3$ | OCH$_3$ | 5-CH$_3$ | CN | H |
| A-632. | OCF$_3$ | OCH$_3$ | 5-OCH$_3$ | CN | H |
| A-633. | OCF$_3$ | CN | 3-F | CN | H |
| A-634. | OCF$_3$ | CN | 3-CH$_3$ | CN | H |
| A-635. | OCF$_3$ | CN | 3-OCH$_3$ | CN | H |
| A-636. | OCF$_3$ | CN | 5-F | CN | H |
| A-637. | OCF$_3$ | CN | 5-CH$_3$ | CN | H |
| A-638. | OCF$_3$ | CN | 5-OCH$_3$ | CN | H |
| A-639. | OCF$_3$ | CH$_2$F | 3-F | CN | H |
| A-640. | OCF$_3$ | CH$_2$F | 3-CH$_3$ | CN | H |
| A-641. | OCF$_3$ | CH$_2$F | 3-OCH$_3$ | CN | H |
| A-642. | OCF$_3$ | CH$_2$F | 5-F | CN | H |
| A-643. | OCF$_3$ | CH$_2$F | 5-CH$_3$ | CN | H |
| A-644. | OCF$_3$ | CH$_2$F | 5-OCH$_3$ | CN | H |
| A-645. | OCF$_3$ | CHF$_2$ | 3-F | CN | H |
| A-646. | OCF$_3$ | CHF$_2$ | 3-CH$_3$ | CN | H |
| A-647. | OCF$_3$ | CHF$_2$ | 3-OCH$_3$ | CN | H |
| A-648. | OCF$_3$ | CHF$_2$ | 5-F | CN | H |
| A-649. | OCF$_3$ | CHF$_2$ | 5-CH$_3$ | CN | H |
| A-650. | OCF$_3$ | CHF$_2$ | 5-OCH$_3$ | CN | H |
| A-651. | OCF$_3$ | CF$_3$ | 3-F | CN | H |
| A-652. | OCF$_3$ | CF$_3$ | 3-CH$_3$ | CN | H |
| A-653. | OCF$_3$ | CF$_3$ | 3-OCH$_3$ | CN | H |
| A-654. | OCF$_3$ | CF$_3$ | 5-F | CN | H |
| A-655. | OCF$_3$ | CF$_3$ | 5-CH$_3$ | CN | H |
| A-656. | OCF$_3$ | CF$_3$ | 5-OCH$_3$ | CN | H |
| A-657. | OCF$_3$ | OCH$_2$F | 3-F | CN | H |
| A-658. | OCF$_3$ | OCH$_2$F | 3-CH$_3$ | CN | H |
| A-659. | OCF$_3$ | OCH$_2$F | 3-OCH$_3$ | CN | H |
| A-660. | OCF$_3$ | OCH$_2$F | 5-F | CN | H |
| A-661. | OCF$_3$ | OCH$_2$F | 5-CH$_3$ | CN | H |
| A-662. | OCF$_3$ | OCH$_2$F | 5-OCH$_3$ | CN | H |
| A-663. | OCF$_3$ | OCHF$_2$ | 3-F | CN | H |
| A-664. | OCF$_3$ | OCHF$_2$ | 3-CH$_3$ | CN | H |
| A-665. | OCF$_3$ | OCHF$_2$ | 3-OCH$_3$ | CN | H |
| A-666. | OCF$_3$ | OCHF$_2$ | 5-F | CN | H |
| A-667. | OCF$_3$ | OCHF$_2$ | 5-CH$_3$ | CN | H |
| A-668. | OCF$_3$ | OCHF$_2$ | 5-OCH$_3$ | CN | H |
| A-669. | OCF$_3$ | OCF$_3$ | 3-F | CN | H |
| A-670. | OCF$_3$ | OCF$_3$ | 3-CH$_3$ | CN | H |
| A-671. | OCF$_3$ | OCF$_3$ | 3-OCH$_3$ | CN | H |
| A-672. | OCF$_3$ | OCF$_3$ | 5-F | CN | H |
| A-673. | OCF$_3$ | OCF$_3$ | 5-CH$_3$ | CN | H |
| A-674. | OCF$_3$ | OCF$_3$ | 5-OCH$_3$ | CN | H |
| A-675. | H | H | H | F | H |
| A-676. | F | H | H | F | H |
| A-677. | CH$_3$ | H | H | F | H |
| A-678. | OCH$_3$ | H | H | F | H |
| A-679. | CH$_2$F | H | H | F | H |
| A-680. | CHF$_2$ | H | H | F | H |
| A-681. | CF$_3$ | H | H | F | H |
| A-682. | OCH$_2$F | H | H | F | H |
| A-683. | OCHF$_2$ | H | H | F | H |
| A-684. | OCF$_3$ | H | H | F | H |
| A-685. | H | F | H | F | H |
| A-686. | H | CH$_3$ | H | F | H |
| A-687. | H | OCH$_3$ | H | F | H |
| A-688. | H | CN | H | F | H |
| A-689. | H | CH$_2$F | H | F | H |
| A-690. | H | CHF$_2$ | H | F | H |
| A-691. | H | CF$_3$ | H | F | H |
| A-692. | H | OCH$_2$F | H | F | H |
| A-693. | H | OCHF$_2$ | H | F | H |
| A-694. | H | OCF$_3$ | H | F | H |
| A-695. | H | H | 3-F | F | H |
| A-696. | H | H | 3-CH$_3$ | F | H |
| A-697. | H | H | 3-OCH$_3$ | F | H |
| A-698. | H | H | 5-F | F | H |
| A-699. | H | H | 5-CH$_3$ | F | H |
| A-700. | H | H | 5-OCH$_3$ | F | H |
| A-701. | F | F | H | F | H |
| A-702. | F | CH$_3$ | H | F | H |
| A-703. | F | OCH$_3$ | H | F | H |
| A-704. | F | CN | H | F | H |
| A-705. | F | CH$_2$F | H | F | H |
| A-706. | F | CHF$_2$ | H | F | H |
| A-707. | F | CF$_3$ | H | F | H |
| A-708. | F | OCH$_2$F | H | F | H |
| A-709. | F | OCHF$_2$ | H | F | H |
| A-710. | F | OCF$_3$ | H | F | H |
| A-711. | F | H | 3-F | F | H |
| A-712. | F | H | 3-CH$_3$ | F | H |
| A-713. | F | H | 3-OCH$_3$ | F | H |
| A-714. | F | H | 5-F | F | H |
| A-715. | F | H | 5-CH$_3$ | F | H |
| A-716. | F | H | 5-OCH$_3$ | F | H |
| A-717. | CH$_3$ | F | H | F | H |
| A-718. | CH$_3$ | CH$_3$ | H | F | H |
| A-719. | CH$_3$ | OCH$_3$ | H | F | H |
| A-720. | CH$_3$ | CN | H | F | H |
| A-721. | CH$_3$ | CH$_2$F | H | F | H |
| A-722. | CH$_3$ | CHF$_2$ | H | F | H |
| A-723. | CH$_3$ | CF$_3$ | H | F | H |
| A-724. | CH$_3$ | OCH$_2$F | H | F | H |
| A-725. | CH$_3$ | OCHF$_2$ | H | F | H |
| A-726. | CH$_3$ | OCF$_3$ | H | F | H |
| A-727. | CH$_3$ | H | 3-F | F | H |
| A-728. | CH$_3$ | H | 3-CH$_3$ | F | H |
| A-729. | CH$_3$ | H | 3-OCH$_3$ | F | H |
| A-730. | CH$_3$ | H | 5-F | F | H |
| A-731. | CH$_3$ | H | 5-CH$_3$ | F | H |
| A-732. | CH$_3$ | H | 5-OCH$_3$ | F | H |
| A-733. | OCH$_3$ | F | H | F | H |
| A-734. | OCH$_3$ | CH$_3$ | H | F | H |
| A-735. | OCH$_3$ | OCH$_3$ | H | F | H |
| A-736. | OCH$_3$ | CN | H | F | H |
| A-737. | OCH$_3$ | CH$_2$F | H | F | H |
| A-738. | OCH$_3$ | CHF$_2$ | H | F | H |
| A-739. | OCH$_3$ | CF$_3$ | H | F | H |
| A-740. | OCH$_3$ | OCH$_2$F | H | F | H |
| A-741. | OCH$_3$ | OCHF$_2$ | H | F | H |
| A-742. | OCH$_3$ | OCF$_3$ | H | F | H |
| A-743. | OCH$_3$ | H | 3-F | F | H |
| A-744. | OCH$_3$ | H | 3-CH$_3$ | F | H |
| A-745. | OCH$_3$ | H | 3-OCH$_3$ | F | H |
| A-746. | OCH$_3$ | H | 5-F | F | H |
| A-747. | OCH$_3$ | H | 5-CH$_3$ | F | H |

TABLE A-continued

| Example No. | R¹ | R² | R³ | R⁶ | R⁷ |
|---|---|---|---|---|---|
| A-748. | OCH₃ | H | 5-OCH₃ | F | H |
| A-749. | H | F | 3-F | F | H |
| A-750. | H | F | 3-CH₃ | F | H |
| A-751. | H | F | 3-OCH₃ | F | H |
| A-752. | H | F | 5-F | F | H |
| A-753. | H | F | 5-CH₃ | F | H |
| A-754. | H | F | 5-OCH₃ | F | H |
| A-755. | H | CH₃ | 3-F | F | H |
| A-756. | H | CH₃ | 3-CH₃ | F | H |
| A-757. | H | CH₃ | 3-OCH₃ | F | H |
| A-758. | H | CH₃ | 5-F | F | H |
| A-759. | H | CH₃ | 5-CH₃ | F | H |
| A-760. | H | CH₃ | 5-OCH₃ | F | H |
| A-761. | H | OCH₃ | 3-F | F | H |
| A-762. | H | OCH₃ | 3-CH₃ | F | H |
| A-763. | H | OCH₃ | 3-OCH₃ | F | H |
| A-764. | H | OCH₃ | 5-F | F | H |
| A-765. | H | OCH₃ | 5-CH₃ | F | H |
| A-766. | H | OCH₃ | 5-OCH₃ | F | H |
| A-767. | H | CN | 3-F | F | H |
| A-768. | H | CN | 3-CH₃ | F | H |
| A-769. | H | CN | 3-OCH₃ | F | H |
| A-770. | H | CN | 5-F | F | H |
| A-771. | H | CN | 5-CH₃ | F | H |
| A-772. | H | CN | 5-OCH₃ | F | H |
| A-773. | H | CH₂F | 3-F | F | H |
| A-774. | H | CH₂F | 3-CH₃ | F | H |
| A-775. | H | CH₂F | 3-OCH₃ | F | H |
| A-776. | H | CH₂F | 5-F | F | H |
| A-777. | H | CH₂F | 5-CH₃ | F | H |
| A-778. | H | CH₂F | 5-OCH₃ | F | H |
| A-779. | H | CHF₂ | 3-F | F | H |
| A-780. | H | CHF₂ | 3-CH₃ | F | H |
| A-781. | H | CHF₂ | 3-OCH₃ | F | H |
| A-782. | H | CHF₂ | 5-F | F | H |
| A-783. | H | CHF₂ | 5-CH₃ | F | H |
| A-784. | H | CHF₂ | 5-OCH₃ | F | H |
| A-785. | H | CF₃ | 3-F | F | H |
| A-786. | H | CF₃ | 3-CH₃ | F | H |
| A-787. | H | CF₃ | 3-OCH₃ | F | H |
| A-788. | H | CF₃ | 5-F | F | H |
| A-789. | H | CF₃ | 5-CH₃ | F | H |
| A-790. | H | CF₃ | 5-OCH₃ | F | H |
| A-791. | H | OCH₂F | 3-F | F | H |
| A-792. | H | OCH₂F | 3-CH₃ | F | H |
| A-793. | H | OCH₂F | 3-OCH₃ | F | H |
| A-794. | H | OCH₂F | 5-F | F | H |
| A-795. | H | OCH₂F | 5-CH₃ | F | H |
| A-796. | H | OCH₂F | 5-OCH₃ | F | H |
| A-797. | H | OCHF₂ | 3-F | F | H |
| A-798. | H | OCHF₂ | 3-CH₃ | F | H |
| A-799. | H | OCHF₂ | 3-OCH₃ | F | H |
| A-800. | H | OCHF₂ | 5-F | F | H |
| A-801. | H | OCHF₂ | 5-CH₃ | F | H |
| A-802. | H | OCHF₂ | 5-OCH₃ | F | H |
| A-803. | H | OCF₃ | 3-F | F | H |
| A-804. | H | OCF₃ | 3-CH₃ | F | H |
| A-805. | H | OCF₃ | 3-OCH₃ | F | H |
| A-806. | H | OCF₃ | 5-F | F | H |
| A-807. | H | OCF₃ | 5-CH₃ | F | H |
| A-808. | H | OCF₃ | 5-OCH₃ | F | H |
| A-809. | F | F | 3-F | F | H |
| A-810. | F | F | 3-CH₃ | F | H |
| A-811. | F | F | 3-OCH₃ | F | H |
| A-812. | F | F | 5-F | F | H |
| A-813. | F | F | 5-CH₃ | F | H |
| A-814. | F | F | 5-OCH₃ | F | H |
| A-815. | F | CH₃ | 3-F | F | H |
| A-816. | F | CH₃ | 3-CH₃ | F | H |
| A-817. | F | CH₃ | 3-OCH₃ | F | H |
| A-818. | F | CH₃ | 5-F | F | H |
| A-819. | F | CH₃ | 5-CH₃ | F | H |
| A-820. | F | CH₃ | 5-OCH₃ | F | H |
| A-821. | F | OCH₃ | 3-F | F | H |
| A-822. | F | OCH₃ | 3-CH₃ | F | H |
| A-823. | F | OCH₃ | 3-OCH₃ | F | H |
| A-824. | F | OCH₃ | 5-F | F | H |
| A-825. | F | OCH₃ | 5-CH₃ | F | H |
| A-826. | F | OCH₃ | 5-OCH₃ | F | H |
| A-827. | F | CN | 3-F | F | H |
| A-828. | F | CN | 3-CH₃ | F | H |
| A-829. | F | CN | 3-OCH₃ | F | H |
| A-830. | F | CN | 5-F | F | H |
| A-831. | F | CN | 5-CH₃ | F | H |
| A-832. | F | CN | 5-OCH₃ | F | H |
| A-833. | F | CH₂F | 3-F | F | H |
| A-834. | F | CH₂F | 3-CH₃ | F | H |
| A-835. | F | CH₂F | 3-OCH₃ | F | H |
| A-836. | F | CH₂F | 5-F | F | H |
| A-837. | F | CH₂F | 5-CH₃ | F | H |
| A-838. | F | CH₂F | 5-OCH₃ | F | H |
| A-839. | F | CHF₂ | 3-F | F | H |
| A-840. | F | CHF₂ | 3-CH₃ | F | H |
| A-841. | F | CHF₂ | 3-OCH₃ | F | H |
| A-842. | F | CHF₂ | 5-F | F | H |
| A-843. | F | CHF₂ | 5-CH₃ | F | H |
| A-844. | F | CHF₂ | 5-OCH₃ | F | H |
| A-845. | F | CF₃ | 3-F | F | H |
| A-846. | F | CF₃ | 3-CH₃ | F | H |
| A-847. | F | CF₃ | 3-OCH₃ | F | H |
| A-848. | F | CF₃ | 5-F | F | H |
| A-849. | F | CF₃ | 5-CH₃ | F | H |
| A-850. | F | CF₃ | 5-OCH₃ | F | H |
| A-851. | F | OCH₂F | 3-F | F | H |
| A-852. | F | OCH₂F | 3-CH₃ | F | H |
| A-853. | F | OCH₂F | 3-OCH₃ | F | H |
| A-854. | F | OCH₂F | 5-F | F | H |
| A-855. | F | OCH₂F | 5-CH₃ | F | H |
| A-856. | F | OCH₂F | 5-OCH₃ | F | H |
| A-857. | F | OCHF₂ | 3-F | F | H |
| A-858. | F | OCHF₂ | 3-CH₃ | F | H |
| A-859. | F | OCHF₂ | 3-OCH₃ | F | H |
| A-860. | F | OCHF₂ | 5-F | F | H |
| A-861. | F | OCHF₂ | 5-CH₃ | F | H |
| A-862. | F | OCHF₂ | 5-OCH₃ | F | H |
| A-863. | F | OCF₃ | 3-F | F | H |
| A-864. | F | OCF₃ | 3-CH₃ | F | H |
| A-865. | F | OCF₃ | 3-OCH₃ | F | H |
| A-866. | F | OCF₃ | 5-F | F | H |
| A-867. | F | OCF₃ | 5-CH₃ | F | H |
| A-868. | F | OCF₃ | 5-OCH₃ | F | H |
| A-869. | CH₃ | F | 3-F | F | H |
| A-870. | CH₃ | F | 3-CH₃ | F | H |
| A-871. | CH₃ | F | 3-OCH₃ | F | H |
| A-872. | CH₃ | F | 5-F | F | H |
| A-873. | CH₃ | F | 5-CH₃ | F | H |
| A-874. | CH₃ | F | 5-OCH₃ | F | H |
| A-875. | CH₃ | CH₃ | 3-F | F | H |
| A-876. | CH₃ | CH₃ | 3-CH₃ | F | H |
| A-877. | CH₃ | CH₃ | 3-OCH₃ | F | H |
| A-878. | CH₃ | CH₃ | 5-F | F | H |
| A-879. | CH₃ | CH₃ | 5-CH₃ | F | H |
| A-880. | CH₃ | CH₃ | 5-OCH₃ | F | H |
| A-881. | CH₃ | OCH₃ | 3-F | F | H |
| A-882. | CH₃ | OCH₃ | 3-CH₃ | F | H |
| A-883. | CH₃ | OCH₃ | 3-OCH₃ | F | H |
| A-884. | CH₃ | OCH₃ | 5-F | F | H |
| A-885. | CH₃ | OCH₃ | 5-CH₃ | F | H |
| A-886. | CH₃ | OCH₃ | 5-OCH₃ | F | H |
| A-887. | CH₃ | CN | 3-F | F | H |
| A-888. | CH₃ | CN | 3-CH₃ | F | H |
| A-889. | CH₃ | CN | 3-OCH₃ | F | H |
| A-890. | CH₃ | CN | 5-F | F | H |
| A-891. | CH₃ | CN | 5-CH₃ | F | H |
| A-892. | CH₃ | CN | 5-OCH₃ | F | H |
| A-893. | CH₃ | CH₂F | 3-F | F | H |
| A-894. | CH₃ | CH₂F | 3-CH₃ | F | H |
| A-895. | CH₃ | CH₂F | 3-OCH₃ | F | H |
| A-896. | CH₃ | CH₂F | 5-F | F | H |
| A-897. | CH₃ | CH₂F | 5-CH₃ | F | H |
| A-898. | CH₃ | CH₂F | 5-OCH₃ | F | H |
| A-899. | CH₃ | CHF₂ | 3-F | F | H |
| A-900. | CH₃ | CHF₂ | 3-CH₃ | F | H |
| A-901. | CH₃ | CHF₂ | 3-OCH₃ | F | H |
| A-902. | CH₃ | CHF₂ | 5-F | F | H |
| A-903. | CH₃ | CHF₂ | 5-CH₃ | F | H |

TABLE A-continued

| Example No. | R¹ | R² | R³ | R⁶ | R⁷ |
|---|---|---|---|---|---|
| A-904. | $CH_3$ | $CHF_2$ | 5-$OCH_3$ | F | H |
| A-905. | $CH_3$ | $CF_3$ | 3-F | F | H |
| A-906. | $CH_3$ | $CF_3$ | 3-$CH_3$ | F | H |
| A-907. | $CH_3$ | $CF_3$ | 3-$OCH_3$ | F | H |
| A-908. | $CH_3$ | $CF_3$ | 5-F | F | H |
| A-909. | $CH_3$ | $CF_3$ | 5-$CH_3$ | F | H |
| A-910. | $CH_3$ | $CF_3$ | 5-$OCH_3$ | F | H |
| A-911. | $CH_3$ | $OCH_2F$ | 3-F | F | H |
| A-912. | $CH_3$ | $OCH_2F$ | 3-$CH_3$ | F | H |
| A-913. | $CH_3$ | $OCH_2F$ | 3-$OCH_3$ | F | H |
| A-914. | $CH_3$ | $OCH_2F$ | 5-F | F | H |
| A-915. | $CH_3$ | $OCH_2F$ | 5-$CH_3$ | F | H |
| A-916. | $CH_3$ | $OCH_2F$ | 5-$OCH_3$ | F | H |
| A-917. | $CH_3$ | $OCHF_2$ | 3-F | F | H |
| A-918. | $CH_3$ | $OCHF_2$ | 3-$CH_3$ | F | H |
| A-919. | $CH_3$ | $OCHF_2$ | 3-$OCH_3$ | F | H |
| A-920. | $CH_3$ | $OCHF_2$ | 5-F | F | H |
| A-921. | $CH_3$ | $OCHF_2$ | 5-$CH_3$ | F | H |
| A-922. | $CH_3$ | $OCHF_2$ | 5-$OCH_3$ | F | H |
| A-923. | $CH_3$ | $OCF_3$ | 3-F | F | H |
| A-924. | $CH_3$ | $OCF_3$ | 3-$CH_3$ | F | H |
| A-925. | $CH_3$ | $OCF_3$ | 3-$OCH_3$ | F | H |
| A-926. | $CH_3$ | $OCF_3$ | 5-F | F | H |
| A-927. | $CH_3$ | $OCF_3$ | 5-$CH_3$ | F | H |
| A-928. | $CH_3$ | $OCF_3$ | 5-$OCH_3$ | F | H |
| A-929. | $OCH_3$ | F | 3-F | F | H |
| A-930. | $OCH_3$ | F | 3-$CH_3$ | F | H |
| A-931. | $OCH_3$ | F | 3-$OCH_3$ | F | H |
| A-932. | $OCH_3$ | F | 5-F | F | H |
| A-933. | $OCH_3$ | F | 5-$CH_3$ | F | H |
| A-934. | $OCH_3$ | F | 5-$OCH_3$ | F | H |
| A-935. | $OCH_3$ | $CH_3$ | 3-F | F | H |
| A-936. | $OCH_3$ | $CH_3$ | 3-$CH_3$ | F | H |
| A-937. | $OCH_3$ | $CH_3$ | 3-$OCH_3$ | F | H |
| A-938. | $OCH_3$ | $CH_3$ | 5-F | F | H |
| A-939. | $OCH_3$ | $CH_3$ | 5-$CH_3$ | F | H |
| A-940. | $OCH_3$ | $CH_3$ | 5-$OCH_3$ | F | H |
| A-941. | $OCH_3$ | $OCH_3$ | 3-F | F | H |
| A-942. | $OCH_3$ | $OCH_3$ | 3-$CH_3$ | F | H |
| A-943. | $OCH_3$ | $OCH_3$ | 3-$OCH_3$ | F | H |
| A-944. | $OCH_3$ | $OCH_3$ | 5-F | F | H |
| A-945. | $OCH_3$ | $OCH_3$ | 5-$CH_3$ | F | H |
| A-946. | $OCH_3$ | $OCH_3$ | 5-$OCH_3$ | F | H |
| A-947. | $OCH_3$ | CN | 3-F | F | H |
| A-948. | $OCH_3$ | CN | 3-$CH_3$ | F | H |
| A-949. | $OCH_3$ | CN | 3-$OCH_3$ | F | H |
| A-950. | $OCH_3$ | CN | 5-F | F | H |
| A-951. | $OCH_3$ | CN | 5-$CH_3$ | F | H |
| A-952. | $OCH_3$ | CN | 5-$OCH_3$ | F | H |
| A-953. | $OCH_3$ | $CH_2F$ | 3-F | F | H |
| A-954. | $OCH_3$ | $CH_2F$ | 3-$CH_3$ | F | H |
| A-955. | $OCH_3$ | $CH_2F$ | 3-$OCH_3$ | F | H |
| A-956. | $OCH_3$ | $CH_2F$ | 5-F | F | H |
| A-957. | $OCH_3$ | $CH_2F$ | 5-$CH_3$ | F | H |
| A-958. | $OCH_3$ | $CH_2F$ | 5-$OCH_3$ | F | H |
| A-959. | $OCH_3$ | $CHF_2$ | 3-F | F | H |
| A-960. | $OCH_3$ | $CHF_2$ | 3-$CH_3$ | F | H |
| A-961. | $OCH_3$ | $CHF_2$ | 3-$OCH_3$ | F | H |
| A-962. | $OCH_3$ | $CHF_2$ | 5-F | F | H |
| A-963. | $OCH_3$ | $CHF_2$ | 5-$CH_3$ | F | H |
| A-964. | $OCH_3$ | $CHF_2$ | 5-$OCH_3$ | F | H |
| A-965. | $OCH_3$ | $CF_3$ | 3-F | F | H |
| A-966. | $OCH_3$ | $CF_3$ | 3-$CH_3$ | F | H |
| A-967. | $OCH_3$ | $CF_3$ | 3-$OCH_3$ | F | H |
| A-968. | $OCH_3$ | $CF_3$ | 5-F | F | H |
| A-969. | $OCH_3$ | $CF_3$ | 5-$CH_3$ | F | H |
| A-970. | $OCH_3$ | $CF_3$ | 5-$OCH_3$ | F | H |
| A-971. | $OCH_3$ | $OCH_2F$ | 3-F | F | H |
| A-972. | $OCH_3$ | $OCH_2F$ | 3-$CH_3$ | F | H |
| A-973. | $OCH_3$ | $OCH_2F$ | 3-$OCH_3$ | F | H |
| A-974. | $OCH_3$ | $OCH_2F$ | 5-F | F | H |
| A-975. | $OCH_3$ | $OCH_2F$ | 5-$CH_3$ | F | H |
| A-976. | $OCH_3$ | $OCH_2F$ | 5-$OCH_3$ | F | H |
| A-977. | $OCH_3$ | $OCHF_2$ | 3-F | F | H |
| A-978. | $OCH_3$ | $OCHF_2$ | 3-$CH_3$ | F | H |
| A-979. | $OCH_3$ | $OCHF_2$ | 3-$OCH_3$ | F | H |
| A-980. | $OCH_3$ | $OCHF_2$ | 5-F | F | H |
| A-981. | $OCH_3$ | $OCHF_2$ | 5-$CH_3$ | F | H |
| A-982. | $OCH_3$ | $OCHF_2$ | 5-$OCH_3$ | F | H |
| A-983. | $OCH_3$ | $OCF_3$ | 3-F | F | H |
| A-984. | $OCH_3$ | $OCF_3$ | 3-$CH_3$ | F | H |
| A-985. | $OCH_3$ | $OCF_3$ | 3-$OCH_3$ | F | H |
| A-986. | $OCH_3$ | $OCF_3$ | 5-F | F | H |
| A-987. | $OCH_3$ | $OCF_3$ | 5-$CH_3$ | F | H |
| A-988. | $OCH_3$ | $OCF_3$ | 5-$OCH_3$ | F | H |
| A-989. | $CH_2F$ | F | 3-F | F | H |
| A-990. | $CH_2F$ | F | 3-$CH_3$ | F | H |
| A-991. | $CH_2F$ | F | 3-$OCH_3$ | F | H |
| A-992. | $CH_2F$ | F | 5-F | F | H |
| A-993. | $CH_2F$ | F | 5-$CH_3$ | F | H |
| A-994. | $CH_2F$ | F | 5-$OCH_3$ | F | H |
| A-995. | $CH_2F$ | $CH_3$ | 3-F | F | H |
| A-996. | $CH_2F$ | $CH_3$ | 3-$CH_3$ | F | H |
| A-997. | $CH_2F$ | $CH_3$ | 3-$OCH_3$ | F | H |
| A-998. | $CH_2F$ | $CH_3$ | 5-F | F | H |
| A-999. | $CH_2F$ | $CH_3$ | 5-$CH_3$ | F | H |
| A-1000. | $CH_2F$ | $CH_3$ | 5-$OCH_3$ | F | H |
| A-1001. | $CH_2F$ | $OCH_3$ | 3-F | F | H |
| A-1002. | $CH_2F$ | $OCH_3$ | 3-$CH_3$ | F | H |
| A-1003. | $CH_2F$ | $OCH_3$ | 3-$OCH_3$ | F | H |
| A-1004. | $CH_2F$ | $OCH_3$ | 5-F | F | H |
| A-1005. | $CH_2F$ | $OCH_3$ | 5-$CH_3$ | F | H |
| A-1006. | $CH_2F$ | $OCH_3$ | 5-$OCH_3$ | F | H |
| A-1007. | $CH_2F$ | CN | 3-F | F | H |
| A-1008. | $CH_2F$ | CN | 3-$CH_3$ | F | H |
| A-1009. | $CH_2F$ | CN | 3-$OCH_3$ | F | H |
| A-1010. | $CH_2F$ | CN | 5-F | F | H |
| A-1011. | $CH_2F$ | CN | 5-$CH_3$ | F | H |
| A-1012. | $CH_2F$ | CN | 5-$OCH_3$ | F | H |
| A-1013. | $CH_2F$ | $CH_2F$ | 3-F | F | H |
| A-1014. | $CH_2F$ | $CH_2F$ | 3-$CH_3$ | F | H |
| A-1015. | $CH_2F$ | $CH_2F$ | 3-$OCH_3$ | F | H |
| A-1016. | $CH_2F$ | $CH_2F$ | 5-F | F | H |
| A-1017. | $CH_2F$ | $CH_2F$ | 5-$CH_3$ | F | H |
| A-1018. | $CH_2F$ | $CH_2F$ | 5-$OCH_3$ | F | H |
| A-1019. | $CH_2F$ | $CHF_2$ | 3-F | F | H |
| A-1020. | $CH_2F$ | $CHF_2$ | 3-$CH_3$ | F | H |
| A-1021. | $CH_2F$ | $CHF_2$ | 3-$OCH_3$ | F | H |
| A-1022. | $CH_2F$ | $CHF_2$ | 5-F | F | H |
| A-1023. | $CH_2F$ | $CHF_2$ | 5-$CH_3$ | F | H |
| A-1024. | $CH_2F$ | $CHF_2$ | 5-$OCH_3$ | F | H |
| A-1025. | $CH_2F$ | $CF_3$ | 3-F | F | H |
| A-1026. | $CH_2F$ | $CF_3$ | 3-$CH_3$ | F | H |
| A-1027. | $CH_2F$ | $CF_3$ | 3-$OCH_3$ | F | H |
| A-1028. | $CH_2F$ | $CF_3$ | 5-F | F | H |
| A-1029. | $CH_2F$ | $CF_3$ | 5-$CH_3$ | F | H |
| A-1030. | $CH_2F$ | $CF_3$ | 5-$OCH_3$ | F | H |
| A-1031. | $CH_2F$ | $OCH_2F$ | 3-F | F | H |
| A-1032. | $CH_2F$ | $OCH_2F$ | 3-$CH_3$ | F | H |
| A-1033. | $CH_2F$ | $OCH_2F$ | 3-$OCH_3$ | F | H |
| A-1034. | $CH_2F$ | $OCH_2F$ | 5-F | F | H |
| A-1035. | $CH_2F$ | $OCH_2F$ | 5-$CH_3$ | F | H |
| A-1036. | $CH_2F$ | $OCH_2F$ | 5-$OCH_3$ | F | H |
| A-1037. | $CH_2F$ | $OCHF_2$ | 3-F | F | H |
| A-1038. | $CH_2F$ | $OCHF_2$ | 3-$CH_3$ | F | H |
| A-1039. | $CH_2F$ | $OCHF_2$ | 3-$OCH_3$ | F | H |
| A-1040. | $CH_2F$ | $OCHF_2$ | 5-F | F | H |
| A-1041. | $CH_2F$ | $OCHF_2$ | 5-$CH_3$ | F | H |
| A-1042. | $CH_2F$ | $OCHF_2$ | 5-$OCH_3$ | F | H |
| A-1043. | $CH_2F$ | $OCF_3$ | 3-F | F | H |
| A-1044. | $CH_2F$ | $OCF_3$ | 3-$CH_3$ | F | H |
| A-1045. | $CH_2F$ | $OCF_3$ | 3-$OCH_3$ | F | H |
| A-1046. | $CH_2F$ | $OCF_3$ | 5-F | F | H |
| A-1047. | $CH_2F$ | $OCF_3$ | 5-$CH_3$ | F | H |
| A-1048. | $CH_2F$ | $OCF_3$ | 5-$OCH_3$ | F | H |
| A-1049. | $CHF_2$ | F | 3-F | F | H |
| A-1050. | $CHF_2$ | F | 3-$CH_3$ | F | H |
| A-1051. | $CHF_2$ | F | 3-$OCH_3$ | F | H |
| A-1052. | $CHF_2$ | F | 5-F | F | H |
| A-1053. | $CHF_2$ | F | 5-$CH_3$ | F | H |
| A-1054. | $CHF_2$ | F | 5-$OCH_3$ | F | H |
| A-1055. | $CHF_2$ | $CH_3$ | 3-F | F | H |
| A-1056. | $CHF_2$ | $CH_3$ | 3-$CH_3$ | F | H |
| A-1057. | $CHF_2$ | $CH_3$ | 3-$OCH_3$ | F | H |
| A-1058. | $CHF_2$ | $CH_3$ | 5-F | F | H |
| A-1059. | $CHF_2$ | $CH_3$ | 5-$CH_3$ | F | H |

TABLE A-continued

| Example No. | R¹ | R² | R³ | R⁶ | R⁷ |
|---|---|---|---|---|---|
| A-1060. | $CHF_2$ | $CH_3$ | 5-$OCH_3$ | F | H |
| A-1061. | $CHF_2$ | $OCH_3$ | 3-F | F | H |
| A-1062. | $CHF_2$ | $OCH_3$ | 3-$CH_3$ | F | H |
| A-1063. | $CHF_2$ | $OCH_3$ | 3-$OCH_3$ | F | H |
| A-1064. | $CHF_2$ | $OCH_3$ | 5-F | F | H |
| A-1065. | $CHF_2$ | $OCH_3$ | 5-$CH_3$ | F | H |
| A-1066. | $CHF_2$ | $OCH_3$ | 5-$OCH_3$ | F | H |
| A-1067. | $CHF_2$ | CN | 3-F | F | H |
| A-1068. | $CHF_2$ | CN | 3-$CH_3$ | F | H |
| A-1069. | $CHF_2$ | CN | 3-$OCH_3$ | F | H |
| A-1070. | $CHF_2$ | CN | 5-F | F | H |
| A-1071. | $CHF_2$ | CN | 5-$CH_3$ | F | H |
| A-1072. | $CHF_2$ | CN | 5-$OCH_3$ | F | H |
| A-1073. | $CHF_2$ | $CH_2F$ | 3-F | F | H |
| A-1074. | $CHF_2$ | $CH_2F$ | 3-$CH_3$ | F | H |
| A-1075. | $CHF_2$ | $CH_2F$ | 3-$OCH_3$ | F | H |
| A-1076. | $CHF_2$ | $CH_2F$ | 5-F | F | H |
| A-1077. | $CHF_2$ | $CH_2F$ | 5-$CH_3$ | F | H |
| A-1078. | $CHF_2$ | $CH_2F$ | 5-$OCH_3$ | F | H |
| A-1079. | $CHF_2$ | $CHF_2$ | 3-F | F | H |
| A-1080. | $CHF_2$ | $CHF_2$ | 3-$CH_3$ | F | H |
| A-1081. | $CHF_2$ | $CHF_2$ | 3-$OCH_3$ | F | H |
| A-1082. | $CHF_2$ | $CHF_2$ | 5-F | F | H |
| A-1083. | $CHF_2$ | $CHF_2$ | 5-$CH_3$ | F | H |
| A-1084. | $CHF_2$ | $CHF_2$ | 5-$OCH_3$ | F | H |
| A-1085. | $CHF_2$ | $CF_3$ | 3-F | F | H |
| A-1086. | $CHF_2$ | $CF_3$ | 3-$CH_3$ | F | H |
| A-1087. | $CHF_2$ | $CF_3$ | 3-$OCH_3$ | F | H |
| A-1088. | $CHF_2$ | $CF_3$ | 5-F | F | H |
| A-1089. | $CHF_2$ | $CF_3$ | 5-$CH_3$ | F | H |
| A-1090. | $CHF_2$ | $CF_3$ | 5-$OCH_3$ | F | H |
| A-1091. | $CHF_2$ | $OCH_2F$ | 3-F | F | H |
| A-1092. | $CHF_2$ | $OCH_2F$ | 3-$CH_3$ | F | H |
| A-1093. | $CHF_2$ | $OCH_2F$ | 3-$OCH_3$ | F | H |
| A-1094. | $CHF_2$ | $OCH_2F$ | 5-F | F | H |
| A-1095. | $CHF_2$ | $OCH_2F$ | 5-$CH_3$ | F | H |
| A-1096. | $CHF_2$ | $OCH_2F$ | 5-$OCH_3$ | F | H |
| A-1097. | $CHF_2$ | $OCHF_2$ | 3-F | F | H |
| A-1098. | $CHF_2$ | $OCHF_2$ | 3-$CH_3$ | F | H |
| A-1099. | $CHF_2$ | $OCHF_2$ | 3-$OCH_3$ | F | H |
| A-1100. | $CHF_2$ | $OCHF_2$ | 5-F | F | H |
| A-1101. | $CHF_2$ | $OCHF_2$ | 5-$CH_3$ | F | H |
| A-1102. | $CHF_2$ | $OCHF_2$ | 5-$OCH_3$ | F | H |
| A-1103. | $CHF_2$ | $OCF_3$ | 3-F | F | H |
| A-1104. | $CHF_2$ | $OCF_3$ | 3-$CH_3$ | F | H |
| A-1105. | $CHF_2$ | $OCF_3$ | 3-$OCH_3$ | F | H |
| A-1106. | $CHF_2$ | $OCF_3$ | 5-F | F | H |
| A-1107. | $CHF_2$ | $OCF_3$ | 5-$CH_3$ | F | H |
| A-1108. | $CHF_2$ | $OCF_3$ | 5-$OCH_3$ | F | H |
| A-1109. | $CF_3$ | F | 3-F | F | H |
| A-1110. | $CF_3$ | F | 3-$CH_3$ | F | H |
| A-1111. | $CF_3$ | F | 3-$OCH_3$ | F | H |
| A-1112. | $CF_3$ | F | 5-F | F | H |
| A-1113. | $CF_3$ | F | 5-$CH_3$ | F | H |
| A-1114. | $CF_3$ | F | 5-$OCH_3$ | F | H |
| A-1115. | $CF_3$ | $CH_3$ | 3-F | F | H |
| A-1116. | $CF_3$ | $CH_3$ | 3-$CH_3$ | F | H |
| A-1117. | $CF_3$ | $CH_3$ | 3-$OCH_3$ | F | H |
| A-1118. | $CF_3$ | $CH_3$ | 5-F | F | H |
| A-1119. | $CF_3$ | $CH_3$ | 5-$CH_3$ | F | H |
| A-1120. | $CF_3$ | $CH_3$ | 5-$OCH_3$ | F | H |
| A-1121. | $CF_3$ | $OCH_3$ | 3-F | F | H |
| A-1122. | $CF_3$ | $OCH_3$ | 3-$CH_3$ | F | H |
| A-1123. | $CF_3$ | $OCH_3$ | 3-$OCH_3$ | F | H |
| A-1124. | $CF_3$ | $OCH_3$ | 5-F | F | H |
| A-1125. | $CF_3$ | $OCH_3$ | 5-$CH_3$ | F | H |
| A-1126. | $CF_3$ | $OCH_3$ | 5-$OCH_3$ | F | H |
| A-1127. | $CF_3$ | CN | 3-F | F | H |
| A-1128. | $CF_3$ | CN | 3-$CH_3$ | F | H |
| A-1129. | $CF_3$ | CN | 3-$OCH_3$ | F | H |
| A-1130. | $CF_3$ | CN | 5-F | F | H |
| A-1131. | $CF_3$ | CN | 5-$CH_3$ | F | H |
| A-1132. | $CF_3$ | CN | 5-$OCH_3$ | F | H |
| A-1133. | $CF_3$ | $CH_2F$ | 3-F | F | H |
| A-1134. | $CF_3$ | $CH_2F$ | 3-$CH_3$ | F | H |
| A-1135. | $CF_3$ | $CH_2F$ | 3-$OCH_3$ | F | H |
| A-1136. | $CF_3$ | $CH_2F$ | 5-F | F | H |
| A-1137. | $CF_3$ | $CH_2F$ | 5-$CH_3$ | F | H |
| A-1138. | $CF_3$ | $CH_2F$ | 5-$OCH_3$ | F | H |
| A-1139. | $CF_3$ | $CHF_2$ | 3-F | F | H |
| A-1140. | $CF_3$ | $CHF_2$ | 3-$CH_3$ | F | H |
| A-1141. | $CF_3$ | $CHF_2$ | 3-$OCH_3$ | F | H |
| A-1142. | $CF_3$ | $CHF_2$ | 5-F | F | H |
| A-1143. | $CF_3$ | $CHF_2$ | 5-$CH_3$ | F | H |
| A-1144. | $CF_3$ | $CHF_2$ | 5-$OCH_3$ | F | H |
| A-1145. | $CF_3$ | $CF_3$ | 3-F | F | H |
| A-1146. | $CF_3$ | $CF_3$ | 3-$CH_3$ | F | H |
| A-1147. | $CF_3$ | $CF_3$ | 3-$OCH_3$ | F | H |
| A-1148. | $CF_3$ | $CF_3$ | 5-F | F | H |
| A-1149. | $CF_3$ | $CF_3$ | 5-$CH_3$ | F | H |
| A-1150. | $CF_3$ | $CF_3$ | 5-$OCH_3$ | F | H |
| A-1151. | $CF_3$ | $OCH_2F$ | 3-F | F | H |
| A-1152. | $CF_3$ | $OCH_2F$ | 3-$CH_3$ | F | H |
| A-1153. | $CF_3$ | $OCH_2F$ | 3-$OCH_3$ | F | H |
| A-1154. | $CF_3$ | $OCH_2F$ | 5-F | F | H |
| A-1155. | $CF_3$ | $OCH_2F$ | 5-$CH_3$ | F | H |
| A-1156. | $CF_3$ | $OCH_2F$ | 5-$OCH_3$ | F | H |
| A-1157. | $CF_3$ | $OCHF_2$ | 3-F | F | H |
| A-1158. | $CF_3$ | $OCHF_2$ | 3-$CH_3$ | F | H |
| A-1159. | $CF_3$ | $OCHF_2$ | 3-$OCH_3$ | F | H |
| A-1160. | $CF_3$ | $OCHF_2$ | 5-F | F | H |
| A-1161. | $CF_3$ | $OCHF_2$ | 5-$CH_3$ | F | H |
| A-1162. | $CF_3$ | $OCHF_2$ | 5-$OCH_3$ | F | H |
| A-1163. | $CF_3$ | $OCF_3$ | 3-F | F | H |
| A-1164. | $CF_3$ | $OCF_3$ | 3-$CH_3$ | F | H |
| A-1165. | $CF_3$ | $OCF_3$ | 3-$OCH_3$ | F | H |
| A-1166. | $CF_3$ | $OCF_3$ | 5-F | F | H |
| A-1167. | $CF_3$ | $OCF_3$ | 5-$CH_3$ | F | H |
| A-1168. | $CF_3$ | $OCF_3$ | 5-$OCH_3$ | F | H |
| A-1169. | $OCH_2F$ | F | 3-F | F | H |
| A-1170. | $OCH_2F$ | F | 3-$CH_3$ | F | H |
| A-1171. | $OCH_2F$ | F | 3-$OCH_3$ | F | H |
| A-1172. | $OCH_2F$ | F | 5-F | F | H |
| A-1173. | $OCH_2F$ | F | 5-$CH_3$ | F | H |
| A-1174. | $OCH_2F$ | F | 5-$OCH_3$ | F | H |
| A-1175. | $OCH_2F$ | $CH_3$ | 3-F | F | H |
| A-1176. | $OCH_2F$ | $CH_3$ | 3-$CH_3$ | F | H |
| A-1177. | $OCH_2F$ | $CH_3$ | 3-$OCH_3$ | F | H |
| A-1178. | $OCH_2F$ | $CH_3$ | 5-F | F | H |
| A-1179. | $OCH_2F$ | $CH_3$ | 5-$CH_3$ | F | H |
| A-1180. | $OCH_2F$ | $CH_3$ | 5-$OCH_3$ | F | H |
| A-1181. | $OCH_2F$ | $OCH_3$ | 3-F | F | H |
| A-1182. | $OCH_2F$ | $OCH_3$ | 3-$CH_3$ | F | H |
| A-1183. | $OCH_2F$ | $OCH_3$ | 3-$OCH_3$ | F | H |
| A-1184. | $OCH_2F$ | $OCH_3$ | 5-F | F | H |
| A-1185. | $OCH_2F$ | $OCH_3$ | 5-$CH_3$ | F | H |
| A-1186. | $OCH_2F$ | $OCH_3$ | 5-$OCH_3$ | F | H |
| A-1187. | $OCH_2F$ | CN | 3-F | F | H |
| A-1188. | $OCH_2F$ | CN | 3-$CH_3$ | F | H |
| A-1189. | $OCH_2F$ | CN | 3-$OCH_3$ | F | H |
| A-1190. | $OCH_2F$ | CN | 5-F | F | H |
| A-1191. | $OCH_2F$ | CN | 5-$CH_3$ | F | H |
| A-1192. | $OCH_2F$ | CN | 5-$OCH_3$ | F | H |
| A-1193. | $OCH_2F$ | $CH_2F$ | 3-F | F | H |
| A-1194. | $OCH_2F$ | $CH_2F$ | 3-$CH_3$ | F | H |
| A-1195. | $OCH_2F$ | $CH_2F$ | 3-$OCH_3$ | F | H |
| A-1196. | $OCH_2F$ | $CH_2F$ | 5-F | F | H |
| A-1197. | $OCH_2F$ | $CH_2F$ | 5-$CH_3$ | F | H |
| A-1198. | $OCH_2F$ | $CH_2F$ | 5-$OCH_3$ | F | H |
| A-1199. | $OCH_2F$ | $CHF_2$ | 3-F | F | H |
| A-1200. | $OCH_2F$ | $CHF_2$ | 3-$CH_3$ | F | H |
| A-1201. | $OCH_2F$ | $CHF_2$ | 3-$OCH_3$ | F | H |
| A-1202. | $OCH_2F$ | $CHF_2$ | 5-F | F | H |
| A-1203. | $OCH_2F$ | $CHF_2$ | 5-$CH_3$ | F | H |
| A-1204. | $OCH_2F$ | $CHF_2$ | 5-$OCH_3$ | F | H |
| A-1205. | $OCH_2F$ | $CF_3$ | 3-F | F | H |
| A-1206. | $OCH_2F$ | $CF_3$ | 3-$CH_3$ | F | H |
| A-1207. | $OCH_2F$ | $CF_3$ | 3-$OCH_3$ | F | H |
| A-1208. | $OCH_2F$ | $CF_3$ | 5-F | F | H |
| A-1209. | $OCH_2F$ | $CF_3$ | 5-$CH_3$ | F | H |
| A-1210. | $OCH_2F$ | $CF_3$ | 5-$OCH_3$ | F | H |
| A-1211. | $OCH_2F$ | $OCH_2F$ | 3-F | F | H |
| A-1212. | $OCH_2F$ | $OCH_2F$ | 3-$CH_3$ | F | H |
| A-1213. | $OCH_2F$ | $OCH_2F$ | 3-$OCH_3$ | F | H |
| A-1214. | $OCH_2F$ | $OCH_2F$ | 5-F | F | H |
| A-1215. | $OCH_2F$ | $OCH_2F$ | 5-$CH_3$ | F | H |

TABLE A-continued

| Example No. | R¹ | R² | R³ | R⁶ | R⁷ |
|---|---|---|---|---|---|
| A-1216. | OCH₂F | OCH₂F | 5-OCH₃ | F | H |
| A-1217. | OCH₂F | OCHF₂ | 3-F | F | H |
| A-1218. | OCH₂F | OCHF₂ | 3-CH₃ | F | H |
| A-1219. | OCH₂F | OCHF₂ | 3-OCH₃ | F | H |
| A-1220. | OCH₂F | OCHF₂ | 5-F | F | H |
| A-1221. | OCH₂F | OCHF₂ | 5-CH₃ | F | H |
| A-1222. | OCH₂F | OCHF₂ | 5-OCH₃ | F | H |
| A-1223. | OCH₂F | OCF₃ | 3-F | F | H |
| A-1224. | OCH₂F | OCF₃ | 3-CH₃ | F | H |
| A-1225. | OCH₂F | OCF₃ | 3-OCH₃ | F | H |
| A-1226. | OCH₂F | OCF₃ | 5-F | F | H |
| A-1227. | OCH₂F | OCF₃ | 5-CH₃ | F | H |
| A-1228. | OCH₂F | OCF₃ | 5-OCH₃ | F | H |
| A-1229. | OCHF₂ | F | 3-F | F | H |
| A-1230. | OCHF₂ | F | 3-CH₃ | F | H |
| A-1231. | OCHF₂ | F | 3-OCH₃ | F | H |
| A-1232. | OCHF₂ | F | 5-F | F | H |
| A-1233. | OCHF₂ | F | 5-CH₃ | F | H |
| A-1234. | OCHF₂ | F | 5-OCH₃ | F | H |
| A-1235. | OCHF₂ | CH₃ | 3-F | F | H |
| A-1236. | OCHF₂ | CH₃ | 3-CH₃ | F | H |
| A-1237. | OCHF₂ | CH₃ | 3-OCH₃ | F | H |
| A-1238. | OCHF₂ | CH₃ | 5-F | F | H |
| A-1239. | OCHF₂ | CH₃ | 5-CH₃ | F | H |
| A-1240. | OCHF₂ | CH₃ | 5-OCH₃ | F | H |
| A-1241. | OCHF₂ | OCH₃ | 3-F | F | H |
| A-1242. | OCHF₂ | OCH₃ | 3-CH₃ | F | H |
| A-1243. | OCHF₂ | OCH₃ | 3-OCH₃ | F | H |
| A-1244. | OCHF₂ | OCH₃ | 5-F | F | H |
| A-1245. | OCHF₂ | OCH₃ | 5-CH₃ | F | H |
| A-1246. | OCHF₂ | OCH₃ | 5-OCH₃ | F | H |
| A-1247. | OCHF₂ | CN | 3-F | F | H |
| A-1248. | OCHF₂ | CN | 3-CH₃ | F | H |
| A-1249. | OCHF₂ | CN | 3-OCH₃ | F | H |
| A-1250. | OCHF₂ | CN | 5-F | F | H |
| A-1251. | OCHF₂ | CN | 5-CH₃ | F | H |
| A-1252. | OCHF₂ | CN | 5-OCH₃ | F | H |
| A-1253. | OCHF₂ | CH₂F | 3-F | F | H |
| A-1254. | OCHF₂ | CH₂F | 3-CH₃ | F | H |
| A-1255. | OCHF₂ | CH₂F | 3-OCH₃ | F | H |
| A-1256. | OCHF₂ | CH₂F | 5-F | F | H |
| A-1257. | OCHF₂ | CH₂F | 5-CH₃ | F | H |
| A-1258. | OCHF₂ | CH₂F | 5-OCH₃ | F | H |
| A-1259. | OCHF₂ | CHF₂ | 3-F | F | H |
| A-1260. | OCHF₂ | CHF₂ | 3-CH₃ | F | H |
| A-1261. | OCHF₂ | CHF₂ | 3-OCH₃ | F | H |
| A-1262. | OCHF₂ | CHF₂ | 5-F | F | H |
| A-1263. | OCHF₂ | CHF₂ | 5-CH₃ | F | H |
| A-1264. | OCHF₂ | CHF₂ | 5-OCH₃ | F | H |
| A-1265. | OCHF₂ | CF₃ | 3-F | F | H |
| A-1266. | OCHF₂ | CF₃ | 3-CH₃ | F | H |
| A-1267. | OCHF₂ | CF₃ | 3-OCH₃ | F | H |
| A-1268. | OCHF₂ | CF₃ | 5-F | F | H |
| A-1269. | OCHF₂ | CF₃ | 5-CH₃ | F | H |
| A-1270. | OCHF₂ | CF₃ | 5-OCH₃ | F | H |
| A-1271. | OCHF₂ | OCH₂F | 3-F | F | H |
| A-1272. | OCHF₂ | OCH₂F | 3-CH₃ | F | H |
| A-1273. | OCHF₂ | OCH₂F | 3-OCH₃ | F | H |
| A-1274. | OCHF₂ | OCH₂F | 5-F | F | H |
| A-1275. | OCHF₂ | OCH₂F | 5-CH₃ | F | H |
| A-1276. | OCHF₂ | OCH₂F | 5-OCH₃ | F | H |
| A-1277. | OCHF₂ | OCHF₂ | 3-F | F | H |
| A-1278. | OCHF₂ | OCHF₂ | 3-CH₃ | F | H |
| A-1279. | OCHF₂ | OCHF₂ | 3-OCH₃ | F | H |
| A-1280. | OCHF₂ | OCHF₂ | 5-F | F | H |
| A-1281. | OCHF₂ | OCHF₂ | 5-CH₃ | F | H |
| A-1282. | OCHF₂ | OCHF₂ | 5-OCH₃ | F | H |
| A-1283. | OCHF₂ | OCF₃ | 3-F | F | H |
| A-1284. | OCHF₂ | OCF₃ | 3-CH₃ | F | H |
| A-1285. | OCHF₂ | OCF₃ | 3-OCH₃ | F | H |
| A-1286. | OCHF₂ | OCF₃ | 5-F | F | H |
| A-1287. | OCHF₂ | OCF₃ | 5-CH₃ | F | H |
| A-1288. | OCHF₂ | OCF₃ | 5-OCH₃ | F | H |
| A-1289. | OCF₃ | F | 3-F | F | H |
| A-1290. | OCF₃ | F | 3-CH₃ | F | H |
| A-1291. | OCF₃ | F | 3-OCH₃ | F | H |
| A-1292. | OCF₃ | F | 5-F | F | H |
| A-1293. | OCF₃ | F | 5-CH₃ | F | H |
| A-1294. | OCF₃ | F | 5-OCH₃ | F | H |
| A-1295. | OCF₃ | CH₃ | 3-F | F | H |
| A-1296. | OCF₃ | CH₃ | 3-CH₃ | F | H |
| A-1297. | OCF₃ | CH₃ | 3-OCH₃ | F | H |
| A-1298. | OCF₃ | CH₃ | 5-F | F | H |
| A-1299. | OCF₃ | CH₃ | 5-CH₃ | F | H |
| A-1300. | OCF₃ | CH₃ | 5-OCH₃ | F | H |
| A-1301. | OCF₃ | OCH₃ | 3-F | F | H |
| A-1302. | OCF₃ | OCH₃ | 3-CH₃ | F | H |
| A-1303. | OCF₃ | OCH₃ | 3-OCH₃ | F | H |
| A-1304. | OCF₃ | OCH₃ | 5-F | F | H |
| A-1305. | OCF₃ | OCH₃ | 5-CH₃ | F | H |
| A-1306. | OCF₃ | OCH₃ | 5-OCH₃ | F | H |
| A-1307. | OCF₃ | CN | 3-F | F | H |
| A-1308. | OCF₃ | CN | 3-CH₃ | F | H |
| A-1309. | OCF₃ | CN | 3-OCH₃ | F | H |
| A-1310. | OCF₃ | CN | 5-F | F | H |
| A-1311. | OCF₃ | CN | 5-CH₃ | F | H |
| A-1312. | OCF₃ | CN | 5-OCH₃ | F | H |
| A-1313. | OCF₃ | CH₂F | 3-F | F | H |
| A-1314. | OCF₃ | CH₂F | 3-CH₃ | F | H |
| A-1315. | OCF₃ | CH₂F | 3-OCH₃ | F | H |
| A-1316. | OCF₃ | CH₂F | 5-F | F | H |
| A-1317. | OCF₃ | CH₂F | 5-CH₃ | F | H |
| A-1318. | OCF₃ | CH₂F | 5-OCH₃ | F | H |
| A-1319. | OCF₃ | CHF₂ | 3-F | F | H |
| A-1320. | OCF₃ | CHF₂ | 3-CH₃ | F | H |
| A-1321. | OCF₃ | CHF₂ | 3-OCH₃ | F | H |
| A-1322. | OCF₃ | CHF₂ | 5-F | F | H |
| A-1323. | OCF₃ | CHF₂ | 5-CH₃ | F | H |
| A-1324. | OCF₃ | CHF₂ | 5-OCH₃ | F | H |
| A-1325. | OCF₃ | CF₃ | 3-F | F | H |
| A-1326. | OCF₃ | CF₃ | 3-CH₃ | F | H |
| A-1327. | OCF₃ | CF₃ | 3-OCH₃ | F | H |
| A-1328. | OCF₃ | CF₃ | 5-F | F | H |
| A-1329. | OCF₃ | CF₃ | 5-CH₃ | F | H |
| A-1330. | OCF₃ | CF₃ | 5-OCH₃ | F | H |
| A-1331. | OCF₃ | OCH₂F | 3-F | F | H |
| A-1332. | OCF₃ | OCH₂F | 3-CH₃ | F | H |
| A-1333. | OCF₃ | OCH₂F | 3-OCH₃ | F | H |
| A-1334. | OCF₃ | OCH₂F | 5-F | F | H |
| A-1335. | OCF₃ | OCH₂F | 5-CH₃ | F | H |
| A-1336. | OCF₃ | OCH₂F | 5-OCH₃ | F | H |
| A-1337. | OCF₃ | OCHF₂ | 3-F | F | H |
| A-1338. | OCF₃ | OCHF₂ | 3-CH₃ | F | H |
| A-1339. | OCF₃ | OCHF₂ | 3-OCH₃ | F | H |
| A-1340. | OCF₃ | OCHF₂ | 5-F | F | H |
| A-1341. | OCF₃ | OCHF₂ | 5-CH₃ | F | H |
| A-1342. | OCF₃ | OCHF₂ | 5-OCH₃ | F | H |
| A-1343. | OCF₃ | OCF₃ | 3-F | F | H |
| A-1344. | OCF₃ | OCF₃ | 3-CH₃ | F | H |
| A-1345. | OCF₃ | OCF₃ | 3-OCH₃ | F | H |
| A-1346. | OCF₃ | OCF₃ | 5-F | F | H |
| A-1347. | OCF₃ | OCF₃ | 5-CH₃ | F | H |
| A-1348. | OCF₃ | OCF₃ | 5-OCH₃ | F | H |
| A-1349. | H | H | H | Cl | H |
| A-1350. | F | H | H | Cl | H |
| A-1351. | CH₃ | H | H | Cl | H |
| A-1352. | OCH₃ | H | H | Cl | H |
| A-1353. | CH₂F | H | H | Cl | H |
| A-1354. | CHF₂ | H | H | Cl | H |
| A-1355. | CF₃ | H | H | Cl | H |
| A-1356. | OCH₂F | H | H | Cl | H |
| A-1357. | OCHF₂ | H | H | Cl | H |
| A-1358. | OCF₃ | H | H | Cl | H |
| A-1359. | H | F | H | Cl | H |
| A-1360. | H | CH₃ | H | Cl | H |
| A-1361. | H | OCH₃ | H | Cl | H |
| A-1362. | H | CN | H | Cl | H |
| A-1363. | H | CH₂F | H | Cl | H |
| A-1364. | H | CHF₂ | H | Cl | H |
| A-1365. | H | CF₃ | H | Cl | H |
| A-1366. | H | OCH₂F | H | Cl | H |
| A-1367. | H | OCHF₂ | H | Cl | H |
| A-1368. | H | OCF₃ | H | Cl | H |
| A-1369. | H | H | 3-F | Cl | H |
| A-1370. | H | H | 3-CH₃ | Cl | H |
| A-1371. | H | H | 3-OCH₃ | Cl | H |

TABLE A-continued

| Example No. | R$^1$ | R$^2$ | R$^3$ | R$^6$ | R$^7$ |
|---|---|---|---|---|---|
| A-1372. | H | H | 5-F | Cl | H |
| A-1373. | H | H | 5-CH$_3$ | Cl | H |
| A-1374. | H | H | 5-OCH$_3$ | Cl | H |
| A-1375. | F | F | H | Cl | H |
| A-1376. | F | CH$_3$ | H | Cl | H |
| A-1377. | F | OCH$_3$ | H | Cl | H |
| A-1378. | F | CN | H | Cl | H |
| A-1379. | F | CH$_2$F | H | Cl | H |
| A-1380. | F | CHF$_2$ | H | Cl | H |
| A-1381. | F | CF$_3$ | H | Cl | H |
| A-1382. | F | OCH$_2$F | H | Cl | H |
| A-1383. | F | OCHF$_2$ | H | Cl | H |
| A-1384. | F | OCF$_3$ | H | Cl | H |
| A-1385. | F | H | 3-F | Cl | H |
| A-1386. | F | H | 3-CH$_3$ | Cl | H |
| A-1387. | F | H | 3-OCH$_3$ | Cl | H |
| A-1388. | F | H | 5-F | Cl | H |
| A-1389. | F | H | 5-CH$_3$ | Cl | H |
| A-1390. | F | H | 5-OCH$_3$ | Cl | H |
| A-1391. | CH$_3$ | F | H | Cl | H |
| A-1392. | CH$_3$ | CH$_3$ | H | Cl | H |
| A-1393. | CH$_3$ | OCH$_3$ | H | Cl | H |
| A-1394. | CH$_3$ | CN | H | Cl | H |
| A-1395. | CH$_3$ | CH$_2$F | H | Cl | H |
| A-1396. | CH$_3$ | CHF$_2$ | H | Cl | H |
| A-1397. | CH$_3$ | CF$_3$ | H | Cl | H |
| A-1398. | CH$_3$ | OCH$_2$F | H | Cl | H |
| A-1399. | CH$_3$ | OCHF$_2$ | H | Cl | H |
| A-1400. | CH$_3$ | OCF$_3$ | H | Cl | H |
| A-1401. | CH$_3$ | H | 3-F | Cl | H |
| A-1402. | CH$_3$ | H | 3-CH$_3$ | Cl | H |
| A-1403. | CH$_3$ | H | 3-OCH$_3$ | Cl | H |
| A-1404. | CH$_3$ | H | 5-F | Cl | H |
| A-1405. | CH$_3$ | H | 5-CH$_3$ | Cl | H |
| A-1406. | CH$_3$ | H | 5-OCH$_3$ | Cl | H |
| A-1407. | OCH$_3$ | F | H | Cl | H |
| A-1408. | OCH$_3$ | CH$_3$ | H | Cl | H |
| A-1409. | OCH$_3$ | OCH$_3$ | H | Cl | H |
| A-1410. | OCH$_3$ | CN | H | Cl | H |
| A-1411. | OCH$_3$ | CH$_2$F | H | Cl | H |
| A-1412. | OCH$_3$ | CHF$_2$ | H | Cl | H |
| A-1413. | OCH$_3$ | CF$_3$ | H | Cl | H |
| A-1414. | OCH$_3$ | OCH$_2$F | H | Cl | H |
| A-1415. | OCH$_3$ | OCHF$_2$ | H | Cl | H |
| A-1416. | OCH$_3$ | OCF$_3$ | H | Cl | H |
| A-1417. | OCH$_3$ | H | 3-F | Cl | H |
| A-1418. | OCH$_3$ | H | 3-CH$_3$ | Cl | H |
| A-1419. | OCH$_3$ | H | 3-OCH$_3$ | Cl | H |
| A-1420. | OCH$_3$ | H | 5-F | Cl | H |
| A-1421. | OCH$_3$ | H | 5-CH$_3$ | Cl | H |
| A-1422. | OCH$_3$ | H | 5-OCH$_3$ | Cl | H |
| A-1423. | H | F | 3-F | Cl | H |
| A-1424. | H | F | 3-CH$_3$ | Cl | H |
| A-1425. | H | F | 3-OCH$_3$ | Cl | H |
| A-1426. | H | F | 5-F | Cl | H |
| A-1427. | H | F | 5-CH$_3$ | Cl | H |
| A-1428. | H | F | 5-OCH$_3$ | Cl | H |
| A-1429. | H | CH$_3$ | 3-F | Cl | H |
| A-1430. | H | CH$_3$ | 3-CH$_3$ | Cl | H |
| A-1431. | H | CH$_3$ | 3-OCH$_3$ | Cl | H |
| A-1432. | H | CH$_3$ | 5-F | Cl | H |
| A-1433. | H | CH$_3$ | 5-CH$_3$ | Cl | H |
| A-1434. | H | CH$_3$ | 5-OCH$_3$ | Cl | H |
| A-1435. | H | OCH$_3$ | 3-F | Cl | H |
| A-1436. | H | OCH$_3$ | 3-CH$_3$ | Cl | H |
| A-1437. | H | OCH$_3$ | 3-OCH$_3$ | Cl | H |
| A-1438. | H | OCH$_3$ | 5-F | Cl | H |
| A-1439. | H | OCH$_3$ | 5-CH$_3$ | Cl | H |
| A-1440. | H | OCH$_3$ | 5-OCH$_3$ | Cl | H |
| A-1441. | H | CN | 3-F | Cl | H |
| A-1442. | H | CN | 3-CH$_3$ | Cl | H |
| A-1443. | H | CN | 3-OCH$_3$ | Cl | H |
| A-1444. | H | CN | 5-F | Cl | H |
| A-1445. | H | CN | 5-CH$_3$ | Cl | H |
| A-1446. | H | CN | 5-OCH$_3$ | Cl | H |
| A-1447. | H | CH$_2$F | 3-F | Cl | H |
| A-1448. | H | CH$_2$F | 3-CH$_3$ | Cl | H |
| A-1449. | H | CH$_2$F | 3-OCH$_3$ | Cl | H |
| A-1450. | H | CH$_2$F | 5-F | Cl | H |
| A-1451. | H | CH$_2$F | 5-CH$_3$ | Cl | H |
| A-1452. | H | CH$_2$F | 5-OCH$_3$ | Cl | H |
| A-1453. | H | CHF$_2$ | 3-F | Cl | H |
| A-1454. | H | CHF$_2$ | 3-CH$_3$ | Cl | H |
| A-1455. | H | CHF$_2$ | 3-OCH$_3$ | Cl | H |
| A-1456. | H | CHF$_2$ | 5-F | Cl | H |
| A-1457. | H | CHF$_2$ | 5-CH$_3$ | Cl | H |
| A-1458. | H | CHF$_2$ | 5-OCH$_3$ | Cl | H |
| A-1459. | H | CF$_3$ | 3-F | Cl | H |
| A-1460. | H | CF$_3$ | 3-CH$_3$ | Cl | H |
| A-1461. | H | CF$_3$ | 3-OCH$_3$ | Cl | H |
| A-1462. | H | CF$_3$ | 5-F | Cl | H |
| A-1463. | H | CF$_3$ | 5-CH$_3$ | Cl | H |
| A-1464. | H | CF$_3$ | 5-OCH$_3$ | Cl | H |
| A-1465. | H | OCH$_2$F | 3-F | Cl | H |
| A-1466. | H | OCH$_2$F | 3-CH$_3$ | Cl | H |
| A-1467. | H | OCH$_2$F | 3-OCH$_3$ | Cl | H |
| A-1468. | H | OCH$_2$F | 5-F | Cl | H |
| A-1469. | H | OCH$_2$F | 5-CH$_3$ | Cl | H |
| A-1470. | H | OCH$_2$F | 5-OCH$_3$ | Cl | H |
| A-1471. | H | OCHF$_2$ | 3-F | Cl | H |
| A-1472. | H | OCHF$_2$ | 3-CH$_3$ | Cl | H |
| A-1473. | H | OCHF$_2$ | 3-OCH$_3$ | Cl | H |
| A-1474. | H | OCHF$_2$ | 5-F | Cl | H |
| A-1475. | H | OCHF$_2$ | 5-CH$_3$ | Cl | H |
| A-1476. | H | OCHF$_2$ | 5-OCH$_3$ | Cl | H |
| A-1477. | H | OCF$_3$ | 3-F | Cl | H |
| A-1478. | H | OCF$_3$ | 3-CH$_3$ | Cl | H |
| A-1479. | H | OCF$_3$ | 3-OCH$_3$ | Cl | H |
| A-1480. | H | OCF$_3$ | 5-F | Cl | H |
| A-1481. | H | OCF$_3$ | 5-CH$_3$ | Cl | H |
| A-1482. | H | OCF$_3$ | 5-OCH$_3$ | Cl | H |
| A-1483. | F | F | 3-F | Cl | H |
| A-1484. | F | F | 3-CH$_3$ | Cl | H |
| A-1485. | F | F | 3-OCH$_3$ | Cl | H |
| A-1486. | F | F | 5-F | Cl | H |
| A-1487. | F | F | 5-CH$_3$ | Cl | H |
| A-1488. | F | F | 5-OCH$_3$ | Cl | H |
| A-1489. | F | CH$_3$ | 3-F | Cl | H |
| A-1490. | F | CH$_3$ | 3-CH$_3$ | Cl | H |
| A-1491. | F | CH$_3$ | 3-OCH$_3$ | Cl | H |
| A-1492. | F | CH$_3$ | 5-F | Cl | H |
| A-1493. | F | CH$_3$ | 5-CH$_3$ | Cl | H |
| A-1494. | F | CH$_3$ | 5-OCH$_3$ | Cl | H |
| A-1495. | F | OCH$_3$ | 3-F | Cl | H |
| A-1496. | F | OCH$_3$ | 3-CH$_3$ | Cl | H |
| A-1497. | F | OCH$_3$ | 3-OCH$_3$ | Cl | H |
| A-1498. | F | OCH$_3$ | 5-F | Cl | H |
| A-1499. | F | OCH$_3$ | 5-CH$_3$ | Cl | H |
| A-1500. | F | OCH$_3$ | 5-OCH$_3$ | Cl | H |
| A-1501. | F | CN | 3-F | Cl | H |
| A-1502. | F | CN | 3-CH$_3$ | Cl | H |
| A-1503. | F | CN | 3-OCH$_3$ | Cl | H |
| A-1504. | F | CN | 5-F | Cl | H |
| A-1505. | F | CN | 5-CH$_3$ | Cl | H |
| A-1506. | F | CN | 5-OCH$_3$ | Cl | H |
| A-1507. | F | CH$_2$F | 3-F | Cl | H |
| A-1508. | F | CH$_2$F | 3-CH$_3$ | Cl | H |
| A-1509. | F | CH$_2$F | 3-OCH$_3$ | Cl | H |
| A-1510. | F | CH$_2$F | 5-F | Cl | H |
| A-1511. | F | CH$_2$F | 5-CH$_3$ | Cl | H |
| A-1512. | F | CH$_2$F | 5-OCH$_3$ | Cl | H |
| A-1513. | F | CHF$_2$ | 3-F | Cl | H |
| A-1514. | F | CHF$_2$ | 3-CH$_3$ | Cl | H |
| A-1515. | F | CHF$_2$ | 3-OCH$_3$ | Cl | H |
| A-1516. | F | CHF$_2$ | 5-F | Cl | H |
| A-1517. | F | CHF$_2$ | 5-CH$_3$ | Cl | H |
| A-1518. | F | CHF$_2$ | 5-OCH$_3$ | Cl | H |
| A-1519. | F | CF$_3$ | 3-F | Cl | H |
| A-1520. | F | CF$_3$ | 3-CH$_3$ | Cl | H |
| A-1521. | F | CF$_3$ | 3-OCH$_3$ | Cl | H |
| A-1522. | F | CF$_3$ | 5-F | Cl | H |
| A-1523. | F | CF$_3$ | 5-CH$_3$ | Cl | H |
| A-1524. | F | CF$_3$ | 5-OCH$_3$ | Cl | H |
| A-1525. | F | OCH$_2$F | 3-F | Cl | H |
| A-1526. | F | OCH$_2$F | 3-CH$_3$ | Cl | H |
| A-1527. | F | OCH$_2$F | 3-OCH$_3$ | Cl | H |

TABLE A-continued

| Example No. | R¹ | R² | R³ | R⁶ | R⁷ |
|---|---|---|---|---|---|
| A-1528. | F | OCH$_2$F | 5-F | Cl | H |
| A-1529. | F | OCH$_2$F | 5-CH$_3$ | Cl | H |
| A-1530. | F | OCH$_2$F | 5-OCH$_3$ | Cl | H |
| A-1531. | F | OCHF$_2$ | 3-F | Cl | H |
| A-1532. | F | OCHF$_2$ | 3-CH$_3$ | Cl | H |
| A-1533. | F | OCHF$_2$ | 3-OCH$_3$ | Cl | H |
| A-1534. | F | OCHF$_2$ | 5-F | Cl | H |
| A-1535. | F | OCHF$_2$ | 5-CH$_3$ | Cl | H |
| A-1536. | F | OCHF$_2$ | 5-OCH$_3$ | Cl | H |
| A-1537. | F | OCF$_3$ | 3-F | Cl | H |
| A-1538. | F | OCF$_3$ | 3-CH$_3$ | Cl | H |
| A-1539. | F | OCF$_3$ | 3-OCH$_3$ | Cl | H |
| A-1540. | F | OCF$_3$ | 5-F | Cl | H |
| A-1541. | F | OCF$_3$ | 5-CH$_3$ | Cl | H |
| A-1542. | F | OCF$_3$ | 5-OCH$_3$ | Cl | H |
| A-1543. | CH$_3$ | F | 3-F | Cl | H |
| A-1544. | CH$_3$ | F | 3-CH$_3$ | Cl | H |
| A-1545. | CH$_3$ | F | 3-OCH$_3$ | Cl | H |
| A-1546. | CH$_3$ | F | 5-F | Cl | H |
| A-1547. | CH$_3$ | F | 5-CH$_3$ | Cl | H |
| A-1548. | CH$_3$ | F | 5-OCH$_3$ | Cl | H |
| A-1549. | CH$_3$ | CH$_3$ | 3-F | Cl | H |
| A-1550. | CH$_3$ | CH$_3$ | 3-CH$_3$ | Cl | H |
| A-1551. | CH$_3$ | CH$_3$ | 3-OCH$_3$ | Cl | H |
| A-1552. | CH$_3$ | CH$_3$ | 5-F | Cl | H |
| A-1553. | CH$_3$ | CH$_3$ | 5-CH$_3$ | Cl | H |
| A-1554. | CH$_3$ | CH$_3$ | 5-OCH$_3$ | Cl | H |
| A-1555. | CH$_3$ | OCH$_3$ | 3-F | Cl | H |
| A-1556. | CH$_3$ | OCH$_3$ | 3-CH$_3$ | Cl | H |
| A-1557. | CH$_3$ | OCH$_3$ | 3-OCH$_3$ | Cl | H |
| A-1558. | CH$_3$ | OCH$_3$ | 5-F | Cl | H |
| A-1559. | CH$_3$ | OCH$_3$ | 5-CH$_3$ | Cl | H |
| A-1560. | CH$_3$ | OCH$_3$ | 5-OCH$_3$ | Cl | H |
| A-1561. | CH$_3$ | CN | 3-F | Cl | H |
| A-1562. | CH$_3$ | CN | 3-CH$_3$ | Cl | H |
| A-1563. | CH$_3$ | CN | 3-OCH$_3$ | Cl | H |
| A-1564. | CH$_3$ | CN | 5-F | Cl | H |
| A-1565. | CH$_3$ | CN | 5-CH$_3$ | Cl | H |
| A-1566. | CH$_3$ | CN | 5-OCH$_3$ | Cl | H |
| A-1567. | CH$_3$ | CH$_2$F | 3-F | Cl | H |
| A-1568. | CH$_3$ | CH$_2$F | 3-CH$_3$ | Cl | H |
| A-1569. | CH$_3$ | CH$_2$F | 3-OCH$_3$ | Cl | H |
| A-1570. | CH$_3$ | CH$_2$F | 5-F | Cl | H |
| A-1571. | CH$_3$ | CH$_2$F | 5-CH$_3$ | Cl | H |
| A-1572. | CH$_3$ | CH$_2$F | 5-OCH$_3$ | Cl | H |
| A-1573. | CH$_3$ | CHF$_2$ | 3-F | Cl | H |
| A-1574. | CH$_3$ | CHF$_2$ | 3-CH$_3$ | Cl | H |
| A-1575. | CH$_3$ | CHF$_2$ | 3-OCH$_3$ | Cl | H |
| A-1576. | CH$_3$ | CHF$_2$ | 5-F | Cl | H |
| A-1577. | CH$_3$ | CHF$_2$ | 5-CH$_3$ | Cl | H |
| A-1578. | CH$_3$ | CHF$_2$ | 5-OCH$_3$ | Cl | H |
| A-1579. | CH$_3$ | CF$_3$ | 3-F | Cl | H |
| A-1580. | CH$_3$ | CF$_3$ | 3-CH$_3$ | Cl | H |
| A-1581. | CH$_3$ | CF$_3$ | 3-OCH$_3$ | Cl | H |
| A-1582. | CH$_3$ | CF$_3$ | 5-F | Cl | H |
| A-1583. | CH$_3$ | CF$_3$ | 5-CH$_3$ | Cl | H |
| A-1584. | CH$_3$ | CF$_3$ | 5-OCH$_3$ | Cl | H |
| A-1585. | CH$_3$ | OCH$_2$F | 3-F | Cl | H |
| A-1586. | CH$_3$ | OCH$_2$F | 3-CH$_3$ | Cl | H |
| A-1587. | CH$_3$ | OCH$_2$F | 3-OCH$_3$ | Cl | H |
| A-1588. | CH$_3$ | OCH$_2$F | 5-F | Cl | H |
| A-1589. | CH$_3$ | OCH$_2$F | 5-CH$_3$ | Cl | H |
| A-1590. | CH$_3$ | OCH$_2$F | 5-OCH$_3$ | Cl | H |
| A-1591. | CH$_3$ | OCHF$_2$ | 3-F | Cl | H |
| A-1592. | CH$_3$ | OCHF$_2$ | 3-CH$_3$ | Cl | H |
| A-1593. | CH$_3$ | OCHF$_2$ | 3-OCH$_3$ | Cl | H |
| A-1594. | CH$_3$ | OCHF$_2$ | 5-F | Cl | H |
| A-1595. | CH$_3$ | OCHF$_2$ | 5-CH$_3$ | Cl | H |
| A-1596. | CH$_3$ | OCHF$_2$ | 5-OCH$_3$ | Cl | H |
| A-1597. | CH$_3$ | OCF$_3$ | 3-F | Cl | H |
| A-1598. | CH$_3$ | OCF$_3$ | 3-CH$_3$ | Cl | H |
| A-1599. | CH$_3$ | OCF$_3$ | 3-OCH$_3$ | Cl | H |
| A-1600. | CH$_3$ | OCF$_3$ | 5-F | Cl | H |
| A-1601. | CH$_3$ | OCF$_3$ | 5-CH$_3$ | Cl | H |
| A-1602. | CH$_3$ | OCF$_3$ | 5-OCH$_3$ | Cl | H |
| A-1603. | OCH$_3$ | F | 3-F | Cl | H |
| A-1604. | OCH$_3$ | F | 3-CH$_3$ | Cl | H |
| A-1605. | OCH$_3$ | F | 3-OCH$_3$ | Cl | H |
| A-1606. | OCH$_3$ | F | 5-F | Cl | H |
| A-1607. | OCH$_3$ | F | 5-CH$_3$ | Cl | H |
| A-1608. | OCH$_3$ | F | 5-OCH$_3$ | Cl | H |
| A-1609. | OCH$_3$ | CH$_3$ | 3-F | Cl | H |
| A-1610. | OCH$_3$ | CH$_3$ | 3-CH$_3$ | Cl | H |
| A-1611. | OCH$_3$ | CH$_3$ | 3-OCH$_3$ | Cl | H |
| A-1612. | OCH$_3$ | CH$_3$ | 5-F | Cl | H |
| A-1613. | OCH$_3$ | CH$_3$ | 5-CH$_3$ | Cl | H |
| A-1614. | OCH$_3$ | CH$_3$ | 5-OCH$_3$ | Cl | H |
| A-1615. | OCH$_3$ | OCH$_3$ | 3-F | Cl | H |
| A-1616. | OCH$_3$ | OCH$_3$ | 3-CH$_3$ | Cl | H |
| A-1617. | OCH$_3$ | OCH$_3$ | 3-OCH$_3$ | Cl | H |
| A-1618. | OCH$_3$ | OCH$_3$ | 5-F | Cl | H |
| A-1619. | OCH$_3$ | OCH$_3$ | 5-CH$_3$ | Cl | H |
| A-1620. | OCH$_3$ | OCH$_3$ | 5-OCH$_3$ | Cl | H |
| A-1621. | OCH$_3$ | CN | 3-F | Cl | H |
| A-1622. | OCH$_3$ | CN | 3-CH$_3$ | Cl | H |
| A-1623. | OCH$_3$ | CN | 3-OCH$_3$ | Cl | H |
| A-1624. | OCH$_3$ | CN | 5-F | Cl | H |
| A-1625. | OCH$_3$ | CN | 5-CH$_3$ | Cl | H |
| A-1626. | OCH$_3$ | CN | 5-OCH$_3$ | Cl | H |
| A-1627. | OCH$_3$ | CH$_2$F | 3-F | Cl | H |
| A-1628. | OCH$_3$ | CH$_2$F | 3-CH$_3$ | Cl | H |
| A-1629. | OCH$_3$ | CH$_2$F | 3-OCH$_3$ | Cl | H |
| A-1630. | OCH$_3$ | CH$_2$F | 5-F | Cl | H |
| A-1631. | OCH$_3$ | CH$_2$F | 5-CH$_3$ | Cl | H |
| A-1632. | OCH$_3$ | CH$_2$F | 5-OCH$_3$ | Cl | H |
| A-1633. | OCH$_3$ | CHF$_2$ | 3-F | Cl | H |
| A-1634. | OCH$_3$ | CHF$_2$ | 3-CH$_3$ | Cl | H |
| A-1635. | OCH$_3$ | CHF$_2$ | 3-OCH$_3$ | Cl | H |
| A-1636. | OCH$_3$ | CHF$_2$ | 5-F | Cl | H |
| A-1637. | OCH$_3$ | CHF$_2$ | 5-CH$_3$ | Cl | H |
| A-1638. | OCH$_3$ | CHF$_2$ | 5-OCH$_3$ | Cl | H |
| A-1639. | OCH$_3$ | CF$_3$ | 3-F | Cl | H |
| A-1640. | OCH$_3$ | CF$_3$ | 3-CH$_3$ | Cl | H |
| A-1641. | OCH$_3$ | CF$_3$ | 3-OCH$_3$ | Cl | H |
| A-1642. | OCH$_3$ | CF$_3$ | 5-F | Cl | H |
| A-1643. | OCH$_3$ | CF$_3$ | 5-CH$_3$ | Cl | H |
| A-1644. | OCH$_3$ | CF$_3$ | 5-OCH$_3$ | Cl | H |
| A-1645. | OCH$_3$ | OCH$_2$F | 3-F | Cl | H |
| A-1646. | OCH$_3$ | OCH$_2$F | 3-CH$_3$ | Cl | H |
| A-1647. | OCH$_3$ | OCH$_2$F | 3-OCH$_3$ | Cl | H |
| A-1648. | OCH$_3$ | OCH$_2$F | 5-F | Cl | H |
| A-1649. | OCH$_3$ | OCH$_2$F | 5-CH$_3$ | Cl | H |
| A-1650. | OCH$_3$ | OCH$_2$F | 5-OCH$_3$ | Cl | H |
| A-1651. | OCH$_3$ | OCHF$_2$ | 3-F | Cl | H |
| A-1652. | OCH$_3$ | OCHF$_2$ | 3-CH$_3$ | Cl | H |
| A-1653. | OCH$_3$ | OCHF$_2$ | 3-OCH$_3$ | Cl | H |
| A-1654. | OCH$_3$ | OCHF$_2$ | 5-F | Cl | H |
| A-1655. | OCH$_3$ | OCHF$_2$ | 5-CH$_3$ | Cl | H |
| A-1656. | OCH$_3$ | OCHF$_2$ | 5-OCH$_3$ | Cl | H |
| A-1657. | OCH$_3$ | OCF$_3$ | 3-F | Cl | H |
| A-1658. | OCH$_3$ | OCF$_3$ | 3-CH$_3$ | Cl | H |
| A-1659. | OCH$_3$ | OCF$_3$ | 3-OCH$_3$ | Cl | H |
| A-1660. | OCH$_3$ | OCF$_3$ | 5-F | Cl | H |
| A-1661. | OCH$_3$ | OCF$_3$ | 5-CH$_3$ | Cl | H |
| A-1662. | OCH$_3$ | OCF$_3$ | 5-OCH$_3$ | Cl | H |
| A-1663. | CH$_2$F | F | 3-F | Cl | H |
| A-1664. | CH$_2$F | F | 3-CH$_3$ | Cl | H |
| A-1665. | CH$_2$F | F | 3-OCH$_3$ | Cl | H |
| A-1666. | CH$_2$F | F | 5-F | Cl | H |
| A-1667. | CH$_2$F | F | 5-CH$_3$ | Cl | H |
| A-1668. | CH$_2$F | F | 5-OCH$_3$ | Cl | H |
| A-1669. | CH$_2$F | CH$_3$ | 3-F | Cl | H |
| A-1670. | CH$_2$F | CH$_3$ | 3-CH$_3$ | Cl | H |
| A-1671. | CH$_2$F | CH$_3$ | 3-OCH$_3$ | Cl | H |
| A-1672. | CH$_2$F | CH$_3$ | 5-F | Cl | H |
| A-1673. | CH$_2$F | CH$_3$ | 5-CH$_3$ | Cl | H |
| A-1674. | CH$_2$F | CH$_3$ | 5-OCH$_3$ | Cl | H |
| A-1675. | CH$_2$F | OCH$_3$ | 3-F | Cl | H |
| A-1676. | CH$_2$F | OCH$_3$ | 3-CH$_3$ | Cl | H |
| A-1677. | CH$_2$F | OCH$_3$ | 3-OCH$_3$ | Cl | H |
| A-1678. | CH$_2$F | OCH$_3$ | 5-F | Cl | H |
| A-1679. | CH$_2$F | OCH$_3$ | 5-CH$_3$ | Cl | H |
| A-1680. | CH$_2$F | OCH$_3$ | 5-OCH$_3$ | Cl | H |
| A-1681. | CH$_2$F | CN | 3-F | Cl | H |
| A-1682. | CH$_2$F | CN | 3-CH$_3$ | Cl | H |
| A-1683. | CH$_2$F | CN | 3-OCH$_3$ | Cl | H |

TABLE A-continued

| Example No. | $R^1$ | $R^2$ | $R^3$ | $R^6$ | $R^7$ |
|---|---|---|---|---|---|
| A-1684. | $CH_2F$ | CN | 5-F | Cl | H |
| A-1685. | $CH_2F$ | CN | 5-$CH_3$ | Cl | H |
| A-1686. | $CH_2F$ | CN | 5-$OCH_3$ | Cl | H |
| A-1687. | $CH_2F$ | $CH_2F$ | 3-F | Cl | H |
| A-1688. | $CH_2F$ | $CH_2F$ | 3-$CH_3$ | Cl | H |
| A-1689. | $CH_2F$ | $CH_2F$ | 3-$OCH_3$ | Cl | H |
| A-1690. | $CH_2F$ | $CH_2F$ | 5-F | Cl | H |
| A-1691. | $CH_2F$ | $CH_2F$ | 5-$CH_3$ | Cl | H |
| A-1692. | $CH_2F$ | $CH_2F$ | 5-$OCH_3$ | Cl | H |
| A-1693. | $CH_2F$ | $CHF_2$ | 3-F | Cl | H |
| A-1694. | $CH_2F$ | $CHF_2$ | 3-$CH_3$ | Cl | H |
| A-1695. | $CH_2F$ | $CHF_2$ | 3-$OCH_3$ | Cl | H |
| A-1696. | $CH_2F$ | $CHF_2$ | 5-F | Cl | H |
| A-1697. | $CH_2F$ | $CHF_2$ | 5-$CH_3$ | Cl | H |
| A-1698. | $CH_2F$ | $CHF_2$ | 5-$OCH_3$ | Cl | H |
| A-1699. | $CH_2F$ | $CF_3$ | 3-F | Cl | H |
| A-1700. | $CH_2F$ | $CF_3$ | 3-$CH_3$ | Cl | H |
| A-1701. | $CH_2F$ | $CF_3$ | 3-$OCH_3$ | Cl | H |
| A-1702. | $CH_2F$ | $CF_3$ | 5-F | Cl | H |
| A-1703. | $CH_2F$ | $CF_3$ | 5-$CH_3$ | Cl | H |
| A-1704. | $CH_2F$ | $CF_3$ | 5-$OCH_3$ | Cl | H |
| A-1705. | $CH_2F$ | $OCH_2F$ | 3-F | Cl | H |
| A-1706. | $CH_2F$ | $OCH_2F$ | 3-$CH_3$ | Cl | H |
| A-1707. | $CH_2F$ | $OCH_2F$ | 3-$OCH_3$ | Cl | H |
| A-1708. | $CH_2F$ | $OCH_2F$ | 5-F | Cl | H |
| A-1709. | $CH_2F$ | $OCH_2F$ | 5-$CH_3$ | Cl | H |
| A-1710. | $CH_2F$ | $OCH_2F$ | 5-$OCH_3$ | Cl | H |
| A-1711. | $CH_2F$ | $OCHF_2$ | 3-F | Cl | H |
| A-1712. | $CH_2F$ | $OCHF_2$ | 3-$CH_3$ | Cl | H |
| A-1713. | $CH_2F$ | $OCHF_2$ | 3-$OCH_3$ | Cl | H |
| A-1714. | $CH_2F$ | $OCHF_2$ | 5-F | Cl | H |
| A-1715. | $CH_2F$ | $OCHF_2$ | 5-$CH_3$ | Cl | H |
| A-1716. | $CH_2F$ | $OCHF_2$ | 5-$OCH_3$ | Cl | H |
| A-1717. | $CH_2F$ | $OCF_3$ | 3-F | Cl | H |
| A-1718. | $CH_2F$ | $OCF_3$ | 3-$CH_3$ | Cl | H |
| A-1719. | $CH_2F$ | $OCF_3$ | 3-$OCH_3$ | Cl | H |
| A-1720. | $CH_2F$ | $OCF_3$ | 5-F | Cl | H |
| A-1721. | $CH_2F$ | $OCF_3$ | 5-$CH_3$ | Cl | H |
| A-1722. | $CH_2F$ | $OCF_3$ | 5-$OCH_3$ | Cl | H |
| A-1723. | $CHF_2$ | F | 3-F | Cl | H |
| A-1724. | $CHF_2$ | F | 3-$CH_3$ | Cl | H |
| A-1725. | $CHF_2$ | F | 3-$OCH_3$ | Cl | H |
| A-1726. | $CHF_2$ | F | 5-F | Cl | H |
| A-1727. | $CHF_2$ | F | 5-$CH_3$ | Cl | H |
| A-1728. | $CHF_2$ | F | 5-$OCH_3$ | Cl | H |
| A-1729. | $CHF_2$ | $CH_3$ | 3-F | Cl | H |
| A-1730. | $CHF_2$ | $CH_3$ | 3-$CH_3$ | Cl | H |
| A-1731. | $CHF_2$ | $CH_3$ | 3-$OCH_3$ | Cl | H |
| A-1732. | $CHF_2$ | $CH_3$ | 5-F | Cl | H |
| A-1733. | $CHF_2$ | $CH_3$ | 5-$CH_3$ | Cl | H |
| A-1734. | $CHF_2$ | $CH_3$ | 5-$OCH_3$ | Cl | H |
| A-1735. | $CHF_2$ | $OCH_3$ | 3-F | Cl | H |
| A-1736. | $CHF_2$ | $OCH_3$ | 3-$CH_3$ | Cl | H |
| A-1737. | $CHF_2$ | $OCH_3$ | 3-$OCH_3$ | Cl | H |
| A-1738. | $CHF_2$ | $OCH_3$ | 5-F | Cl | H |
| A-1739. | $CHF_2$ | $OCH_3$ | 5-$CH_3$ | Cl | H |
| A-1740. | $CHF_2$ | $OCH_3$ | 5-$OCH_3$ | Cl | H |
| A-1741. | $CHF_2$ | CN | 3-F | Cl | H |
| A-1742. | $CHF_2$ | CN | 3-$CH_3$ | Cl | H |
| A-1743. | $CHF_2$ | CN | 3-$OCH_3$ | Cl | H |
| A-1744. | $CHF_2$ | CN | 5-F | Cl | H |
| A-1745. | $CHF_2$ | CN | 5-$CH_3$ | Cl | H |
| A-1746. | $CHF_2$ | CN | 5-$OCH_3$ | Cl | H |
| A-1747. | $CHF_2$ | $CH_2F$ | 3-F | Cl | H |
| A-1748. | $CHF_2$ | $CH_2F$ | 3-$CH_3$ | Cl | H |
| A-1749. | $CHF_2$ | $CH_2F$ | 3-$OCH_3$ | Cl | H |
| A-1750. | $CHF_2$ | $CH_2F$ | 5-F | Cl | H |
| A-1751. | $CHF_2$ | $CH_2F$ | 5-$CH_3$ | Cl | H |
| A-1752. | $CHF_2$ | $CH_2F$ | 5-$OCH_3$ | Cl | H |
| A-1753. | $CHF_2$ | $CHF_2$ | 3-F | Cl | H |
| A-1754. | $CHF_2$ | $CHF_2$ | 3-$CH_3$ | Cl | H |
| A-1755. | $CHF_2$ | $CHF_2$ | 3-$OCH_3$ | Cl | H |
| A-1756. | $CHF_2$ | $CHF_2$ | 5-F | Cl | H |
| A-1757. | $CHF_2$ | $CHF_2$ | 5-$CH_3$ | Cl | H |
| A-1758. | $CHF_2$ | $CHF_2$ | 5-$OCH_3$ | Cl | H |
| A-1759. | $CHF_2$ | $CF_3$ | 3-F | Cl | H |
| A-1760. | $CHF_2$ | $CF_3$ | 3-$CH_3$ | Cl | H |
| A-1761. | $CHF_2$ | $CF_3$ | 3-$OCH_3$ | Cl | H |
| A-1762. | $CHF_2$ | $CF_3$ | 5-F | Cl | H |
| A-1763. | $CHF_2$ | $CF_3$ | 5-$CH_3$ | Cl | H |
| A-1764. | $CHF_2$ | $CF_3$ | 5-$OCH_3$ | Cl | H |
| A-1765. | $CHF_2$ | $OCH_2F$ | 3-F | Cl | H |
| A-1766. | $CHF_2$ | $OCH_2F$ | 3-$CH_3$ | Cl | H |
| A-1767. | $CHF_2$ | $OCH_2F$ | 3-$OCH_3$ | Cl | H |
| A-1768. | $CHF_2$ | $OCH_2F$ | 5-F | Cl | H |
| A-1769. | $CHF_2$ | $OCH_2F$ | 5-$CH_3$ | Cl | H |
| A-1770. | $CHF_2$ | $OCH_2F$ | 5-$OCH_3$ | Cl | H |
| A-1771. | $CHF_2$ | $OCHF_2$ | 3-F | Cl | H |
| A-1772. | $CHF_2$ | $OCHF_2$ | 3-$CH_3$ | Cl | H |
| A-1773. | $CHF_2$ | $OCHF_2$ | 3-$OCH_3$ | Cl | H |
| A-1774. | $CHF_2$ | $OCHF_2$ | 5-F | Cl | H |
| A-1775. | $CHF_2$ | $OCHF_2$ | 5-$CH_3$ | Cl | H |
| A-1776. | $CHF_2$ | $OCHF_2$ | 5-$OCH_3$ | Cl | H |
| A-1777. | $CHF_2$ | $OCF_3$ | 3-F | Cl | H |
| A-1778. | $CHF_2$ | $OCF_3$ | 3-$CH_3$ | Cl | H |
| A-1779. | $CHF_2$ | $OCF_3$ | 3-$OCH_3$ | Cl | H |
| A-1780. | $CHF_2$ | $OCF_3$ | 5-F | Cl | H |
| A-1781. | $CHF_2$ | $OCF_3$ | 5-$CH_3$ | Cl | H |
| A-1782. | $CHF_2$ | $OCF_3$ | 5-$OCH_3$ | Cl | H |
| A-1783. | $CF_3$ | F | 3-F | Cl | H |
| A-1784. | $CF_3$ | F | 3-$CH_3$ | Cl | H |
| A-1785. | $CF_3$ | F | 3-$OCH_3$ | Cl | H |
| A-1786. | $CF_3$ | F | 5-F | Cl | H |
| A-1787. | $CF_3$ | F | 5-$CH_3$ | Cl | H |
| A-1788. | $CF_3$ | F | 5-$OCH_3$ | Cl | H |
| A-1789. | $CF_3$ | $CH_3$ | 3-F | Cl | H |
| A-1790. | $CF_3$ | $CH_3$ | 3-$CH_3$ | Cl | H |
| A-1791. | $CF_3$ | $CH_3$ | 3-$OCH_3$ | Cl | H |
| A-1792. | $CF_3$ | $CH_3$ | 5-F | Cl | H |
| A-1793. | $CF_3$ | $CH_3$ | 5-$CH_3$ | Cl | H |
| A-1794. | $CF_3$ | $CH_3$ | 5-$OCH_3$ | Cl | H |
| A-1795. | $CF_3$ | $OCH_3$ | 3-F | Cl | H |
| A-1796. | $CF_3$ | $OCH_3$ | 3-$CH_3$ | Cl | H |
| A-1797. | $CF_3$ | $OCH_3$ | 3-$OCH_3$ | Cl | H |
| A-1798. | $CF_3$ | $OCH_3$ | 5-F | Cl | H |
| A-1799. | $CF_3$ | $OCH_3$ | 5-$CH_3$ | Cl | H |
| A-1800. | $CF_3$ | $OCH_3$ | 5-$OCH_3$ | Cl | H |
| A-1801. | $CF_3$ | CN | 3-F | Cl | H |
| A-1802. | $CF_3$ | CN | 3-$CH_3$ | Cl | H |
| A-1803. | $CF_3$ | CN | 3-$OCH_3$ | Cl | H |
| A-1804. | $CF_3$ | CN | 5-F | Cl | H |
| A-1805. | $CF_3$ | CN | 5-$CH_3$ | Cl | H |
| A-1806. | $CF_3$ | CN | 5-$OCH_3$ | Cl | H |
| A-1807. | $CF_3$ | $CH_2F$ | 3-F | Cl | H |
| A-1808. | $CF_3$ | $CH_2F$ | 3-$CH_3$ | Cl | H |
| A-1809. | $CF_3$ | $CH_2F$ | 3-$OCH_3$ | Cl | H |
| A-1810. | $CF_3$ | $CH_2F$ | 5-F | Cl | H |
| A-1811. | $CF_3$ | $CH_2F$ | 5-$CH_3$ | Cl | H |
| A-1812. | $CF_3$ | $CH_2F$ | 5-$OCH_3$ | Cl | H |
| A-1813. | $CF_3$ | $CHF_2$ | 3-F | Cl | H |
| A-1814. | $CF_3$ | $CHF_2$ | 3-$CH_3$ | Cl | H |
| A-1815. | $CF_3$ | $CHF_2$ | 3-$OCH_3$ | Cl | H |
| A-1816. | $CF_3$ | $CHF_2$ | 5-F | Cl | H |
| A-1817. | $CF_3$ | $CHF_2$ | 5-$CH_3$ | Cl | H |
| A-1818. | $CF_3$ | $CHF_2$ | 5-$OCH_3$ | Cl | H |
| A-1819. | $CF_3$ | $CF_3$ | 3-F | Cl | H |
| A-1820. | $CF_3$ | $CF_3$ | 3-$CH_3$ | Cl | H |
| A-1821. | $CF_3$ | $CF_3$ | 3-$OCH_3$ | Cl | H |
| A-1822. | $CF_3$ | $CF_3$ | 5-F | Cl | H |
| A-1823. | $CF_3$ | $CF_3$ | 5-$CH_3$ | Cl | H |
| A-1824. | $CF_3$ | $CF_3$ | 5-$OCH_3$ | Cl | H |
| A-1825. | $CF_3$ | $OCH_2F$ | 3-F | Cl | H |
| A-1826. | $CF_3$ | $OCH_2F$ | 3-$CH_3$ | Cl | H |
| A-1827. | $CF_3$ | $OCH_2F$ | 3-$OCH_3$ | Cl | H |
| A-1828. | $CF_3$ | $OCH_2F$ | 5-F | Cl | H |
| A-1829. | $CF_3$ | $OCH_2F$ | 5-$CH_3$ | Cl | H |
| A-1830. | $CF_3$ | $OCH_2F$ | 5-$OCH_3$ | Cl | H |
| A-1831. | $CF_3$ | $OCHF_2$ | 3-F | Cl | H |
| A-1832. | $CF_3$ | $OCHF_2$ | 3-$CH_3$ | Cl | H |
| A-1833. | $CF_3$ | $OCHF_2$ | 3-$OCH_3$ | Cl | H |
| A-1834. | $CF_3$ | $OCHF_2$ | 5-F | Cl | H |
| A-1835. | $CF_3$ | $OCHF_2$ | 5-$CH_3$ | Cl | H |
| A-1836. | $CF_3$ | $OCHF_2$ | 5-$OCH_3$ | Cl | H |
| A-1837. | $CF_3$ | $OCF_3$ | 3-F | Cl | H |
| A-1838. | $CF_3$ | $OCF_3$ | 3-$CH_3$ | Cl | H |
| A-1839. | $CF_3$ | $OCF_3$ | 3-$OCH_3$ | Cl | H |

TABLE A-continued

| Example No. | R¹ | R² | R³ | R⁶ | R⁷ |
|---|---|---|---|---|---|
| A-1840. | CF₃ | OCF₃ | 5-F | Cl | H |
| A-1841. | CF₃ | OCF₃ | 5-CH₃ | Cl | H |
| A-1842. | CF₃ | OCF₃ | 5-OCH₃ | Cl | H |
| A-1843. | OCH₂F | F | 3-F | Cl | H |
| A-1844. | OCH₂F | F | 3-CH₃ | Cl | H |
| A-1845. | OCH₂F | F | 3-OCH₃ | Cl | H |
| A-1846. | OCH₂F | F | 5-F | Cl | H |
| A-1847. | OCH₂F | F | 5-CH₃ | Cl | H |
| A-1848. | OCH₂F | F | 5-OCH₃ | Cl | H |
| A-1849. | OCH₂F | CH₃ | 3-F | Cl | H |
| A-1850. | OCH₂F | CH₃ | 3-CH₃ | Cl | H |
| A-1851. | OCH₂F | CH₃ | 3-OCH₃ | Cl | H |
| A-1852. | OCH₂F | CH₃ | 5-F | Cl | H |
| A-1853. | OCH₂F | CH₃ | 5-CH₃ | Cl | H |
| A-1854. | OCH₂F | CH₃ | 5-OCH₃ | Cl | H |
| A-1855. | OCH₂F | OCH₃ | 3-F | Cl | H |
| A-1856. | OCH₂F | OCH₃ | 3-CH₃ | Cl | H |
| A-1857. | OCH₂F | OCH₃ | 3-OCH₃ | Cl | H |
| A-1858. | OCH₂F | OCH₃ | 5-F | Cl | H |
| A-1859. | OCH₂F | OCH₃ | 5-CH₃ | Cl | H |
| A-1860. | OCH₂F | OCH₃ | 5-OCH₃ | Cl | H |
| A-1861. | OCH₂F | CN | 3-F | Cl | H |
| A-1862. | OCH₂F | CN | 3-CH₃ | Cl | H |
| A-1863. | OCH₂F | CN | 3-OCH₃ | Cl | H |
| A-1864. | OCH₂F | CN | 5-F | Cl | H |
| A-1865. | OCH₂F | CN | 5-CH₃ | Cl | H |
| A-1866. | OCH₂F | CN | 5-OCH₃ | Cl | H |
| A-1867. | OCH₂F | CH₂F | 3-F | Cl | H |
| A-1868. | OCH₂F | CH₂F | 3-CH₃ | Cl | H |
| A-1869. | OCH₂F | CH₂F | 3-OCH₃ | Cl | H |
| A-1870. | OCH₂F | CH₂F | 5-F | Cl | H |
| A-1871. | OCH₂F | CH₂F | 5-CH₃ | Cl | H |
| A-1872. | OCH₂F | CH₂F | 5-OCH₃ | Cl | H |
| A-1873. | OCH₂F | CHF₂ | 3-F | Cl | H |
| A-1874. | OCH₂F | CHF₂ | 3-CH₃ | Cl | H |
| A-1875. | OCH₂F | CHF₂ | 3-OCH₃ | Cl | H |
| A-1876. | OCH₂F | CHF₂ | 5-F | Cl | H |
| A-1877. | OCH₂F | CHF₂ | 5-CH₃ | Cl | H |
| A-1878. | OCH₂F | CHF₂ | 5-OCH₃ | Cl | H |
| A-1879. | OCH₂F | CF₃ | 3-F | Cl | H |
| A-1880. | OCH₂F | CF₃ | 3-CH₃ | Cl | H |
| A-1881. | OCH₂F | CF₃ | 3-OCH₃ | Cl | H |
| A-1882. | OCH₂F | CF₃ | 5-F | Cl | H |
| A-1883. | OCH₂F | CF₃ | 5-CH₃ | Cl | H |
| A-1884. | OCH₂F | CF₃ | 5-OCH₃ | Cl | H |
| A-1885. | OCH₂F | OCH₂F | 3-F | Cl | H |
| A-1886. | OCH₂F | OCH₂F | 3-CH₃ | Cl | H |
| A-1887. | OCH₂F | OCH₂F | 3-OCH₃ | Cl | H |
| A-1888. | OCH₂F | OCH₂F | 5-F | Cl | H |
| A-1889. | OCH₂F | OCH₂F | 5-CH₃ | Cl | H |
| A-1890. | OCH₂F | OCH₂F | 5-OCH₃ | Cl | H |
| A-1891. | OCH₂F | OCHF₂ | 3-F | Cl | H |
| A-1892. | OCH₂F | OCHF₂ | 3-CH₃ | Cl | H |
| A-1893. | OCH₂F | OCHF₂ | 3-OCH₃ | Cl | H |
| A-1894. | OCH₂F | OCHF₂ | 5-F | Cl | H |
| A-1895. | OCH₂F | OCHF₂ | 5-CH₃ | Cl | H |
| A-1896. | OCH₂F | OCHF₂ | 5-OCH₃ | Cl | H |
| A-1897. | OCH₂F | OCF₃ | 3-F | Cl | H |
| A-1898. | OCH₂F | OCF₃ | 3-CH₃ | Cl | H |
| A-1899. | OCH₂F | OCF₃ | 3-OCH₃ | Cl | H |
| A-1900. | OCH₂F | OCF₃ | 5-F | Cl | H |
| A-1901. | OCH₂F | OCF₃ | 5-CH₃ | Cl | H |
| A-1902. | OCH₂F | OCF₃ | 5-OCH₃ | Cl | H |
| A-1903. | OCHF₂ | F | 3-F | Cl | H |
| A-1904. | OCHF₂ | F | 3-CH₃ | Cl | H |
| A-1905. | OCHF₂ | F | 3-OCH₃ | Cl | H |
| A-1906. | OCHF₂ | F | 5-F | Cl | H |
| A-1907. | OCHF₂ | F | 5-CH₃ | Cl | H |
| A-1908. | OCHF₂ | F | 5-OCH₃ | Cl | H |
| A-1909. | OCHF₂ | CH₃ | 3-F | Cl | H |
| A-1910. | OCHF₂ | CH₃ | 3-CH₃ | Cl | H |
| A-1911. | OCHF₂ | CH₃ | 3-OCH₃ | Cl | H |
| A-1912. | OCHF₂ | CH₃ | 5-F | Cl | H |
| A-1913. | OCHF₂ | CH₃ | 5-CH₃ | Cl | H |
| A-1914. | OCHF₂ | CH₃ | 5-OCH₃ | Cl | H |
| A-1915. | OCHF₂ | OCH₃ | 3-F | Cl | H |
| A-1916. | OCHF₂ | OCH₃ | 3-CH₃ | Cl | H |
| A-1917. | OCHF₂ | OCH₃ | 3-OCH₃ | Cl | H |
| A-1918. | OCHF₂ | OCH₃ | 5-F | Cl | H |
| A-1919. | OCHF₂ | OCH₃ | 5-CH₃ | Cl | H |
| A-1920. | OCHF₂ | OCH₃ | 5-OCH₃ | Cl | H |
| A-1921. | OCHF₂ | CN | 3-F | Cl | H |
| A-1922. | OCHF₂ | CN | 3-CH₃ | Cl | H |
| A-1923. | OCHF₂ | CN | 3-OCH₃ | Cl | H |
| A-1924. | OCHF₂ | CN | 5-F | Cl | H |
| A-1925. | OCHF₂ | CN | 5-CH₃ | Cl | H |
| A-1926. | OCHF₂ | CN | 5-OCH₃ | Cl | H |
| A-1927. | OCHF₂ | CH₂F | 3-F | Cl | H |
| A-1928. | OCHF₂ | CH₂F | 3-CH₃ | Cl | H |
| A-1929. | OCHF₂ | CH₂F | 3-OCH₃ | Cl | H |
| A-1930. | OCHF₂ | CH₂F | 5-F | Cl | H |
| A-1931. | OCHF₂ | CH₂F | 5-CH₃ | Cl | H |
| A-1932. | OCHF₂ | CH₂F | 5-OCH₃ | Cl | H |
| A-1933. | OCHF₂ | CHF₂ | 3-F | Cl | H |
| A-1934. | OCHF₂ | CHF₂ | 3-CH₃ | Cl | H |
| A-1935. | OCHF₂ | CHF₂ | 3-OCH₃ | Cl | H |
| A-1936. | OCHF₂ | CHF₂ | 5-F | Cl | H |
| A-1937. | OCHF₂ | CHF₂ | 5-CH₃ | Cl | H |
| A-1938. | OCHF₂ | CHF₂ | 5-OCH₃ | Cl | H |
| A-1939. | OCHF₂ | CF₃ | 3-F | Cl | H |
| A-1940. | OCHF₂ | CF₃ | 3-CH₃ | Cl | H |
| A-1941. | OCHF₂ | CF₃ | 3-OCH₃ | Cl | H |
| A-1942. | OCHF₂ | CF₃ | 5-F | Cl | H |
| A-1943. | OCHF₂ | CF₃ | 5-CH₃ | Cl | H |
| A-1944. | OCHF₂ | CF₃ | 5-OCH₃ | Cl | H |
| A-1945. | OCHF₂ | OCH₂F | 3-F | Cl | H |
| A-1946. | OCHF₂ | OCH₂F | 3-CH₃ | Cl | H |
| A-1947. | OCHF₂ | OCH₂F | 3-OCH₃ | Cl | H |
| A-1948. | OCHF₂ | OCH₂F | 5-F | Cl | H |
| A-1949. | OCHF₂ | OCH₂F | 5-CH₃ | Cl | H |
| A-1950. | OCHF₂ | OCH₂F | 5-OCH₃ | Cl | H |
| A-1951. | OCHF₂ | OCHF₂ | 3-F | Cl | H |
| A-1952. | OCHF₂ | OCHF₂ | 3-CH₃ | Cl | H |
| A-1953. | OCHF₂ | OCHF₂ | 3-OCH₃ | Cl | H |
| A-1954. | OCHF₂ | OCHF₂ | 5-F | Cl | H |
| A-1955. | OCHF₂ | OCHF₂ | 5-CH₃ | Cl | H |
| A-1956. | OCHF₂ | OCHF₂ | 5-OCH₃ | Cl | H |
| A-1957. | OCHF₂ | OCF₃ | 3-F | Cl | H |
| A-1958. | OCHF₂ | OCF₃ | 3-CH₃ | Cl | H |
| A-1959. | OCHF₂ | OCF₃ | 3-OCH₃ | Cl | H |
| A-1960. | OCHF₂ | OCF₃ | 5-F | Cl | H |
| A-1961. | OCHF₂ | OCF₃ | 5-CH₃ | Cl | H |
| A-1962. | OCHF₂ | OCF₃ | 5-OCH₃ | Cl | H |
| A-1963. | OCF₃ | F | 3-F | Cl | H |
| A-1964. | OCF₃ | F | 3-CH₃ | Cl | H |
| A-1965. | OCF₃ | F | 3-OCH₃ | Cl | H |
| A-1966. | OCF₃ | F | 5-F | Cl | H |
| A-1967. | OCF₃ | F | 5-CH₃ | Cl | H |
| A-1968. | OCF₃ | F | 5-OCH₃ | Cl | H |
| A-1969. | OCF₃ | CH₃ | 3-F | Cl | H |
| A-1970. | OCF₃ | CH₃ | 3-CH₃ | Cl | H |
| A-1971. | OCF₃ | CH₃ | 3-OCH₃ | Cl | H |
| A-1972. | OCF₃ | CH₃ | 5-F | Cl | H |
| A-1973. | OCF₃ | CH₃ | 5-CH₃ | Cl | H |
| A-1974. | OCF₃ | CH₃ | 5-OCH₃ | Cl | H |
| A-1975. | OCF₃ | OCH₃ | 3-F | Cl | H |
| A-1976. | OCF₃ | OCH₃ | 3-CH₃ | Cl | H |
| A-1977. | OCF₃ | OCH₃ | 3-OCH₃ | Cl | H |
| A-1978. | OCF₃ | OCH₃ | 5-F | Cl | H |
| A-1979. | OCF₃ | OCH₃ | 5-CH₃ | Cl | H |
| A-1980. | OCF₃ | OCH₃ | 5-OCH₃ | Cl | H |
| A-1981. | OCF₃ | CN | 3-F | Cl | H |
| A-1982. | OCF₃ | CN | 3-CH₃ | Cl | H |
| A-1983. | OCF₃ | CN | 3-OCH₃ | Cl | H |
| A-1984. | OCF₃ | CN | 5-F | Cl | H |
| A-1985. | OCF₃ | CN | 5-CH₃ | Cl | H |
| A-1986. | OCF₃ | CN | 5-OCH₃ | Cl | H |
| A-1987. | OCF₃ | CH₂F | 3-F | Cl | H |
| A-1988. | OCF₃ | CH₂F | 3-CH₃ | Cl | H |
| A-1989. | OCF₃ | CH₂F | 3-OCH₃ | Cl | H |
| A-1990. | OCF₃ | CH₂F | 5-F | Cl | H |
| A-1991. | OCF₃ | CH₂F | 5-CH₃ | Cl | H |
| A-1992. | OCF₃ | CH₂F | 5-OCH₃ | Cl | H |
| A-1993. | OCF₃ | CHF₂ | 3-F | Cl | H |
| A-1994. | OCF₃ | CHF₂ | 3-CH₃ | Cl | H |
| A-1995. | OCF₃ | CHF₂ | 3-OCH₃ | Cl | H |

TABLE A-continued

| Example No. | R¹ | R² | R³ | R⁶ | R⁷ |
|---|---|---|---|---|---|
| A-1996. | OCF₃ | CHF₂ | 5-F | Cl | H |
| A-1997. | OCF₃ | CHF₂ | 5-CH₃ | Cl | H |
| A-1998. | OCF₃ | CHF₂ | 5-OCH₃ | Cl | H |
| A-1999. | OCF₃ | CF₃ | 3-F | Cl | H |
| A-2000. | OCF₃ | CF₃ | 3-CH₃ | Cl | H |
| A-2001. | OCF₃ | CF₃ | 3-OCH₃ | Cl | H |
| A-2002. | OCF₃ | CF₃ | 5-F | Cl | H |
| A-2003. | OCF₃ | CF₃ | 5-CH₃ | Cl | H |
| A-2004. | OCF₃ | CF₃ | 5-OCH₃ | Cl | H |
| A-2005. | OCF₃ | OCH₂F | 3-F | Cl | H |
| A-2006. | OCF₃ | OCH₂F | 3-CH₃ | Cl | H |
| A-2007. | OCF₃ | OCH₂F | 3-OCH₃ | Cl | H |
| A-2008. | OCF₃ | OCH₂F | 5-F | Cl | H |
| A-2009. | OCF₃ | OCH₂F | 5-CH₃ | Cl | H |
| A-2010. | OCF₃ | OCH₂F | 5-OCH₃ | Cl | H |
| A-2011. | OCF₃ | OCHF₂ | 3-F | Cl | H |
| A-2012. | OCF₃ | OCHF₂ | 3-CH₃ | Cl | H |
| A-2013. | OCF₃ | OCHF₂ | 3-OCH₃ | Cl | H |
| A-2014. | OCF₃ | OCHF₂ | 5-F | Cl | H |
| A-2015. | OCF₃ | OCHF₂ | 5-CH₃ | Cl | H |
| A-2016. | OCF₃ | OCHF₂ | 5-OCH₃ | Cl | H |
| A-2017. | OCF₃ | OCF₃ | 3-F | Cl | H |
| A-2018. | OCF₃ | OCF₃ | 3-CH₃ | Cl | H |
| A-2019. | OCF₃ | OCF₃ | 3-OCH₃ | Cl | H |
| A-2020. | OCF₃ | OCF₃ | 5-F | Cl | H |
| A-2021. | OCF₃ | OCF₃ | 5-CH₃ | Cl | H |
| A-2022. | OCF₃ | OCF₃ | 5-OCH₃ | Cl | H |
| A-2023. | H | H | H | CN | F |
| A-2024. | F | H | H | CN | F |
| A-2025. | CH₃ | H | H | CN | F |
| A-2026. | OCH₃ | H | H | CN | F |
| A-2027. | CH₂F | H | H | CN | F |
| A-2028. | CHF₂ | H | H | CN | F |
| A-2029. | CF₃ | H | H | CN | F |
| A-2030. | OCH₂F | H | H | CN | F |
| A-2031. | OCHF₂ | H | H | CN | F |
| A-2032. | OCF₃ | H | H | CN | F |
| A-2033. | H | F | H | CN | F |
| A-2034. | H | CH₃ | H | CN | F |
| A-2035. | H | OCH₃ | H | CN | F |
| A-2036. | H | CN | H | CN | F |
| A-2037. | H | CH₂F | H | CN | F |
| A-2038. | H | CHF₂ | H | CN | F |
| A-2039. | H | CF₃ | H | CN | F |
| A-2040. | H | OCH₂F | H | CN | F |
| A-2041. | H | OCHF₂ | H | CN | F |
| A-2042. | H | OCF₃ | H | CN | F |
| A-2043. | H | H | 3-F | CN | F |
| A-2044. | H | H | 3-CH₃ | CN | F |
| A-2045. | H | H | 3-OCH₃ | CN | F |
| A-2046. | H | H | 5-F | CN | F |
| A-2047. | H | H | 5-CH₃ | CN | F |
| A-2048. | H | H | 5-OCH₃ | CN | F |
| A-2049. | F | F | H | CN | F |
| A-2050. | F | CH₃ | H | CN | F |
| A-2051. | F | OCH₃ | H | CN | F |
| A-2052. | F | CN | H | CN | F |
| A-2053. | F | CH₂F | H | CN | F |
| A-2054. | F | CHF₂ | H | CN | F |
| A-2055. | F | CF₃ | H | CN | F |
| A-2056. | F | OCH₂F | H | CN | F |
| A-2057. | F | OCHF₂ | H | CN | F |
| A-2058. | F | OCF₃ | H | CN | F |
| A-2059. | F | H | 3-F | CN | F |
| A-2060. | F | H | 3-CH₃ | CN | F |
| A-2061. | F | H | 3-OCH₃ | CN | F |
| A-2062. | F | H | 5-F | CN | F |
| A-2063. | F | H | 5-CH₃ | CN | F |
| A-2064. | F | H | 5-OCH₃ | CN | F |
| A-2065. | CH₃ | F | H | CN | F |
| A-2066. | CH₃ | CH₃ | H | CN | F |
| A-2067. | CH₃ | OCH₃ | H | CN | F |
| A-2068. | CH₃ | CN | H | CN | F |
| A-2069. | CH₃ | CH₂F | H | CN | F |
| A-2070. | CH₃ | CHF₂ | H | CN | F |
| A-2071. | CH₃ | CF₃ | H | CN | F |
| A-2072. | CH₃ | OCH₂F | H | CN | F |
| A-2073. | CH₃ | OCHF₂ | H | CN | F |
| A-2074. | CH₃ | OCF₃ | H | CN | F |
| A-2075. | CH₃ | H | 3-F | CN | F |
| A-2076. | CH₃ | H | 3-CH₃ | CN | F |
| A-2077. | CH₃ | H | 3-OCH₃ | CN | F |
| A-2078. | CH₃ | H | 5-F | CN | F |
| A-2079. | CH₃ | H | 5-CH₃ | CN | F |
| A-2080. | CH₃ | H | 5-OCH₃ | CN | F |
| A-2081. | OCH₃ | F | H | CN | F |
| A-2082. | OCH₃ | CH₃ | H | CN | F |
| A-2083. | OCH₃ | OCH₃ | H | CN | F |
| A-2084. | OCH₃ | CN | H | CN | F |
| A-2085. | OCH₃ | CH₂F | H | CN | F |
| A-2086. | OCH₃ | CHF₂ | H | CN | F |
| A-2087. | OCH₃ | CF₃ | H | CN | F |
| A-2088. | OCH₃ | OCH₂F | H | CN | F |
| A-2089. | OCH₃ | OCHF₂ | H | CN | F |
| A-2090. | OCH₃ | OCF₃ | H | CN | F |
| A-2091. | OCH₃ | H | 3-F | CN | F |
| A-2092. | OCH₃ | H | 3-CH₃ | CN | F |
| A-2093. | OCH₃ | H | 3-OCH₃ | CN | F |
| A-2094. | OCH₃ | H | 5-F | CN | F |
| A-2095. | OCH₃ | H | 5-CH₃ | CN | F |
| A-2096. | OCH₃ | H | 5-OCH₃ | CN | F |
| A-2097. | H | F | 3-F | CN | F |
| A-2098. | H | F | 3-CH₃ | CN | F |
| A-2099. | H | F | 3-OCH₃ | CN | F |
| A-2100. | H | F | 5-F | CN | F |
| A-2101. | H | F | 5-CH₃ | CN | F |
| A-2102. | H | F | 5-OCH₃ | CN | F |
| A-2103. | H | CH₃ | 3-F | CN | F |
| A-2104. | H | CH₃ | 3-CH₃ | CN | F |
| A-2105. | H | CH₃ | 3-OCH₃ | CN | F |
| A-2106. | H | CH₃ | 5-F | CN | F |
| A-2107. | H | CH₃ | 5-CH₃ | CN | F |
| A-2108. | H | CH₃ | 5-OCH₃ | CN | F |
| A-2109. | H | OCH₃ | 3-F | CN | F |
| A-2110. | H | OCH₃ | 3-CH₃ | CN | F |
| A-2111. | H | OCH₃ | 3-OCH₃ | CN | F |
| A-2112. | H | OCH₃ | 5-F | CN | F |
| A-2113. | H | OCH₃ | 5-CH₃ | CN | F |
| A-2114. | H | OCH₃ | 5-OCH₃ | CN | F |
| A-2115. | H | CN | 3-F | CN | F |
| A-2116. | H | CN | 3-CH₃ | CN | F |
| A-2117. | H | CN | 3-OCH₃ | CN | F |
| A-2118. | H | CN | 5-F | CN | F |
| A-2119. | H | CN | 5-CH₃ | CN | F |
| A-2120. | H | CN | 5-OCH₃ | CN | F |
| A-2121. | H | CH₂F | 3-F | CN | F |
| A-2122. | H | CH₂F | 3-CH₃ | CN | F |
| A-2123. | H | CH₂F | 3-OCH₃ | CN | F |
| A-2124. | H | CH₂F | 5-F | CN | F |
| A-2125. | H | CH₂F | 5-CH₃ | CN | F |
| A-2126. | H | CH₂F | 5-OCH₃ | CN | F |
| A-2127. | H | CHF₂ | 3-F | CN | F |
| A-2128. | H | CHF₂ | 3-CH₃ | CN | F |
| A-2129. | H | CHF₂ | 3-OCH₃ | CN | F |
| A-2130. | H | CHF₂ | 5-F | CN | F |
| A-2131. | H | CHF₂ | 5-CH₃ | CN | F |
| A-2132. | H | CHF₂ | 5-OCH₃ | CN | F |
| A-2133. | H | CF₃ | 3-F | CN | F |
| A-2134. | H | CF₃ | 3-CH₃ | CN | F |
| A-2135. | H | CF₃ | 3-OCH₃ | CN | F |
| A-2136. | H | CF₃ | 5-F | CN | F |
| A-2137. | H | CF₃ | 5-CH₃ | CN | F |
| A-2138. | H | CF₃ | 5-OCH₃ | CN | F |
| A-2139. | H | OCH₂F | 3-F | CN | F |
| A-2140. | H | OCH₂F | 3-CH₃ | CN | F |
| A-2141. | H | OCH₂F | 3-OCH₃ | CN | F |
| A-2142. | H | OCH₂F | 5-F | CN | F |
| A-2143. | H | OCH₂F | 5-CH₃ | CN | F |
| A-2144. | H | OCH₂F | 5-OCH₃ | CN | F |
| A-2145. | H | OCHF₂ | 3-F | CN | F |
| A-2146. | H | OCHF₂ | 3-CH₃ | CN | F |
| A-2147. | H | OCHF₂ | 3-OCH₃ | CN | F |
| A-2148. | H | OCHF₂ | 5-F | CN | F |
| A-2149. | H | OCHF₂ | 5-CH₃ | CN | F |
| A-2150. | H | OCHF₂ | 5-OCH₃ | CN | F |
| A-2151. | H | OCF₃ | 3-F | CN | F |

TABLE A-continued

| Example No. | R¹ | R² | R³ | R⁶ | R⁷ |
|---|---|---|---|---|---|
| A-2152. | H | OCF$_3$ | 3-CH$_3$ | CN | F |
| A-2153. | H | OCF$_3$ | 3-OCH$_3$ | CN | F |
| A-2154. | H | OCF$_3$ | 5-F | CN | F |
| A-2155. | H | OCF$_3$ | 5-CH$_3$ | CN | F |
| A-2156. | H | OCF$_3$ | 5-OCH$_3$ | CN | F |
| A-2157. | F | F | 3-F | CN | F |
| A-2158. | F | F | 3-CH$_3$ | CN | F |
| A-2159. | F | F | 3-OCH$_3$ | CN | F |
| A-2160. | F | F | 5-F | CN | F |
| A-2161. | F | F | 5-CH$_3$ | CN | F |
| A-2162. | F | F | 5-OCH$_3$ | CN | F |
| A-2163. | F | CH$_3$ | 3-F | CN | F |
| A-2164. | F | CH$_3$ | 3-CH$_3$ | CN | F |
| A-2165. | F | CH$_3$ | 3-OCH$_3$ | CN | F |
| A-2166. | F | CH$_3$ | 5-F | CN | F |
| A-2167. | F | CH$_3$ | 5-CH$_3$ | CN | F |
| A-2168. | F | CH$_3$ | 5-OCH$_3$ | CN | F |
| A-2169. | F | OCH$_3$ | 3-F | CN | F |
| A-2170. | F | OCH$_3$ | 3-CH$_3$ | CN | F |
| A-2171. | F | OCH$_3$ | 3-OCH$_3$ | CN | F |
| A-2172. | F | OCH$_3$ | 5-F | CN | F |
| A-2173. | F | OCH$_3$ | 5-CH$_3$ | CN | F |
| A-2174. | F | OCH$_3$ | 5-OCH$_3$ | CN | F |
| A-2175. | F | CN | 3-F | CN | F |
| A-2176. | F | CN | 3-CH$_3$ | CN | F |
| A-2177. | F | CN | 3-OCH$_3$ | CN | F |
| A-2178. | F | CN | 5-F | CN | F |
| A-2179. | F | CN | 5-CH$_3$ | CN | F |
| A-2180. | F | CN | 5-OCH$_3$ | CN | F |
| A-2181. | F | CH$_2$F | 3-F | CN | F |
| A-2182. | F | CH$_2$F | 3-CH$_3$ | CN | F |
| A-2183. | F | CH$_2$F | 3-OCH$_3$ | CN | F |
| A-2184. | F | CH$_2$F | 5-F | CN | F |
| A-2185. | F | CH$_2$F | 5-CH$_3$ | CN | F |
| A-2186. | F | CH$_2$F | 5-OCH$_3$ | CN | F |
| A-2187. | F | CHF$_2$ | 3-F | CN | F |
| A-2188. | F | CHF$_2$ | 3-CH$_3$ | CN | F |
| A-2189. | F | CHF$_2$ | 3-OCH$_3$ | CN | F |
| A-2190. | F | CHF$_2$ | 5-F | CN | F |
| A-2191. | F | CHF$_2$ | 5-CH$_3$ | CN | F |
| A-2192. | F | CHF$_2$ | 5-OCH$_3$ | CN | F |
| A-2193. | F | CF$_3$ | 3-F | CN | F |
| A-2194. | F | CF$_3$ | 3-CH$_3$ | CN | F |
| A-2195. | F | CF$_3$ | 3-OCH$_3$ | CN | F |
| A-2196. | F | CF$_3$ | 5-F | CN | F |
| A-2197. | F | CF$_3$ | 5-CH$_3$ | CN | F |
| A-2198. | F | CF$_3$ | 5-OCH$_3$ | CN | F |
| A-2199. | F | OCH$_2$F | 3-F | CN | F |
| A-2200. | F | OCH$_2$F | 3-CH$_3$ | CN | F |
| A-2201. | F | OCH$_2$F | 3-OCH$_3$ | CN | F |
| A-2202. | F | OCH$_2$F | 5-F | CN | F |
| A-2203. | F | OCH$_2$F | 5-CH$_3$ | CN | F |
| A-2204. | F | OCH$_2$F | 5-OCH$_3$ | CN | F |
| A-2205. | F | OCHF$_2$ | 3-F | CN | F |
| A-2206. | F | OCHF$_2$ | 3-CH$_3$ | CN | F |
| A-2207. | F | OCHF$_2$ | 3-OCH$_3$ | CN | F |
| A-2208. | F | OCHF$_2$ | 5-F | CN | F |
| A-2209. | F | OCHF$_2$ | 5-CH$_3$ | CN | F |
| A-2210. | F | OCHF$_2$ | 5-OCH$_3$ | CN | F |
| A-2211. | F | OCF$_3$ | 3-F | CN | F |
| A-2212. | F | OCF$_3$ | 3-CH$_3$ | CN | F |
| A-2213. | F | OCF$_3$ | 3-OCH$_3$ | CN | F |
| A-2214. | F | OCF$_3$ | 5-F | CN | F |
| A-2215. | F | OCF$_3$ | 5-CH$_3$ | CN | F |
| A-2216. | F | OCF$_3$ | 5-OCH$_3$ | CN | F |
| A-2217. | CH$_3$ | F | 3-F | CN | F |
| A-2218. | CH$_3$ | F | 3-CH$_3$ | CN | F |
| A-2219. | CH$_3$ | F | 3-OCH$_3$ | CN | F |
| A-2220. | CH$_3$ | F | 5-F | CN | F |
| A-2221. | CH$_3$ | F | 5-CH$_3$ | CN | F |
| A-2222. | CH$_3$ | F | 5-OCH$_3$ | CN | F |
| A-2223. | CH$_3$ | CH$_3$ | 3-F | CN | F |
| A-2224. | CH$_3$ | CH$_3$ | 3-CH$_3$ | CN | F |
| A-2225. | CH$_3$ | CH$_3$ | 3-OCH$_3$ | CN | F |
| A-2226. | CH$_3$ | CH$_3$ | 5-F | CN | F |
| A-2227. | CH$_3$ | CH$_3$ | 5-CH$_3$ | CN | F |
| A-2228. | CH$_3$ | CH$_3$ | 5-OCH$_3$ | CN | F |
| A-2229. | CH$_3$ | OCH$_3$ | 3-F | CN | F |
| A-2230. | CH$_3$ | OCH$_3$ | 3-CH$_3$ | CN | F |
| A-2231. | CH$_3$ | OCH$_3$ | 3-OCH$_3$ | CN | F |
| A-2232. | CH$_3$ | OCH$_3$ | 5-F | CN | F |
| A-2233. | CH$_3$ | OCH$_3$ | 5-CH$_3$ | CN | F |
| A-2234. | CH$_3$ | OCH$_3$ | 5-OCH$_3$ | CN | F |
| A-2235. | CH$_3$ | CN | 3-F | CN | F |
| A-2236. | CH$_3$ | CN | 3-CH$_3$ | CN | F |
| A-2237. | CH$_3$ | CN | 3-OCH$_3$ | CN | F |
| A-2238. | CH$_3$ | CN | 5-F | CN | F |
| A-2239. | CH$_3$ | CN | 5-CH$_3$ | CN | F |
| A-2240. | CH$_3$ | CN | 5-OCH$_3$ | CN | F |
| A-2241. | CH$_3$ | CH$_2$F | 3-F | CN | F |
| A-2242. | CH$_3$ | CH$_2$F | 3-CH$_3$ | CN | F |
| A-2243. | CH$_3$ | CH$_2$F | 3-OCH$_3$ | CN | F |
| A-2244. | CH$_3$ | CH$_2$F | 5-F | CN | F |
| A-2245. | CH$_3$ | CH$_2$F | 5-CH$_3$ | CN | F |
| A-2246. | CH$_3$ | CH$_2$F | 5-OCH$_3$ | CN | F |
| A-2247. | CH$_3$ | CHF$_2$ | 3-F | CN | F |
| A-2248. | CH$_3$ | CHF$_2$ | 3-CH$_3$ | CN | F |
| A-2249. | CH$_3$ | CHF$_2$ | 3-OCH$_3$ | CN | F |
| A-2250. | CH$_3$ | CHF$_2$ | 5-F | CN | F |
| A-2251. | CH$_3$ | CHF$_2$ | 5-CH$_3$ | CN | F |
| A-2252. | CH$_3$ | CHF$_2$ | 5-OCH$_3$ | CN | F |
| A-2253. | CH$_3$ | CF$_3$ | 3-F | CN | F |
| A-2254. | CH$_3$ | CF$_3$ | 3-CH$_3$ | CN | F |
| A-2255. | CH$_3$ | CF$_3$ | 3-OCH$_3$ | CN | F |
| A-2256. | CH$_3$ | CF$_3$ | 5-F | CN | F |
| A-2257. | CH$_3$ | CF$_3$ | 5-CH$_3$ | CN | F |
| A-2258. | CH$_3$ | CF$_3$ | 5-OCH$_3$ | CN | F |
| A-2259. | CH$_3$ | OCH$_2$F | 3-F | CN | F |
| A-2260. | CH$_3$ | OCH$_2$F | 3-CH$_3$ | CN | F |
| A-2261. | CH$_3$ | OCH$_2$F | 3-OCH$_3$ | CN | F |
| A-2262. | CH$_3$ | OCH$_2$F | 5-F | CN | F |
| A-2263. | CH$_3$ | OCH$_2$F | 5-CH$_3$ | CN | F |
| A-2264. | CH$_3$ | OCH$_2$F | 5-OCH$_3$ | CN | F |
| A-2265. | CH$_3$ | OCHF$_2$ | 3-F | CN | F |
| A-2266. | CH$_3$ | OCHF$_2$ | 3-CH$_3$ | CN | F |
| A-2267. | CH$_3$ | OCHF$_2$ | 3-OCH$_3$ | CN | F |
| A-2268. | CH$_3$ | OCHF$_2$ | 5-F | CN | F |
| A-2269. | CH$_3$ | OCHF$_2$ | 5-CH$_3$ | CN | F |
| A-2270. | CH$_3$ | OCHF$_2$ | 5-OCH$_3$ | CN | F |
| A-2271. | CH$_3$ | OCF$_3$ | 3-F | CN | F |
| A-2272. | CH$_3$ | OCF$_3$ | 3-CH$_3$ | CN | F |
| A-2273. | CH$_3$ | OCF$_3$ | 3-OCH$_3$ | CN | F |
| A-2274. | CH$_3$ | OCF$_3$ | 5-F | CN | F |
| A-2275. | CH$_3$ | OCF$_3$ | 5-CH$_3$ | CN | F |
| A-2276. | CH$_3$ | OCF$_3$ | 5-OCH$_3$ | CN | F |
| A-2277. | OCH$_3$ | F | 3-F | CN | F |
| A-2278. | OCH$_3$ | F | 3-CH$_3$ | CN | F |
| A-2279. | OCH$_3$ | F | 3-OCH$_3$ | CN | F |
| A-2280. | OCH$_3$ | F | 5-F | CN | F |
| A-2281. | OCH$_3$ | F | 5-CH$_3$ | CN | F |
| A-2282. | OCH$_3$ | F | 5-OCH$_3$ | CN | F |
| A-2283. | OCH$_3$ | CH$_3$ | 3-F | CN | F |
| A-2284. | OCH$_3$ | CH$_3$ | 3-CH$_3$ | CN | F |
| A-2285. | OCH$_3$ | CH$_3$ | 3-OCH$_3$ | CN | F |
| A-2286. | OCH$_3$ | CH$_3$ | 5-F | CN | F |
| A-2287. | OCH$_3$ | CH$_3$ | 5-CH$_3$ | CN | F |
| A-2288. | OCH$_3$ | CH$_3$ | 5-OCH$_3$ | CN | F |
| A-2289. | OCH$_3$ | OCH$_3$ | 3-F | CN | F |
| A-2290. | OCH$_3$ | OCH$_3$ | 3-CH$_3$ | CN | F |
| A-2291. | OCH$_3$ | OCH$_3$ | 3-OCH$_3$ | CN | F |
| A-2292. | OCH$_3$ | OCH$_3$ | 5-F | CN | F |
| A-2293. | OCH$_3$ | OCH$_3$ | 5-CH$_3$ | CN | F |
| A-2294. | OCH$_3$ | OCH$_3$ | 5-OCH$_3$ | CN | F |
| A-2295. | OCH$_3$ | CN | 3-F | CN | F |
| A-2296. | OCH$_3$ | CN | 3-CH$_3$ | CN | F |
| A-2297. | OCH$_3$ | CN | 3-OCH$_3$ | CN | F |
| A-2298. | OCH$_3$ | CN | 5-F | CN | F |
| A-2299. | OCH$_3$ | CN | 5-CH$_3$ | CN | F |
| A-2300. | OCH$_3$ | CN | 5-OCH$_3$ | CN | F |
| A-2301. | OCH$_3$ | CH$_2$F | 3-F | CN | F |
| A-2302. | OCH$_3$ | CH$_2$F | 3-CH$_3$ | CN | F |
| A-2303. | OCH$_3$ | CH$_2$F | 3-OCH$_3$ | CN | F |
| A-2304. | OCH$_3$ | CH$_2$F | 5-F | CN | F |
| A-2305. | OCH$_3$ | CH$_2$F | 5-CH$_3$ | CN | F |
| A-2306. | OCH$_3$ | CH$_2$F | 5-OCH$_3$ | CN | F |
| A-2307. | OCH$_3$ | CHF$_2$ | 3-F | CN | F |

TABLE A-continued

| Example No. | R¹ | R² | R³ | R⁶ | R⁷ |
|---|---|---|---|---|---|
| A-2308. | OCH₃ | CHF₂ | 3-CH₃ | CN | F |
| A-2309. | OCH₃ | CHF₂ | 3-OCH₃ | CN | F |
| A-2310. | OCH₃ | CHF₂ | 5-F | CN | F |
| A-2311. | OCH₃ | CHF₂ | 5-CH₃ | CN | F |
| A-2312. | OCH₃ | CHF₂ | 5-OCH₃ | CN | F |
| A-2313. | OCH₃ | CF₃ | 3-F | CN | F |
| A-2314. | OCH₃ | CF₃ | 3-CH₃ | CN | F |
| A-2315. | OCH₃ | CF₃ | 3-OCH₃ | CN | F |
| A-2316. | OCH₃ | CF₃ | 5-F | CN | F |
| A-2317. | OCH₃ | CF₃ | 5-CH₃ | CN | F |
| A-2318. | OCH₃ | CF₃ | 5-OCH₃ | CN | F |
| A-2319. | OCH₃ | OCH₂F | 3-F | CN | F |
| A-2320. | OCH₃ | OCH₂F | 3-CH₃ | CN | F |
| A-2321. | OCH₃ | OCH₂F | 3-OCH₃ | CN | F |
| A-2322. | OCH₃ | OCH₂F | 5-F | CN | F |
| A-2323. | OCH₃ | OCH₂F | 5-CH₃ | CN | F |
| A-2324. | OCH₃ | OCH₂F | 5-OCH₃ | CN | F |
| A-2325. | OCH₃ | OCHF₂ | 3-F | CN | F |
| A-2326. | OCH₃ | OCHF₂ | 3-CH₃ | CN | F |
| A-2327. | OCH₃ | OCHF₂ | 3-OCH₃ | CN | F |
| A-2328. | OCH₃ | OCHF₂ | 5-F | CN | F |
| A-2329. | OCH₃ | OCHF₂ | 5-CH₃ | CN | F |
| A-2330. | OCH₃ | OCHF₂ | 5-OCH₃ | CN | F |
| A-2331. | OCH₃ | OCF₃ | 3-F | CN | F |
| A-2332. | OCH₃ | OCF₃ | 3-CH₃ | CN | F |
| A-2333. | OCH₃ | OCF₃ | 3-OCH₃ | CN | F |
| A-2334. | OCH₃ | OCF₃ | 5-F | CN | F |
| A-2335. | OCH₃ | OCF₃ | 5-CH₃ | CN | F |
| A-2336. | OCH₃ | OCF₃ | 5-OCH₃ | CN | F |
| A-2337. | CH₂F | F | 3-F | CN | F |
| A-2338. | CH₂F | F | 3-CH₃ | CN | F |
| A-2339. | CH₂F | F | 3-OCH₃ | CN | F |
| A-2340. | CH₂F | F | 5-F | CN | F |
| A-2341. | CH₂F | F | 5-CH₃ | CN | F |
| A-2342. | CH₂F | F | 5-OCH₃ | CN | F |
| A-2343. | CH₂F | CH₃ | 3-F | CN | F |
| A-2344. | CH₂F | CH₃ | 3-CH₃ | CN | F |
| A-2345. | CH₂F | CH₃ | 3-OCH₃ | CN | F |
| A-2346. | CH₂F | CH₃ | 5-F | CN | F |
| A-2347. | CH₂F | CH₃ | 5-CH₃ | CN | F |
| A-2348. | CH₂F | CH₃ | 5-OCH₃ | CN | F |
| A-2349. | CH₂F | OCH₃ | 3-F | CN | F |
| A-2350. | CH₂F | OCH₃ | 3-CH₃ | CN | F |
| A-2351. | CH₂F | OCH₃ | 3-OCH₃ | CN | F |
| A-2352. | CH₂F | OCH₃ | 5-F | CN | F |
| A-2353. | CH₂F | OCH₃ | 5-CH₃ | CN | F |
| A-2354. | CH₂F | OCH₃ | 5-OCH₃ | CN | F |
| A-2355. | CH₂F | CN | 3-F | CN | F |
| A-2356. | CH₂F | CN | 3-CH₃ | CN | F |
| A-2357. | CH₂F | CN | 3-OCH₃ | CN | F |
| A-2358. | CH₂F | CN | 5-F | CN | F |
| A-2359. | CH₂F | CN | 5-CH₃ | CN | F |
| A-2360. | CH₂F | CN | 5-OCH₃ | CN | F |
| A-2361. | CH₂F | CH₂F | 3-F | CN | F |
| A-2362. | CH₂F | CH₂F | 3-CH₃ | CN | F |
| A-2363. | CH₂F | CH₂F | 3-OCH₃ | CN | F |
| A-2364. | CH₂F | CH₂F | 5-F | CN | F |
| A-2365. | CH₂F | CH₂F | 5-CH₃ | CN | F |
| A-2366. | CH₂F | CH₂F | 5-OCH₃ | CN | F |
| A-2367. | CH₂F | CHF₂ | 3-F | CN | F |
| A-2368. | CH₂F | CHF₂ | 3-CH₃ | CN | F |
| A-2369. | CH₂F | CHF₂ | 3-OCH₃ | CN | F |
| A-2370. | CH₂F | CHF₂ | 5-F | CN | F |
| A-2371. | CH₂F | CHF₂ | 5-CH₃ | CN | F |
| A-2372. | CH₂F | CHF₂ | 5-OCH₃ | CN | F |
| A-2373. | CH₂F | CF₃ | 3-F | CN | F |
| A-2374. | CH₂F | CF₃ | 3-CH₃ | CN | F |
| A-2375. | CH₂F | CF₃ | 3-OCH₃ | CN | F |
| A-2376. | CH₂F | CF₃ | 5-F | CN | F |
| A-2377. | CH₂F | CF₃ | 5-CH₃ | CN | F |
| A-2378. | CH₂F | CF₃ | 5-OCH₃ | CN | F |
| A-2379. | CH₂F | OCH₂F | 3-F | CN | F |
| A-2380. | CH₂F | OCH₂F | 3-CH₃ | CN | F |
| A-2381. | CH₂F | OCH₂F | 3-OCH₃ | CN | F |
| A-2382. | CH₂F | OCH₂F | 5-F | CN | F |
| A-2383. | CH₂F | OCH₂F | 5-CH₃ | CN | F |
| A-2384. | CH₂F | OCH₂F | 5-OCH₃ | CN | F |
| A-2385. | CH₂F | OCHF₂ | 3-F | CN | F |
| A-2386. | CH₂F | OCHF₂ | 3-CH₃ | CN | F |
| A-2387. | CH₂F | OCHF₂ | 3-OCH₃ | CN | F |
| A-2388. | CH₂F | OCHF₂ | 5-F | CN | F |
| A-2389. | CH₂F | OCHF₂ | 5-CH₃ | CN | F |
| A-2390. | CH₂F | OCHF₂ | 5-OCH₃ | CN | F |
| A-2391. | CH₂F | OCF₃ | 3-F | CN | F |
| A-2392. | CH₂F | OCF₃ | 3-CH₃ | CN | F |
| A-2393. | CH₂F | OCF₃ | 3-OCH₃ | CN | F |
| A-2394. | CH₂F | OCF₃ | 5-F | CN | F |
| A-2395. | CH₂F | OCF₃ | 5-CH₃ | CN | F |
| A-2396. | CH₂F | OCF₃ | 5-OCH₃ | CN | F |
| A-2397. | CHF₂ | F | 3-F | CN | F |
| A-2398. | CHF₂ | F | 3-CH₃ | CN | F |
| A-2399. | CHF₂ | F | 3-OCH₃ | CN | F |
| A-2400. | CHF₂ | F | 5-F | CN | F |
| A-2401. | CHF₂ | F | 5-CH₃ | CN | F |
| A-2402. | CHF₂ | F | 5-OCH₃ | CN | F |
| A-2403. | CHF₂ | CH₃ | 3-F | CN | F |
| A-2404. | CHF₂ | CH₃ | 3-CH₃ | CN | F |
| A-2405. | CHF₂ | CH₃ | 3-OCH₃ | CN | F |
| A-2406. | CHF₂ | CH₃ | 5-F | CN | F |
| A-2407. | CHF₂ | CH₃ | 5-CH₃ | CN | F |
| A-2408. | CHF₂ | CH₃ | 5-OCH₃ | CN | F |
| A-2409. | CHF₂ | OCH₃ | 3-F | CN | F |
| A-2410. | CHF₂ | OCH₃ | 3-CH₃ | CN | F |
| A-2411. | CHF₂ | OCH₃ | 3-OCH₃ | CN | F |
| A-2412. | CHF₂ | OCH₃ | 5-F | CN | F |
| A-2413. | CHF₂ | OCH₃ | 5-CH₃ | CN | F |
| A-2414. | CHF₂ | OCH₃ | 5-OCH₃ | CN | F |
| A-2415. | CHF₂ | CN | 3-F | CN | F |
| A-2416. | CHF₂ | CN | 3-CH₃ | CN | F |
| A-2417. | CHF₂ | CN | 3-OCH₃ | CN | F |
| A-2418. | CHF₂ | CN | 5-F | CN | F |
| A-2419. | CHF₂ | CN | 5-CH₃ | CN | F |
| A-2420. | CHF₂ | CN | 5-OCH₃ | CN | F |
| A-2421. | CHF₂ | CH₂F | 3-F | CN | F |
| A-2422. | CHF₂ | CH₂F | 3-CH₃ | CN | F |
| A-2423. | CHF₂ | CH₂F | 3-OCH₃ | CN | F |
| A-2424. | CHF₂ | CH₂F | 5-F | CN | F |
| A-2425. | CHF₂ | CH₂F | 5-CH₃ | CN | F |
| A-2426. | CHF₂ | CH₂F | 5-OCH₃ | CN | F |
| A-2427. | CHF₂ | CHF₂ | 3-F | CN | F |
| A-2428. | CHF₂ | CHF₂ | 3-CH₃ | CN | F |
| A-2429. | CHF₂ | CHF₂ | 3-OCH₃ | CN | F |
| A-2430. | CHF₂ | CHF₂ | 5-F | CN | F |
| A-2431. | CHF₂ | CHF₂ | 5-CH₃ | CN | F |
| A-2432. | CHF₂ | CHF₂ | 5-OCH₃ | CN | F |
| A-2433. | CHF₂ | CF₃ | 3-F | CN | F |
| A-2434. | CHF₂ | CF₃ | 3-CH₃ | CN | F |
| A-2435. | CHF₂ | CF₃ | 3-OCH₃ | CN | F |
| A-2436. | CHF₂ | CF₃ | 5-F | CN | F |
| A-2437. | CHF₂ | CF₃ | 5-CH₃ | CN | F |
| A-2438. | CHF₂ | CF₃ | 5-OCH₃ | CN | F |
| A-2439. | CHF₂ | OCH₂F | 3-F | CN | F |
| A-2440. | CHF₂ | OCH₂F | 3-CH₃ | CN | F |
| A-2441. | CHF₂ | OCH₂F | 3-OCH₃ | CN | F |
| A-2442. | CHF₂ | OCH₂F | 5-F | CN | F |
| A-2443. | CHF₂ | OCH₂F | 5-CH₃ | CN | F |
| A-2444. | CHF₂ | OCH₂F | 5-OCH₃ | CN | F |
| A-2445. | CHF₂ | OCHF₂ | 3-F | CN | F |
| A-2446. | CHF₂ | OCHF₂ | 3-CH₃ | CN | F |
| A-2447. | CHF₂ | OCHF₂ | 3-OCH₃ | CN | F |
| A-2448. | CHF₂ | OCHF₂ | 5-F | CN | F |
| A-2449. | CHF₂ | OCHF₂ | 5-CH₃ | CN | F |
| A-2450. | CHF₂ | OCHF₂ | 5-OCH₃ | CN | F |
| A-2451. | CHF₂ | OCF₃ | 3-F | CN | F |
| A-2452. | CHF₂ | OCF₃ | 3-CH₃ | CN | F |
| A-2453. | CHF₂ | OCF₃ | 3-OCH₃ | CN | F |
| A-2454. | CHF₂ | OCF₃ | 5-F | CN | F |
| A-2455. | CHF₂ | OCF₃ | 5-CH₃ | CN | F |
| A-2456. | CHF₂ | OCF₃ | 5-OCH₃ | CN | F |
| A-2457. | CF₃ | F | 3-F | CN | F |
| A-2458. | CF₃ | F | 3-CH₃ | CN | F |
| A-2459. | CF₃ | F | 3-OCH₃ | CN | F |
| A-2460. | CF₃ | F | 5-F | CN | F |
| A-2461. | CF₃ | F | 5-CH₃ | CN | F |
| A-2462. | CF₃ | F | 5-OCH₃ | CN | F |
| A-2463. | CF₃ | CH₃ | 3-F | CN | F |

TABLE A-continued

| Example No. | R¹ | R² | R³ | R⁶ | R⁷ |
|---|---|---|---|---|---|
| A-2464. | $CF_3$ | $CH_3$ | 3-$CH_3$ | CN | F |
| A-2465. | $CF_3$ | $CH_3$ | 3-$OCH_3$ | CN | F |
| A-2466. | $CF_3$ | $CH_3$ | 5-F | CN | F |
| A-2467. | $CF_3$ | $CH_3$ | 5-$CH_3$ | CN | F |
| A-2468. | $CF_3$ | $CH_3$ | 5-$OCH_3$ | CN | F |
| A-2469. | $CF_3$ | $OCH_3$ | 3-F | CN | F |
| A-2470. | $CF_3$ | $OCH_3$ | 3-$CH_3$ | CN | F |
| A-2471. | $CF_3$ | $OCH_3$ | 3-$OCH_3$ | CN | F |
| A-2472. | $CF_3$ | $OCH_3$ | 5-F | CN | F |
| A-2473. | $CF_3$ | $OCH_3$ | 5-$CH_3$ | CN | F |
| A-2474. | $CF_3$ | $OCH_3$ | 5-$OCH_3$ | CN | F |
| A-2475. | $CF_3$ | CN | 3-F | CN | F |
| A-2476. | $CF_3$ | CN | 3-$CH_3$ | CN | F |
| A-2477. | $CF_3$ | CN | 3-$OCH_3$ | CN | F |
| A-2478. | $CF_3$ | CN | 5-F | CN | F |
| A-2479. | $CF_3$ | CN | 5-$CH_3$ | CN | F |
| A-2480. | $CF_3$ | CN | 5-$OCH_3$ | CN | F |
| A-2481. | $CF_3$ | $CH_2F$ | 3-F | CN | F |
| A-2482. | $CF_3$ | $CH_2F$ | 3-$CH_3$ | CN | F |
| A-2483. | $CF_3$ | $CH_2F$ | 3-$OCH_3$ | CN | F |
| A-2484. | $CF_3$ | $CH_2F$ | 5-F | CN | F |
| A-2485. | $CF_3$ | $CH_2F$ | 5-$CH_3$ | CN | F |
| A-2486. | $CF_3$ | $CH_2F$ | 5-$OCH_3$ | CN | F |
| A-2487. | $CF_3$ | $CHF_2$ | 3-F | CN | F |
| A-2488. | $CF_3$ | $CHF_2$ | 3-$CH_3$ | CN | F |
| A-2489. | $CF_3$ | $CHF_2$ | 3-$OCH_3$ | CN | F |
| A-2490. | $CF_3$ | $CHF_2$ | 5-F | CN | F |
| A-2491. | $CF_3$ | $CHF_2$ | 5-$CH_3$ | CN | F |
| A-2492. | $CF_3$ | $CHF_2$ | 5-$OCH_3$ | CN | F |
| A-2493. | $CF_3$ | $CF_3$ | 3-F | CN | F |
| A-2494. | $CF_3$ | $CF_3$ | 3-$CH_3$ | CN | F |
| A-2495. | $CF_3$ | $CF_3$ | 3-$OCH_3$ | CN | F |
| A-2496. | $CF_3$ | $CF_3$ | 5-F | CN | F |
| A-2497. | $CF_3$ | $CF_3$ | 5-$CH_3$ | CN | F |
| A-2498. | $CF_3$ | $CF_3$ | 5-$OCH_3$ | CN | F |
| A-2499. | $CF_3$ | $OCH_2F$ | 3-F | CN | F |
| A-2500. | $CF_3$ | $OCH_2F$ | 3-$CH_3$ | CN | F |
| A-2501. | $CF_3$ | $OCH_2F$ | 3-$OCH_3$ | CN | F |
| A-2502. | $CF_3$ | $OCH_2F$ | 5-F | CN | F |
| A-2503. | $CF_3$ | $OCH_2F$ | 5-$CH_3$ | CN | F |
| A-2504. | $CF_3$ | $OCH_2F$ | 5-$OCH_3$ | CN | F |
| A-2505. | $CF_3$ | $OCHF_2$ | 3-F | CN | F |
| A-2506. | $CF_3$ | $OCHF_2$ | 3-$CH_3$ | CN | F |
| A-2507. | $CF_3$ | $OCHF_2$ | 3-$OCH_3$ | CN | F |
| A-2508. | $CF_3$ | $OCHF_2$ | 5-F | CN | F |
| A-2509. | $CF_3$ | $OCHF_2$ | 5-$CH_3$ | CN | F |
| A-2510. | $CF_3$ | $OCHF_2$ | 5-$OCH_3$ | CN | F |
| A-2511. | $CF_3$ | $OCF_3$ | 3-F | CN | F |
| A-2512. | $CF_3$ | $OCF_3$ | 3-$CH_3$ | CN | F |
| A-2513. | $CF_3$ | $OCF_3$ | 3-$OCH_3$ | CN | F |
| A-2514. | $CF_3$ | $OCF_3$ | 5-F | CN | F |
| A-2515. | $CF_3$ | $OCF_3$ | 5-$CH_3$ | CN | F |
| A-2516. | $CF_3$ | $OCF_3$ | 5-$OCH_3$ | CN | F |
| A-2517. | $OCH_2F$ | F | 3-F | CN | F |
| A-2518. | $OCH_2F$ | F | 3-$CH_3$ | CN | F |
| A-2519. | $OCH_2F$ | F | 3-$OCH_3$ | CN | F |
| A-2520. | $OCH_2F$ | F | 5-F | CN | F |
| A-2521. | $OCH_2F$ | F | 5-$CH_3$ | CN | F |
| A-2522. | $OCH_2F$ | F | 5-$OCH_3$ | CN | F |
| A-2523. | $OCH_2F$ | $CH_3$ | 3-F | CN | F |
| A-2524. | $OCH_2F$ | $CH_3$ | 3-$CH_3$ | CN | F |
| A-2525. | $OCH_2F$ | $CH_3$ | 3-$OCH_3$ | CN | F |
| A-2526. | $OCH_2F$ | $CH_3$ | 5-F | CN | F |
| A-2527. | $OCH_2F$ | $CH_3$ | 5-$CH_3$ | CN | F |
| A-2528. | $OCH_2F$ | $CH_3$ | 5-$OCH_3$ | CN | F |
| A-2529. | $OCH_2F$ | $OCH_3$ | 3-F | CN | F |
| A-2530. | $OCH_2F$ | $OCH_3$ | 3-$CH_3$ | CN | F |
| A-2531. | $OCH_2F$ | $OCH_3$ | 3-$OCH_3$ | CN | F |
| A-2532. | $OCH_2F$ | $OCH_3$ | 5-F | CN | F |
| A-2533. | $OCH_2F$ | $OCH_3$ | 5-$CH_3$ | CN | F |
| A-2534. | $OCH_2F$ | $OCH_3$ | 5-$OCH_3$ | CN | F |
| A-2535. | $OCH_2F$ | CN | 3-F | CN | F |
| A-2536. | $OCH_2F$ | CN | 3-$CH_3$ | CN | F |
| A-2537. | $OCH_2F$ | CN | 3-$OCH_3$ | CN | F |
| A-2538. | $OCH_2F$ | CN | 5-F | CN | F |
| A-2539. | $OCH_2F$ | CN | 5-$CH_3$ | CN | F |
| A-2540. | $OCH_2F$ | CN | 5-$OCH_3$ | CN | F |
| A-2541. | $OCH_2F$ | $CH_2F$ | 3-F | CN | F |
| A-2542. | $OCH_2F$ | $CH_2F$ | 3-$CH_3$ | CN | F |
| A-2543. | $OCH_2F$ | $CH_2F$ | 3-$OCH_3$ | CN | F |
| A-2544. | $OCH_2F$ | $CH_2F$ | 5-F | CN | F |
| A-2545. | $OCH_2F$ | $CH_2F$ | 5-$CH_3$ | CN | F |
| A-2546. | $OCH_2F$ | $CH_2F$ | 5-$OCH_3$ | CN | F |
| A-2547. | $OCH_2F$ | $CHF_2$ | 3-F | CN | F |
| A-2548. | $OCH_2F$ | $CHF_2$ | 3-$CH_3$ | CN | F |
| A-2549. | $OCH_2F$ | $CHF_2$ | 3-$OCH_3$ | CN | F |
| A-2550. | $OCH_2F$ | $CHF_2$ | 5-F | CN | F |
| A-2551. | $OCH_2F$ | $CHF_2$ | 5-$CH_3$ | CN | F |
| A-2552. | $OCH_2F$ | $CHF_2$ | 5-$OCH_3$ | CN | F |
| A-2553. | $OCH_2F$ | $CF_3$ | 3-F | CN | F |
| A-2554. | $OCH_2F$ | $CF_3$ | 3-$CH_3$ | CN | F |
| A-2555. | $OCH_2F$ | $CF_3$ | 3-$OCH_3$ | CN | F |
| A-2556. | $OCH_2F$ | $CF_3$ | 5-F | CN | F |
| A-2557. | $OCH_2F$ | $CF_3$ | 5-$CH_3$ | CN | F |
| A-2558. | $OCH_2F$ | $CF_3$ | 5-$OCH_3$ | CN | F |
| A-2559. | $OCH_2F$ | $OCH_2F$ | 3-F | CN | F |
| A-2560. | $OCH_2F$ | $OCH_2F$ | 3-$CH_3$ | CN | F |
| A-2561. | $OCH_2F$ | $OCH_2F$ | 3-$OCH_3$ | CN | F |
| A-2562. | $OCH_2F$ | $OCH_2F$ | 5-F | CN | F |
| A-2563. | $OCH_2F$ | $OCH_2F$ | 5-$CH_3$ | CN | F |
| A-2564. | $OCH_2F$ | $OCH_2F$ | 5-$OCH_3$ | CN | F |
| A-2565. | $OCH_2F$ | $OCHF_2$ | 3-F | CN | F |
| A-2566. | $OCH_2F$ | $OCHF_2$ | 3-$CH_3$ | CN | F |
| A-2567. | $OCH_2F$ | $OCHF_2$ | 3-$OCH_3$ | CN | F |
| A-2568. | $OCH_2F$ | $OCHF_2$ | 5-F | CN | F |
| A-2569. | $OCH_2F$ | $OCHF_2$ | 5-$CH_3$ | CN | F |
| A-2570. | $OCH_2F$ | $OCHF_2$ | 5-$OCH_3$ | CN | F |
| A-2571. | $OCH_2F$ | $OCF_3$ | 3-F | CN | F |
| A-2572. | $OCH_2F$ | $OCF_3$ | 3-$CH_3$ | CN | F |
| A-2573. | $OCH_2F$ | $OCF_3$ | 3-$OCH_3$ | CN | F |
| A-2574. | $OCH_2F$ | $OCF_3$ | 5-F | CN | F |
| A-2575. | $OCH_2F$ | $OCF_3$ | 5-$CH_3$ | CN | F |
| A-2576. | $OCH_2F$ | $OCF_3$ | 5-$OCH_3$ | CN | F |
| A-2577. | $OCHF_2$ | F | 3-F | CN | F |
| A-2578. | $OCHF_2$ | F | 3-$CH_3$ | CN | F |
| A-2579. | $OCHF_2$ | F | 3-$OCH_3$ | CN | F |
| A-2580. | $OCHF_2$ | F | 5-F | CN | F |
| A-2581. | $OCHF_2$ | F | 5-$CH_3$ | CN | F |
| A-2582. | $OCHF_2$ | F | 5-$OCH_3$ | CN | F |
| A-2583. | $OCHF_2$ | $CH_3$ | 3-F | CN | F |
| A-2584. | $OCHF_2$ | $CH_3$ | 3-$CH_3$ | CN | F |
| A-2585. | $OCHF_2$ | $CH_3$ | 3-$OCH_3$ | CN | F |
| A-2586. | $OCHF_2$ | $CH_3$ | 5-F | CN | F |
| A-2587. | $OCHF_2$ | $CH_3$ | 5-$CH_3$ | CN | F |
| A-2588. | $OCHF_2$ | $CH_3$ | 5-$OCH_3$ | CN | F |
| A-2589. | $OCHF_2$ | $OCH_3$ | 3-F | CN | F |
| A-2590. | $OCHF_2$ | $OCH_3$ | 3-$CH_3$ | CN | F |
| A-2591. | $OCHF_2$ | $OCH_3$ | 3-$OCH_3$ | CN | F |
| A-2592. | $OCHF_2$ | $OCH_3$ | 5-F | CN | F |
| A-2593. | $OCHF_2$ | $OCH_3$ | 5-$CH_3$ | CN | F |
| A-2594. | $OCHF_2$ | $OCH_3$ | 5-$OCH_3$ | CN | F |
| A-2595. | $OCHF_2$ | CN | 3-F | CN | F |
| A-2596. | $OCHF_2$ | CN | 3-$CH_3$ | CN | F |
| A-2597. | $OCHF_2$ | CN | 3-$OCH_3$ | CN | F |
| A-2598. | $OCHF_2$ | CN | 5-F | CN | F |
| A-2599. | $OCHF_2$ | CN | 5-$CH_3$ | CN | F |
| A-2600. | $OCHF_2$ | CN | 5-$OCH_3$ | CN | F |
| A-2601. | $OCHF_2$ | $CH_2F$ | 3-F | CN | F |
| A-2602. | $OCHF_2$ | $CH_2F$ | 3-$CH_3$ | CN | F |
| A-2603. | $OCHF_2$ | $CH_2F$ | 3-$OCH_3$ | CN | F |
| A-2604. | $OCHF_2$ | $CH_2F$ | 5-F | CN | F |
| A-2605. | $OCHF_2$ | $CH_2F$ | 5-$CH_3$ | CN | F |
| A-2606. | $OCHF_2$ | $CH_2F$ | 5-$OCH_3$ | CN | F |
| A-2607. | $OCHF_2$ | $CHF_2$ | 3-F | CN | F |
| A-2608. | $OCHF_2$ | $CHF_2$ | 3-$CH_3$ | CN | F |
| A-2609. | $OCHF_2$ | $CHF_2$ | 3-$OCH_3$ | CN | F |
| A-2610. | $OCHF_2$ | $CHF_2$ | 5-F | CN | F |
| A-2611. | $OCHF_2$ | $CHF_2$ | 5-$CH_3$ | CN | F |
| A-2612. | $OCHF_2$ | $CHF_2$ | 5-$OCH_3$ | CN | F |
| A-2613. | $OCHF_2$ | $CF_3$ | 3-F | CN | F |
| A-2614. | $OCHF_2$ | $CF_3$ | 3-$CH_3$ | CN | F |
| A-2615. | $OCHF_2$ | $CF_3$ | 3-$OCH_3$ | CN | F |
| A-2616. | $OCHF_2$ | $CF_3$ | 5-F | CN | F |
| A-2617. | $OCHF_2$ | $CF_3$ | 5-$CH_3$ | CN | F |
| A-2618. | $OCHF_2$ | $CF_3$ | 5-$OCH_3$ | CN | F |
| A-2619. | $OCHF_2$ | $OCH_2F$ | 3-F | CN | F |

TABLE A-continued

| Example No. | R¹ | R² | R³ | R⁶ | R⁷ |
|---|---|---|---|---|---|
| A-2620. | OCHF₂ | OCH₂F | 3-CH₃ | CN | F |
| A-2621. | OCHF₂ | OCH₂F | 3-OCH₃ | CN | F |
| A-2622. | OCHF₂ | OCH₂F | 5-F | CN | F |
| A-2623. | OCHF₂ | OCH₂F | 5-CH₃ | CN | F |
| A-2624. | OCHF₂ | OCH₂F | 5-OCH₃ | CN | F |
| A-2625. | OCHF₂ | OCHF₂ | 3-F | CN | F |
| A-2626. | OCHF₂ | OCHF₂ | 3-CH₃ | CN | F |
| A-2627. | OCHF₂ | OCHF₂ | 3-OCH₃ | CN | F |
| A-2628. | OCHF₂ | OCHF₂ | 5-F | CN | F |
| A-2629. | OCHF₂ | OCHF₂ | 5-CH₃ | CN | F |
| A-2630. | OCHF₂ | OCHF₂ | 5-OCH₃ | CN | F |
| A-2631. | OCHF₂ | OCF₃ | 3-F | CN | F |
| A-2632. | OCHF₂ | OCF₃ | 3-CH₃ | CN | F |
| A-2633. | OCHF₂ | OCF₃ | 3-OCH₃ | CN | F |
| A-2634. | OCHF₂ | OCF₃ | 5-F | CN | F |
| A-2635. | OCHF₂ | OCF₃ | 5-CH₃ | CN | F |
| A-2636. | OCHF₂ | OCF₃ | 5-OCH₃ | CN | F |
| A-2637. | OCF₃ | F | 3-F | CN | F |
| A-2638. | OCF₃ | F | 3-CH₃ | CN | F |
| A-2639. | OCF₃ | F | 3-OCH₃ | CN | F |
| A-2640. | OCF₃ | F | 5-F | CN | F |
| A-2641. | OCF₃ | F | 5-CH₃ | CN | F |
| A-2642. | OCF₃ | F | 5-OCH₃ | CN | F |
| A-2643. | OCF₃ | CH₃ | 3-F | CN | F |
| A-2644. | OCF₃ | CH₃ | 3-CH₃ | CN | F |
| A-2645. | OCF₃ | CH₃ | 3-OCH₃ | CN | F |
| A-2646. | OCF₃ | CH₃ | 5-F | CN | F |
| A-2647. | OCF₃ | CH₃ | 5-CH₃ | CN | F |
| A-2648. | OCF₃ | CH₃ | 5-OCH₃ | CN | F |
| A-2649. | OCF₃ | OCH₃ | 3-F | CN | F |
| A-2650. | OCF₃ | OCH₃ | 3-CH₃ | CN | F |
| A-2651. | OCF₃ | OCH₃ | 3-OCH₃ | CN | F |
| A-2652. | OCF₃ | OCH₃ | 5-F | CN | F |
| A-2653. | OCF₃ | OCH₃ | 5-CH₃ | CN | F |
| A-2654. | OCF₃ | OCH₃ | 5-OCH₃ | CN | F |
| A-2655. | OCF₃ | CN | 3-F | CN | F |
| A-2656. | OCF₃ | CN | 3-CH₃ | CN | F |
| A-2657. | OCF₃ | CN | 3-OCH₃ | CN | F |
| A-2658. | OCF₃ | CN | 5-F | CN | F |
| A-2659. | OCF₃ | CN | 5-CH₃ | CN | F |
| A-2660. | OCF₃ | CN | 5-OCH₃ | CN | F |
| A-2661. | OCF₃ | CH₂F | 3-F | CN | F |
| A-2662. | OCF₃ | CH₂F | 3-CH₃ | CN | F |
| A-2663. | OCF₃ | CH₂F | 3-OCH₃ | CN | F |
| A-2664. | OCF₃ | CH₂F | 5-F | CN | F |
| A-2665. | OCF₃ | CH₂F | 5-CH₃ | CN | F |
| A-2666. | OCF₃ | CH₂F | 5-OCH₃ | CN | F |
| A-2667. | OCF₃ | CHF₂ | 3-F | CN | F |
| A-2668. | OCF₃ | CHF₂ | 3-CH₃ | CN | F |
| A-2669. | OCF₃ | CHF₂ | 3-OCH₃ | CN | F |
| A-2670. | OCF₃ | CHF₂ | 5-F | CN | F |
| A-2671. | OCF₃ | CHF₂ | 5-CH₃ | CN | F |
| A-2672. | OCF₃ | CHF₂ | 5-OCH₃ | CN | F |
| A-2673. | OCF₃ | CF₃ | 3-F | CN | F |
| A-2674. | OCF₃ | CF₃ | 3-CH₃ | CN | F |
| A-2675. | OCF₃ | CF₃ | 3-OCH₃ | CN | F |
| A-2676. | OCF₃ | CF₃ | 5-F | CN | F |
| A-2677. | OCF₃ | CF₃ | 5-CH₃ | CN | F |
| A-2678. | OCF₃ | CF₃ | 5-OCH₃ | CN | F |
| A-2679. | OCF₃ | OCH₂F | 3-F | CN | F |
| A-2680. | OCF₃ | OCH₂F | 3-CH₃ | CN | F |
| A-2681. | OCF₃ | OCH₂F | 3-OCH₃ | CN | F |
| A-2682. | OCF₃ | OCH₂F | 5-F | CN | F |
| A-2683. | OCF₃ | OCH₂F | 5-CH₃ | CN | F |
| A-2684. | OCF₃ | OCH₂F | 5-OCH₃ | CN | F |
| A-2685. | OCF₃ | OCHF₂ | 3-F | CN | F |
| A-2686. | OCF₃ | OCHF₂ | 3-CH₃ | CN | F |
| A-2687. | OCF₃ | OCHF₂ | 3-OCH₃ | CN | F |
| A-2688. | OCF₃ | OCHF₂ | 5-F | CN | F |
| A-2689. | OCF₃ | OCHF₂ | 5-CH₃ | CN | F |
| A-2690. | OCF₃ | OCHF₂ | 5-OCH₃ | CN | F |
| A-2691. | OCF₃ | OCF₃ | 3-F | CN | F |
| A-2692. | OCF₃ | OCF₃ | 3-CH₃ | CN | F |
| A-2693. | OCF₃ | OCF₃ | 3-OCH₃ | CN | F |
| A-2694. | OCF₃ | OCF₃ | 5-F | CN | F |
| A-2695. | OCF₃ | OCF₃ | 5-CH₃ | CN | F |
| A-2696. | OCF₃ | OCF₃ | 5-OCH₃ | CN | F |
| A-2697. | H | H | H | F | F |
| A-2698. | F | H | H | F | F |
| A-2699. | CH₃ | H | H | F | F |
| A-2700. | OCH₃ | H | H | F | F |
| A-2701. | CH₂F | H | H | F | F |
| A-2702. | CHF₂ | H | H | F | F |
| A-2703. | CF₃ | H | H | F | F |
| A-2704. | OCH₂F | H | H | F | F |
| A-2705. | OCHF₂ | H | H | F | F |
| A-2706. | OCF₃ | H | H | F | F |
| A-2707. | H | F | H | F | F |
| A-2708. | H | CH₃ | H | F | F |
| A-2709. | H | OCH₃ | H | F | F |
| A-2710. | H | CN | H | F | F |
| A-2711. | H | CH₂F | H | F | F |
| A-2712. | H | CHF₂ | H | F | F |
| A-2713. | H | CF₃ | H | F | F |
| A-2714. | H | OCH₂F | H | F | F |
| A-2715. | H | OCHF₂ | H | F | F |
| A-2716. | H | OCF₃ | H | F | F |
| A-2717. | H | H | 3-F | F | F |
| A-2718. | H | H | 3-CH₃ | F | F |
| A-2719. | H | H | 3-OCH₃ | F | F |
| A-2720. | H | H | 5-F | F | F |
| A-2721. | H | H | 5-CH₃ | F | F |
| A-2722. | H | H | 5-OCH₃ | F | F |
| A-2723. | F | F | H | F | F |
| A-2724. | F | CH₃ | H | F | F |
| A-2725. | F | OCH₃ | H | F | F |
| A-2726. | F | CN | H | F | F |
| A-2727. | F | CH₂F | H | F | F |
| A-2728. | F | CHF₂ | H | F | F |
| A-2729. | F | CF₃ | H | F | F |
| A-2730. | F | OCH₂F | H | F | F |
| A-2731. | F | OCHF₂ | H | F | F |
| A-2732. | F | OCF₃ | H | F | F |
| A-2733. | F | H | 3-F | F | F |
| A-2734. | F | H | 3-CH₃ | F | F |
| A-2735. | F | H | 3-OCH₃ | F | F |
| A-2736. | F | H | 5-F | F | F |
| A-2737. | F | H | 5-CH₃ | F | F |
| A-2738. | F | H | 5-OCH₃ | F | F |
| A-2739. | CH₃ | F | H | F | F |
| A-2740. | CH₃ | CH₃ | H | F | F |
| A-2741. | CH₃ | OCH₃ | H | F | F |
| A-2742. | CH₃ | CN | H | F | F |
| A-2743. | CH₃ | CH₂F | H | F | F |
| A-2744. | CH₃ | CHF₂ | H | F | F |
| A-2745. | CH₃ | CF₃ | H | F | F |
| A-2746. | CH₃ | OCH₂F | H | F | F |
| A-2747. | CH₃ | OCHF₂ | H | F | F |
| A-2748. | CH₃ | OCF₃ | H | F | F |
| A-2749. | CH₃ | H | 3-F | F | F |
| A-2750. | CH₃ | H | 3-CH₃ | F | F |
| A-2751. | CH₃ | H | 3-OCH₃ | F | F |
| A-2752. | CH₃ | H | 5-F | F | F |
| A-2753. | CH₃ | H | 5-CH₃ | F | F |
| A-2754. | CH₃ | H | 5-OCH₃ | F | F |
| A-2755. | OCH₃ | F | H | F | F |
| A-2756. | OCH₃ | CH₃ | H | F | F |
| A-2757. | OCH₃ | OCH₃ | H | F | F |
| A-2758. | OCH₃ | CN | H | F | F |
| A-2759. | OCH₃ | CH₂F | H | F | F |
| A-2760. | OCH₃ | CHF₂ | H | F | F |
| A-2761. | OCH₃ | CF₃ | H | F | F |
| A-2762. | OCH₃ | OCH₂F | H | F | F |
| A-2763. | OCH₃ | OCHF₂ | H | F | F |
| A-2764. | OCH₃ | OCF₃ | H | F | F |
| A-2765. | OCH₃ | H | 3-F | F | F |
| A-2766. | OCH₃ | H | 3-CH₃ | F | F |
| A-2767. | OCH₃ | H | 3-OCH₃ | F | F |
| A-2768. | OCH₃ | H | 5-F | F | F |
| A-2769. | OCH₃ | H | 5-CH₃ | F | F |
| A-2770. | OCH₃ | H | 5-OCH₃ | F | F |
| A-2771. | H | F | 3-F | F | F |
| A-2772. | H | F | 3-CH₃ | F | F |
| A-2773. | H | F | 3-OCH₃ | F | F |
| A-2774. | H | F | 5-F | F | F |
| A-2775. | H | F | 5-CH₃ | F | F |

TABLE A-continued

| Example No. | $R^1$ | $R^2$ | $R^3$ | $R^6$ | $R^7$ |
|---|---|---|---|---|---|
| A-2776. | H | F | 5-OCH$_3$ | F | F |
| A-2777. | H | CH$_3$ | 3-F | F | F |
| A-2778. | H | CH$_3$ | 3-CH$_3$ | F | F |
| A-2779. | H | CH$_3$ | 3-OCH$_3$ | F | F |
| A-2780. | H | CH$_3$ | 5-F | F | F |
| A-2781. | H | CH$_3$ | 5-CH$_3$ | F | F |
| A-2782. | H | CH$_3$ | 5-OCH$_3$ | F | F |
| A-2783. | H | OCH$_3$ | 3-F | F | F |
| A-2784. | H | OCH$_3$ | 3-CH$_3$ | F | F |
| A-2785. | H | OCH$_3$ | 3-OCH$_3$ | F | F |
| A-2786. | H | OCH$_3$ | 5-F | F | F |
| A-2787. | H | OCH$_3$ | 5-CH$_3$ | F | F |
| A-2788. | H | OCH$_3$ | 5-OCH$_3$ | F | F |
| A-2789. | H | CN | 3-F | F | F |
| A-2790. | H | CN | 3-CH$_3$ | F | F |
| A-2791. | H | CN | 3-OCH$_3$ | F | F |
| A-2792. | H | CN | 5-F | F | F |
| A-2793. | H | CN | 5-CH$_3$ | F | F |
| A-2794. | H | CN | 5-OCH$_3$ | F | F |
| A-2795. | H | CH$_2$F | 3-F | F | F |
| A-2796. | H | CH$_2$F | 3-CH$_3$ | F | F |
| A-2797. | H | CH$_2$F | 3-OCH$_3$ | F | F |
| A-2798. | H | CH$_2$F | 5-F | F | F |
| A-2799. | H | CH$_2$F | 5-CH$_3$ | F | F |
| A-2800. | H | CH$_2$F | 5-OCH$_3$ | F | F |
| A-2801. | H | CHF$_2$ | 3-F | F | F |
| A-2802. | H | CHF$_2$ | 3-CH$_3$ | F | F |
| A-2803. | H | CHF$_2$ | 3-OCH$_3$ | F | F |
| A-2804. | H | CHF$_2$ | 5-F | F | F |
| A-2805. | H | CHF$_2$ | 5-CH$_3$ | F | F |
| A-2806. | H | CHF$_2$ | 5-OCH$_3$ | F | F |
| A-2807. | H | CF$_3$ | 3-F | F | F |
| A-2808. | H | CF$_3$ | 3-CH$_3$ | F | F |
| A-2809. | H | CF$_3$ | 3-OCH$_3$ | F | F |
| A-2810. | H | CF$_3$ | 5-F | F | F |
| A-2811. | H | CF$_3$ | 5-CH$_3$ | F | F |
| A-2812. | H | CF$_3$ | 5-OCH$_3$ | F | F |
| A-2813. | H | OCH$_2$F | 3-F | F | F |
| A-2814. | H | OCH$_2$F | 3-CH$_3$ | F | F |
| A-2815. | H | OCH$_2$F | 3-OCH$_3$ | F | F |
| A-2816. | H | OCH$_2$F | 5-F | F | F |
| A-2817. | H | OCH$_2$F | 5-CH$_3$ | F | F |
| A-2818. | H | OCH$_2$F | 5-OCH$_3$ | F | F |
| A-2819. | H | OCHF$_2$ | 3-F | F | F |
| A-2820. | H | OCHF$_2$ | 3-CH$_3$ | F | F |
| A-2821. | H | OCHF$_2$ | 3-OCH$_3$ | F | F |
| A-2822. | H | OCHF$_2$ | 5-F | F | F |
| A-2823. | H | OCHF$_2$ | 5-CH$_3$ | F | F |
| A-2824. | H | OCHF$_2$ | 5-OCH$_3$ | F | F |
| A-2825. | H | OCF$_3$ | 3-F | F | F |
| A-2826. | H | OCF$_3$ | 3-CH$_3$ | F | F |
| A-2827. | H | OCF$_3$ | 3-OCH$_3$ | F | F |
| A-2828. | H | OCF$_3$ | 5-F | F | F |
| A-2829. | H | OCF$_3$ | 5-CH$_3$ | F | F |
| A-2830. | H | OCF$_3$ | 5-OCH$_3$ | F | F |
| A-2831. | F | F | 3-F | F | F |
| A-2832. | F | F | 3-CH$_3$ | F | F |
| A-2833. | F | F | 3-OCH$_3$ | F | F |
| A-2834. | F | F | 5-F | F | F |
| A-2835. | F | F | 5-CH$_3$ | F | F |
| A-2836. | F | F | 5-OCH$_3$ | F | F |
| A-2837. | F | CH$_3$ | 3-F | F | F |
| A-2838. | F | CH$_3$ | 3-CH$_3$ | F | F |
| A-2839. | F | CH$_3$ | 3-OCH$_3$ | F | F |
| A-2840. | F | CH$_3$ | 5-F | F | F |
| A-2841. | F | CH$_3$ | 5-CH$_3$ | F | F |
| A-2842. | F | CH$_3$ | 5-OCH$_3$ | F | F |
| A-2843. | F | OCH$_3$ | 3-F | F | F |
| A-2844. | F | OCH$_3$ | 3-CH$_3$ | F | F |
| A-2845. | F | OCH$_3$ | 3-OCH$_3$ | F | F |
| A-2846. | F | OCH$_3$ | 5-F | F | F |
| A-2847. | F | OCH$_3$ | 5-CH$_3$ | F | F |
| A-2848. | F | OCH$_3$ | 5-OCH$_3$ | F | F |
| A-2849. | F | CN | 3-F | F | F |
| A-2850. | F | CN | 3-CH$_3$ | F | F |
| A-2851. | F | CN | 3-OCH$_3$ | F | F |
| A-2852. | F | CN | 5-F | F | F |
| A-2853. | F | CN | 5-CH$_3$ | F | F |
| A-2854. | F | CN | 5-OCH$_3$ | F | F |
| A-2855. | F | CH$_2$F | 3-F | F | F |
| A-2856. | F | CH$_2$F | 3-CH$_3$ | F | F |
| A-2857. | F | CH$_2$F | 3-OCH$_3$ | F | F |
| A-2858. | F | CH$_2$F | 5-F | F | F |
| A-2859. | F | CH$_2$F | 5-CH$_3$ | F | F |
| A-2860. | F | CH$_2$F | 5-OCH$_3$ | F | F |
| A-2861. | F | CHF$_2$ | 3-F | F | F |
| A-2862. | F | CHF$_2$ | 3-CH$_3$ | F | F |
| A-2863. | F | CHF$_2$ | 3-OCH$_3$ | F | F |
| A-2864. | F | CHF$_2$ | 5-F | F | F |
| A-2865. | F | CHF$_2$ | 5-CH$_3$ | F | F |
| A-2866. | F | CHF$_2$ | 5-OCH$_3$ | F | F |
| A-2867. | F | CF$_3$ | 3-F | F | F |
| A-2868. | F | CF$_3$ | 3-CH$_3$ | F | F |
| A-2869. | F | CF$_3$ | 3-OCH$_3$ | F | F |
| A-2870. | F | CF$_3$ | 5-F | F | F |
| A-2871. | F | CF$_3$ | 5-CH$_3$ | F | F |
| A-2872. | F | CF$_3$ | 5-OCH$_3$ | F | F |
| A-2873. | F | OCH$_2$F | 3-F | F | F |
| A-2874. | F | OCH$_2$F | 3-CH$_3$ | F | F |
| A-2875. | F | OCH$_2$F | 3-OCH$_3$ | F | F |
| A-2876. | F | OCH$_2$F | 5-F | F | F |
| A-2877. | F | OCH$_2$F | 5-CH$_3$ | F | F |
| A-2878. | F | OCH$_2$F | 5-OCH$_3$ | F | F |
| A-2879. | F | OCHF$_2$ | 3-F | F | F |
| A-2880. | F | OCHF$_2$ | 3-CH$_3$ | F | F |
| A-2881. | F | OCHF$_2$ | 3-OCH$_3$ | F | F |
| A-2882. | F | OCHF$_2$ | 5-F | F | F |
| A-2883. | F | OCHF$_2$ | 5-CH$_3$ | F | F |
| A-2884. | F | OCHF$_2$ | 5-OCH$_3$ | F | F |
| A-2885. | F | OCF$_3$ | 3-F | F | F |
| A-2886. | F | OCF$_3$ | 3-CH$_3$ | F | F |
| A-2887. | F | OCF$_3$ | 3-OCH$_3$ | F | F |
| A-2888. | F | OCF$_3$ | 5-F | F | F |
| A-2889. | F | OCF$_3$ | 5-CH$_3$ | F | F |
| A-2890. | F | OCF$_3$ | 5-OCH$_3$ | F | F |
| A-2891. | CH$_3$ | F | 3-F | F | F |
| A-2892. | CH$_3$ | F | 3-CH$_3$ | F | F |
| A-2893. | CH$_3$ | F | 3-OCH$_3$ | F | F |
| A-2894. | CH$_3$ | F | 5-F | F | F |
| A-2895. | CH$_3$ | F | 5-CH$_3$ | F | F |
| A-2896. | CH$_3$ | F | 5-OCH$_3$ | F | F |
| A-2897. | CH$_3$ | CH$_3$ | 3-F | F | F |
| A-2898. | CH$_3$ | CH$_3$ | 3-CH$_3$ | F | F |
| A-2899. | CH$_3$ | CH$_3$ | 3-OCH$_3$ | F | F |
| A-2900. | CH$_3$ | CH$_3$ | 5-F | F | F |
| A-2901. | CH$_3$ | CH$_3$ | 5-CH$_3$ | F | F |
| A-2902. | CH$_3$ | CH$_3$ | 5-OCH$_3$ | F | F |
| A-2903. | CH$_3$ | OCH$_3$ | 3-F | F | F |
| A-2904. | CH$_3$ | OCH$_3$ | 3-CH$_3$ | F | F |
| A-2905. | CH$_3$ | OCH$_3$ | 3-OCH$_3$ | F | F |
| A-2906. | CH$_3$ | OCH$_3$ | 5-F | F | F |
| A-2907. | CH$_3$ | OCH$_3$ | 5-CH$_3$ | F | F |
| A-2908. | CH$_3$ | OCH$_3$ | 5-OCH$_3$ | F | F |
| A-2909. | CH$_3$ | CN | 3-F | F | F |
| A-2910. | CH$_3$ | CN | 3-CH$_3$ | F | F |
| A-2911. | CH$_3$ | CN | 3-OCH$_3$ | F | F |
| A-2912. | CH$_3$ | CN | 5-F | F | F |
| A-2913. | CH$_3$ | CN | 5-CH$_3$ | F | F |
| A-2914. | CH$_3$ | CN | 5-OCH$_3$ | F | F |
| A-2915. | CH$_3$ | CH$_2$F | 3-F | F | F |
| A-2916. | CH$_3$ | CH$_2$F | 3-CH$_3$ | F | F |
| A-2917. | CH$_3$ | CH$_2$F | 3-OCH$_3$ | F | F |
| A-2918. | CH$_3$ | CH$_2$F | 5-F | F | F |
| A-2919. | CH$_3$ | CH$_2$F | 5-CH$_3$ | F | F |
| A-2920. | CH$_3$ | CH$_2$F | 5-OCH$_3$ | F | F |
| A-2921. | CH$_3$ | CHF$_2$ | 3-F | F | F |
| A-2922. | CH$_3$ | CHF$_2$ | 3-CH$_3$ | F | F |
| A-2923. | CH$_3$ | CHF$_2$ | 3-OCH$_3$ | F | F |
| A-2924. | CH$_3$ | CHF$_2$ | 5-F | F | F |
| A-2925. | CH$_3$ | CHF$_2$ | 5-CH$_3$ | F | F |
| A-2926. | CH$_3$ | CHF$_2$ | 5-OCH$_3$ | F | F |
| A-2927. | CH$_3$ | CF$_3$ | 3-F | F | F |
| A-2928. | CH$_3$ | CF$_3$ | 3-CH$_3$ | F | F |
| A-2929. | CH$_3$ | CF$_3$ | 3-OCH$_3$ | F | F |
| A-2930. | CH$_3$ | CF$_3$ | 5-F | F | F |
| A-2931. | CH$_3$ | CF$_3$ | 5-CH$_3$ | F | F |

TABLE A-continued

| Example No. | R$^1$ | R$^2$ | R$^3$ | R$^6$ | R$^7$ |
|---|---|---|---|---|---|
| A-2932. | CH$_3$ | CF$_3$ | 5-OCH$_3$ | F | F |
| A-2933. | CH$_3$ | OCH$_2$F | 3-F | F | F |
| A-2934. | CH$_3$ | OCH$_2$F | 3-CH$_3$ | F | F |
| A-2935. | CH$_3$ | OCH$_2$F | 3-OCH$_3$ | F | F |
| A-2936. | CH$_3$ | OCH$_2$F | 5-F | F | F |
| A-2937. | CH$_3$ | OCH$_2$F | 5-CH$_3$ | F | F |
| A-2938. | CH$_3$ | OCH$_2$F | 5-OCH$_3$ | F | F |
| A-2939. | CH$_3$ | OCHF$_2$ | 3-F | F | F |
| A-2940. | CH$_3$ | OCHF$_2$ | 3-CH$_3$ | F | F |
| A-2941. | CH$_3$ | OCHF$_2$ | 3-OCH$_3$ | F | F |
| A-2942. | CH$_3$ | OCHF$_2$ | 5-F | F | F |
| A-2943. | CH$_3$ | OCHF$_2$ | 5-CH$_3$ | F | F |
| A-2944. | CH$_3$ | OCHF$_2$ | 5-OCH$_3$ | F | F |
| A-2945. | CH$_3$ | OCF$_3$ | 3-F | F | F |
| A-2946. | CH$_3$ | OCF$_3$ | 3-CH$_3$ | F | F |
| A-2947. | CH$_3$ | OCF$_3$ | 3-OCH$_3$ | F | F |
| A-2948. | CH$_3$ | OCF$_3$ | 5-F | F | F |
| A-2949. | CH$_3$ | OCF$_3$ | 5-CH$_3$ | F | F |
| A-2950. | CH$_3$ | OCF$_3$ | 5-OCH$_3$ | F | F |
| A-2951. | OCH$_3$ | F | 3-F | F | F |
| A-2952. | OCH$_3$ | F | 3-CH$_3$ | F | F |
| A-2953. | OCH$_3$ | F | 3-OCH$_3$ | F | F |
| A-2954. | OCH$_3$ | F | 5-F | F | F |
| A-2955. | OCH$_3$ | F | 5-CH$_3$ | F | F |
| A-2956. | OCH$_3$ | F | 5-OCH$_3$ | F | F |
| A-2957. | OCH$_3$ | CH$_3$ | 3-F | F | F |
| A-2958. | OCH$_3$ | CH$_3$ | 3-CH$_3$ | F | F |
| A-2959. | OCH$_3$ | CH$_3$ | 3-OCH$_3$ | F | F |
| A-2960. | OCH$_3$ | CH$_3$ | 5-F | F | F |
| A-2961. | OCH$_3$ | CH$_3$ | 5-CH$_3$ | F | F |
| A-2962. | OCH$_3$ | CH$_3$ | 5-OCH$_3$ | F | F |
| A-2963. | OCH$_3$ | OCH$_3$ | 3-F | F | F |
| A-2964. | OCH$_3$ | OCH$_3$ | 3-CH$_3$ | F | F |
| A-2965. | OCH$_3$ | OCH$_3$ | 3-OCH$_3$ | F | F |
| A-2966. | OCH$_3$ | OCH$_3$ | 5-F | F | F |
| A-2967. | OCH$_3$ | OCH$_3$ | 5-CH$_3$ | F | F |
| A-2968. | OCH$_3$ | OCH$_3$ | 5-OCH$_3$ | F | F |
| A-2969. | OCH$_3$ | CN | 3-F | F | F |
| A-2970. | OCH$_3$ | CN | 3-CH$_3$ | F | F |
| A-2971. | OCH$_3$ | CN | 3-OCH$_3$ | F | F |
| A-2972. | OCH$_3$ | CN | 5-F | F | F |
| A-2973. | OCH$_3$ | CN | 5-CH$_3$ | F | F |
| A-2974. | OCH$_3$ | CN | 5-OCH$_3$ | F | F |
| A-2975. | OCH$_3$ | CH$_2$F | 3-F | F | F |
| A-2976. | OCH$_3$ | CH$_2$F | 3-CH$_3$ | F | F |
| A-2977. | OCH$_3$ | CH$_2$F | 3-OCH$_3$ | F | F |
| A-2978. | OCH$_3$ | CH$_2$F | 5-F | F | F |
| A-2979. | OCH$_3$ | CH$_2$F | 5-CH$_3$ | F | F |
| A-2980. | OCH$_3$ | CH$_2$F | 5-OCH$_3$ | F | F |
| A-2981. | OCH$_3$ | CHF$_2$ | 3-F | F | F |
| A-2982. | OCH$_3$ | CHF$_2$ | 3-CH$_3$ | F | F |
| A-2983. | OCH$_3$ | CHF$_2$ | 3-OCH$_3$ | F | F |
| A-2984. | OCH$_3$ | CHF$_2$ | 5-F | F | F |
| A-2985. | OCH$_3$ | CHF$_2$ | 5-CH$_3$ | F | F |
| A-2986. | OCH$_3$ | CHF$_2$ | 5-OCH$_3$ | F | F |
| A-2987. | OCH$_3$ | CF$_3$ | 3-F | F | F |
| A-2988. | OCH$_3$ | CF$_3$ | 3-CH$_3$ | F | F |
| A-2989. | OCH$_3$ | CF$_3$ | 3-OCH$_3$ | F | F |
| A-2990. | OCH$_3$ | CF$_3$ | 5-F | F | F |
| A-2991. | OCH$_3$ | CF$_3$ | 5-CH$_3$ | F | F |
| A-2992. | OCH$_3$ | CF$_3$ | 5-OCH$_3$ | F | F |
| A-2993. | OCH$_3$ | OCH$_2$F | 3-F | F | F |
| A-2994. | OCH$_3$ | OCH$_2$F | 3-CH$_3$ | F | F |
| A-2995. | OCH$_3$ | OCH$_2$F | 3-OCH$_3$ | F | F |
| A-2996. | OCH$_3$ | OCH$_2$F | 5-F | F | F |
| A-2997. | OCH$_3$ | OCH$_2$F | 5-CH$_3$ | F | F |
| A-2998. | OCH$_3$ | OCH$_2$F | 5-OCH$_3$ | F | F |
| A-2999. | OCH$_3$ | OCHF$_2$ | 3-F | F | F |
| A-3000. | OCH$_3$ | OCHF$_2$ | 3-CH$_3$ | F | F |
| A-3001. | OCH$_3$ | OCHF$_2$ | 3-OCH$_3$ | F | F |
| A-3002. | OCH$_3$ | OCHF$_2$ | 5-F | F | F |
| A-3003. | OCH$_3$ | OCHF$_2$ | 5-CH$_3$ | F | F |
| A-3004. | OCH$_3$ | OCHF$_2$ | 5-OCH$_3$ | F | F |
| A-3005. | OCH$_3$ | OCF$_3$ | 3-F | F | F |
| A-3006. | OCH$_3$ | OCF$_3$ | 3-CH$_3$ | F | F |
| A-3007. | OCH$_3$ | OCF$_3$ | 3-OCH$_3$ | F | F |
| A-3008. | OCH$_3$ | OCF$_3$ | 5-F | F | F |
| A-3009. | OCH$_3$ | OCF$_3$ | 5-CH$_3$ | F | F |
| A-3010. | OCH$_3$ | OCF$_3$ | 5-OCH$_3$ | F | F |
| A-3011. | CH$_2$F | F | 3-F | F | F |
| A-3012. | CH$_2$F | F | 3-CH$_3$ | F | F |
| A-3013. | CH$_2$F | F | 3-OCH$_3$ | F | F |
| A-3014. | CH$_2$F | F | 5-F | F | F |
| A-3015. | CH$_2$F | F | 5-CH$_3$ | F | F |
| A-3016. | CH$_2$F | F | 5-OCH$_3$ | F | F |
| A-3017. | CH$_2$F | CH$_3$ | 3-F | F | F |
| A-3018. | CH$_2$F | CH$_3$ | 3-CH$_3$ | F | F |
| A-3019. | CH$_2$F | CH$_3$ | 3-OCH$_3$ | F | F |
| A-3020. | CH$_2$F | CH$_3$ | 5-F | F | F |
| A-3021. | CH$_2$F | CH$_3$ | 5-CH$_3$ | F | F |
| A-3022. | CH$_2$F | CH$_3$ | 5-OCH$_3$ | F | F |
| A-3023. | CH$_2$F | OCH$_3$ | 3-F | F | F |
| A-3024. | CH$_2$F | OCH$_3$ | 3-CH$_3$ | F | F |
| A-3025. | CH$_2$F | OCH$_3$ | 3-OCH$_3$ | F | F |
| A-3026. | CH$_2$F | OCH$_3$ | 5-F | F | F |
| A-3027. | CH$_2$F | OCH$_3$ | 5-CH$_3$ | F | F |
| A-3028. | CH$_2$F | OCH$_3$ | 5-OCH$_3$ | F | F |
| A-3029. | CH$_2$F | CN | 3-F | F | F |
| A-3030. | CH$_2$F | CN | 3-CH$_3$ | F | F |
| A-3031. | CH$_2$F | CN | 3-OCH$_3$ | F | F |
| A-3032. | CH$_2$F | CN | 5-F | F | F |
| A-3033. | CH$_2$F | CN | 5-CH$_3$ | F | F |
| A-3034. | CH$_2$F | CN | 5-OCH$_3$ | F | F |
| A-3035. | CH$_2$F | CH$_2$F | 3-F | F | F |
| A-3036. | CH$_2$F | CH$_2$F | 3-CH$_3$ | F | F |
| A-3037. | CH$_2$F | CH$_2$F | 3-OCH$_3$ | F | F |
| A-3038. | CH$_2$F | CH$_2$F | 5-F | F | F |
| A-3039. | CH$_2$F | CH$_2$F | 5-CH$_3$ | F | F |
| A-3040. | CH$_2$F | CH$_2$F | 5-OCH$_3$ | F | F |
| A-3041. | CH$_2$F | CHF$_2$ | 3-F | F | F |
| A-3042. | CH$_2$F | CHF$_2$ | 3-CH$_3$ | F | F |
| A-3043. | CH$_2$F | CHF$_2$ | 3-OCH$_3$ | F | F |
| A-3044. | CH$_2$F | CHF$_2$ | 5-F | F | F |
| A-3045. | CH$_2$F | CHF$_2$ | 5-CH$_3$ | F | F |
| A-3046. | CH$_2$F | CHF$_2$ | 5-OCH$_3$ | F | F |
| A-3047. | CH$_2$F | CF$_3$ | 3-F | F | F |
| A-3048. | CH$_2$F | CF$_3$ | 3-CH$_3$ | F | F |
| A-3049. | CH$_2$F | CF$_3$ | 3-OCH$_3$ | F | F |
| A-3050. | CH$_2$F | CF$_3$ | 5-F | F | F |
| A-3051. | CH$_2$F | CF$_3$ | 5-CH$_3$ | F | F |
| A-3052. | CH$_2$F | CF$_3$ | 5-OCH$_3$ | F | F |
| A-3053. | CH$_2$F | OCH$_2$F | 3-F | F | F |
| A-3054. | CH$_2$F | OCH$_2$F | 3-CH$_3$ | F | F |
| A-3055. | CH$_2$F | OCH$_2$F | 3-OCH$_3$ | F | F |
| A-3056. | CH$_2$F | OCH$_2$F | 5-F | F | F |
| A-3057. | CH$_2$F | OCH$_2$F | 5-CH$_3$ | F | F |
| A-3058. | CH$_2$F | OCH$_2$F | 5-OCH$_3$ | F | F |
| A-3059. | CH$_2$F | OCHF$_2$ | 3-F | F | F |
| A-3060. | CH$_2$F | OCHF$_2$ | 3-CH$_3$ | F | F |
| A-3061. | CH$_2$F | OCHF$_2$ | 3-OCH$_3$ | F | F |
| A-3062. | CH$_2$F | OCHF$_2$ | 5-F | F | F |
| A-3063. | CH$_2$F | OCHF$_2$ | 5-CH$_3$ | F | F |
| A-3064. | CH$_2$F | OCHF$_2$ | 5-OCH$_3$ | F | F |
| A-3065. | CH$_2$F | OCF$_3$ | 3-F | F | F |
| A-3066. | CH$_2$F | OCF$_3$ | 3-CH$_3$ | F | F |
| A-3067. | CH$_2$F | OCF$_3$ | 3-OCH$_3$ | F | F |
| A-3068. | CH$_2$F | OCF$_3$ | 5-F | F | F |
| A-3069. | CH$_2$F | OCF$_3$ | 5-CH$_3$ | F | F |
| A-3070. | CH$_2$F | OCF$_3$ | 5-OCH$_3$ | F | F |
| A-3071. | CHF$_2$ | F | 3-F | F | F |
| A-3072. | CHF$_2$ | F | 3-CH$_3$ | F | F |
| A-3073. | CHF$_2$ | F | 3-OCH$_3$ | F | F |
| A-3074. | CHF$_2$ | F | 5-F | F | F |
| A-3075. | CHF$_2$ | F | 5-CH$_3$ | F | F |
| A-3076. | CHF$_2$ | F | 5-OCH$_3$ | F | F |
| A-3077. | CHF$_2$ | CH$_3$ | 3-F | F | F |
| A-3078. | CHF$_2$ | CH$_3$ | 3-CH$_3$ | F | F |
| A-3079. | CHF$_2$ | CH$_3$ | 3-OCH$_3$ | F | F |
| A-3080. | CHF$_2$ | CH$_3$ | 5-F | F | F |
| A-3081. | CHF$_2$ | CH$_3$ | 5-CH$_3$ | F | F |
| A-3082. | CHF$_2$ | CH$_3$ | 5-OCH$_3$ | F | F |
| A-3083. | CHF$_2$ | OCH$_3$ | 3-F | F | F |
| A-3084. | CHF$_2$ | OCH$_3$ | 3-CH$_3$ | F | F |
| A-3085. | CHF$_2$ | OCH$_3$ | 3-OCH$_3$ | F | F |
| A-3086. | CHF$_2$ | OCH$_3$ | 5-F | F | F |
| A-3087. | CHF$_2$ | OCH$_3$ | 5-CH$_3$ | F | F |

TABLE A-continued

| Example No. | R¹ | R² | R³ | R⁶ | R⁷ |
|---|---|---|---|---|---|
| A-3088. | CHF$_2$ | OCH$_3$ | 5-OCH$_3$ | F | F |
| A-3089. | CHF$_2$ | CN | 3-F | F | F |
| A-3090. | CHF$_2$ | CN | 3-CH$_3$ | F | F |
| A-3091. | CHF$_2$ | CN | 3-OCH$_3$ | F | F |
| A-3092. | CHF$_2$ | CN | 5-F | F | F |
| A-3093. | CHF$_2$ | CN | 5-CH$_3$ | F | F |
| A-3094. | CHF$_2$ | CN | 5-OCH$_3$ | F | F |
| A-3095. | CHF$_2$ | CH$_2$F | 3-F | F | F |
| A-3096. | CHF$_2$ | CH$_2$F | 3-CH$_3$ | F | F |
| A-3097. | CHF$_2$ | CH$_2$F | 3-OCH$_3$ | F | F |
| A-3098. | CHF$_2$ | CH$_2$F | 5-F | F | F |
| A-3099. | CHF$_2$ | CH$_2$F | 5-CH$_3$ | F | F |
| A-3100. | CHF$_2$ | CH$_2$F | 5-OCH$_3$ | F | F |
| A-3101. | CHF$_2$ | CHF$_2$ | 3-F | F | F |
| A-3102. | CHF$_2$ | CHF$_2$ | 3-CH$_3$ | F | F |
| A-3103. | CHF$_2$ | CHF$_2$ | 3-OCH$_3$ | F | F |
| A-3104. | CHF$_2$ | CHF$_2$ | 5-F | F | F |
| A-3105. | CHF$_2$ | CHF$_2$ | 5-CH$_3$ | F | F |
| A-3106. | CHF$_2$ | CHF$_2$ | 5-OCH$_3$ | F | F |
| A-3107. | CHF$_2$ | CF$_3$ | 3-F | F | F |
| A-3108. | CHF$_2$ | CF$_3$ | 3-CH$_3$ | F | F |
| A-3109. | CHF$_2$ | CF$_3$ | 3-OCH$_3$ | F | F |
| A-3110. | CHF$_2$ | CF$_3$ | 5-F | F | F |
| A-3111. | CHF$_2$ | CF$_3$ | 5-CH$_3$ | F | F |
| A-3112. | CHF$_2$ | CF$_3$ | 5-OCH$_3$ | F | F |
| A-3113. | CHF$_2$ | OCH$_2$F | 3-F | F | F |
| A-3114. | CHF$_2$ | OCH$_2$F | 3-CH$_3$ | F | F |
| A-3115. | CHF$_2$ | OCH$_2$F | 3-OCH$_3$ | F | F |
| A-3116. | CHF$_2$ | OCH$_2$F | 5-F | F | F |
| A-3117. | CHF$_2$ | OCH$_2$F | 5-CH$_3$ | F | F |
| A-3118. | CHF$_2$ | OCH$_2$F | 5-OCH$_3$ | F | F |
| A-3119. | CHF$_2$ | OCHF$_2$ | 3-F | F | F |
| A-3120. | CHF$_2$ | OCHF$_2$ | 3-CH$_3$ | F | F |
| A-3121. | CHF$_2$ | OCHF$_2$ | 3-OCH$_3$ | F | F |
| A-3122. | CHF$_2$ | OCHF$_2$ | 5-F | F | F |
| A-3123. | CHF$_2$ | OCHF$_2$ | 5-CH$_3$ | F | F |
| A-3124. | CHF$_2$ | OCHF$_2$ | 5-OCH$_3$ | F | F |
| A-3125. | CHF$_2$ | OCF$_3$ | 3-F | F | F |
| A-3126. | CHF$_2$ | OCF$_3$ | 3-CH$_3$ | F | F |
| A-3127. | CHF$_2$ | OCF$_3$ | 3-OCH$_3$ | F | F |
| A-3128. | CHF$_2$ | OCF$_3$ | 5-F | F | F |
| A-3129. | CHF$_2$ | OCF$_3$ | 5-CH$_3$ | F | F |
| A-3130. | CHF$_2$ | OCF$_3$ | 5-OCH$_3$ | F | F |
| A-3131. | CF$_3$ | F | 3-F | F | F |
| A-3132. | CF$_3$ | F | 3-CH$_3$ | F | F |
| A-3133. | CF$_3$ | F | 3-OCH$_3$ | F | F |
| A-3134. | CF$_3$ | F | 5-F | F | F |
| A-3135. | CF$_3$ | F | 5-CH$_3$ | F | F |
| A-3136. | CF$_3$ | F | 5-OCH$_3$ | F | F |
| A-3137. | CF$_3$ | CH$_3$ | 3-F | F | F |
| A-3138. | CF$_3$ | CH$_3$ | 3-CH$_3$ | F | F |
| A-3139. | CF$_3$ | CH$_3$ | 3-OCH$_3$ | F | F |
| A-3140. | CF$_3$ | CH$_3$ | 5-F | F | F |
| A-3141. | CF$_3$ | CH$_3$ | 5-CH$_3$ | F | F |
| A-3142. | CF$_3$ | CH$_3$ | 5-OCH$_3$ | F | F |
| A-3143. | CF$_3$ | OCH$_3$ | 3-F | F | F |
| A-3144. | CF$_3$ | OCH$_3$ | 3-CH$_3$ | F | F |
| A-3145. | CF$_3$ | OCH$_3$ | 3-OCH$_3$ | F | F |
| A-3146. | CF$_3$ | OCH$_3$ | 5-F | F | F |
| A-3147. | CF$_3$ | OCH$_3$ | 5-CH$_3$ | F | F |
| A-3148. | CF$_3$ | OCH$_3$ | 5-OCH$_3$ | F | F |
| A-3149. | CF$_3$ | CN | 3-F | F | F |
| A-3150. | CF$_3$ | CN | 3-CH$_3$ | F | F |
| A-3151. | CF$_3$ | CN | 3-OCH$_3$ | F | F |
| A-3152. | CF$_3$ | CN | 5-F | F | F |
| A-3153. | CF$_3$ | CN | 5-CH$_3$ | F | F |
| A-3154. | CF$_3$ | CN | 5-OCH$_3$ | F | F |
| A-3155. | CF$_3$ | CH$_2$F | 3-F | F | F |
| A-3156. | CF$_3$ | CH$_2$F | 3-CH$_3$ | F | F |
| A-3157. | CF$_3$ | CH$_2$F | 3-OCH$_3$ | F | F |
| A-3158. | CF$_3$ | CH$_2$F | 5-F | F | F |
| A-3159. | CF$_3$ | CH$_2$F | 5-CH$_3$ | F | F |
| A-3160. | CF$_3$ | CH$_2$F | 5-OCH$_3$ | F | F |
| A-3161. | CF$_3$ | CHF$_2$ | 3-F | F | F |
| A-3162. | CF$_3$ | CHF$_2$ | 3-CH$_3$ | F | F |
| A-3163. | CF$_3$ | CHF$_2$ | 3-OCH$_3$ | F | F |
| A-3164. | CF$_3$ | CHF$_2$ | 5-F | F | F |
| A-3165. | CF$_3$ | CHF$_2$ | 5-CH$_3$ | F | F |
| A-3166. | CF$_3$ | CHF$_2$ | 5-OCH$_3$ | F | F |
| A-3167. | CF$_3$ | CF$_3$ | 3-F | F | F |
| A-3168. | CF$_3$ | CF$_3$ | 3-CH$_3$ | F | F |
| A-3169. | CF$_3$ | CF$_3$ | 3-OCH$_3$ | F | F |
| A-3170. | CF$_3$ | CF$_3$ | 5-F | F | F |
| A-3171. | CF$_3$ | CF$_3$ | 5-CH$_3$ | F | F |
| A-3172. | CF$_3$ | CF$_3$ | 5-OCH$_3$ | F | F |
| A-3173. | CF$_3$ | OCH$_2$F | 3-F | F | F |
| A-3174. | CF$_3$ | OCH$_2$F | 3-CH$_3$ | F | F |
| A-3175. | CF$_3$ | OCH$_2$F | 3-OCH$_3$ | F | F |
| A-3176. | CF$_3$ | OCH$_2$F | 5-F | F | F |
| A-3177. | CF$_3$ | OCH$_2$F | 5-CH$_3$ | F | F |
| A-3178. | CF$_3$ | OCH$_2$F | 5-OCH$_3$ | F | F |
| A-3179. | CF$_3$ | OCHF$_2$ | 3-F | F | F |
| A-3180. | CF$_3$ | OCHF$_2$ | 3-CH$_3$ | F | F |
| A-3181. | CF$_3$ | OCHF$_2$ | 3-OCH$_3$ | F | F |
| A-3182. | CF$_3$ | OCHF$_2$ | 5-F | F | F |
| A-3183. | CF$_3$ | OCHF$_2$ | 5-CH$_3$ | F | F |
| A-3184. | CF$_3$ | OCHF$_2$ | 5-OCH$_3$ | F | F |
| A-3185. | CF$_3$ | OCF$_3$ | 3-F | F | F |
| A-3186. | CF$_3$ | OCF$_3$ | 3-CH$_3$ | F | F |
| A-3187. | CF$_3$ | OCF$_3$ | 3-OCH$_3$ | F | F |
| A-3188. | CF$_3$ | OCF$_3$ | 5-F | F | F |
| A-3189. | CF$_3$ | OCF$_3$ | 5-CH$_3$ | F | F |
| A-3190. | CF$_3$ | OCF$_3$ | 5-OCH$_3$ | F | F |
| A-3191. | OCH$_2$F | F | 3-F | F | F |
| A-3192. | OCH$_2$F | F | 3-CH$_3$ | F | F |
| A-3193. | OCH$_2$F | F | 3-OCH$_3$ | F | F |
| A-3194. | OCH$_2$F | F | 5-F | F | F |
| A-3195. | OCH$_2$F | F | 5-CH$_3$ | F | F |
| A-3196. | OCH$_2$F | F | 5-OCH$_3$ | F | F |
| A-3197. | OCH$_2$F | CH$_3$ | 3-F | F | F |
| A-3198. | OCH$_2$F | CH$_3$ | 3-CH$_3$ | F | F |
| A-3199. | OCH$_2$F | CH$_3$ | 3-OCH$_3$ | F | F |
| A-3200. | OCH$_2$F | CH$_3$ | 5-F | F | F |
| A-3201. | OCH$_2$F | CH$_3$ | 5-CH$_3$ | F | F |
| A-3202. | OCH$_2$F | CH$_3$ | 5-OCH$_3$ | F | F |
| A-3203. | OCH$_2$F | OCH$_3$ | 3-F | F | F |
| A-3204. | OCH$_2$F | OCH$_3$ | 3-CH$_3$ | F | F |
| A-3205. | OCH$_2$F | OCH$_3$ | 3-OCH$_3$ | F | F |
| A-3206. | OCH$_2$F | OCH$_3$ | 5-F | F | F |
| A-3207. | OCH$_2$F | OCH$_3$ | 5-CH$_3$ | F | F |
| A-3208. | OCH$_2$F | OCH$_3$ | 5-OCH$_3$ | F | F |
| A-3209. | OCH$_2$F | CN | 3-F | F | F |
| A-3210. | OCH$_2$F | CN | 3-CH$_3$ | F | F |
| A-3211. | OCH$_2$F | CN | 3-OCH$_3$ | F | F |
| A-3212. | OCH$_2$F | CN | 5-F | F | F |
| A-3213. | OCH$_2$F | CN | 5-CH$_3$ | F | F |
| A-3214. | OCH$_2$F | CN | 5-OCH$_3$ | F | F |
| A-3215. | OCH$_2$F | CH$_2$F | 3-F | F | F |
| A-3216. | OCH$_2$F | CH$_2$F | 3-CH$_3$ | F | F |
| A-3217. | OCH$_2$F | CH$_2$F | 3-OCH$_3$ | F | F |
| A-3218. | OCH$_2$F | CH$_2$F | 5-F | F | F |
| A-3219. | OCH$_2$F | CH$_2$F | 5-CH$_3$ | F | F |
| A-3220. | OCH$_2$F | CH$_2$F | 5-OCH$_3$ | F | F |
| A-3221. | OCH$_2$F | CHF$_2$ | 3-F | F | F |
| A-3222. | OCH$_2$F | CHF$_2$ | 3-CH$_3$ | F | F |
| A-3223. | OCH$_2$F | CHF$_2$ | 3-OCH$_3$ | F | F |
| A-3224. | OCH$_2$F | CHF$_2$ | 5-F | F | F |
| A-3225. | OCH$_2$F | CHF$_2$ | 5-CH$_3$ | F | F |
| A-3226. | OCH$_2$F | CHF$_2$ | 5-OCH$_3$ | F | F |
| A-3227. | OCH$_2$F | CF$_3$ | 3-F | F | F |
| A-3228. | OCH$_2$F | CF$_3$ | 3-CH$_3$ | F | F |
| A-3229. | OCH$_2$F | CF$_3$ | 3-OCH$_3$ | F | F |
| A-3230. | OCH$_2$F | CF$_3$ | 5-F | F | F |
| A-3231. | OCH$_2$F | CF$_3$ | 5-CH$_3$ | F | F |
| A-3232. | OCH$_2$F | CF$_3$ | 5-OCH$_3$ | F | F |
| A-3233. | OCH$_2$F | OCH$_2$F | 3-F | F | F |
| A-3234. | OCH$_2$F | OCH$_2$F | 3-CH$_3$ | F | F |
| A-3235. | OCH$_2$F | OCH$_2$F | 3-OCH$_3$ | F | F |
| A-3236. | OCH$_2$F | OCH$_2$F | 5-F | F | F |
| A-3237. | OCH$_2$F | OCH$_2$F | 5-CH$_3$ | F | F |
| A-3238. | OCH$_2$F | OCH$_2$F | 5-OCH$_3$ | F | F |
| A-3239. | OCH$_2$F | OCHF$_2$ | 3-F | F | F |
| A-3240. | OCH$_2$F | OCHF$_2$ | 3-CH$_3$ | F | F |
| A-3241. | OCH$_2$F | OCHF$_2$ | 3-OCH$_3$ | F | F |
| A-3242. | OCH$_2$F | OCHF$_2$ | 5-F | F | F |
| A-3243. | OCH$_2$F | OCHF$_2$ | 5-CH$_3$ | F | F |

TABLE A-continued

| Example No. | R¹ | R² | R³ | R⁶ | R⁷ |
|---|---|---|---|---|---|
| A-3244. | OCH$_2$F | OCHF$_2$ | 5-OCH$_3$ | F | F |
| A-3245. | OCH$_2$F | OCF$_3$ | 3-F | F | F |
| A-3246. | OCH$_2$F | OCF$_3$ | 3-CH$_3$ | F | F |
| A-3247. | OCH$_2$F | OCF$_3$ | 3-OCH$_3$ | F | F |
| A-3248. | OCH$_2$F | OCF$_3$ | 5-F | F | F |
| A-3249. | OCH$_2$F | OCF$_3$ | 5-CH$_3$ | F | F |
| A-3250. | OCH$_2$F | OCF$_3$ | 5-OCH$_3$ | F | F |
| A-3251. | OCHF$_2$ | F | 3-F | F | F |
| A-3252. | OCHF$_2$ | F | 3-CH$_3$ | F | F |
| A-3253. | OCHF$_2$ | F | 3-OCH$_3$ | F | F |
| A-3254. | OCHF$_2$ | F | 5-F | F | F |
| A-3255. | OCHF$_2$ | F | 5-CH$_3$ | F | F |
| A-3256. | OCHF$_2$ | F | 5-OCH$_3$ | F | F |
| A-3257. | OCHF$_2$ | CH$_3$ | 3-F | F | F |
| A-3258. | OCHF$_2$ | CH$_3$ | 3-CH$_3$ | F | F |
| A-3259. | OCHF$_2$ | CH$_3$ | 3-OCH$_3$ | F | F |
| A-3260. | OCHF$_2$ | CH$_3$ | 5-F | F | F |
| A-3261. | OCHF$_2$ | CH$_3$ | 5-CH$_3$ | F | F |
| A-3262. | OCHF$_2$ | CH$_3$ | 5-OCH$_3$ | F | F |
| A-3263. | OCHF$_2$ | OCH$_3$ | 3-F | F | F |
| A-3264. | OCHF$_2$ | OCH$_3$ | 3-CH$_3$ | F | F |
| A-3265. | OCHF$_2$ | OCH$_3$ | 3-OCH$_3$ | F | F |
| A-3266. | OCHF$_2$ | OCH$_3$ | 5-F | F | F |
| A-3267. | OCHF$_2$ | OCH$_3$ | 5-CH$_3$ | F | F |
| A-3268. | OCHF$_2$ | OCH$_3$ | 5-OCH$_3$ | F | F |
| A-3269. | OCHF$_2$ | CN | 3-F | F | F |
| A-3270. | OCHF$_2$ | CN | 3-CH$_3$ | F | F |
| A-3271. | OCHF$_2$ | CN | 3-OCH$_3$ | F | F |
| A-3272. | OCHF$_2$ | CN | 5-F | F | F |
| A-3273. | OCHF$_2$ | CN | 5-CH$_3$ | F | F |
| A-3274. | OCHF$_2$ | CN | 5-OCH$_3$ | F | F |
| A-3275. | OCHF$_2$ | CH$_2$F | 3-F | F | F |
| A-3276. | OCHF$_2$ | CH$_2$F | 3-CH$_3$ | F | F |
| A-3277. | OCHF$_2$ | CH$_2$F | 3-OCH$_3$ | F | F |
| A-3278. | OCHF$_2$ | CH$_2$F | 5-F | F | F |
| A-3279. | OCHF$_2$ | CH$_2$F | 5-CH$_3$ | F | F |
| A-3280. | OCHF$_2$ | CH$_2$F | 5-OCH$_3$ | F | F |
| A-3281. | OCHF$_2$ | CHF$_2$ | 3-F | F | F |
| A-3282. | OCHF$_2$ | CHF$_2$ | 3-CH$_3$ | F | F |
| A-3283. | OCHF$_2$ | CHF$_2$ | 3-OCH$_3$ | F | F |
| A-3284. | OCHF$_2$ | CHF$_2$ | 5-F | F | F |
| A-3285. | OCHF$_2$ | CHF$_2$ | 5-CH$_3$ | F | F |
| A-3286. | OCHF$_2$ | CHF$_2$ | 5-OCH$_3$ | F | F |
| A-3287. | OCHF$_2$ | CF$_3$ | 3-F | F | F |
| A-3288. | OCHF$_2$ | CF$_3$ | 3-CH$_3$ | F | F |
| A-3289. | OCHF$_2$ | CF$_3$ | 3-OCH$_3$ | F | F |
| A-3290. | OCHF$_2$ | CF$_3$ | 5-F | F | F |
| A-3291. | OCHF$_2$ | CF$_3$ | 5-CH$_3$ | F | F |
| A-3292. | OCHF$_2$ | CF$_3$ | 5-OCH$_3$ | F | F |
| A-3293. | OCHF$_2$ | OCH$_2$F | 3-F | F | F |
| A-3294. | OCHF$_2$ | OCH$_2$F | 3-CH$_3$ | F | F |
| A-3295. | OCHF$_2$ | OCH$_2$F | 3-OCH$_3$ | F | F |
| A-3296. | OCHF$_2$ | OCH$_2$F | 5-F | F | F |
| A-3297. | OCHF$_2$ | OCH$_2$F | 5-CH$_3$ | F | F |
| A-3298. | OCHF$_2$ | OCH$_2$F | 5-OCH$_3$ | F | F |
| A-3299. | OCHF$_2$ | OCHF$_2$ | 3-F | F | F |
| A-3300. | OCHF$_2$ | OCHF$_2$ | 3-CH$_3$ | F | F |
| A-3301. | OCHF$_2$ | OCHF$_2$ | 3-OCH$_3$ | F | F |
| A-3302. | OCHF$_2$ | OCHF$_2$ | 5-F | F | F |
| A-3303. | OCHF$_2$ | OCHF$_2$ | 5-CH$_3$ | F | F |
| A-3304. | OCHF$_2$ | OCHF$_2$ | 5-OCH$_3$ | F | F |
| A-3305. | OCHF$_2$ | OCF$_3$ | 3-F | F | F |
| A-3306. | OCHF$_2$ | OCF$_3$ | 3-CH$_3$ | F | F |
| A-3307. | OCHF$_2$ | OCF$_3$ | 3-OCH$_3$ | F | F |
| A-3308. | OCHF$_2$ | OCF$_3$ | 5-F | F | F |
| A-3309. | OCHF$_2$ | OCF$_3$ | 5-CH$_3$ | F | F |
| A-3310. | OCHF$_2$ | OCF$_3$ | 5-OCH$_3$ | F | F |
| A-3311. | OCF$_3$ | F | 3-F | F | F |
| A-3312. | OCF$_3$ | F | 3-CH$_3$ | F | F |
| A-3313. | OCF$_3$ | F | 3-OCH$_3$ | F | F |
| A-3314. | OCF$_3$ | F | 5-F | F | F |
| A-3315. | OCF$_3$ | F | 5-CH$_3$ | F | F |
| A-3316. | OCF$_3$ | F | 5-OCH$_3$ | F | F |
| A-3317. | OCF$_3$ | CH$_3$ | 3-F | F | F |
| A-3318. | OCF$_3$ | CH$_3$ | 3-CH$_3$ | F | F |
| A-3319. | OCF$_3$ | CH$_3$ | 3-OCH$_3$ | F | F |
| A-3320. | OCF$_3$ | CH$_3$ | 5-F | F | F |
| A-3321. | OCF$_3$ | CH$_3$ | 5-CH$_3$ | F | F |
| A-3322. | OCF$_3$ | CH$_3$ | 5-OCH$_3$ | F | F |
| A-3323. | OCF$_3$ | OCH$_3$ | 3-F | F | F |
| A-3324. | OCF$_3$ | OCH$_3$ | 3-CH$_3$ | F | F |
| A-3325. | OCF$_3$ | OCH$_3$ | 3-OCH$_3$ | F | F |
| A-3326. | OCF$_3$ | OCH$_3$ | 5-F | F | F |
| A-3327. | OCF$_3$ | OCH$_3$ | 5-CH$_3$ | F | F |
| A-3328. | OCF$_3$ | OCH$_3$ | 5-OCH$_3$ | F | F |
| A-3329. | OCF$_3$ | CN | 3-F | F | F |
| A-3330. | OCF$_3$ | CN | 3-CH$_3$ | F | F |
| A-3331. | OCF$_3$ | CN | 3-OCH$_3$ | F | F |
| A-3332. | OCF$_3$ | CN | 5-F | F | F |
| A-3333. | OCF$_3$ | CN | 5-CH$_3$ | F | F |
| A-3334. | OCF$_3$ | CN | 5-OCH$_3$ | F | F |
| A-3335. | OCF$_3$ | CH$_2$F | 3-F | F | F |
| A-3336. | OCF$_3$ | CH$_2$F | 3-CH$_3$ | F | F |
| A-3337. | OCF$_3$ | CH$_2$F | 3-OCH$_3$ | F | F |
| A-3338. | OCF$_3$ | CH$_2$F | 5-F | F | F |
| A-3339. | OCF$_3$ | CH$_2$F | 5-CH$_3$ | F | F |
| A-3340. | OCF$_3$ | CH$_2$F | 5-OCH$_3$ | F | F |
| A-3341. | OCF$_3$ | CHF$_2$ | 3-F | F | F |
| A-3342. | OCF$_3$ | CHF$_2$ | 3-CH$_3$ | F | F |
| A-3343. | OCF$_3$ | CHF$_2$ | 3-OCH$_3$ | F | F |
| A-3344. | OCF$_3$ | CHF$_2$ | 5-F | F | F |
| A-3345. | OCF$_3$ | CHF$_2$ | 5-CH$_3$ | F | F |
| A-3346. | OCF$_3$ | CHF$_2$ | 5-OCH$_3$ | F | F |
| A-3347. | OCF$_3$ | CF$_3$ | 3-F | F | F |
| A-3348. | OCF$_3$ | CF$_3$ | 3-CH$_3$ | F | F |
| A-3349. | OCF$_3$ | CF$_3$ | 3-OCH$_3$ | F | F |
| A-3350. | OCF$_3$ | CF$_3$ | 5-F | F | F |
| A-3351. | OCF$_3$ | CF$_3$ | 5-CH$_3$ | F | F |
| A-3352. | OCF$_3$ | CF$_3$ | 5-OCH$_3$ | F | F |
| A-3353. | OCF$_3$ | OCH$_2$F | 3-F | F | F |
| A-3354. | OCF$_3$ | OCH$_2$F | 3-CH$_3$ | F | F |
| A-3355. | OCF$_3$ | OCH$_2$F | 3-OCH$_3$ | F | F |
| A-3356. | OCF$_3$ | OCH$_2$F | 5-F | F | F |
| A-3357. | OCF$_3$ | OCH$_2$F | 5-CH$_3$ | F | F |
| A-3358. | OCF$_3$ | OCH$_2$F | 5-OCH$_3$ | F | F |
| A-3359. | OCF$_3$ | OCHF$_2$ | 3-F | F | F |
| A-3360. | OCF$_3$ | OCHF$_2$ | 3-CH$_3$ | F | F |
| A-3361. | OCF$_3$ | OCHF$_2$ | 3-OCH$_3$ | F | F |
| A-3362. | OCF$_3$ | OCHF$_2$ | 5-F | F | F |
| A-3363. | OCF$_3$ | OCHF$_2$ | 5-CH$_3$ | F | F |
| A-3364. | OCF$_3$ | OCHF$_2$ | 5-OCH$_3$ | F | F |
| A-3365. | OCF$_3$ | OCF$_3$ | 3-F | F | F |
| A-3366. | OCF$_3$ | OCF$_3$ | 3-CH$_3$ | F | F |
| A-3367. | OCF$_3$ | OCF$_3$ | 3-OCH$_3$ | F | F |
| A-3368. | OCF$_3$ | OCF$_3$ | 5-F | F | F |
| A-3369. | OCF$_3$ | OCF$_3$ | 5-CH$_3$ | F | F |
| A-3370. | OCF$_3$ | OCF$_3$ | 5-OCH$_3$ | F | F |
| A-3371. | H | H | H | Cl | F |
| A-3372. | F | H | H | Cl | F |
| A-3373. | CH$_3$ | H | H | Cl | F |
| A-3374. | OCH$_3$ | H | H | Cl | F |
| A-3375. | CH$_2$F | H | H | Cl | F |
| A-3376. | CHF$_2$ | H | H | Cl | F |
| A-3377. | CF$_3$ | H | H | Cl | F |
| A-3378. | OCH$_2$F | H | H | Cl | F |
| A-3379. | OCHF$_2$ | H | H | Cl | F |
| A-3380. | OCF$_3$ | H | H | Cl | F |
| A-3381. | H | F | H | Cl | F |
| A-3382. | H | CH$_3$ | H | Cl | F |
| A-3383. | H | OCH$_3$ | H | Cl | F |
| A-3384. | H | CN | H | Cl | F |
| A-3385. | H | CH$_2$F | H | Cl | F |
| A-3386. | H | CHF$_2$ | H | Cl | F |
| A-3387. | H | CF$_3$ | H | Cl | F |
| A-3388. | H | OCH$_2$F | H | Cl | F |
| A-3389. | H | OCHF$_2$ | H | Cl | F |
| A-3390. | H | OCF$_3$ | H | Cl | F |
| A-3391. | H | H | 3-F | Cl | F |
| A-3392. | H | H | 3-CH$_3$ | Cl | F |
| A-3393. | H | H | 3-OCH$_3$ | Cl | F |
| A-3394. | H | H | 5-F | Cl | F |
| A-3395. | H | H | 5-CH$_3$ | Cl | F |
| A-3396. | H | H | 5-OCH$_3$ | Cl | F |
| A-3397. | F | F | H | Cl | F |
| A-3398. | F | CH$_3$ | H | Cl | F |
| A-3399. | F | OCH$_3$ | H | Cl | F |

TABLE A-continued

| Example No. | R¹ | R² | R³ | R⁶ | R⁷ |
|---|---|---|---|---|---|
| A-3400. | F | CN | H | Cl | F |
| A-3401. | F | CH₂F | H | Cl | F |
| A-3402. | F | CHF₂ | H | Cl | F |
| A-3403. | F | CF₃ | H | Cl | F |
| A-3404. | F | OCH₂F | H | Cl | F |
| A-3405. | F | OCHF₂ | H | Cl | F |
| A-3406. | F | OCF₃ | H | Cl | F |
| A-3407. | F | H | 3-F | Cl | F |
| A-3408. | F | H | 3-CH₃ | Cl | F |
| A-3409. | F | H | 3-OCH₃ | Cl | F |
| A-3410. | F | H | 5-F | Cl | F |
| A-3411. | F | H | 5-CH₃ | Cl | F |
| A-3412. | F | H | 5-OCH₃ | Cl | F |
| A-3413. | CH₃ | F | H | Cl | F |
| A-3414. | CH₃ | CH₃ | H | Cl | F |
| A-3415. | CH₃ | OCH₃ | H | Cl | F |
| A-3416. | CH₃ | CN | H | Cl | F |
| A-3417. | CH₃ | CH₂F | H | Cl | F |
| A-3418. | CH₃ | CHF₂ | H | Cl | F |
| A-3419. | CH₃ | CF₃ | H | Cl | F |
| A-3420. | CH₃ | OCH₂F | H | Cl | F |
| A-3421. | CH₃ | OCHF₂ | H | Cl | F |
| A-3422. | CH₃ | OCF₃ | H | Cl | F |
| A-3423. | CH₃ | H | 3-F | Cl | F |
| A-3424. | CH₃ | H | 3-CH₃ | Cl | F |
| A-3425. | CH₃ | H | 3-OCH₃ | Cl | F |
| A-3426. | CH₃ | H | 5-F | Cl | F |
| A-3427. | CH₃ | H | 5-CH₃ | Cl | F |
| A-3428. | CH₃ | H | 5-OCH₃ | Cl | F |
| A-3429. | OCH₃ | F | H | Cl | F |
| A-3430. | OCH₃ | CH₃ | H | Cl | F |
| A-3431. | OCH₃ | OCH₃ | H | Cl | F |
| A-3432. | OCH₃ | CN | H | Cl | F |
| A-3433. | OCH₃ | CH₂F | H | Cl | F |
| A-3434. | OCH₃ | CHF₂ | H | Cl | F |
| A-3435. | OCH₃ | CF₃ | H | Cl | F |
| A-3436. | OCH₃ | OCH₂F | H | Cl | F |
| A-3437. | OCH₃ | OCHF₂ | H | Cl | F |
| A-3438. | OCH₃ | OCF₃ | H | Cl | F |
| A-3439. | OCH₃ | H | 3-F | Cl | F |
| A-3440. | OCH₃ | H | 3-CH₃ | Cl | F |
| A-3441. | OCH₃ | H | 3-OCH₃ | Cl | F |
| A-3442. | OCH₃ | H | 5-F | Cl | F |
| A-3443. | OCH₃ | H | 5-CH₃ | Cl | F |
| A-3444. | OCH₃ | H | 5-OCH₃ | Cl | F |
| A-3445. | H | F | 3-F | Cl | F |
| A-3446. | H | F | 3-CH₃ | Cl | F |
| A-3447. | H | F | 3-OCH₃ | Cl | F |
| A-3448. | H | F | 5-F | Cl | F |
| A-3449. | H | F | 5-CH₃ | Cl | F |
| A-3450. | H | F | 5-OCH₃ | Cl | F |
| A-3451. | H | CH₃ | 3-F | Cl | F |
| A-3452. | H | CH₃ | 3-CH₃ | Cl | F |
| A-3453. | H | CH₃ | 3-OCH₃ | Cl | F |
| A-3454. | H | CH₃ | 5-F | Cl | F |
| A-3455. | H | CH₃ | 5-CH₃ | Cl | F |
| A-3456. | H | CH₃ | 5-OCH₃ | Cl | F |
| A-3457. | H | OCH₃ | 3-F | Cl | F |
| A-3458. | H | OCH₃ | 3-CH₃ | Cl | F |
| A-3459. | H | OCH₃ | 3-OCH₃ | Cl | F |
| A-3460. | H | OCH₃ | 5-F | Cl | F |
| A-3461. | H | OCH₃ | 5-CH₃ | Cl | F |
| A-3462. | H | OCH₃ | 5-OCH₃ | Cl | F |
| A-3463. | H | CN | 3-F | Cl | F |
| A-3464. | H | CN | 3-CH₃ | Cl | F |
| A-3465. | H | CN | 3-OCH₃ | Cl | F |
| A-3466. | H | CN | 5-F | Cl | F |
| A-3467. | H | CN | 5-CH₃ | Cl | F |
| A-3468. | H | CN | 5-OCH₃ | Cl | F |
| A-3469. | H | CH₂F | 3-F | Cl | F |
| A-3470. | H | CH₂F | 3-CH₃ | Cl | F |
| A-3471. | H | CH₂F | 3-OCH₃ | Cl | F |
| A-3472. | H | CH₂F | 5-F | Cl | F |
| A-3473. | H | CH₂F | 5-CH₃ | Cl | F |
| A-3474. | H | CH₂F | 5-OCH₃ | Cl | F |
| A-3475. | H | CHF₂ | 3-F | Cl | F |
| A-3476. | H | CHF₂ | 3-CH₃ | Cl | F |
| A-3477. | H | CHF₂ | 3-OCH₃ | Cl | F |
| A-3478. | H | CHF₂ | 5-F | Cl | F |
| A-3479. | H | CHF₂ | 5-CH₃ | Cl | F |
| A-3480. | H | CHF₂ | 5-OCH₃ | Cl | F |
| A-3481. | H | CF₃ | 3-F | Cl | F |
| A-3482. | H | CF₃ | 3-CH₃ | Cl | F |
| A-3483. | H | CF₃ | 3-OCH₃ | Cl | F |
| A-3484. | H | CF₃ | 5-F | Cl | F |
| A-3485. | H | CF₃ | 5-CH₃ | Cl | F |
| A-3486. | H | CF₃ | 5-OCH₃ | Cl | F |
| A-3487. | H | OCH₂F | 3-F | Cl | F |
| A-3488. | H | OCH₂F | 3-CH₃ | Cl | F |
| A-3489. | H | OCH₂F | 3-OCH₃ | Cl | F |
| A-3490. | H | OCH₂F | 5-F | Cl | F |
| A-3491. | H | OCH₂F | 5-CH₃ | Cl | F |
| A-3492. | H | OCH₂F | 5-OCH₃ | Cl | F |
| A-3493. | H | OCHF₂ | 3-F | Cl | F |
| A-3494. | H | OCHF₂ | 3-CH₃ | Cl | F |
| A-3495. | H | OCHF₂ | 3-OCH₃ | Cl | F |
| A-3496. | H | OCHF₂ | 5-F | Cl | F |
| A-3497. | H | OCHF₂ | 5-CH₃ | Cl | F |
| A-3498. | H | OCHF₂ | 5-OCH₃ | Cl | F |
| A-3499. | H | OCF₃ | 3-F | Cl | F |
| A-3500. | H | OCF₃ | 3-CH₃ | Cl | F |
| A-3501. | H | OCF₃ | 3-OCH₃ | Cl | F |
| A-3502. | H | OCF₃ | 5-F | Cl | F |
| A-3503. | H | OCF₃ | 5-CH₃ | Cl | F |
| A-3504. | H | OCF₃ | 5-OCH₃ | Cl | F |
| A-3505. | F | F | 3-F | Cl | F |
| A-3506. | F | F | 3-CH₃ | Cl | F |
| A-3507. | F | F | 3-OCH₃ | Cl | F |
| A-3508. | F | F | 5-F | Cl | F |
| A-3509. | F | F | 5-CH₃ | Cl | F |
| A-3510. | F | F | 5-OCH₃ | Cl | F |
| A-3511. | F | CH₃ | 3-F | Cl | F |
| A-3512. | F | CH₃ | 3-CH₃ | Cl | F |
| A-3513. | F | CH₃ | 3-OCH₃ | Cl | F |
| A-3514. | F | CH₃ | 5-F | Cl | F |
| A-3515. | F | CH₃ | 5-CH₃ | Cl | F |
| A-3516. | F | CH₃ | 5-OCH₃ | Cl | F |
| A-3517. | F | OCH₃ | 3-F | Cl | F |
| A-3518. | F | OCH₃ | 3-CH₃ | Cl | F |
| A-3519. | F | OCH₃ | 3-OCH₃ | Cl | F |
| A-3520. | F | OCH₃ | 5-F | Cl | F |
| A-3521. | F | OCH₃ | 5-CH₃ | Cl | F |
| A-3522. | F | OCH₃ | 5-OCH₃ | Cl | F |
| A-3523. | F | CN | 3-F | Cl | F |
| A-3524. | F | CN | 3-CH₃ | Cl | F |
| A-3525. | F | CN | 3-OCH₃ | Cl | F |
| A-3526. | F | CN | 5-F | Cl | F |
| A-3527. | F | CN | 5-CH₃ | Cl | F |
| A-3528. | F | CN | 5-OCH₃ | Cl | F |
| A-3529. | F | CH₂F | 3-F | Cl | F |
| A-3530. | F | CH₂F | 3-CH₃ | Cl | F |
| A-3531. | F | CH₂F | 3-OCH₃ | Cl | F |
| A-3532. | F | CH₂F | 5-F | Cl | F |
| A-3533. | F | CH₂F | 5-CH₃ | Cl | F |
| A-3534. | F | CH₂F | 5-OCH₃ | Cl | F |
| A-3535. | F | CHF₂ | 3-F | Cl | F |
| A-3536. | F | CHF₂ | 3-CH₃ | Cl | F |
| A-3537. | F | CHF₂ | 3-OCH₃ | Cl | F |
| A-3538. | F | CHF₂ | 5-F | Cl | F |
| A-3539. | F | CHF₂ | 5-CH₃ | Cl | F |
| A-3540. | F | CHF₂ | 5-OCH₃ | Cl | F |
| A-3541. | F | CF₃ | 3-F | Cl | F |
| A-3542. | F | CF₃ | 3-CH₃ | Cl | F |
| A-3543. | F | CF₃ | 3-OCH₃ | Cl | F |
| A-3544. | F | CF₃ | 5-F | Cl | F |
| A-3545. | F | CF₃ | 5-CH₃ | Cl | F |
| A-3546. | F | CF₃ | 5-OCH₃ | Cl | F |
| A-3547. | F | OCH₂F | 3-F | Cl | F |
| A-3548. | F | OCH₂F | 3-CH₃ | Cl | F |
| A-3549. | F | OCH₂F | 3-OCH₃ | Cl | F |
| A-3550. | F | OCH₂F | 5-F | Cl | F |
| A-3551. | F | OCH₂F | 5-CH₃ | Cl | F |
| A-3552. | F | OCH₂F | 5-OCH₃ | Cl | F |
| A-3553. | F | OCHF₂ | 3-F | Cl | F |
| A-3554. | F | OCHF₂ | 3-CH₃ | Cl | F |
| A-3555. | F | OCHF₂ | 3-OCH₃ | Cl | F |

TABLE A-continued

| Example No. | R¹ | R² | R³ | R⁶ | R⁷ |
|---|---|---|---|---|---|
| A-3556. | F | OCHF₂ | 5-F | Cl | F |
| A-3557. | F | OCHF₂ | 5-CH₃ | Cl | F |
| A-3558. | F | OCHF₂ | 5-OCH₃ | Cl | F |
| A-3559. | F | OCF₃ | 3-F | Cl | F |
| A-3560. | F | OCF₃ | 3-CH₃ | Cl | F |
| A-3561. | F | OCF₃ | 3-OCH₃ | Cl | F |
| A-3562. | F | OCF₃ | 5-F | Cl | F |
| A-3563. | F | OCF₃ | 5-CH₃ | Cl | F |
| A-3564. | F | OCF₃ | 5-OCH₃ | Cl | F |
| A-3565. | CH₃ | F | 3-F | Cl | F |
| A-3566. | CH₃ | F | 3-CH₃ | Cl | F |
| A-3567. | CH₃ | F | 3-OCH₃ | Cl | F |
| A-3568. | CH₃ | F | 5-F | Cl | F |
| A-3569. | CH₃ | F | 5-CH₃ | Cl | F |
| A-3570. | CH₃ | F | 5-OCH₃ | Cl | F |
| A-3571. | CH₃ | CH₃ | 3-F | Cl | F |
| A-3572. | CH₃ | CH₃ | 3-CH₃ | Cl | F |
| A-3573. | CH₃ | CH₃ | 3-OCH₃ | Cl | F |
| A-3574. | CH₃ | CH₃ | 5-F | Cl | F |
| A-3575. | CH₃ | CH₃ | 5-CH₃ | Cl | F |
| A-3576. | CH₃ | CH₃ | 5-OCH₃ | Cl | F |
| A-3577. | CH₃ | OCH₃ | 3-F | Cl | F |
| A-3578. | CH₃ | OCH₃ | 3-CH₃ | Cl | F |
| A-3579. | CH₃ | OCH₃ | 3-OCH₃ | Cl | F |
| A-3580. | CH₃ | OCH₃ | 5-F | Cl | F |
| A-3581. | CH₃ | OCH₃ | 5-CH₃ | Cl | F |
| A-3582. | CH₃ | OCH₃ | 5-OCH₃ | Cl | F |
| A-3583. | CH₃ | CN | 3-F | Cl | F |
| A-3584. | CH₃ | CN | 3-CH₃ | Cl | F |
| A-3585. | CH₃ | CN | 3-OCH₃ | Cl | F |
| A-3586. | CH₃ | CN | 5-F | Cl | F |
| A-3587. | CH₃ | CN | 5-CH₃ | Cl | F |
| A-3588. | CH₃ | CN | 5-OCH₃ | Cl | F |
| A-3589. | CH₃ | CH₂F | 3-F | Cl | F |
| A-3590. | CH₃ | CH₂F | 3-CH₃ | Cl | F |
| A-3591. | CH₃ | CH₂F | 3-OCH₃ | Cl | F |
| A-3592. | CH₃ | CH₂F | 5-F | Cl | F |
| A-3593. | CH₃ | CH₂F | 5-CH₃ | Cl | F |
| A-3594. | CH₃ | CH₂F | 5-OCH₃ | Cl | F |
| A-3595. | CH₃ | CHF₂ | 3-F | Cl | F |
| A-3596. | CH₃ | CHF₂ | 3-CH₃ | Cl | F |
| A-3597. | CH₃ | CHF₂ | 3-OCH₃ | Cl | F |
| A-3598. | CH₃ | CHF₂ | 5-F | Cl | F |
| A-3599. | CH₃ | CHF₂ | 5-CH₃ | Cl | F |
| A-3600. | CH₃ | CHF₂ | 5-OCH₃ | Cl | F |
| A-3601. | CH₃ | CF₃ | 3-F | Cl | F |
| A-3602. | CH₃ | CF₃ | 3-CH₃ | Cl | F |
| A-3603. | CH₃ | CF₃ | 3-OCH₃ | Cl | F |
| A-3604. | CH₃ | CF₃ | 5-F | Cl | F |
| A-3605. | CH₃ | CF₃ | 5-CH₃ | Cl | F |
| A-3606. | CH₃ | CF₃ | 5-OCH₃ | Cl | F |
| A-3607. | CH₃ | OCH₂F | 3-F | Cl | F |
| A-3608. | CH₃ | OCH₂F | 3-CH₃ | Cl | F |
| A-3609. | CH₃ | OCH₂F | 3-OCH₃ | Cl | F |
| A-3610. | CH₃ | OCH₂F | 5-F | Cl | F |
| A-3611. | CH₃ | OCH₂F | 5-CH₃ | Cl | F |
| A-3612. | CH₃ | OCH₂F | 5-OCH₃ | Cl | F |
| A-3613. | CH₃ | OCHF₂ | 3-F | Cl | F |
| A-3614. | CH₃ | OCHF₂ | 3-CH₃ | Cl | F |
| A-3615. | CH₃ | OCHF₂ | 3-OCH₃ | Cl | F |
| A-3616. | CH₃ | OCHF₂ | 5-F | Cl | F |
| A-3617. | CH₃ | OCHF₂ | 5-CH₃ | Cl | F |
| A-3618. | CH₃ | OCHF₂ | 5-OCH₃ | Cl | F |
| A-3619. | CH₃ | OCF₃ | 3-F | Cl | F |
| A-3620. | CH₃ | OCF₃ | 3-CH₃ | Cl | F |
| A-3621. | CH₃ | OCF₃ | 3-OCH₃ | Cl | F |
| A-3622. | CH₃ | OCF₃ | 5-F | Cl | F |
| A-3623. | CH₃ | OCF₃ | 5-CH₃ | Cl | F |
| A-3624. | CH₃ | OCF₃ | 5-OCH₃ | Cl | F |
| A-3625. | OCH₃ | F | 3-F | Cl | F |
| A-3626. | OCH₃ | F | 3-CH₃ | Cl | F |
| A-3627. | OCH₃ | F | 3-OCH₃ | Cl | F |
| A-3628. | OCH₃ | F | 5-F | Cl | F |
| A-3629. | OCH₃ | F | 5-CH₃ | Cl | F |
| A-3630. | OCH₃ | F | 5-OCH₃ | Cl | F |
| A-3631. | OCH₃ | CH₃ | 3-F | Cl | F |
| A-3632. | OCH₃ | CH₃ | 3-CH₃ | Cl | F |
| A-3633. | OCH₃ | CH₃ | 3-OCH₃ | Cl | F |
| A-3634. | OCH₃ | CH₃ | 5-F | Cl | F |
| A-3635. | OCH₃ | CH₃ | 5-CH₃ | Cl | F |
| A-3636. | OCH₃ | CH₃ | 5-OCH₃ | Cl | F |
| A-3637. | OCH₃ | OCH₃ | 3-F | Cl | F |
| A-3638. | OCH₃ | OCH₃ | 3-CH₃ | Cl | F |
| A-3639. | OCH₃ | OCH₃ | 3-OCH₃ | Cl | F |
| A-3640. | OCH₃ | OCH₃ | 5-F | Cl | F |
| A-3641. | OCH₃ | OCH₃ | 5-CH₃ | Cl | F |
| A-3642. | OCH₃ | OCH₃ | 5-OCH₃ | Cl | F |
| A-3643. | OCH₃ | CN | 3-F | Cl | F |
| A-3644. | OCH₃ | CN | 3-CH₃ | Cl | F |
| A-3645. | OCH₃ | CN | 3-OCH₃ | Cl | F |
| A-3646. | OCH₃ | CN | 5-F | Cl | F |
| A-3647. | OCH₃ | CN | 5-CH₃ | Cl | F |
| A-3648. | OCH₃ | CN | 5-OCH₃ | Cl | F |
| A-3649. | OCH₃ | CH₂F | 3-F | Cl | F |
| A-3650. | OCH₃ | CH₂F | 3-CH₃ | Cl | F |
| A-3651. | OCH₃ | CH₂F | 3-OCH₃ | Cl | F |
| A-3652. | OCH₃ | CH₂F | 5-F | Cl | F |
| A-3653. | OCH₃ | CH₂F | 5-CH₃ | Cl | F |
| A-3654. | OCH₃ | CH₂F | 5-OCH₃ | Cl | F |
| A-3655. | OCH₃ | CHF₂ | 3-F | Cl | F |
| A-3656. | OCH₃ | CHF₂ | 3-CH₃ | Cl | F |
| A-3657. | OCH₃ | CHF₂ | 3-OCH₃ | Cl | F |
| A-3658. | OCH₃ | CHF₂ | 5-F | Cl | F |
| A-3659. | OCH₃ | CHF₂ | 5-CH₃ | Cl | F |
| A-3660. | OCH₃ | CHF₂ | 5-OCH₃ | Cl | F |
| A-3661. | OCH₃ | CF₃ | 3-F | Cl | F |
| A-3662. | OCH₃ | CF₃ | 3-CH₃ | Cl | F |
| A-3663. | OCH₃ | CF₃ | 3-OCH₃ | Cl | F |
| A-3664. | OCH₃ | CF₃ | 5-F | Cl | F |
| A-3665. | OCH₃ | CF₃ | 5-CH₃ | Cl | F |
| A-3666. | OCH₃ | CF₃ | 5-OCH₃ | Cl | F |
| A-3667. | OCH₃ | OCH₂F | 3-F | Cl | F |
| A-3668. | OCH₃ | OCH₂F | 3-CH₃ | Cl | F |
| A-3669. | OCH₃ | OCH₂F | 3-OCH₃ | Cl | F |
| A-3670. | OCH₃ | OCH₂F | 5-F | Cl | F |
| A-3671. | OCH₃ | OCH₂F | 5-CH₃ | Cl | F |
| A-3672. | OCH₃ | OCH₂F | 5-OCH₃ | Cl | F |
| A-3673. | OCH₃ | OCHF₂ | 3-F | Cl | F |
| A-3674. | OCH₃ | OCHF₂ | 3-CH₃ | Cl | F |
| A-3675. | OCH₃ | OCHF₂ | 3-OCH₃ | Cl | F |
| A-3676. | OCH₃ | OCHF₂ | 5-F | Cl | F |
| A-3677. | OCH₃ | OCHF₂ | 5-CH₃ | Cl | F |
| A-3678. | OCH₃ | OCHF₂ | 5-OCH₃ | Cl | F |
| A-3679. | OCH₃ | OCF₃ | 3-F | Cl | F |
| A-3680. | OCH₃ | OCF₃ | 3-CH₃ | Cl | F |
| A-3681. | OCH₃ | OCF₃ | 3-OCH₃ | Cl | F |
| A-3682. | OCH₃ | OCF₃ | 5-F | Cl | F |
| A-3683. | OCH₃ | OCF₃ | 5-CH₃ | Cl | F |
| A-3684. | OCH₃ | OCF₃ | 5-OCH₃ | Cl | F |
| A-3685. | CH₂F | F | 3-F | Cl | F |
| A-3686. | CH₂F | F | 3-CH₃ | Cl | F |
| A-3687. | CH₂F | F | 3-OCH₃ | Cl | F |
| A-3688. | CH₂F | F | 5-F | Cl | F |
| A-3689. | CH₂F | F | 5-CH₃ | Cl | F |
| A-3690. | CH₂F | F | 5-OCH₃ | Cl | F |
| A-3691. | CH₂F | CH₃ | 3-F | Cl | F |
| A-3692. | CH₂F | CH₃ | 3-CH₃ | Cl | F |
| A-3693. | CH₂F | CH₃ | 3-OCH₃ | Cl | F |
| A-3694. | CH₂F | CH₃ | 5-F | Cl | F |
| A-3695. | CH₂F | CH₃ | 5-CH₃ | Cl | F |
| A-3696. | CH₂F | CH₃ | 5-OCH₃ | Cl | F |
| A-3697. | CH₂F | OCH₃ | 3-F | Cl | F |
| A-3698. | CH₂F | OCH₃ | 3-CH₃ | Cl | F |
| A-3699. | CH₂F | OCH₃ | 3-OCH₃ | Cl | F |
| A-3700. | CH₂F | OCH₃ | 5-F | Cl | F |
| A-3701. | CH₂F | OCH₃ | 5-CH₃ | Cl | F |
| A-3702. | CH₂F | OCH₃ | 5-OCH₃ | Cl | F |
| A-3703. | CH₂F | CN | 3-F | Cl | F |
| A-3704. | CH₂F | CN | 3-CH₃ | Cl | F |
| A-3705. | CH₂F | CN | 3-OCH₃ | Cl | F |
| A-3706. | CH₂F | CN | 5-F | Cl | F |
| A-3707. | CH₂F | CN | 5-CH₃ | Cl | F |
| A-3708. | CH₂F | CN | 5-OCH₃ | Cl | F |
| A-3709. | CH₂F | CH₂F | 3-F | Cl | F |
| A-3710. | CH₂F | CH₂F | 3-CH₃ | Cl | F |
| A-3711. | CH₂F | CH₂F | 3-OCH₃ | Cl | F |

TABLE A-continued

| Example No. | R¹ | R² | R³ | R⁶ | R⁷ |
|---|---|---|---|---|---|
| A-3712. | CH₂F | CH₂F | 5-F | Cl | F |
| A-3713. | CH₂F | CH₂F | 5-CH₃ | Cl | F |
| A-3714. | CH₂F | CH₂F | 5-OCH₃ | Cl | F |
| A-3715. | CH₂F | CHF₂ | 3-F | Cl | F |
| A-3716. | CH₂F | CHF₂ | 3-CH₃ | Cl | F |
| A-3717. | CH₂F | CHF₂ | 3-OCH₃ | Cl | F |
| A-3718. | CH₂F | CHF₂ | 5-F | Cl | F |
| A-3719. | CH₂F | CHF₂ | 5-CH₃ | Cl | F |
| A-3720. | CH₂F | CHF₂ | 5-OCH₃ | Cl | F |
| A-3721. | CH₂F | CF₃ | 3-F | Cl | F |
| A-3722. | CH₂F | CF₃ | 3-CH₃ | Cl | F |
| A-3723. | CH₂F | CF₃ | 3-OCH₃ | Cl | F |
| A-3724. | CH₂F | CF₃ | 5-F | Cl | F |
| A-3725. | CH₂F | CF₃ | 5-CH₃ | Cl | F |
| A-3726. | CH₂F | CF₃ | 5-OCH₃ | Cl | F |
| A-3727. | CH₂F | OCH₂F | 3-F | Cl | F |
| A-3728. | CH₂F | OCH₂F | 3-CH₃ | Cl | F |
| A-3729. | CH₂F | OCH₂F | 3-OCH₃ | Cl | F |
| A-3730. | CH₂F | OCH₂F | 5-F | Cl | F |
| A-3731. | CH₂F | OCH₂F | 5-CH₃ | Cl | F |
| A-3732. | CH₂F | OCH₂F | 5-OCH₃ | Cl | F |
| A-3733. | CH₂F | OCHF₂ | 3-F | Cl | F |
| A-3734. | CH₂F | OCHF₂ | 3-CH₃ | Cl | F |
| A-3735. | CH₂F | OCHF₂ | 3-OCH₃ | Cl | F |
| A-3736. | CH₂F | OCHF₂ | 5-F | Cl | F |
| A-3737. | CH₂F | OCHF₂ | 5-CH₃ | Cl | F |
| A-3738. | CH₂F | OCHF₂ | 5-OCH₃ | Cl | F |
| A-3739. | CH₂F | OCF₃ | 3-F | Cl | F |
| A-3740. | CH₂F | OCF₃ | 3-CH₃ | Cl | F |
| A-3741. | CH₂F | OCF₃ | 3-OCH₃ | Cl | F |
| A-3742. | CH₂F | OCF₃ | 5-F | Cl | F |
| A-3743. | CH₂F | OCF₃ | 5-CH₃ | Cl | F |
| A-3744. | CH₂F | OCF₃ | 5-OCH₃ | Cl | F |
| A-3745. | CHF₂ | F | 3-F | Cl | F |
| A-3746. | CHF₂ | F | 3-CH₃ | Cl | F |
| A-3747. | CHF₂ | F | 3-OCH₃ | Cl | F |
| A-3748. | CHF₂ | F | 5-F | Cl | F |
| A-3749. | CHF₂ | F | 5-CH₃ | Cl | F |
| A-3750. | CHF₂ | F | 5-OCH₃ | Cl | F |
| A-3751. | CHF₂ | CH₃ | 3-F | Cl | F |
| A-3752. | CHF₂ | CH₃ | 3-CH₃ | Cl | F |
| A-3753. | CHF₂ | CH₃ | 3-OCH₃ | Cl | F |
| A-3754. | CHF₂ | CH₃ | 5-F | Cl | F |
| A-3755. | CHF₂ | CH₃ | 5-CH₃ | Cl | F |
| A-3756. | CHF₂ | CH₃ | 5-OCH₃ | Cl | F |
| A-3757. | CHF₂ | OCH₃ | 3-F | Cl | F |
| A-3758. | CHF₂ | OCH₃ | 3-CH₃ | Cl | F |
| A-3759. | CHF₂ | OCH₃ | 3-OCH₃ | Cl | F |
| A-3760. | CHF₂ | OCH₃ | 5-F | Cl | F |
| A-3761. | CHF₂ | OCH₃ | 5-CH₃ | Cl | F |
| A-3762. | CHF₂ | OCH₃ | 5-OCH₃ | Cl | F |
| A-3763. | CHF₂ | CN | 3-F | Cl | F |
| A-3764. | CHF₂ | CN | 3-CH₃ | Cl | F |
| A-3765. | CHF₂ | CN | 3-OCH₃ | Cl | F |
| A-3766. | CHF₂ | CN | 5-F | Cl | F |
| A-3767. | CHF₂ | CN | 5-CH₃ | Cl | F |
| A-3768. | CHF₂ | CN | 5-OCH₃ | Cl | F |
| A-3769. | CHF₂ | CH₂F | 3-F | Cl | F |
| A-3770. | CHF₂ | CH₂F | 3-CH₃ | Cl | F |
| A-3771. | CHF₂ | CH₂F | 3-OCH₃ | Cl | F |
| A-3772. | CHF₂ | CH₂F | 5-F | Cl | F |
| A-3773. | CHF₂ | CH₂F | 5-CH₃ | Cl | F |
| A-3774. | CHF₂ | CH₂F | 5-OCH₃ | Cl | F |
| A-3775. | CHF₂ | CHF₂ | 3-F | Cl | F |
| A-3776. | CHF₂ | CHF₂ | 3-CH₃ | Cl | F |
| A-3777. | CHF₂ | CHF₂ | 3-OCH₃ | Cl | F |
| A-3778. | CHF₂ | CHF₂ | 5-F | Cl | F |
| A-3779. | CHF₂ | CHF₂ | 5-CH₃ | Cl | F |
| A-3780. | CHF₂ | CHF₂ | 5-OCH₃ | Cl | F |
| A-3781. | CHF₂ | CF₃ | 3-F | Cl | F |
| A-3782. | CHF₂ | CF₃ | 3-CH₃ | Cl | F |
| A-3783. | CHF₂ | CF₃ | 3-OCH₃ | Cl | F |
| A-3784. | CHF₂ | CF₃ | 5-F | Cl | F |
| A-3785. | CHF₂ | CF₃ | 5-CH₃ | Cl | F |
| A-3786. | CHF₂ | CF₃ | 5-OCH₃ | Cl | F |
| A-3787. | CHF₂ | OCH₂F | 3-F | Cl | F |
| A-3788. | CHF₂ | OCH₂F | 3-CH₃ | Cl | F |
| A-3789. | CHF₂ | OCH₂F | 3-OCH₃ | Cl | F |
| A-3790. | CHF₂ | OCH₂F | 5-F | Cl | F |
| A-3791. | CHF₂ | OCH₂F | 5-CH₃ | Cl | F |
| A-3792. | CHF₂ | OCH₂F | 5-OCH₃ | Cl | F |
| A-3793. | CHF₂ | OCHF₂ | 3-F | Cl | F |
| A-3794. | CHF₂ | OCHF₂ | 3-CH₃ | Cl | F |
| A-3795. | CHF₂ | OCHF₂ | 3-OCH₃ | Cl | F |
| A-3796. | CHF₂ | OCHF₂ | 5-F | Cl | F |
| A-3797. | CHF₂ | OCHF₂ | 5-CH₃ | Cl | F |
| A-3798. | CHF₂ | OCHF₂ | 5-OCH₃ | Cl | F |
| A-3799. | CHF₂ | OCF₃ | 3-F | Cl | F |
| A-3800. | CHF₂ | OCF₃ | 3-CH₃ | Cl | F |
| A-3801. | CHF₂ | OCF₃ | 3-OCH₃ | Cl | F |
| A-3802. | CHF₂ | OCF₃ | 5-F | Cl | F |
| A-3803. | CHF₂ | OCF₃ | 5-CH₃ | Cl | F |
| A-3804. | CHF₂ | OCF₃ | 5-OCH₃ | Cl | F |
| A-3805. | CF₃ | F | 3-F | Cl | F |
| A-3806. | CF₃ | F | 3-CH₃ | Cl | F |
| A-3807. | CF₃ | F | 3-OCH₃ | Cl | F |
| A-3808. | CF₃ | F | 5-F | Cl | F |
| A-3809. | CF₃ | F | 5-CH₃ | Cl | F |
| A-3810. | CF₃ | F | 5-OCH₃ | Cl | F |
| A-3811. | CF₃ | CH₃ | 3-F | Cl | F |
| A-3812. | CF₃ | CH₃ | 3-CH₃ | Cl | F |
| A-3813. | CF₃ | CH₃ | 3-OCH₃ | Cl | F |
| A-3814. | CF₃ | CH₃ | 5-F | Cl | F |
| A-3815. | CF₃ | CH₃ | 5-CH₃ | Cl | F |
| A-3816. | CF₃ | CH₃ | 5-OCH₃ | Cl | F |
| A-3817. | CF₃ | OCH₃ | 3-F | Cl | F |
| A-3818. | CF₃ | OCH₃ | 3-CH₃ | Cl | F |
| A-3819. | CF₃ | OCH₃ | 3-OCH₃ | Cl | F |
| A-3820. | CF₃ | OCH₃ | 5-F | Cl | F |
| A-3821. | CF₃ | OCH₃ | 5-CH₃ | Cl | F |
| A-3822. | CF₃ | OCH₃ | 5-OCH₃ | Cl | F |
| A-3823. | CF₃ | CN | 3-F | Cl | F |
| A-3824. | CF₃ | CN | 3-CH₃ | Cl | F |
| A-3825. | CF₃ | CN | 3-OCH₃ | Cl | F |
| A-3826. | CF₃ | CN | 5-F | Cl | F |
| A-3827. | CF₃ | CN | 5-CH₃ | Cl | F |
| A-3828. | CF₃ | CN | 5-OCH₃ | Cl | F |
| A-3829. | CF₃ | CH₂F | 3-F | Cl | F |
| A-3830. | CF₃ | CH₂F | 3-CH₃ | Cl | F |
| A-3831. | CF₃ | CH₂F | 3-OCH₃ | Cl | F |
| A-3832. | CF₃ | CH₂F | 5-F | Cl | F |
| A-3833. | CF₃ | CH₂F | 5-CH₃ | Cl | F |
| A-3834. | CF₃ | CH₂F | 5-OCH₃ | Cl | F |
| A-3835. | CF₃ | CHF₂ | 3-F | Cl | F |
| A-3836. | CF₃ | CHF₂ | 3-CH₃ | Cl | F |
| A-3837. | CF₃ | CHF₂ | 3-OCH₃ | Cl | F |
| A-3838. | CF₃ | CHF₂ | 5-F | Cl | F |
| A-3839. | CF₃ | CHF₂ | 5-CH₃ | Cl | F |
| A-3840. | CF₃ | CHF₂ | 5-OCH₃ | Cl | F |
| A-3841. | CF₃ | CF₃ | 3-F | Cl | F |
| A-3842. | CF₃ | CF₃ | 3-CH₃ | Cl | F |
| A-3843. | CF₃ | CF₃ | 3-OCH₃ | Cl | F |
| A-3844. | CF₃ | CF₃ | 5-F | Cl | F |
| A-3845. | CF₃ | CF₃ | 5-CH₃ | Cl | F |
| A-3846. | CF₃ | CF₃ | 5-OCH₃ | Cl | F |
| A-3847. | CF₃ | OCH₂F | 3-F | Cl | F |
| A-3848. | CF₃ | OCH₂F | 3-CH₃ | Cl | F |
| A-3849. | CF₃ | OCH₂F | 3-OCH₃ | Cl | F |
| A-3850. | CF₃ | OCH₂F | 5-F | Cl | F |
| A-3851. | CF₃ | OCH₂F | 5-CH₃ | Cl | F |
| A-3852. | CF₃ | OCH₂F | 5-OCH₃ | Cl | F |
| A-3853. | CF₃ | OCHF₂ | 3-F | Cl | F |
| A-3854. | CF₃ | OCHF₂ | 3-CH₃ | Cl | F |
| A-3855. | CF₃ | OCHF₂ | 3-OCH₃ | Cl | F |
| A-3856. | CF₃ | OCHF₂ | 5-F | Cl | F |
| A-3857. | CF₃ | OCHF₂ | 5-CH₃ | Cl | F |
| A-3858. | CF₃ | OCHF₂ | 5-OCH₃ | Cl | F |
| A-3859. | CF₃ | OCF₃ | 3-F | Cl | F |
| A-3860. | CF₃ | OCF₃ | 3-CH₃ | Cl | F |
| A-3861. | CF₃ | OCF₃ | 3-OCH₃ | Cl | F |
| A-3862. | CF₃ | OCF₃ | 5-F | Cl | F |
| A-3863. | CF₃ | OCF₃ | 5-CH₃ | Cl | F |
| A-3864. | CF₃ | OCF₃ | 5-OCH₃ | Cl | F |
| A-3865. | OCH₂F | F | 3-F | Cl | F |
| A-3866. | OCH₂F | F | 3-CH₃ | Cl | F |
| A-3867. | OCH₂F | F | 3-OCH₃ | Cl | F |

TABLE A-continued

| Example No. | R¹ | R² | R³ | R⁶ | R⁷ |
|---|---|---|---|---|---|
| A-3868. | OCH₂F | F | 5-F | Cl | F |
| A-3869. | OCH₂F | F | 5-CH₃ | Cl | F |
| A-3870. | OCH₂F | F | 5-OCH₃ | Cl | F |
| A-3871. | OCH₂F | CH₃ | 3-F | Cl | F |
| A-3872. | OCH₂F | CH₃ | 3-CH₃ | Cl | F |
| A-3873. | OCH₂F | CH₃ | 3-OCH₃ | Cl | F |
| A-3874. | OCH₂F | CH₃ | 5-F | Cl | F |
| A-3875. | OCH₂F | CH₃ | 5-CH₃ | Cl | F |
| A-3876. | OCH₂F | CH₃ | 5-OCH₃ | Cl | F |
| A-3877. | OCH₂F | OCH₃ | 3-F | Cl | F |
| A-3878. | OCH₂F | OCH₃ | 3-CH₃ | Cl | F |
| A-3879. | OCH₂F | OCH₃ | 3-OCH₃ | Cl | F |
| A-3880. | OCH₂F | OCH₃ | 5-F | Cl | F |
| A-3881. | OCH₂F | OCH₃ | 5-CH₃ | Cl | F |
| A-3882. | OCH₂F | OCH₃ | 5-OCH₃ | Cl | F |
| A-3883. | OCH₂F | CN | 3-F | Cl | F |
| A-3884. | OCH₂F | CN | 3-CH₃ | Cl | F |
| A-3885. | OCH₂F | CN | 3-OCH₃ | Cl | F |
| A-3886. | OCH₂F | CN | 5-F | Cl | F |
| A-3887. | OCH₂F | CN | 5-CH₃ | Cl | F |
| A-3888. | OCH₂F | CN | 5-OCH₃ | Cl | F |
| A-3889. | OCH₂F | CH₂F | 3-F | Cl | F |
| A-3890. | OCH₂F | CH₂F | 3-CH₃ | Cl | F |
| A-3891. | OCH₂F | CH₂F | 3-OCH₃ | Cl | F |
| A-3892. | OCH₂F | CH₂F | 5-F | Cl | F |
| A-3893. | OCH₂F | CH₂F | 5-CH₃ | Cl | F |
| A-3894. | OCH₂F | CH₂F | 5-OCH₃ | Cl | F |
| A-3895. | OCH₂F | CHF₂ | 3-F | Cl | F |
| A-3896. | OCH₂F | CHF₂ | 3-CH₃ | Cl | F |
| A-3897. | OCH₂F | CHF₂ | 3-OCH₃ | Cl | F |
| A-3898. | OCH₂F | CHF₂ | 5-F | Cl | F |
| A-3899. | OCH₂F | CHF₂ | 5-CH₃ | Cl | F |
| A-3900. | OCH₂F | CHF₂ | 5-OCH₃ | Cl | F |
| A-3901. | OCH₂F | CF₃ | 3-F | Cl | F |
| A-3902. | OCH₂F | CF₃ | 3-CH₃ | Cl | F |
| A-3903. | OCH₂F | CF₃ | 3-OCH₃ | Cl | F |
| A-3904. | OCH₂F | CF₃ | 5-F | Cl | F |
| A-3905. | OCH₂F | CF₃ | 5-CH₃ | Cl | F |
| A-3906. | OCH₂F | CF₃ | 5-OCH₃ | Cl | F |
| A-3907. | OCH₂F | OCH₂F | 3-F | Cl | F |
| A-3908. | OCH₂F | OCH₂F | 3-CH₃ | Cl | F |
| A-3909. | OCH₂F | OCH₂F | 3-OCH₃ | Cl | F |
| A-3910. | OCH₂F | OCH₂F | 5-F | Cl | F |
| A-3911. | OCH₂F | OCH₂F | 5-CH₃ | Cl | F |
| A-3912. | OCH₂F | OCH₂F | 5-OCH₃ | Cl | F |
| A-3913. | OCH₂F | OCHF₂ | 3-F | Cl | F |
| A-3914. | OCH₂F | OCHF₂ | 3-CH₃ | Cl | F |
| A-3915. | OCH₂F | OCHF₂ | 3-OCH₃ | Cl | F |
| A-3916. | OCH₂F | OCHF₂ | 5-F | Cl | F |
| A-3917. | OCH₂F | OCHF₂ | 5-CH₃ | Cl | F |
| A-3918. | OCH₂F | OCHF₂ | 5-OCH₃ | Cl | F |
| A-3919. | OCH₂F | OCF₃ | 3-F | Cl | F |
| A-3920. | OCH₂F | OCF₃ | 3-CH₃ | Cl | F |
| A-3921. | OCH₂F | OCF₃ | 3-OCH₃ | Cl | F |
| A-3922. | OCH₂F | OCF₃ | 5-F | Cl | F |
| A-3923. | OCH₂F | OCF₃ | 5-CH₃ | Cl | F |
| A-3924. | OCH₂F | OCF₃ | 5-OCH₃ | Cl | F |
| A-3925. | OCHF₂ | F | 3-F | Cl | F |
| A-3926. | OCHF₂ | F | 3-CH₃ | Cl | F |
| A-3927. | OCHF₂ | F | 3-OCH₃ | Cl | F |
| A-3928. | OCHF₂ | F | 5-F | Cl | F |
| A-3929. | OCHF₂ | F | 5-CH₃ | Cl | F |
| A-3930. | OCHF₂ | F | 5-OCH₃ | Cl | F |
| A-3931. | OCHF₂ | CH₃ | 3-F | Cl | F |
| A-3932. | OCHF₂ | CH₃ | 3-CH₃ | Cl | F |
| A-3933. | OCHF₂ | CH₃ | 3-OCH₃ | Cl | F |
| A-3934. | OCHF₂ | CH₃ | 5-F | Cl | F |
| A-3935. | OCHF₂ | CH₃ | 5-CH₃ | Cl | F |
| A-3936. | OCHF₂ | CH₃ | 5-OCH₃ | Cl | F |
| A-3937. | OCHF₂ | OCH₃ | 3-F | Cl | F |
| A-3938. | OCHF₂ | OCH₃ | 3-CH₃ | Cl | F |
| A-3939. | OCHF₂ | OCH₃ | 3-OCH₃ | Cl | F |
| A-3940. | OCHF₂ | OCH₃ | 5-F | Cl | F |
| A-3941. | OCHF₂ | OCH₃ | 5-CH₃ | Cl | F |
| A-3942. | OCHF₂ | OCH₃ | 5-OCH₃ | Cl | F |
| A-3943. | OCHF₂ | CN | 3-F | Cl | F |
| A-3944. | OCHF₂ | CN | 3-CH₃ | Cl | F |
| A-3945. | OCHF₂ | CN | 3-OCH₃ | Cl | F |
| A-3946. | OCHF₂ | CN | 5-F | Cl | F |
| A-3947. | OCHF₂ | CN | 5-CH₃ | Cl | F |
| A-3948. | OCHF₂ | CN | 5-OCH₃ | Cl | F |
| A-3949. | OCHF₂ | CH₂F | 3-F | Cl | F |
| A-3950. | OCHF₂ | CH₂F | 3-CH₃ | Cl | F |
| A-3951. | OCHF₂ | CH₂F | 3-OCH₃ | Cl | F |
| A-3952. | OCHF₂ | CH₂F | 5-F | Cl | F |
| A-3953. | OCHF₂ | CH₂F | 5-CH₃ | Cl | F |
| A-3954. | OCHF₂ | CH₂F | 5-OCH₃ | Cl | F |
| A-3955. | OCHF₂ | CHF₂ | 3-F | Cl | F |
| A-3956. | OCHF₂ | CHF₂ | 3-CH₃ | Cl | F |
| A-3957. | OCHF₂ | CHF₂ | 3-OCH₃ | Cl | F |
| A-3958. | OCHF₂ | CHF₂ | 5-F | Cl | F |
| A-3959. | OCHF₂ | CHF₂ | 5-CH₃ | Cl | F |
| A-3960. | OCHF₂ | CHF₂ | 5-OCH₃ | Cl | F |
| A-3961. | OCHF₂ | CF₃ | 3-F | Cl | F |
| A-3962. | OCHF₂ | CF₃ | 3-CH₃ | Cl | F |
| A-3963. | OCHF₂ | CF₃ | 3-OCH₃ | Cl | F |
| A-3964. | OCHF₂ | CF₃ | 5-F | Cl | F |
| A-3965. | OCHF₂ | CF₃ | 5-CH₃ | Cl | F |
| A-3966. | OCHF₂ | CF₃ | 5-OCH₃ | Cl | F |
| A-3967. | OCHF₂ | OCH₂F | 3-F | Cl | F |
| A-3968. | OCHF₂ | OCH₂F | 3-CH₃ | Cl | F |
| A-3969. | OCHF₂ | OCH₂F | 3-OCH₃ | Cl | F |
| A-3970. | OCHF₂ | OCH₂F | 5-F | Cl | F |
| A-3971. | OCHF₂ | OCH₂F | 5-CH₃ | Cl | F |
| A-3972. | OCHF₂ | OCH₂F | 5-OCH₃ | Cl | F |
| A-3973. | OCHF₂ | OCHF₂ | 3-F | Cl | F |
| A-3974. | OCHF₂ | OCHF₂ | 3-CH₃ | Cl | F |
| A-3975. | OCHF₂ | OCHF₂ | 3-OCH₃ | Cl | F |
| A-3976. | OCHF₂ | OCHF₂ | 5-F | Cl | F |
| A-3977. | OCHF₂ | OCHF₂ | 5-CH₃ | Cl | F |
| A-3978. | OCHF₂ | OCHF₂ | 5-OCH₃ | Cl | F |
| A-3979. | OCHF₂ | OCF₃ | 3-F | Cl | F |
| A-3980. | OCHF₂ | OCF₃ | 3-CH₃ | Cl | F |
| A-3981. | OCHF₂ | OCF₃ | 3-OCH₃ | Cl | F |
| A-3982. | OCHF₂ | OCF₃ | 5-F | Cl | F |
| A-3983. | OCHF₂ | OCF₃ | 5-CH₃ | Cl | F |
| A-3984. | OCHF₂ | OCF₃ | 5-OCH₃ | Cl | F |
| A-3985. | OCF₃ | F | 3-F | Cl | F |
| A-3986. | OCF₃ | F | 3-CH₃ | Cl | F |
| A-3987. | OCF₃ | F | 3-OCH₃ | Cl | F |
| A-3988. | OCF₃ | F | 5-F | Cl | F |
| A-3989. | OCF₃ | F | 5-CH₃ | Cl | F |
| A-3990. | OCF₃ | F | 5-OCH₃ | Cl | F |
| A-3991. | OCF₃ | CH₃ | 3-F | Cl | F |
| A-3992. | OCF₃ | CH₃ | 3-CH₃ | Cl | F |
| A-3993. | OCF₃ | CH₃ | 3-OCH₃ | Cl | F |
| A-3994. | OCF₃ | CH₃ | 5-F | Cl | F |
| A-3995. | OCF₃ | CH₃ | 5-CH₃ | Cl | F |
| A-3996. | OCF₃ | CH₃ | 5-OCH₃ | Cl | F |
| A-3997. | OCF₃ | OCH₃ | 3-F | Cl | F |
| A-3998. | OCF₃ | OCH₃ | 3-CH₃ | Cl | F |
| A-3999. | OCF₃ | OCH₃ | 3-OCH₃ | Cl | F |
| A-4000. | OCF₃ | OCH₃ | 5-F | Cl | F |
| A-4001. | OCF₃ | OCH₃ | 5-CH₃ | Cl | F |
| A-4002. | OCF₃ | OCH₃ | 5-OCH₃ | Cl | F |
| A-4003. | OCF₃ | CN | 3-F | Cl | F |
| A-4004. | OCF₃ | CN | 3-CH₃ | Cl | F |
| A-4005. | OCF₃ | CN | 3-OCH₃ | Cl | F |
| A-4006. | OCF₃ | CN | 5-F | Cl | F |
| A-4007. | OCF₃ | CN | 5-CH₃ | Cl | F |
| A-4008. | OCF₃ | CN | 5-OCH₃ | Cl | F |
| A-4009. | OCF₃ | CH₂F | 3-F | Cl | F |
| A-4010. | OCF₃ | CH₂F | 3-CH₃ | Cl | F |
| A-4011. | OCF₃ | CH₂F | 3-OCH₃ | Cl | F |
| A-4012. | OCF₃ | CH₂F | 5-F | Cl | F |
| A-4013. | OCF₃ | CH₂F | 5-CH₃ | Cl | F |
| A-4014. | OCF₃ | CH₂F | 5-OCH₃ | Cl | F |
| A-4015. | OCF₃ | CHF₂ | 3-F | Cl | F |
| A-4016. | OCF₃ | CHF₂ | 3-CH₃ | Cl | F |
| A-4017. | OCF₃ | CHF₂ | 3-OCH₃ | Cl | F |
| A-4018. | OCF₃ | CHF₂ | 5-F | Cl | F |
| A-4019. | OCF₃ | CHF₂ | 5-CH₃ | Cl | F |
| A-4020. | OCF₃ | CHF₂ | 5-OCH₃ | Cl | F |
| A-4021. | OCF₃ | CF₃ | 3-F | Cl | F |
| A-4022. | OCF₃ | CF₃ | 3-CH₃ | Cl | F |
| A-4023. | OCF₃ | CF₃ | 3-OCH₃ | Cl | F |

TABLE A-continued

| Example No. | R¹ | R² | R³ | R⁶ | R⁷ |
| --- | --- | --- | --- | --- | --- |
| A-4024. | $OCF_3$ | $CF_3$ | 5-F | Cl | F |
| A-4025. | $OCF_3$ | $CF_3$ | 5-$CH_3$ | Cl | F |
| A-4026. | $OCF_3$ | $CF_3$ | 5-$OCH_3$ | Cl | F |
| A-4027. | $OCF_3$ | $OCH_2F$ | 3-F | Cl | F |
| A-4028. | $OCF_3$ | $OCH_2F$ | 3-$CH_3$ | Cl | F |
| A-4029. | $OCF_3$ | $OCH_2F$ | 3-$OCH_3$ | Cl | F |
| A-4030. | $OCF_3$ | $OCH_2F$ | 5-F | Cl | F |
| A-4031. | $OCF_3$ | $OCH_2F$ | 5-$CH_3$ | Cl | F |
| A-4032. | $OCF_3$ | $OCH_2F$ | 5-$OCH_3$ | Cl | F |
| A-4033. | $OCF_3$ | $OCHF_2$ | 3-F | Cl | F |
| A-4034. | $OCF_3$ | $OCHF_2$ | 3-$CH_3$ | Cl | F |
| A-4035. | $OCF_3$ | $OCHF_2$ | 3-$OCH_3$ | Cl | F |
| A-4036. | $OCF_3$ | $OCHF_2$ | 5-F | Cl | F |
| A-4037. | $OCF_3$ | $OCHF_2$ | 5-$CH_3$ | Cl | F |
| A-4038. | $OCF_3$ | $OCHF_2$ | 5-$OCH_3$ | Cl | F |
| A-4039. | $OCF_3$ | $OCF_3$ | 3-F | Cl | F |
| A-4040. | $OCF_3$ | $OCF_3$ | 3-$CH_3$ | Cl | F |
| A-4041. | $OCF_3$ | $OCF_3$ | 3-$OCH_3$ | Cl | F |
| A-4042. | $OCF_3$ | $OCF_3$ | 5-F | Cl | F |
| A-4043. | $OCF_3$ | $OCF_3$ | 5-$CH_3$ | Cl | F |
| A-4044. | $OCF_3$ | $OCF_3$ | 5-$OCH_3$ | Cl | F |

TABLE B

| Example No. | R² | R³ | R⁶ | R⁷ |
| --- | --- | --- | --- | --- |
| B-1. | H | H | CN | H |
| B-2. | F | H | CN | H |
| B-3. | $CH_3$ | H | CN | H |
| B-4. | $OCH_3$ | H | CN | H |
| B-5. | CN | H | CN | H |
| B-6. | $CH_2F$ | H | CN | H |
| B-7. | $CHF_2$ | H | CN | H |
| B-8. | $CF_3$ | H | CN | H |
| B-9. | $OCH_2F$ | H | CN | H |
| B-10. | $OCHF_2$ | H | CN | H |
| B-11. | $OCF_3$ | H | CN | H |
| B-12. | H | 3-F | CN | H |
| B-13. | H | 3-$CH_3$ | CN | H |
| B-14. | H | 3-$OCH_3$ | CN | H |
| B-15. | H | 5-F | CN | H |
| B-16. | H | 5-$CH_3$ | CN | H |
| B-17. | H | 5-$OCH_3$ | CN | H |
| B-18. | H | 6-F | CN | H |
| B-19. | H | 6-$CH_3$ | CN | H |
| B-20. | H | 6-$OCH_3$ | CN | H |
| B-21. | F | 3-F | CN | H |
| B-22. | F | 3-$CH_3$ | CN | H |
| B-23. | F | 3-$OCH_3$ | CN | H |
| B-24. | F | 5-F | CN | H |
| B-25. | F | 5-$CH_3$ | CN | H |
| B-26. | F | 5-$OCH_3$ | CN | H |
| B-27. | F | 6-F | CN | H |
| B-28. | F | 6-$CH_3$ | CN | H |
| B-29. | F | 6-$OCH_3$ | CN | H |
| B-30. | $CH_3$ | 3-F | CN | H |
| B-31. | $CH_3$ | 3-$CH_3$ | CN | H |
| B-32. | $CH_3$ | 3-$OCH_3$ | CN | H |
| B-33. | $CH_3$ | 5-F | CN | H |
| B-34. | $CH_3$ | 5-$CH_3$ | CN | H |
| B-35. | $CH_3$ | 5-$OCH_3$ | CN | H |
| B-36. | $CH_3$ | 6-F | CN | H |
| B-37. | $CH_3$ | 6-$CH_3$ | CN | H |
| B-38. | $CH_3$ | 6-$OCH_3$ | CN | H |
| B-39. | $OCH_3$ | 3-F | CN | H |
| B-40. | $OCH_3$ | 3-$CH_3$ | CN | H |
| B-41. | $OCH_3$ | 3-$OCH_3$ | CN | H |
| B-42. | $OCH_3$ | 5-F | CN | H |
| B-43. | $OCH_3$ | 5-$CH_3$ | CN | H |
| B-44. | $OCH_3$ | 5-$OCH_3$ | CN | H |
| B-45. | $OCH_3$ | 6-F | CN | H |
| B-46. | $OCH_3$ | 6-$CH_3$ | CN | H |
| B-47. | $OCH_3$ | 6-$OCH_3$ | CN | H |
| B-48. | CN | 3-F | CN | H |
| B-49. | CN | 3-$CH_3$ | CN | H |
| B-50. | CN | 3-$OCH_3$ | CN | H |
| B-51. | CN | 5-F | CN | H |
| B-52. | CN | 5-$CH_3$ | CN | H |
| B-53. | CN | 5-$OCH_3$ | CN | H |
| B-54. | CN | 6-F | CN | H |
| B-55. | CN | 6-$CH_3$ | CN | H |
| B-56. | CN | 6-$OCH_3$ | CN | H |
| B-57. | $CH_2F$ | 3-F | CN | H |
| B-58. | $CH_2F$ | 3-$CH_3$ | CN | H |
| B-59. | $CH_2F$ | 3-$OCH_3$ | CN | H |
| B-60. | $CH_2F$ | 5-F | CN | H |
| B-61. | $CH_2F$ | 5-$CH_3$ | CN | H |
| B-62. | $CH_2F$ | 5-$OCH_3$ | CN | H |
| B-63. | $CH_2F$ | 6-F | CN | H |
| B-64. | $CH_2F$ | 6-$CH_3$ | CN | H |
| B-65. | $CH_2F$ | 6-$OCH_3$ | CN | H |
| B-66. | $CHF_2$ | 3-F | CN | H |
| B-67. | $CHF_2$ | 3-$CH_3$ | CN | H |
| B-68. | $CHF_2$ | 3-$OCH_3$ | CN | H |
| B-69. | $CHF_2$ | 5-F | CN | H |
| B-70. | $CHF_2$ | 5-$CH_3$ | CN | H |
| B-71. | $CHF_2$ | 5-$OCH_3$ | CN | H |
| B-72. | $CHF_2$ | 6-F | CN | H |
| B-73. | $CHF_2$ | 6-$CH_3$ | CN | H |
| B-74. | $CHF_2$ | 6-$OCH_3$ | CN | H |
| B-75. | $CF_3$ | 3-F | CN | H |
| B-76. | $CF_3$ | 3-$CH_3$ | CN | H |
| B-77. | $CF_3$ | 3-$OCH_3$ | CN | H |
| B-78. | $CF_3$ | 5-F | CN | H |
| B-79. | $CF_3$ | 5-$CH_3$ | CN | H |
| B-80. | $CF_3$ | 5-$OCH_3$ | CN | H |
| B-81. | $CF_3$ | 6-F | CN | H |
| B-82. | $CF_3$ | 6-$CH_3$ | CN | H |
| B-83. | $CF_3$ | 6-$OCH_3$ | CN | H |
| B-84. | $OCH_2F$ | 3-F | CN | H |
| B-85. | $OCH_2F$ | 3-$CH_3$ | CN | H |
| B-86. | $OCH_2F$ | 3-$OCH_3$ | CN | H |
| B-87. | $OCH_2F$ | 5-F | CN | H |
| B-88. | $OCH_2F$ | 5-$CH_3$ | CN | H |
| B-89. | $OCH_2F$ | 5-$OCH_3$ | CN | H |
| B-90. | $OCH_2F$ | 6-F | CN | H |
| B-91. | $OCH_2F$ | 6-$CH_3$ | CN | H |
| B-92. | $OCH_2F$ | 6-$OCH_3$ | CN | H |
| B-93. | $OCHF_2$ | 3-F | CN | H |
| B-94. | $OCHF_2$ | 3-$CH_3$ | CN | H |
| B-95. | $OCHF_2$ | 3-$OCH_3$ | CN | H |
| B-96. | $OCHF_2$ | 5-F | CN | H |
| B-97. | $OCHF_2$ | 5-$CH_3$ | CN | H |
| B-98. | $OCHF_2$ | 5-$OCH_3$ | CN | H |
| B-99. | $OCHF_2$ | 6-F | CN | H |
| B-100. | $OCHF_2$ | 6-$CH_3$ | CN | H |
| B-101. | $OCHF_2$ | 6-$OCH_3$ | CN | H |
| B-102. | $OCF_3$ | 3-F | CN | H |
| B-103. | $OCF_3$ | 3-$CH_3$ | CN | H |
| B-104. | $OCF_3$ | 3-$OCH_3$ | CN | H |
| B-105. | $OCF_3$ | 5-F | CN | H |
| B-106. | $OCF_3$ | 5-$CH_3$ | CN | H |
| B-107. | $OCF_3$ | 5-$OCH_3$ | CN | H |
| B-108. | $OCF_3$ | 6-F | CN | H |
| B-109. | $OCF_3$ | 6-$CH_3$ | CN | H |
| B-110. | $OCF_3$ | 6-$OCH_3$ | CN | H |
| B-111. | H | H | F | H |
| B-112. | F | H | F | H |
| B-113. | $CH_3$ | H | F | H |
| B-114. | $OCH_3$ | H | F | H |
| B-115. | CN | H | F | H |
| B-116. | $CH_2F$ | H | F | H |
| B-117. | $CHF_2$ | H | F | H |
| B-118. | $CF_3$ | H | F | H |
| B-119. | $OCH_2F$ | H | F | H |
| B-120. | $OCHF_2$ | H | F | H |
| B-121. | $OCF_3$ | H | F | H |
| B-122. | H | 3-F | F | H |
| B-123. | H | 3-$CH_3$ | F | H |
| B-124. | H | 3-$OCH_3$ | F | H |
| B-125. | H | 5-F | F | H |
| B-126. | H | 5-$CH_3$ | F | H |
| B-127. | H | 5-$OCH_3$ | F | H |

TABLE B-continued

| Example No. | R² | R³ | R⁶ | R⁷ |
|---|---|---|---|---|
| B-128. | H | 6-F | F | H |
| B-129. | H | 6-CH₃ | F | H |
| B-130. | H | 6-OCH₃ | F | H |
| B-131. | F | 3-F | F | H |
| B-132. | F | 3-CH₃ | F | H |
| B-133. | F | 3-OCH₃ | F | H |
| B-134. | F | 5-F | F | H |
| B-135. | F | 5-CH₃ | F | H |
| B-136. | F | 5-OCH₃ | F | H |
| B-137. | F | 6-F | F | H |
| B-138. | F | 6-CH₃ | F | H |
| B-139. | F | 6-OCH₃ | F | H |
| B-140. | CH₃ | 3-F | F | H |
| B-141. | CH₃ | 3-CH₃ | F | H |
| B-142. | CH₃ | 3-OCH₃ | F | H |
| B-143. | CH₃ | 5-F | F | H |
| B-144. | CH₃ | 5-CH₃ | F | H |
| B-145. | CH₃ | 5-OCH₃ | F | H |
| B-146. | CH₃ | 6-F | F | H |
| B-147. | CH₃ | 6-CH₃ | F | H |
| B-148. | CH₃ | 6-OCH₃ | F | H |
| B-149. | OCH₃ | 3-F | F | H |
| B-150. | OCH₃ | 3-CH₃ | F | H |
| B-151. | OCH₃ | 3-OCH₃ | F | H |
| B-152. | OCH₃ | 5-F | F | H |
| B-153. | OCH₃ | 5-CH₃ | F | H |
| B-154. | OCH₃ | 5-OCH₃ | F | H |
| B-155. | OCH₃ | 6-F | F | H |
| B-156. | OCH₃ | 6-CH₃ | F | H |
| B-157. | OCH₃ | 6-OCH₃ | F | H |
| B-158. | CN | 3-F | F | H |
| B-159. | CN | 3-CH₃ | F | H |
| B-160. | CN | 3-OCH₃ | F | H |
| B-161. | CN | 5-F | F | H |
| B-162. | CN | 5-CH₃ | F | H |
| B-163. | CN | 5-OCH₃ | F | H |
| B-164. | CN | 6-F | F | H |
| B-165. | CN | 6-CH₃ | F | H |
| B-166. | CN | 6-OCH₃ | F | H |
| B-167. | CH₂F | 3-F | F | H |
| B-168. | CH₂F | 3-CH₃ | F | H |
| B-169. | CH₂F | 3-OCH₃ | F | H |
| B-170. | CH₂F | 5-F | F | H |
| B-171. | CH₂F | 5-CH₃ | F | H |
| B-172. | CH₂F | 5-OCH₃ | F | H |
| B-173. | CH₂F | 6-F | F | H |
| B-174. | CH₂F | 6-CH₃ | F | H |
| B-175. | CH₂F | 6-OCH₃ | F | H |
| B-176. | CHF₂ | 3-F | F | H |
| B-177. | CHF₂ | 3-CH₃ | F | H |
| B-178. | CHF₂ | 3-OCH₃ | F | H |
| B-179. | CHF₂ | 5-F | F | H |
| B-180. | CHF₂ | 5-CH₃ | F | H |
| B-181. | CHF₂ | 5-OCH₃ | F | H |
| B-182. | CHF₂ | 6-F | F | H |
| B-183. | CHF₂ | 6-CH₃ | F | H |
| B-184. | CHF₂ | 6-OCH₃ | F | H |
| B-185. | CF₃ | 3-F | F | H |
| B-186. | CF₃ | 3-CH₃ | F | H |
| B-187. | CF₃ | 3-OCH₃ | F | H |
| B-188. | CF₃ | 5-F | F | H |
| B-189. | CF₃ | 5-CH₃ | F | H |
| B-190. | CF₃ | 5-OCH₃ | F | H |
| B-191. | CF₃ | 6-F | F | H |
| B-192. | CF₃ | 6-CH₃ | F | H |
| B-193. | CF₃ | 6-OCH₃ | F | H |
| B-194. | OCH₂F | 3-F | F | H |
| B-195. | OCH₂F | 3-CH₃ | F | H |
| B-196. | OCH₂F | 3-OCH₃ | F | H |
| B-197. | OCH₂F | 5-F | F | H |
| B-198. | OCH₂F | 5-CH₃ | F | H |
| B-199. | OCH₂F | 5-OCH₃ | F | H |
| B-200. | OCH₂F | 6-F | F | H |
| B-201. | OCH₂F | 6-CH₃ | F | H |
| B-202. | OCH₂F | 6-OCH₃ | F | H |
| B-203. | OCHF₂ | 3-F | F | H |
| B-204. | OCHF₂ | 3-CH₃ | F | H |
| B-205. | OCHF₂ | 3-OCH₃ | F | H |
| B-206. | OCHF₂ | 5-F | F | H |
| B-207. | OCHF₂ | 5-CH₃ | F | H |
| B-208. | OCHF₂ | 5-OCH₃ | F | H |
| B-209. | OCHF₂ | 6-F | F | H |
| B-210. | OCHF₂ | 6-CH₃ | F | H |
| B-211. | OCHF₂ | 6-OCH₃ | F | H |
| B-212. | OCF₃ | 3-F | F | H |
| B-213. | OCF₃ | 3-CH₃ | F | H |
| B-214. | OCF₃ | 3-OCH₃ | F | H |
| B-215. | OCF₃ | 5-F | F | H |
| B-216. | OCF₃ | 5-CH₃ | F | H |
| B-217. | OCF₃ | 5-OCH₃ | F | H |
| B-218. | OCF₃ | 6-F | F | H |
| B-219. | OCF₃ | 6-CH₃ | F | H |
| B-220. | OCF₃ | 6-OCH₃ | F | H |
| B-221. | H | H | Cl | H |
| B-222. | F | H | Cl | H |
| B-223. | CH₃ | H | Cl | H |
| B-224. | OCH₃ | H | Cl | H |
| B-225. | CN | H | Cl | H |
| B-226. | CH₂F | H | Cl | H |
| B-227. | CHF₂ | H | Cl | H |
| B-228. | CF₃ | H | Cl | H |
| B-229. | OCH₂F | H | Cl | H |
| B-230. | OCHF₂ | H | Cl | H |
| B-231. | OCF₃ | H | Cl | H |
| B-232. | H | 3-F | Cl | H |
| B-233. | H | 3-CH₃ | Cl | H |
| B-234. | H | 3-OCH₃ | Cl | H |
| B-235. | H | 5-F | Cl | H |
| B-236. | H | 5-CH₃ | Cl | H |
| B-237. | H | 5-OCH₃ | Cl | H |
| B-238. | H | 6-F | Cl | H |
| B-239. | H | 6-CH₃ | Cl | H |
| B-240. | H | 6-OCH₃ | Cl | H |
| B-241. | F | 3-F | Cl | H |
| B-242. | F | 3-CH₃ | Cl | H |
| B-243. | F | 3-OCH₃ | Cl | H |
| B-244. | F | 5-F | Cl | H |
| B-245. | F | 5-CH₃ | Cl | H |
| B-246. | F | 5-OCH₃ | Cl | H |
| B-247. | F | 6-F | Cl | H |
| B-248. | F | 6-CH₃ | Cl | H |
| B-249. | F | 6-OCH₃ | Cl | H |
| B-250. | CH₃ | 3-F | Cl | H |
| B-251. | CH₃ | 3-CH₃ | Cl | H |
| B-252. | CH₃ | 3-OCH₃ | Cl | H |
| B-253. | CH₃ | 5-F | Cl | H |
| B-254. | CH₃ | 5-CH₃ | Cl | H |
| B-255. | CH₃ | 5-OCH₃ | Cl | H |
| B-256. | CH₃ | 6-F | Cl | H |
| B-257. | CH₃ | 6-CH₃ | Cl | H |
| B-258. | CH₃ | 6-OCH₃ | Cl | H |
| B-259. | OCH₃ | 3-F | Cl | H |
| B-260. | OCH₃ | 3-CH₃ | Cl | H |
| B-261. | OCH₃ | 3-OCH₃ | Cl | H |
| B-262. | OCH₃ | 5-F | Cl | H |
| B-263. | OCH₃ | 5-CH₃ | Cl | H |
| B-264. | OCH₃ | 5-OCH₃ | Cl | H |
| B-265. | OCH₃ | 6-F | Cl | H |
| B-266. | OCH₃ | 6-CH₃ | Cl | H |
| B-267. | OCH₃ | 6-OCH₃ | Cl | H |
| B-268. | CN | 3-F | Cl | H |
| B-269. | CN | 3-CH₃ | Cl | H |
| B-270. | CN | 3-OCH₃ | Cl | H |
| B-271. | CN | 5-F | Cl | H |
| B-272. | CN | 5-CH₃ | Cl | H |
| B-273. | CN | 5-OCH₃ | Cl | H |
| B-274. | CN | 6-F | Cl | H |
| B-275. | CN | 6-CH₃ | Cl | H |
| B-276. | CN | 6-OCH₃ | Cl | H |
| B-277. | CH₂F | 3-F | Cl | H |
| B-278. | CH₂F | 3-CH₃ | Cl | H |
| B-279. | CH₂F | 3-OCH₃ | Cl | H |
| B-280. | CH₂F | 5-F | Cl | H |
| B-281. | CH₂F | 5-CH₃ | Cl | H |
| B-282. | CH₂F | 5-OCH₃ | Cl | H |
| B-283. | CH₂F | 6-F | Cl | H |

TABLE B-continued

| Example No. | $R^2$ | $R^3$ | $R^6$ | $R^7$ |
|---|---|---|---|---|
| B-284. | $CH_2F$ | 6-$CH_3$ | Cl | H |
| B-285. | $CH_2F$ | 6-$OCH_3$ | Cl | H |
| B-286. | $CHF_2$ | 3-F | Cl | H |
| B-287. | $CHF_2$ | 3-$CH_3$ | Cl | H |
| B-288. | $CHF_2$ | 3-$OCH_3$ | Cl | H |
| B-289. | $CHF_2$ | 5-F | Cl | H |
| B-290. | $CHF_2$ | 5-$CH_3$ | Cl | H |
| B-291. | $CHF_2$ | 5-$OCH_3$ | Cl | H |
| B-292. | $CHF_2$ | 6-F | Cl | H |
| B-293. | $CHF_2$ | 6-$CH_3$ | Cl | H |
| B-294. | $CHF_2$ | 6-$OCH_3$ | Cl | H |
| B-295. | $CF_3$ | 3-F | Cl | H |
| B-296. | $CF_3$ | 3-$CH_3$ | Cl | H |
| B-297. | $CF_3$ | 3-$OCH_3$ | Cl | H |
| B-298. | $CF_3$ | 5-F | Cl | H |
| B-299. | $CF_3$ | 5-$CH_3$ | Cl | H |
| B-300. | $CF_3$ | 5-$OCH_3$ | Cl | H |
| B-301. | $CF_3$ | 6-F | Cl | H |
| B-302. | $CF_3$ | 6-$CH_3$ | Cl | H |
| B-303. | $CF_3$ | 6-$OCH_3$ | Cl | H |
| B-304. | $OCH_2F$ | 3-F | Cl | H |
| B-305. | $OCH_2F$ | 3-$CH_3$ | Cl | H |
| B-306. | $OCH_2F$ | 3-$OCH_3$ | Cl | H |
| B-307. | $OCH_2F$ | 5-F | Cl | H |
| B-308. | $OCH_2F$ | 5-$CH_3$ | Cl | H |
| B-309. | $OCH_2F$ | 5-$OCH_3$ | Cl | H |
| B-310. | $OCH_2F$ | 6-F | Cl | H |
| B-311. | $OCH_2F$ | 6-$CH_3$ | Cl | H |
| B-312. | $OCH_2F$ | 6-$OCH_3$ | Cl | H |
| B-313. | $OCHF_2$ | 3-F | Cl | H |
| B-314. | $OCHF_2$ | 3-$CH_3$ | Cl | H |
| B-315. | $OCHF_2$ | 3-$OCH_3$ | Cl | H |
| B-316. | $OCHF_2$ | 5-F | Cl | H |
| B-317. | $OCHF_2$ | 5-$CH_3$ | Cl | H |
| B-318. | $OCHF_2$ | 5-$OCH_3$ | Cl | H |
| B-319. | $OCHF_2$ | 6-F | Cl | H |
| B-320. | $OCHF_2$ | 6-$CH_3$ | Cl | H |
| B-321. | $OCHF_2$ | 6-$OCH_3$ | Cl | H |
| B-322. | $OCF_3$ | 3-F | Cl | H |
| B-323. | $OCF_3$ | 3-$CH_3$ | Cl | H |
| B-324. | $OCF_3$ | 3-$OCH_3$ | Cl | H |
| B-325. | $OCF_3$ | 5-F | Cl | H |
| B-326. | $OCF_3$ | 5-$CH_3$ | Cl | H |
| B-327. | $OCF_3$ | 5-$OCH_3$ | Cl | H |
| B-328. | $OCF_3$ | 6-F | Cl | H |
| B-329. | $OCF_3$ | 6-$CH_3$ | Cl | H |
| B-330. | $OCF_3$ | 6-$OCH_3$ | Cl | H |
| B-331. | H | H | CN | F |
| B-332. | F | H | CN | F |
| B-333. | $CH_3$ | H | CN | F |
| B-334. | $OCH_3$ | H | CN | F |
| B-335. | CN | H | CN | F |
| B-336. | $CH_2F$ | H | CN | F |
| B-337. | $CHF_2$ | H | CN | F |
| B-338. | $CF_3$ | H | CN | F |
| B-339. | $OCH_2F$ | H | CN | F |
| B-340. | $OCHF_2$ | H | CN | F |
| B-341. | $OCF_3$ | H | CN | F |
| B-342. | H | 3-F | CN | F |
| B-343. | H | 3-$CH_3$ | CN | F |
| B-344. | H | 3-$OCH_3$ | CN | F |
| B-345. | H | 5-F | CN | F |
| B-346. | H | 5-$CH_3$ | CN | F |
| B-347. | H | 5-$OCH_3$ | CN | F |
| B-348. | H | 6-F | CN | F |
| B-349. | H | 6-$CH_3$ | CN | F |
| B-350. | H | 6-$OCH_3$ | CN | F |
| B-351. | F | 3-F | CN | F |
| B-352. | F | 3-$CH_3$ | CN | F |
| B-353. | F | 3-$OCH_3$ | CN | F |
| B-354. | F | 5-F | CN | F |
| B-355. | F | 5-$CH_3$ | CN | F |
| B-356. | F | 5-$OCH_3$ | CN | F |
| B-357. | F | 6-F | CN | F |
| B-358. | F | 6-$CH_3$ | CN | F |
| B-359. | F | 6-$OCH_3$ | CN | F |
| B-360. | $CH_3$ | 3-F | CN | F |
| B-361. | $CH_3$ | 3-$CH_3$ | CN | F |
| B-362. | $CH_3$ | 3-$OCH_3$ | CN | F |
| B-363. | $CH_3$ | 5-F | CN | F |
| B-364. | $CH_3$ | 5-$CH_3$ | CN | F |
| B-365. | $CH_3$ | 5-$OCH_3$ | CN | F |
| B-366. | $CH_3$ | 6-F | CN | F |
| B-367. | $CH_3$ | 6-$CH_3$ | CN | F |
| B-368. | $CH_3$ | 6-$OCH_3$ | CN | F |
| B-369. | $OCH_3$ | 3-F | CN | F |
| B-370. | $OCH_3$ | 3-$CH_3$ | CN | F |
| B-371. | $OCH_3$ | 3-$OCH_3$ | CN | F |
| B-372. | $OCH_3$ | 5-F | CN | F |
| B-373. | $OCH_3$ | 5-$CH_3$ | CN | F |
| B-374. | $OCH_3$ | 5-$OCH_3$ | CN | F |
| B-375. | $OCH_3$ | 6-F | CN | F |
| B-376. | $OCH_3$ | 6-$CH_3$ | CN | F |
| B-377. | $OCH_3$ | 6-$OCH_3$ | CN | F |
| B-378. | CN | 3-F | CN | F |
| B-379. | CN | 3-$CH_3$ | CN | F |
| B-380. | CN | 3-$OCH_3$ | CN | F |
| B-381. | CN | 5-F | CN | F |
| B-382. | CN | 5-$CH_3$ | CN | F |
| B-383. | CN | 5-$OCH_3$ | CN | F |
| B-384. | CN | 6-F | CN | F |
| B-385. | CN | 6-$CH_3$ | CN | F |
| B-386. | CN | 6-$OCH_3$ | CN | F |
| B-387. | $CH_2F$ | 3-F | CN | F |
| B-388. | $CH_2F$ | 3-$CH_3$ | CN | F |
| B-389. | $CH_2F$ | 3-$OCH_3$ | CN | F |
| B-390. | $CH_2F$ | 5-F | CN | F |
| B-391. | $CH_2F$ | 5-$CH_3$ | CN | F |
| B-392. | $CH_2F$ | 5-$OCH_3$ | CN | F |
| B-393. | $CH_2F$ | 6-F | CN | F |
| B-394. | $CH_2F$ | 6-$CH_3$ | CN | F |
| B-395. | $CH_2F$ | 6-$OCH_3$ | CN | F |
| B-396. | $CHF_2$ | 3-F | CN | F |
| B-397. | $CHF_2$ | 3-$CH_3$ | CN | F |
| B-398. | $CHF_2$ | 3-$OCH_3$ | CN | F |
| B-399. | $CHF_2$ | 5-F | CN | F |
| B-400. | $CHF_2$ | 5-$CH_3$ | CN | F |
| B-401. | $CHF_2$ | 5-$OCH_3$ | CN | F |
| B-402. | $CHF_2$ | 6-F | CN | F |
| B-403. | $CHF_2$ | 6-$CH_3$ | CN | F |
| B-404. | $CHF_2$ | 6-$OCH_3$ | CN | F |
| B-405. | $CF_3$ | 3-F | CN | F |
| B-406. | $CF_3$ | 3-$CH_3$ | CN | F |
| B-407. | $CF_3$ | 3-$OCH_3$ | CN | F |
| B-408. | $CF_3$ | 5-F | CN | F |
| B-409. | $CF_3$ | 5-$CH_3$ | CN | F |
| B-410. | $CF_3$ | 5-$OCH_3$ | CN | F |
| B-411. | $CF_3$ | 6-F | CN | F |
| B-412. | $CF_3$ | 6-$CH_3$ | CN | F |
| B-413. | $CF_3$ | 6-$OCH_3$ | CN | F |
| B-414. | $OCH_2F$ | 3-F | CN | F |
| B-415. | $OCH_2F$ | 3-$CH_3$ | CN | F |
| B-416. | $OCH_2F$ | 3-$OCH_3$ | CN | F |
| B-417. | $OCH_2F$ | 5-F | CN | F |
| B-418. | $OCH_2F$ | 5-$CH_3$ | CN | F |
| B-419. | $OCH_2F$ | 5-$OCH_3$ | CN | F |
| B-420. | $OCH_2F$ | 6-F | CN | F |
| B-421. | $OCH_2F$ | 6-$CH_3$ | CN | F |
| B-422. | $OCH_2F$ | 6-$OCH_3$ | CN | F |
| B-423. | $OCHF_2$ | 3-F | CN | F |
| B-424. | $OCHF_2$ | 3-$CH_3$ | CN | F |
| B-425. | $OCHF_2$ | 3-$OCH_3$ | CN | F |
| B-426. | $OCHF_2$ | 5-F | CN | F |
| B-427. | $OCHF_2$ | 5-$CH_3$ | CN | F |
| B-428. | $OCHF_2$ | 5-$OCH_3$ | CN | F |
| B-429. | $OCHF_2$ | 6-F | CN | F |
| B-430. | $OCHF_2$ | 6-$CH_3$ | CN | F |
| B-431. | $OCHF_2$ | 6-$OCH_3$ | CN | F |
| B-432. | $OCF_3$ | 3-F | CN | F |
| B-433. | $OCF_3$ | 3-$CH_3$ | CN | F |
| B-434. | $OCF_3$ | 3-$OCH_3$ | CN | F |
| B-435. | $OCF_3$ | 5-F | CN | F |
| B-436. | $OCF_3$ | 5-$CH_3$ | CN | F |
| B-437. | $OCF_3$ | 5-$OCH_3$ | CN | F |
| B-438. | $OCF_3$ | 6-F | CN | F |
| B-439. | $OCF_3$ | 6-$CH_3$ | CN | F |

TABLE B-continued

| Example No. | $R^2$ | $R^3$ | $R^6$ | $R^7$ |
|---|---|---|---|---|
| B-440. | $OCF_3$ | 6-$OCH_3$ | CN | F |
| B-441. | H | H | F | F |
| B-442. | F | H | F | F |
| B-443. | $CH_3$ | H | F | F |
| B-444. | $OCH_3$ | H | F | F |
| B-445. | CN | H | F | F |
| B-446. | $CH_2F$ | H | F | F |
| B-447. | $CHF_2$ | H | F | F |
| B-448. | $CF_3$ | H | F | F |
| B-449. | $OCH_2F$ | H | F | F |
| B-450. | $OCHF_2$ | H | F | F |
| B-451. | $OCF_3$ | H | F | F |
| B-452. | H | 3-F | F | F |
| B-453. | H | 3-$CH_3$ | F | F |
| B-454. | H | 3-$OCH_3$ | F | F |
| B-455. | H | 5-F | F | F |
| B-456. | H | 5-$CH_3$ | F | F |
| B-457. | H | 5-$OCH_3$ | F | F |
| B-458. | H | 6-F | F | F |
| B-459. | H | 6-$CH_3$ | F | F |
| B-460. | H | 6-$OCH_3$ | F | F |
| B-461. | F | 3-F | F | F |
| B-462. | F | 3-$CH_3$ | F | F |
| B-463. | F | 3-$OCH_3$ | F | F |
| B-464. | F | 5-F | F | F |
| B-465. | F | 5-$CH_3$ | F | F |
| B-466. | F | 5-$OCH_3$ | F | F |
| B-467. | F | 6-F | F | F |
| B-468. | F | 6-$CH_3$ | F | F |
| B-469. | F | 6-$OCH_3$ | F | F |
| B-470. | $CH_3$ | 3-F | F | F |
| B-471. | $CH_3$ | 3-$CH_3$ | F | F |
| B-472. | $CH_3$ | 3-$OCH_3$ | F | F |
| B-473. | $CH_3$ | 5-F | F | F |
| B-474. | $CH_3$ | 5-$CH_3$ | F | F |
| B-475. | $CH_3$ | 5-$OCH_3$ | F | F |
| B-476. | $CH_3$ | 6-F | F | F |
| B-477. | $CH_3$ | 6-$CH_3$ | F | F |
| B-478. | $CH_3$ | 6-$OCH_3$ | F | F |
| B-479. | $OCH_3$ | 3-F | F | F |
| B-480. | $OCH_3$ | 3-$CH_3$ | F | F |
| B-481. | $OCH_3$ | 3-$OCH_3$ | F | F |
| B-482. | $OCH_3$ | 5-F | F | F |
| B-483. | $OCH_3$ | 5-$CH_3$ | F | F |
| B-484. | $OCH_3$ | 5-$OCH_3$ | F | F |
| B-485. | $OCH_3$ | 6-F | F | F |
| B-486. | $OCH_3$ | 6-$CH_3$ | F | F |
| B-487. | $OCH_3$ | 6-$OCH_3$ | F | F |
| B-488. | CN | 3-F | F | F |
| B-489. | CN | 3-$CH_3$ | F | F |
| B-490. | CN | 3-$OCH_3$ | F | F |
| B-491. | CN | 5-F | F | F |
| B-492. | CN | 5-$CH_3$ | F | F |
| B-493. | CN | 5-$OCH_3$ | F | F |
| B-494. | CN | 6-F | F | F |
| B-495. | CN | 6-$CH_3$ | F | F |
| B-496. | CN | 6-$OCH_3$ | F | F |
| B-497. | $CH_2F$ | 3-F | F | F |
| B-498. | $CH_2F$ | 3-$CH_3$ | F | F |
| B-499. | $CH_2F$ | 3-$OCH_3$ | F | F |
| B-500. | $CH_2F$ | 5-F | F | F |
| B-501. | $CH_2F$ | 5-$CH_3$ | F | F |
| B-502. | $CH_2F$ | 5-$OCH_3$ | F | F |
| B-503. | $CH_2F$ | 6-F | F | F |
| B-504. | $CH_2F$ | 6-$CH_3$ | F | F |
| B-505. | $CH_2F$ | 6-$OCH_3$ | F | F |
| B-506. | $CHF_2$ | 3-F | F | F |
| B-507. | $CHF_2$ | 3-$CH_3$ | F | F |
| B-508. | $CHF_2$ | 3-$OCH_3$ | F | F |
| B-509. | $CHF_2$ | 5-F | F | F |
| B-510. | $CHF_2$ | 5-$CH_3$ | F | F |
| B-511. | $CHF_2$ | 5-$OCH_3$ | F | F |
| B-512. | $CHF_2$ | 6-F | F | F |
| B-513. | $CHF_2$ | 6-$CH_3$ | F | F |
| B-514. | $CHF_2$ | 6-$OCH_3$ | F | F |
| B-515. | $CF_3$ | 3-F | F | F |
| B-516. | $CF_3$ | 3-$CH_3$ | F | F |
| B-517. | $CF_3$ | 3-$OCH_3$ | F | F |
| B-518. | $CF_3$ | 5-F | F | F |
| B-519. | $CF_3$ | 5-$CH_3$ | F | F |
| B-520. | $CF_3$ | 5-$OCH_3$ | F | F |
| B-521. | $CF_3$ | 6-F | F | F |
| B-522. | $CF_3$ | 6-$CH_3$ | F | F |
| B-523. | $CF_3$ | 6-$OCH_3$ | F | F |
| B-524. | $OCH_2F$ | 3-F | F | F |
| B-525. | $OCH_2F$ | 3-$CH_3$ | F | F |
| B-526. | $OCH_2F$ | 3-$OCH_3$ | F | F |
| B-527. | $OCH_2F$ | 5-F | F | F |
| B-528. | $OCH_2F$ | 5-$CH_3$ | F | F |
| B-529. | $OCH_2F$ | 5-$OCH_3$ | F | F |
| B-530. | $OCH_2F$ | 6-F | F | F |
| B-531. | $OCH_2F$ | 6-$CH_3$ | F | F |
| B-532. | $OCH_2F$ | 6-$OCH_3$ | F | F |
| B-533. | $OCHF_2$ | 3-F | F | F |
| B-534. | $OCHF_2$ | 3-$CH_3$ | F | F |
| B-535. | $OCHF_2$ | 3-$OCH_3$ | F | F |
| B-536. | $OCHF_2$ | 5-F | F | F |
| B-537. | $OCHF_2$ | 5-$CH_3$ | F | F |
| B-538. | $OCHF_2$ | 5-$OCH_3$ | F | F |
| B-539. | $OCHF_2$ | 6-F | F | F |
| B-540. | $OCHF_2$ | 6-$CH_3$ | F | F |
| B-541. | $OCHF_2$ | 6-$OCH_3$ | F | F |
| B-542. | $OCF_3$ | 3-F | F | F |
| B-543. | $OCF_3$ | 3-$CH_3$ | F | F |
| B-544. | $OCF_3$ | 3-$OCH_3$ | F | F |
| B-545. | $OCF_3$ | 5-F | F | F |
| B-546. | $OCF_3$ | 5-$CH_3$ | F | F |
| B-547. | $OCF_3$ | 5-$OCH_3$ | F | F |
| B-548. | $OCF_3$ | 6-F | F | F |
| B-549. | $OCF_3$ | 6-$CH_3$ | F | F |
| B-550. | $OCF_3$ | 6-$OCH_3$ | F | F |
| B-551. | H | H | Cl | F |
| B-552. | F | H | Cl | F |
| B-553. | $CH_3$ | H | Cl | F |
| B-554. | $OCH_3$ | H | Cl | F |
| B-555. | CN | H | Cl | F |
| B-556. | $CH_2F$ | H | Cl | F |
| B-557. | $CHF_2$ | H | Cl | F |
| B-558. | $CF_3$ | H | Cl | F |
| B-559. | $OCH_2F$ | H | Cl | F |
| B-560. | $OCHF_2$ | H | Cl | F |
| B-561. | $OCF_3$ | H | Cl | F |
| B-562. | H | 3-F | Cl | F |
| B-563. | H | 3-$CH_3$ | Cl | F |
| B-564. | H | 3-$OCH_3$ | Cl | F |
| B-565. | H | 5-F | Cl | F |
| B-566. | H | 5-$CH_3$ | Cl | F |
| B-567. | H | 5-$OCH_3$ | Cl | F |
| B-568. | H | 6-F | Cl | F |
| B-569. | H | 6-$CH_3$ | Cl | F |
| B-570. | H | 6-$OCH_3$ | Cl | F |
| B-571. | F | 3-F | Cl | F |
| B-572. | F | 3-$CH_3$ | Cl | F |
| B-573. | F | 3-$OCH_3$ | Cl | F |
| B-574. | F | 5-F | Cl | F |
| B-575. | F | 5-$CH_3$ | Cl | F |
| B-576. | F | 5-$OCH_3$ | Cl | F |
| B-577. | F | 6-F | Cl | F |
| B-578. | F | 6-$CH_3$ | Cl | F |
| B-579. | F | 6-$OCH_3$ | Cl | F |
| B-580. | $CH_3$ | 3-F | Cl | F |
| B-581. | $CH_3$ | 3-$CH_3$ | Cl | F |
| B-582. | $CH_3$ | 3-$OCH_3$ | Cl | F |
| B-583. | $CH_3$ | 5-F | Cl | F |
| B-584. | $CH_3$ | 5-$CH_3$ | Cl | F |
| B-585. | $CH_3$ | 5-$OCH_3$ | Cl | F |
| B-586. | $CH_3$ | 6-F | Cl | F |
| B-587. | $CH_3$ | 6-$CH_3$ | Cl | F |
| B-588. | $CH_3$ | 6-$OCH_3$ | Cl | F |
| B-589. | $OCH_3$ | 3-F | Cl | F |
| B-590. | $OCH_3$ | 3-$CH_3$ | Cl | F |
| B-591. | $OCH_3$ | 3-$OCH_3$ | Cl | F |
| B-592. | $OCH_3$ | 5-F | Cl | F |
| B-593. | $OCH_3$ | 5-$CH_3$ | Cl | F |
| B-594. | $OCH_3$ | 5-$OCH_3$ | Cl | F |
| B-595. | $OCH_3$ | 6-F | Cl | F |

TABLE B-continued

| Example No. | R² | R³ | R⁶ | R⁷ |
|---|---|---|---|---|
| B-596. | OCH₃ | 6-CH₃ | Cl | F |
| B-597. | OCH₃ | 6-OCH₃ | Cl | F |
| B-598. | CN | 3-F | Cl | F |
| B-599. | CN | 3-CH₃ | Cl | F |
| B-600. | CN | 3-OCH₃ | Cl | F |
| B-601. | CN | 5-F | Cl | F |
| B-602. | CN | 5-CH₃ | Cl | F |
| B-603. | CN | 5-OCH₃ | Cl | F |
| B-604. | CN | 6-F | Cl | F |
| B-605. | CN | 6-CH₃ | Cl | F |
| B-606. | CN | 6-OCH₃ | Cl | F |
| B-607. | CH₂F | 3-F | Cl | F |
| B-608. | CH₂F | 3-CH₃ | Cl | F |
| B-609. | CH₂F | 3-OCH₃ | Cl | F |
| B-610. | CH₂F | 5-F | Cl | F |
| B-611. | CH₂F | 5-CH₃ | Cl | F |
| B-612. | CH₂F | 5-OCH₃ | Cl | F |
| B-613. | CH₂F | 6-F | Cl | F |
| B-614. | CH₂F | 6-CH₃ | Cl | F |
| B-615. | CH₂F | 6-OCH₃ | Cl | F |
| B-616. | CHF₂ | 3-F | Cl | F |
| B-617. | CHF₂ | 3-CH₃ | Cl | F |
| B-618. | CHF₂ | 3-OCH₃ | Cl | F |
| B-619. | CHF₂ | 5-F | Cl | F |
| B-620. | CHF₂ | 5-CH₃ | Cl | F |
| B-621. | CHF₂ | 5-OCH₃ | Cl | F |
| B-622. | CHF₂ | 6-F | Cl | F |
| B-623. | CHF₂ | 6-CH₃ | Cl | F |
| B-624. | CHF₂ | 6-OCH₃ | Cl | F |
| B-625. | CF₃ | 3-F | Cl | F |
| B-626. | CF₃ | 3-CH₃ | Cl | F |
| B-627. | CF₃ | 3-OCH₃ | Cl | F |
| B-628. | CF₃ | 5-F | Cl | F |
| B-629. | CF₃ | 5-CH₃ | Cl | F |
| B-630. | CF₃ | 5-OCH₃ | Cl | F |
| B-631. | CF₃ | 6-F | Cl | F |
| B-632. | CF₃ | 6-CH₃ | Cl | F |
| B-633. | CF₃ | 6-OCH₃ | Cl | F |
| B-634. | OCH₂F | 3-F | Cl | F |
| B-635. | OCH₂F | 3-CH₃ | Cl | F |
| B-636. | OCH₂F | 3-OCH₃ | Cl | F |
| B-637. | OCH₂F | 5-F | Cl | F |
| B-638. | OCH₂F | 5-CH₃ | Cl | F |
| B-639. | OCH₂F | 5-OCH₃ | Cl | F |
| B-640. | OCH₂F | 6-F | Cl | F |
| B-641. | OCH₂F | 6-CH₃ | Cl | F |
| B-642. | OCH₂F | 6-OCH₃ | Cl | F |
| B-643. | OCHF₂ | 3-F | Cl | F |
| B-644. | OCHF₂ | 3-CH₃ | Cl | F |
| B-645. | OCHF₂ | 3-OCH₃ | Cl | F |
| B-646. | OCHF₂ | 5-F | Cl | F |
| B-647. | OCHF₂ | 5-CH₃ | Cl | F |
| B-648. | OCHF₂ | 5-OCH₃ | Cl | F |
| B-649. | OCHF₂ | 6-F | Cl | F |
| B-650. | OCHF₂ | 6-CH₃ | Cl | F |
| B-651. | OCHF₂ | 6-OCH₃ | Cl | F |
| B-652. | OCF₃ | 3-F | Cl | F |
| B-653. | OCF₃ | 3-CH₃ | Cl | F |
| B-654. | OCF₃ | 3-OCH₃ | Cl | F |
| B-655. | OCF₃ | 5-F | Cl | F |
| B-656. | OCF₃ | 5-CH₃ | Cl | F |
| B-657. | OCF₃ | 5-OCH₃ | Cl | F |
| B-658. | OCF₃ | 6-F | Cl | F |
| B-659. | OCF₃ | 6-CH₃ | Cl | F |
| B-660. | OCF₃ | 6-OCH₃ | Cl | F |

The positions (e.g. 3-/5-/6-) of $R^3$ are relative to the 2- and 4-positions of radicals $R^1$ and $R^2$ and to the 1-position of the attachment point of the ring to the $SO_2$ group.

The preferred compounds among the compounds I.1 to I.40 mentioned above are those of the formulae I.1, I.6, I.11, I.16, I.21, I.26, I.31 and I.36, and especially compounds of the formulae I.1, I.6, I.16 and I.21. Particularly preferred are compounds of the formulae I.1 and I.6.

In a specific embodiment, the compounds I are selected from the compounds specified in the examples, either as a free base or in form of a pharmaceutically acceptable salt, an N-oxide or a stereoisomer thereof or as their racemate or any other mixture of their steroisomers.

The compounds I of the invention have a center of chirality in position 3 of the 2-oxindole ring. The compounds of the invention may therefore be in the form of a 1:1 mixture of enantiomers (racemate) or of a nonracemic mixture of enantiomers in which one of the two enantiomers, either the enantiomer which rotates the plane of vibration of linearly polarized light to the left (i.e. minus rotation) (hereinafter (−) enantiomer) or the enantiomer which rotates the plane of vibration of linearly polarized light to the right (i.e. plus rotation) (hereinafter (+) enantiomer), is enriched, or of substantially enantiopure compounds, that is to say of substantially enantiopure (−) enantiomer or (+) enantiomer.

Since the compounds of the invention have a single center of asymmetry and no axis/plane of chirality, a nonracemic mixture can also be defined as a mixture of enantiomers in which either the R or the S enantiomer predominates. Substantially enantiopure compounds can accordingly also be defined as substantially enantiopure R enantiomer or substantially enantiopure S enantiomer.

"Substantially enantiopure compounds" means in the context of the present invention those compounds having an enantiomeric excess (ee; % ee=(R−S)/(R+S)×100 or (S−R)/(S+R)×100) of at least 80% ee, preferably at least 85% ee, more preferably at least 90% ee, even more preferably at least 95% ee and in particular at least 98% ee.

In one embodiment of the invention, the compounds of the invention are in the form of substantially enantiopure compounds. Particularly preferred compounds have an enantiomeric excess of at least 85% ee, more preferably of at least 90% ee, even more preferably of at least 95% ee and in particular of at least 98% ee.

The invention thus relates both to the pure enantiomers and to mixtures thereof, e.g. mixtures in which one enantiomer is present in enriched form, but also to the racemates. The invention also relates to the pharmaceutically acceptable salts of the pure enantiomers of compounds I, and the mixtures of enantiomers in the form of the pharmaceutically acceptable salts of compounds I.

Preferred embodiments of the invention are compounds of the formula I as detailed above which are characterized in that they are in optically active form, and the enantiomer of the relevant compound of the formula I is the S-enantiomer, in the form of a free base, or a pharmaceutically acceptable salt thereof.

Particularly preference is given to compounds of the general formula I and their pharmaceutically acceptable salts as detailed above in which the corresponding S-enantiomer is present in an optical purity (enantiomeric excess, ee) of more than 50% ee, particularly preferably of at least 80% ee, more preferably of at least 90% ee and even more preferably of at least 95% ee and in particular of at least 98% ee.

Likewise preferred embodiments of the invention are compounds of the general formula I as detailed above which are characterized in that they are in optically inactive form, i.e. in the form of the racemate, or in the form of a pharmaceutically acceptable salt of the racemate.

Examples of synthetic routes for preparing the oxindole derivatives of the invention are described below.

The compounds of the invention can be prepared by using methods described in WO 2005/030755, WO 2006/005609 and the other references mentioned in the outset for synthesizing analogous compounds, and the preparation is outlined by way of example in the below synthesis schemes. The variables $X^1$, $X^2$, $R^2$, $R^3$, $R^4$, $R^5$, $R^6$, $R^7$, $R^8$, $R^9$, $R^{10}$, $R^{11}$, a and b in these synthetic schemes have the same meanings as in formula I.

Scheme 1

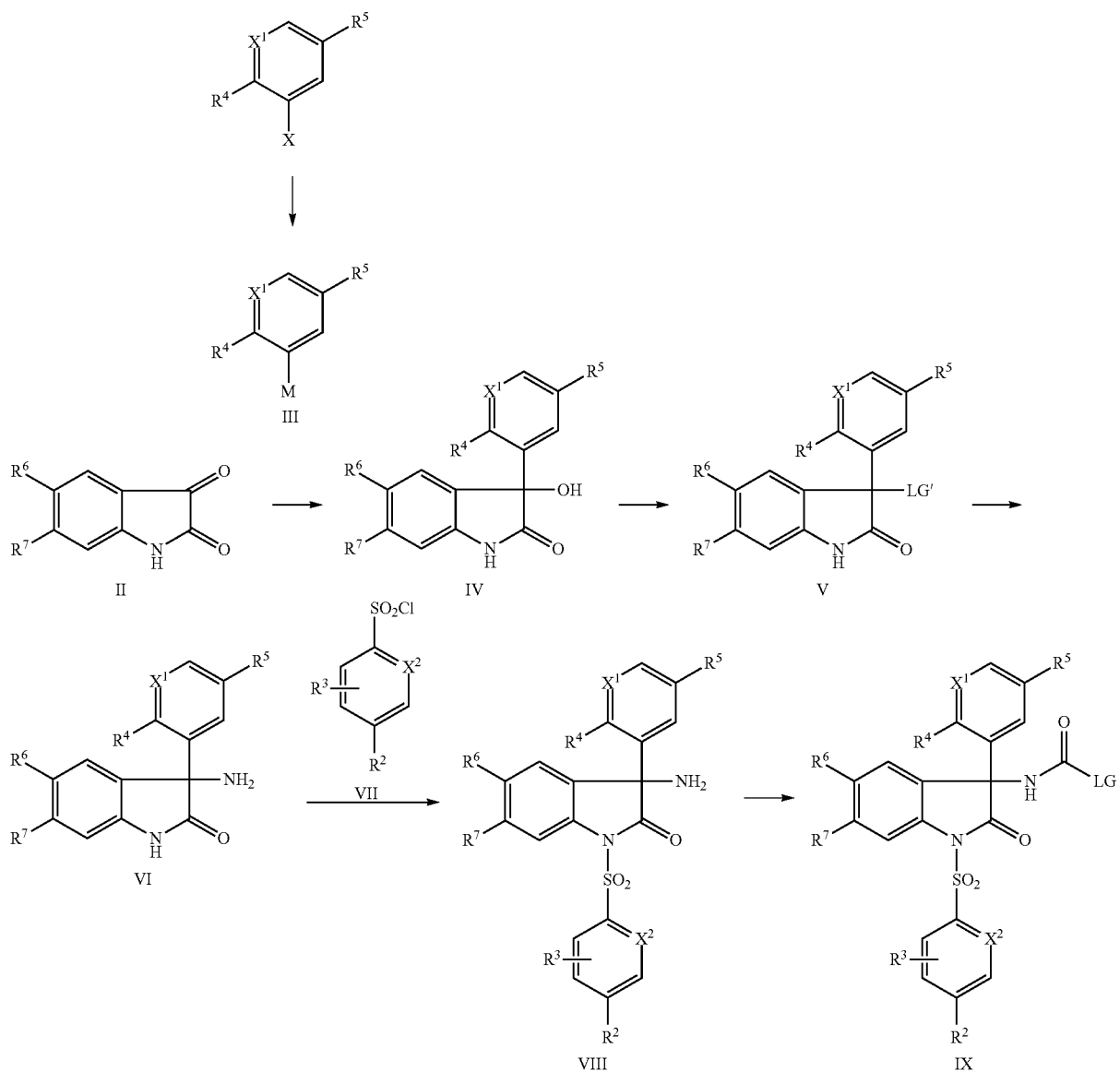

As shown in scheme 1, 3-hydroxy-1,3-dihydroindol-2-ones IV can be obtained by addition of metallated heterocycles III onto the 3-keto group of the isatins II. The metallated heterocycles, such as, for example, the corresponding Grignard (Mg) or organyllithium compound III (M=MgX or Li; ×=I or Br), can be obtained in any conventional way from halogen or hydrocarbon compounds by reaction with Mg or lithium-organic compounds. Exemplary methods are described in Houben-Weyl, Methoden der Organischen Chemie, vol. 13, 1-2, chapter on Mg and Li compounds. The isatins II are either commercially available or were prepared in analogy to methods described in the literature (Advances in Heterocyclic Chemistry, A. R. Katritzky and A. J. Boulton, Academic Press, New York, 1975, 18, 2-58; J. Brazil. Chem. Soc. 12, 273-324, 2001).

The 3-hydroxyoxindoles IV can be converted into the compounds V which have a leaving group LG' in position 3, where the leaving group LG' is a conventional leaving group such as, for example, chlorine or bromide. The intermediate V with for example LG'=Cl can be prepared by treating the alcohol IV with thionyl chloride in the presence of a base such as, for example, pyridine, in a suitable solvent such as, for example, dichloromethane. The compounds V can subsequently be reacted with amines, such as, for example, ammonia, in a substitution reaction to give the amines VI.

The amines VI are converted into the sulfonylated product VIII by treatment with sulfonyl chlorides VII after deprotonation with a strong base such as, for example, potassium tert-butoxide or sodium hydride in DMF. Sulfonyl chlorides VII employed can either be purchased or be prepared by known processes (for example J. Med. Chem. 40, 1149 (1997)). Compounds VIII are then reacted with carbonic acid halide, such as phenyl chloroformate, in the presence of a base such as, for example, pyridine, to give the corresponding carbamate IX (LG=leaving group; in case of using phenyl chloroformate, LG=phenoxy).

Scheme 2
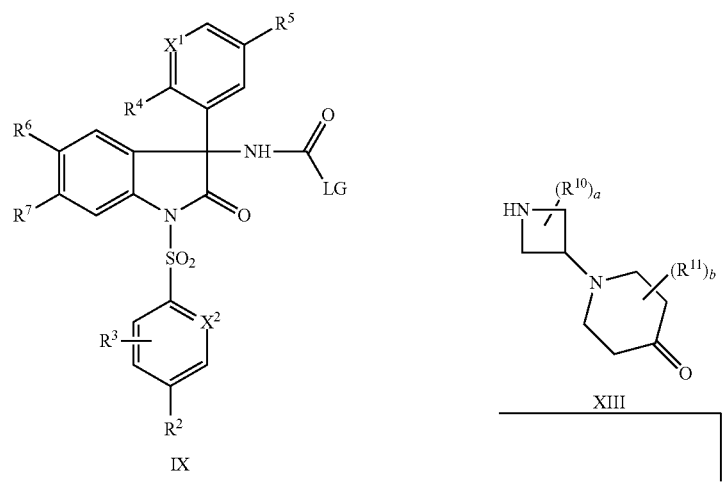
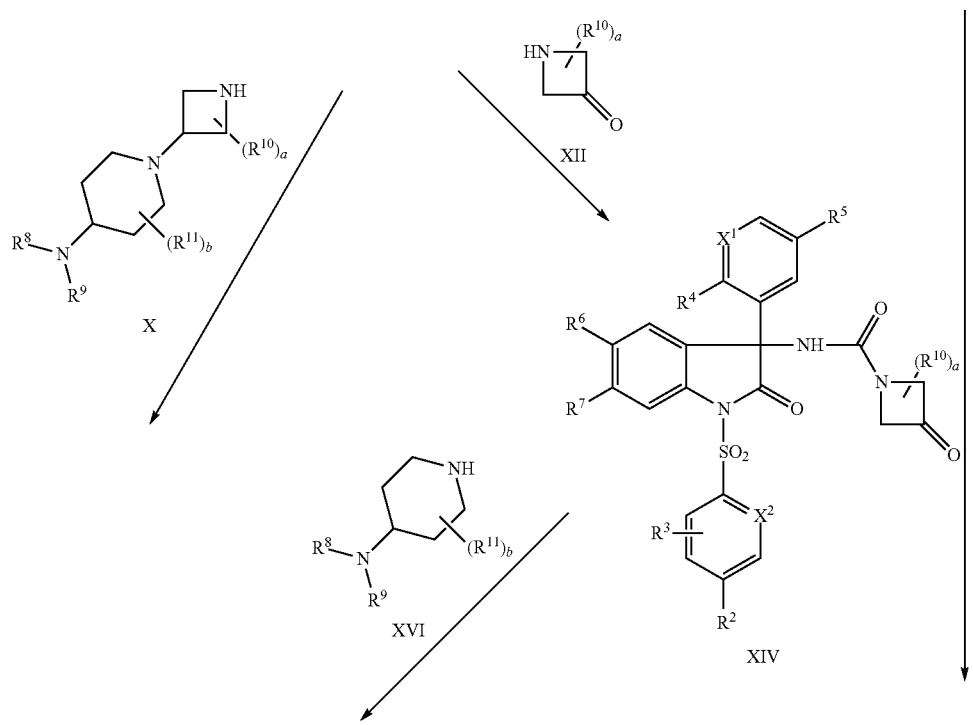

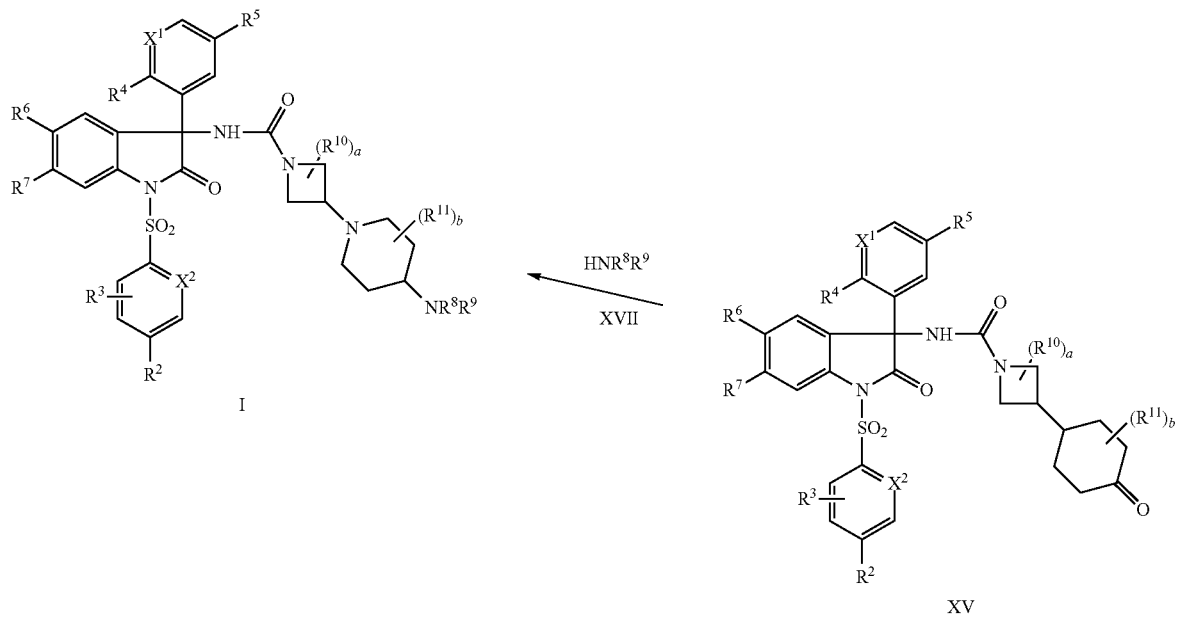

As shown in scheme 2, in a first variant, intermediate IX can then be reacted with an appropriate amine X to give directly the compounds of the general formula I; this conversion can be done at room temperature or elevated temperature and with the addition of auxiliary bases such as, for example, triethylamine or diisopropylethylamine.

In a second variant compounds of the general formula I are prepared from intermediates IX in a two-step sequence: intermediate IX can be reacted with an appropriate azetidine-3-one XII or 1-(3-azetidinyl)-4-piperidinone XIII employing the same method and conditions as described above to give the corresponding oxo compounds XIV or XV. Reductive amination of compounds XIV or XV with the appropriate amines XVI or XVII then gives the compounds of the general formula I. The latter reaction is carried out in the presence of a suitable reduction agent, e.g. boron-based reduction agent, typically a boronic ester, such as sodium triacetoxyhydroborate, or cyanoborohydride; where appropriate a Lewis acid such as e.g. zinc chloride or titanium isopropoxide is added to the reaction. General examples for reductive amination are described in the literature, e.g. Comprehensive Organic Transformations $2^{nd}$ ed, R. Larock, Wiley VCH, 835-846.

Scheme 3

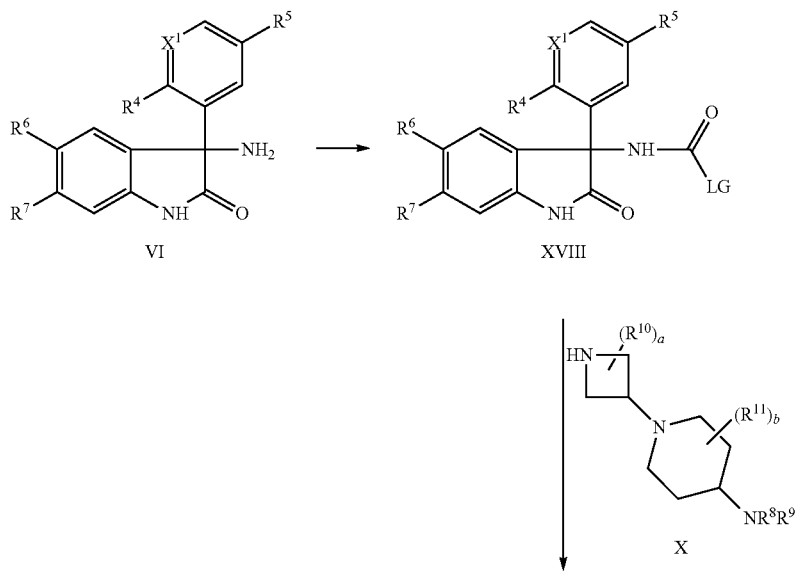

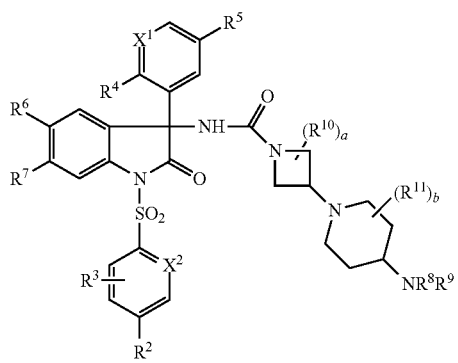

I

-continued

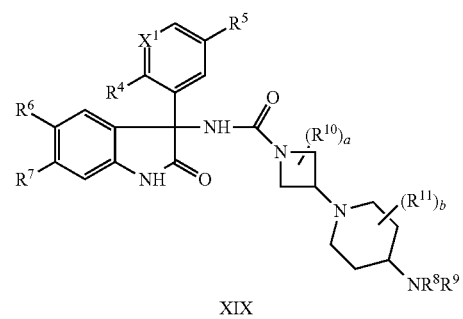

XIX

As shown in scheme 3, in a third variant compounds of the general formula I are prepared from amines VI in a three-step sequence: amines VI are first reacted with a carbonic acid halide, such as phenyl chloroformate, in the presence of a base such as, for example, pyridine, to give the corresponding carbamate XVIII (LG=leaving group; in case of using phenyl chloroformate, LG=phenoxy), and then reacted further with an appropriate amine at room temperature or elevated temperature and with the addition of auxiliary bases such as, for example, pyridine, triethylamine or diisopropylethylamine to give intermediate XIX. Sulfonylation of compounds XIX by treatment with sulfonyl chlorides VII after deprotonation with a strong base such as, for example, potassium tert-butoxide or sodium hydride in DMF, then gives the compounds of the general formula I.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the preparation methods are within routine techniques.

Suitable protecting groups and the methods for protecting and deprotecting different substituents using such suitable protecting groups are well known to those skilled in the art; examples of which may be found in T. Greene and P. Wuts, Protective Groups in Organic Synthesis (3rd ed.), John Wiley & Sons, NY (1999), which is incorporated herein by reference in its entirety. Synthesis of the compounds of the invention may be accomplished by methods analogous to those described in the synthetic scheme described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

The present invention moreover relates to compounds of formula I as defined above, wherein at least one of the atoms has been replaced by its stable, non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Of course, the compounds according to the invention contain more of the respective isotope than this naturally occurs and thus is anyway present in the compounds I.

Stable isotopes (e.g., deuterium, $^{13}C$, $^{15}N$, $^{18}O$) are non-radioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10): 927-932 (1995); Kushner et al., Can. J. Physiol. Pharmacol., 77, 79-88 (1999).

Incorporation of a heavy atom, particularly substitution of deuterium for hydrogen, can give rise to an isotope effect that could alter the pharmacokinetics of the drug.

Stable isotope labeling of a drug can alter its physico-chemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

A further aspect of the present invention relates to a pharmaceutical composition comprising at least one compound of the general formula I and/or an N-oxide, a stereoisomer or a pharmaceutically acceptable salt thereof as detailed above, and a pharmaceutically acceptable carrier; or comprising at least one compound I wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance. Suitable carriers depend inter alia on the dosage form of the composition and are known in principle to the skilled worker. Some suitable carriers are described hereinafter.

The present invention furthermore relates to a compound I as defined above or an N-oxide, a stereoisomer or a pharmaceutically acceptable salt thereof for use as a medicament. The present invention also relates to a compound I as defined above or an N-oxide, a stereoisomer or a pharmaceutically acceptable salt thereof for the treatment of vasopressin-related diseases, especially of disorders which respond to the modulation of the vasopressin receptor and in particular of the V1b receptor.

A further aspect of the present invention relates to the use of compounds of the formula I and/or of an N-oxide, a stereoisomer or of pharmaceutically acceptable salts thereof for the manufacture of a medicament for the treatment and/or prophylaxis of vasopressin-related diseases, especially of disorders which respond to the modulation of the vasopressin receptor and in particular of the V1b receptor.

Vasopressin-related diseases are those in which the progress of the disease is at least partly dependent on vasopressin, i.e. diseases which show an elevated vasopressin level which may contribute directly or indirectly to the pathological condition. In other words, vasopressin-related diseases are those which can be influenced by modulating the vasopressin receptor, for example by administration of a vasopressin receptor ligand (agonist, antagonist, partial antagonist/agonist, inverse agonist etc.).

In a preferred embodiment, the present invention relates to the use of compounds of the invention of the formula I or of an N-oxide, a stereoisomer or of pharmaceutically acceptable salts thereof for the manufacture of a medicament for the treatment and/or prophylaxis of diseases selected from diabetes, insulin resistance, nocturnal enuresis, incontinence and diseases in which impairments of blood clotting occur, and/or for delaying micturition. The term "diabetes" means all types of diabetes, especially diabetes mellitus (including type I and especially type II), diabetes renalis and in particular diabetes insipidus. The types of diabetes are preferably diabetes mellitus of type II (with insulin resistance) or diabetes insipidus.

In a further preferred embodiment, the present invention relates to the use of compounds of the invention of the formula I or of an N-oxide, a stereoisomer or of pharmaceutically acceptable salts thereof for the manufacture of a medicament for the treatment and/or prophylaxis of diseases selected from hypertension, pulmonary hypertension, heart failure, myocardial infarction, coronary spasm, unstable angina, PTCA (percutaneous transluminal coronary angioplasty), ischemias of the heart, impairments of the renal system, edemas, renal vasospasm, necrosis of the renal cortex, hyponatremia, hypokalemia, Schwartz-Bartter syndrome, impairments of the gastrointestinal tract, gastric vasospasm, hepatocirrhosis, gastric and intestinal ulcers, emesis, emesis occurring during chemotherapy, and travel sickness.

The compounds of the invention of the formula I or their N-oxides, stereoisomers or pharmaceutically acceptable salts or the pharmaceutical composition of the invention can also be used for the treatment of various vasopressin-related complaints which have central nervous causes or alterations in the HPA axis (hypothalamic pituitary adrenal axis), for example for affective disorders such as depressive disorders and anxiety disorders. Depressive disorders include for example dysthymic disorders, major depression, seasonal depression, treatment-resistant depression disorders, bipolar disorders, or childhood onset mood disorders. Anxiety disorders include for example phobias, post-traumatic stress disorders, general anxiety disorders, panic disorders, drug withdrawal-induced anxiety disorders, and obsessive-compulsive disorders.

Vasopressin-related complaints which have central nervous causes or alterations in the HPA axis are further cognitive disorders such as Alzheimer's disease, MCI (Mild Cognitive Impairment) and CIAS (Cognitive Impairment Associated with Schizophrenia).

The compounds of the invention of the formula I and their N-oxides, a stereoisomers or pharmaceutically acceptable salts or the pharmaceutical composition of the invention can likewise be employed for the treatment of anxiety disorders and stress-dependent anxiety disorders, such as, for example, generalized anxiety disorders, phobias, post-traumatic anxiety disorders, panic anxiety disorders, obsessive-compulsive anxiety disorders, acute stress-dependent anxiety disorders, drug withdrawal-induced anxiety disorders and social phobia.

The compounds of the invention of the formula I and their N-oxides, stereoisomers or pharmaceutically acceptable salts or the pharmaceutical composition of the invention can likewise be employed for the treatment and/or prophylaxis of social impairment, such as autism or social impairment related with schizophrenia.

The compounds of the invention of the formula I and their N-oxides, stereoisomers or pharmaceutically acceptable salts or the pharmaceutical composition of the invention can likewise be employed for the treatment and/or prophylaxis of increased aggression in conditions such as Alzheimer's disease and schizophrenia.

The compounds of the invention can furthermore also be employed for the treatment of memory impairments, Alzheimer's disease, psychoses, psychotic disorders, sleep disorders and/or Cushing's syndrome, and all stress-dependent diseases.

Accordingly, a further preferred embodiment of the present invention relates to the use of compounds of the invention of the formula I or of an N-oxide, a stereoisomer or pharmaceutically acceptable salts thereof for the manufacture of a medicament for the treatment of affective disorders.

In a further preferred embodiment, the present invention relates to the use of compounds of the invention of the formula I or of an N-oxide, a stereoisomer or pharmaceutically acceptable salts thereof for the manufacture of a medicament for the treatment of anxiety disorders and/or stress-dependent anxiety disorders.

In a further preferred embodiment, the present invention relates to the use of compounds of the invention of the formula I or of an N-oxide, a stereoisomer or pharmaceutically acceptable salts thereof for the manufacture of a medicament for the treatment of memory impairments and/or Alzheimer's disease.

In a further preferred embodiment, the present invention relates to the use of compounds of the invention of the formula I or of an N-oxide, a stereoisomer or pharmaceutically acceptable salts thereof for the manufacture of a medicament for the treatment of psychoses and/or psychotic disorders.

In a further preferred embodiment, the present invention relates to the use of compounds of the invention of the formula I or of an N-oxide, a stereoisomer or pharmaceutically acceptable salts thereof for the manufacture of a medicament for the treatment of Cushing's syndrome or other stress-dependent diseases.

In a further preferred embodiment, the present invention relates to the use of compounds of the invention of the formula I or of an N-oxide, a stereoisomer or pharmaceutically acceptable salts thereof for the manufacture of a medicament for the treatment of sleep disorders.

In a further preferred embodiment, the present invention relates to the use of compounds of the invention of the formula I or of an N-oxide, a stereoisomer or pharmaceutically acceptable salts thereof for the manufacture of a medicament for the treatment of depressive disorders. In the case of depressive disorders, specific mention is to be made of childhood onset mood disorders, i.e. depressive moods having their onset in childhood, but also of major depression, seasonal depression, bipolar disorders and dysthymic disorders, and especially of major depression and seasonal depression as well as of the depressive phases of bipolar disorders. The invention also relates to compounds of the formula I or N-oxides, stereoisomers or pharmaceutically acceptable salts thereof for the manufacture of a medicament for the treatment of treatment-resistant depression disorders and for the use in an add-on therapy of depressive disorders.

In a further preferred embodiment, the present invention relates to the use of compounds of the invention of the formula I or of an N-oxide, a stereoisomer or pharmaceutically acceptable salts thereof for the manufacture of a medicament for the treatment of vasomotor symptoms and/or thermoregulatory dysfunctions such as, for example, the hot flush symptom.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of drug or pharmaceutical dependencies and/or dependencies mediated by other factors, for the treatment of drug-use disorders, for the treatment and/or prophylaxis of stress caused by withdrawal of one or more factors mediating the dependence and/or for the treatment and/or prophylaxis of stress-induced relapses into drug or pharmaceutical dependencies and/or dependencies mediated by other factors. To be more precise, the present invention relates to the use of compounds of the invention of the formula I or of an N-oxide, a stereoisomer or pharmaceutically acceptable salts thereof for the manufacture of a medicament for the treatment and/or prophylaxis of substance-related and addictive disorders such as substance use disorder, substance-induced disorder, alcohol use disorder, alcohol intoxication, alcohol withdrawal, unspecified alcohol-related disorder, caffeine intoxication, caffeine withdrawal, unspecified caffeine disorder, cannabis use disorder, cannabis withdrawal, unspecified cannabis-related disorder, phencyclidine use disorder, other hallucinogen use disorders, phencyclidine intoxication, other hallucinogen disorders, hallucinogen persisting perception disorder, unspecified phencyclidine disorder, inhalant use disorder, inhalant intoxication, opioid use disorder, opioid withdrawal, sedative, hypnotic or anxiolytic use disorder, sedative, hypnotic or anxiolytic withdrawal, stimulant use disorder, stimulant intoxication, stimulant withdrawal, tobacco use disorder, tobacco withdrawal, unspecified tobacco-related disorder, other (or unknown) substance use disorders, other (or unknown) substance intoxication, other (or unknown) substance withdrawal, other (or unknown) substance related disorder and gambling disorder; as well as to compounds of the invention of the formula I or of an N-oxide, a stereoisomer or of pharmaceutically acceptable salts thereof for the treatment and/or prophylaxis of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of schizophrenia and/or psychosis.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of pain, e.g. acute or chronic pain, preferably chronic pain, especially neuropathic pain. Chronic pain may be a complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

A further aspect of the invention relates to a compound I or pharmaceutically acceptable salts thereof for use as a medicament, and to a compound I or an N-oxide, a stereoisomer or pharmaceutically acceptable salts thereof for the manufacture of a medicament for the treatment and/or prophylaxis of the above-defined diseases.

A further aspect of the invention relates to a method for the treatment and/or prophylaxis of vasopressin-related diseases, in which an effective amount of at least one compound of the invention of the formula I or of an N-oxide, a stereoisomer or of at least one pharmaceutically acceptable salt thereof or of a pharmaceutical composition of the invention is administered to a patient.

Concerning the definition of vasopressin-related diseases, reference is made to the above statements.

In a preferred embodiment of the invention, the method of the invention serves for the treatment and/or prophylaxis of disorders selected from diabetes, insulin resistance, nocturnal enuresis, incontinence and diseases in which impairments of blood clotting occur, and/or for delaying micturition. Concerning the definition of diabetes, reference is made to the above statements.

In a further preferred embodiment, the method of the invention serves for the treatment and/or prophylaxis of disorders selected from hypertension, pulmonary hypertension, heart failure, myocardial infarction, coronary spasm, unstable angina, PTCA (percutaneous transluminal coronary angioplasty), ischemias of the heart, impairments of the renal system, edemas, renal vasospasm, necrosis of the renal cortex, hyponatremia, hypokalemia, Schwartz-Bartter syndrome, impairments of the gastrointestinal tract, gastritic vasospasm, hepatocirrhosis, gastric and intestinal ulcers, emesis, emesis occurring during chemotherapy, and travel sickness.

In a further preferred embodiment, the method of the invention serves for the treatment and/or prophylaxis of affective disorders.

In a further preferred embodiment, the method of the invention serves for the treatment and/or prophylaxis of anxiety disorders and/or stress-dependent anxiety disorders.

In a further preferred embodiment, the method of the invention serves for the treatment and/or prophylaxis of memory impairments and/or Alzheimer's disease.

In a further preferred embodiment, the method of the invention serves for the treatment and/or prophylaxis of psychoses and/or psychotic disorders.

In a further preferred embodiment, the method of the invention serves for the treatment and/or prophylaxis of Cushing's syndrome.

In a further preferred embodiment, the method of the invention serves for the treatment and/or prophylaxis of sleep disorders in a patient.

In a further preferred embodiment, the method of the invention serves for the treatment and/or prophylaxis of depressive disorders. In the case of depressive disorders, specific mention is to be made of major depression, seasonal depression, bipolar disorders, dysthymic disorders and childhood onset mood disorders, i.e. depressive moods having their onset in childhood, and especially of major depression and seasonal depression as well as of the depressive phases of bipolar disorders. The method of the invention also serves for the treatment of treatment-resistant depression disorders and as an add-on therapy of depressive disorders.

In a further preferred embodiment, the method of the invention serves for the treatment and/or prophylaxis of vasomotor symptoms and/or thermoregulatory dysfunctions, such as, for example, the hot flush symptom.

In a further preferred embodiment, the method of the invention serves for the treatment and/or prophylaxis of drug or pharmaceutical dependencies and/or dependencies mediated by other factors, for the treatment of drug-use disorders, for the treatment and/or prophylaxis of stress caused by withdrawal of one or more factors mediating the dependence, and/or for the treatment and/or prophylaxis of stress-induced relapses into drug or pharmaceutical dependencies and/or dependencies mediated by other factors.

In a further preferred embodiment, the method of the invention serves for the treatment and/or prophylaxis of schizophrenia and/or psychosis.

In a further preferred embodiment, the method of the invention serves for the treatment and/or prophylaxis of pain, e.g. acute or chronic pain, preferably chronic pain, especially neuropathic pain.

The patient to be treated prophylactically or therapeutically with the method of the invention is preferably a mammal, for example a human or a nonhuman mammal or a nonhuman transgenic mammal. Specifically it is a human.

The compounds of the general formula I and their pharmaceutically acceptable salts as detailed above can be prepared by a skilled worker with knowledge of the technical teaching of the invention in implementing and/or in analogous implementation of process steps known per se.

The compounds I and/or their pharmaceutically acceptable salts, N-oxides and their stereoisomers are distinguished by having a selectivity for the vasopressin V1b receptor subtype vis-à-vis at least one of the closely related vasopressin/oxytocin receptor subtypes (for example vasopressin V1a, vasopressin V2 and/or oxytocin).

Alternatively, or preferably in addition, the compounds I and/or their pharmaceutically acceptable salts, N-oxides and a stereoisomers are distinguished by having an improved metabolic stability.

The metabolic stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible in this connection to conclude from an observed longer half-life that the metabolic stability of the compound is improved. The stability in the presence of human liver microsomes is of particular interest because it makes it possible to predict the metabolic degradation of the compound in the human liver. Compounds with increased metabolic stability (measured in the liver microsome test) are therefore probably also degraded more slowly in the liver. The slower metabolic degradation in the liver may lead to higher and/or longer-lasting concentrations (active levels) of the compound in the body, so that the elimination half-life of the compounds of the invention is increased. Increased and/or longer-lasting active levels may lead to a better activity of the compound in the treatment or prophylaxis of various vasopressin-related diseases. In addition, an improved metabolic stability may lead to an increased bioavailability after oral administration, because the compound is subject, after absorption in the intestine, to less metabolic degradation in the liver (so-called first pass effect). An increased oral bioavailability may, owing to an increased concentration (active level) of the compound, lead to a better activity of the compound after oral administration.

The compounds of the invention are effective after administration by various routes. Possible examples are intravenous, intramuscular, subcutaneous, topical, intratracheal, intranasal, transdermal, vaginal, rectal, sublingual, buccal or oral administration, and administration is frequently intravenous, intramuscular or, in particular, oral.

The present invention also relates to pharmaceutical compositions which comprise an effective dose of a compound I of the invention and/or an N-oxide, a stereoisomer and/or a pharmaceutically acceptable salt thereof and suitable pharmaceutical carriers (drug carriers).

These drug carriers are chosen according to the pharmaceutical form and the desired mode of administration and are known in principle to the skilled worker.

The compounds of the invention of the formula I, their N-oxides, steroisomers or optionally suitable salts of these compounds can be used to produce pharmaceutical compositions for oral, sublingual, buccal, subcutaneous, intramuscular, intravenous, topical, intratracheal, intranasal, transdermal, vaginal or rectal administration, and be administered to animals or humans in uniform administration forms, mixed with conventional pharmaceutical carriers, for the prophylaxis or treatment of the above disorders or diseases.

The suitable administration forms (dose units) include forms for oral administration such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active ingredient can vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered once to 5 times a day, so that a daily dose of from 0.5 to 25 000 mg, preferably 1 to 5000 mg, is administered.

If a solid composition is prepared in the form of tablets, the active ingredient is mixed with a solid pharmaceutical carrier such as gelatin, starch, lactose, magnesium stearate, talc, silicon dioxide or the like.

The tablets can be coated with sucrose, a cellulose derivative or another suitable substance or be treated otherwise in order to display a sustained or delayed activity and to release a predetermined amount of the active ingredient continuously.

A preparation in the form of gelatin capsules is obtained by mixing the active ingredient with an extender and including the resulting mixture in soft or hard gelatin capsules.

A preparation in the form of a syrup or elixir or for administration in the form of drops may contain active ingredients together with a sweetener, which is preferably calorie-free, methylparaben or propylparaben as antiseptics, a flavoring and a suitable coloring substance.

Water-dispersible powders or granules may comprise the active ingredients mixed with dispersants, wetting agents or suspending agents, such as polyvinylpyrrolidones, and sweeteners or masking flavors.

Rectal or vaginal administration is achieved by using suppositories which are prepared with binders which melt at rectal temperature, for example cocoa butter or polyethylene glycols. Parenteral administration is effected by using aqueous suspensions, isotonic saline solutions or sterile and injectable solutions which comprise pharmacologically acceptable dispersants and/or wetting agents, for example propylene glycol or polyethylene glycol.

The active ingredient may also be formulated as microcapsules or centrosomes, if suitable with one or more carriers or additives.

The compositions of the invention may, in addition to the compounds of the invention, comprise other active ingredients which may be beneficial for the treatment of the disorders or diseases indicated above.

The present invention thus further relates to pharmaceutical compositions in which a plurality of active ingredients are present together, where at least one of these is a compound I of the invention, or salt thereof.

The invention is explained in more detail below by means of examples, but the examples are not to be understood to be restrictive.

The compounds of the invention can be prepared by various synthetic routes. The methods mentioned, as described accordingly in synthesis schemes 1, 2 and 3, are explained in greater detail merely by way of example using the given examples without being exclusively restricted to synthesis route 1, 2 or 3 or analogous methods.

EXPERIMENTAL SECTION

Abbreviations Used $Et_3N$: Triethylamine
THF: Tetrahydrofuran
DMF: N,N-Dimethylformamide
DMSO: Dimethyl sulfoxide
TFA: Trifluoroacetic acid
RT room temperature
p: pseudo (for example pt pseudo triplet)
b: broad (for example bs broad singlet)
s: singlet
d: doublet
t: triplet
m: multiplet
dd: doublet of doublets
dt: doublet of triplets
tt: triplet of triplets I. Preparation of the Starting Compounds 1.) (S)—N-(5-cyano-1-((2,4-dimethoxyphenyl)sulfonyl)-3-(2-ethoxypyridin-3-yl)-2-oxoindolin-3-yl)-3-oxoazetidine-1-carboxamide To a solution of (S)-phenyl (5-cyano-1-((2,4-dimethoxyphenyl)sulfonyl)-3-(2-ethoxypyridin-3-yl)-2-oxoindolin-3-yl)carbamate (425 mg, 0.691 mmol) and azetidin-3-one hydrochloride (80 mg, 0.744 mmol) in DMF (6 ml) $Et_3N$ (1 ml, 7.17 mmol) was added and the mixture stirred over night at room temperature. Subsequently 40 ml of water and 10 ml $NaHCO_3$-solution were added and the mixture extracted twice with ethyl acetate. The combined organic layers were washed 3× with brine, dried over $MgSO_4$, filtered off and evaporated to give 430 mg of a yellow solid.

Flash chromatography (silica gel/gradient from 0 to 5% methanol in dichloromethane) yielded 330 mg of the title compound as white solid.

ESI-MS $[M+H]^+$=592.2

2.) (S)—N-(5-cyano-1-((2,4-dimethoxyphenyl)sulfonyl)-3-(2-methoxypyridin-3-yl)-2-oxoindolin-3-yl)-3-oxoazetidine-1-carboxamide To a solution of (S)-phenyl(5-cyano-1-((2,4-dimethoxyphenyl)sulfonyl)-3-(2-methoxypyridin-3-yl)-2-oxoindolin-3-yl)carbamate (1 g, 1.665 mmol) and azetidin-3-one hydrochloride (220 mg, 2.046 mmol) in 10 ml of DMF $Et_3N$ (1.5 ml, 10.76 mmol) was added and the mixture stirred over night at room temperature. 70 ml of water and 10 ml of 10% $NaHCO_3$-solution were added, the mixture extracted twice with ethyl acetate, the combined organic layers washed twice with brine, dried over MgSO4, filtered and concentrated to leave 1.3 g of the crude product as yellow oil. Flash chromatography (silica gel/gradient from 0 to 5% methanol in dichloromethane) yielded 610 mg of the title compound as an off-white solid.

ESI-MS $[M+H]^+$=578.1

Following the procedures as described for intermediates 1 and 2 and using the appropriate starting material were prepared:

3.) (S)—N-(5-chloro-1-((2,4-dimethoxyphenyl)sulfonyl)-3-(2-ethoxypyridin-3-yl)-2-oxoindolin-3-yl)-3-oxoazetidine-1-carboxamide

ESI-MS $[M+H]^+$=602.1.

II. Preparation of the Compounds of the Formula I

Enantiomers of the compounds I were prepared by using enantiomerically pure starting compounds.

Example 1

N-[(3S)-5-cyano-1-(2,4-dimethoxyphenyl)sulfonyl-3-(2-ethoxy-3-pyridyl)-2-oxoindolin-3-yl]-3-[4-(1-piperidyl)-1-piperidyl]azetidine-1-carboxamide (Compound of Formula I.1, Wherein $R^1$ is Methoxy, $R^2$ is Methoxy, $R^3$ is Hydrogen, $R^6$ is Cyano, $R^7$ is Hydrogen, $R^8$ and $R^9$ Together with the Nitrogen Atom they are Bond to, Form piperidin-1-yl)

A solution of (S)—N-(5-cyano-1-((2,4-dimethoxyphenyl) sulfonyl)-3-(2-ethoxypyridin-3-yl)-2-oxoindolin-3-yl)-3-oxoazetidine-1-carboxamide (50 mg, 0.085 mmol) and 4-piperidinopiperidin (40 mg, 0.238 mmol) in THF (1.5 ml) was stirred over night at room temperature, then sodium cyanoborohydride (10 mg, 0.159 mmol) and acetic acid (40 μl, 0.699 mmol) added and stirring continued for 2 hr. Subsequently 10 ml of water, 2 ml of 10% $NaHCO_3$-solution and 2 ml of dichloromethane were added to the mixture, the layers separated using a 30 ml Chromabond PTS-cartridge, the aqueous layer extracted with 1 ml of dichlormethane, and the combined organic layer evaporated to leave a gummy oil. Flash chromatography of the crude product (silica gel/gradient from 0 to 25% methanol in dichloromethane) afforded 32 mg of the title compound as white solid.

ESI-MS $[M+H]^+$=744.3.
$^1$H-NMR (600 MHz DMSO), δ [ppm]: 8.14 (dd, 1H), 7.88 (d, 1H), 7.83 (m, 2H), 7.66 (s, 1H), 7.54 (s, 1H), 7.05 (dd, 1H), 6.70 (dd, 1H), 6.66 (d, 1H), 4.09 (q, 2H), 3.86 (s, 3H), 3.78 and 3.58 (each m, broad, 2H), 3.46 (s, 3H), 2.94 (m, 1H), 2.73 (m, 2H), 2.41 (m, 4H), 2.17 (m, 1H), 1.68 (m, 4H), 1.40 (m, 8H), 0.95 (t, 3H).

The following compounds were obtained according to the procedures described for example 1 using the appropriate starting materials.

Example 2

(S)—N-(5-cyano-1-((2,4-dimethoxyphenyl)sulfonyl)-3-(2-ethoxypyridin-3-yl)-2-oxoindolin-3-yl)-3-(4-(dimethylamino)piperidin-1-yl)azetidine-1-carboxamide (Compound of Formula I.1, Wherein $R^1$ is Methoxy, $R^2$ is Methoxy, $R^3$ is Hydrogen, $R^6$ is Cyano, $R^7$ is Hydrogen, $R^8$ is Methyl and $R^9$ is Methyl)

ESI-MS [M+H]$^+$=704.3

$^1$H NMR (600 MHz, DMSO) δ 8.14 (dd, 1H), 7.89 (d, 1H), 7.83 (m, 3H), 7.66 (s, 1H), 7.55 (s, 1H), 7.05 (dd, 1H), 6.70 (dd, 1H), 6.66 (d, 1H), 4.09 (q, 2H), 3.86 (s, 3H), 3.74 (m broad, 2H), 3.58 (m broad, 2H), 3.46 (s, 3H), 2.94 (m, 1H), 2.70 (m, 2H), 2.15 (s broad, 6H), 2.07 (m, 1H), 1.70 (m, 4H), 1.35 (m, 2H), 0.96 (t, 3H).

Example 3

(S)—N-(5-cyano-1-((2,4-dimethoxyphenyl)sulfonyl)-3-(2-ethoxypyridin-3-yl)-2-oxoindolin-3-yl)-3-(4-(diethylamino)piperidin-1-yl)azetidine-1-carboxamide (Compound of Formula I.1, Wherein $R^1$ is Methoxy, $R^2$ is Methoxy, $R^3$ is Hydrogen, $R^6$ is Cyano, $R^7$ is Hydrogen, $R^8$ is Ethyl, and $R^9$ is Ethyl)

ESI-MS [M+H]$^+$=732.3

Example 4

(S)—N-(5-cyano-1-((2,4-dimethoxyphenyl)sulfonyl)-3-(2-ethoxypyridin-3-yl)-2-oxoindolin-3-yl)-3-(4-(pyrrolidin-1-yl)piperidin-1-yl)azetidine-1-carboxamide (Compound of Formula I.1, Wherein $R^1$ is Methoxy, $R^2$ is Methoxy, $R^3$ is Hydrogen, $R^6$ is Cyano, $R^7$ is Hydrogen, $R^8$ and $R^9$ Together with the Nitrogen Atom they are Bond to, Form pyrrolidin-1-yl)

ESI-MS [M+H]$^+$=730.3

$^1$H NMR (600 MHz, DMSO) δ 8.14 (dd, 1H), 7.88 (d, 1H), 7.83 (m, 3H), 7.66 (s, 1H), 7.54 (s, 1H), 7.05 (dd, 1H), 6.70 (dd, 1H), 6.66 (d, 1H), 4.09 (q, 2H), 3.86 (s, 3H), 3.73 (m broad, 2H), 3.58 (m broad, 2H), 3.46 (s, 3H), 2.95 (m, 1H), 2.62 (m, 2H), 2.42 (m, 4H), 1.92 (m, 1H), 1.76 (m, 4H), 1.66 (m, 4H), 1.35 (m, 2H), 0.95 (t, 3H).

Example 5

(S)-3-([1,4'-bipiperidin]-1'-yl)-N-(5-cyano-1-((2,4-dimethoxyphenyl)sulfonyl)-3-(2-methoxypyridin-3-yl)-2-oxoindolin-3-yl)azetidine-1-carboxamide (Compound of Formula I.6, Wherein $R^1$ is Methoxy, $R^2$ is Methoxy, $R^3$ is Hydrogen, $R^6$ is Cyano, $R^7$ is Hydrogen, $R^8$ and $R^9$ Together with the Nitrogen Atom they are Bond to, Form piperidin-1-yl)

To a solution of (S)—N-(5-cyano-1-((2,4-dimethoxyphenyl)sulfonyl)-3-(2-methoxypyridin-3-yl)-2-oxoindolin-3-yl)-3-oxoazetidine-1-carboxamide (80 mg, 0.139 mmol) and 4-piperidinopiperidine (50 mg, 0.297 mmol) ethanol (2 ml) and THF (2 ml) titanium isopropoxide (200 μl, 0.672 mmol) was added and the mixture stirred over night at room temperature and 50 min at 60° C. After cooling to room temperature sodium cyanoborohydride (25 mg, 0.398 mmol) was added and stirring continued for 30 min. The reaction mixture was diluted with 2 ml of water, then 2 ml of 10% NaHCO$_3$-solution added, the resulting suspension concentrated, and the obtained residue treated with 20 ml of water and 20 ml of dichloromethane. The formed solid was filtered off over celite, washed with dichlormethane, the organic layer separated, dried over MgSO4, filtered and evaporated to leave 100 mg of a yellow solid. Flash chromatography of the crude product (silica gel/gradient from 0 to 25% methanol in dichloromethane) afforded 33 mg of the title compound as an off-white solid.

ESI-MS [M+H]$^+$=730.3

$^1$H NMR (600 MHz, DMSO) δ 8.14 (dd, 1H), 7.91 (d, 1H), 7.86 (d, 1H), 7.80 (m, 2H), 7.70 (d, 1H), 7.58 (s, 1H), 7.06 (dd, 1H), 6.72 (dd, 1H), 6.68 (d, 1H), 3.87 (s, 3H), 3.75 (m broad, 2H), 3.65 (s, 3H), 3.58 (m, 2H), 3.52 (s, 3H), 2.94 (m, 1H), 2.73 (m, 2H), 2.39 (m, 4H), 1.70 (m, 4H), 1.53-1.30 (m 8H).

Example 6

(S)—N-(5-cyano-1-((2,4-dimethoxyphenyl)sulfonyl)-3-(2-methoxypyridin-3-yl)-2-oxoindolin-3-yl)-3-(4-(pyrrolidin-1-yl)piperidin-1-yl)azetidine-1-carboxamide (Compound of Formula I.6, Wherein $R^1$ is Methoxy, $R^2$ is Methoxy, $R^3$ is Hydrogen, $R^6$ is Cyano, $R^7$ is Hydrogen, $R^8$ and $R^9$ Together with the Nitrogen Atom they are Bond to, Form pyrrolidin-1-yl)

ESI-MS [M+H]$^+$=716.3

Example 7

(S)-3-(4-(azetidin-1-yl)piperidin-1-yl)-N-(5-cyano-1-((2,4-dimethoxyphenyl)sulfonyl)-3-(2-ethoxypyridin-3-yl)-2-oxoindolin-3-yl)azetidine-1-carboxamide (Compound of Formula I.1, Wherein $R^1$ is Methoxy, $R^2$ is Methoxy, $R^3$ is Hydrogen, $R^6$ is Cyano, $R^7$ is Hydrogen, $R^8$ and $R^9$ Together with the Nitrogen Atom they are Bond to, Form azetidin-1-yl)

To a solution of (S)—N-(5-cyano-1-((2,4-dimethoxyphenyl)sulfonyl)-3-(2-ethoxypyridin-3-yl)-2-oxoindolin-3-yl)-3-(4-oxopiperidin-1-yl)azetidine-1-carboxamide (65 mg, 0.096 mmol) and azetidine (10 μl, 0.166 mmol) in methanol (3 ml) first zinc chloride (25 mg, 0.183 mmol), and after stirring for 10 min, sodium cyanoborohydride (15 mg, 0.239 mmol) was added and the mixture stirred over night at room temperature. Then 5 ml of 10% NaHCO$_3$-solution were added, methanol removed under vacuum, and the remaining suspension digested with 50 ml of water and 20 ml of ethyl acetate. The aqueous layer was re-extracted with ethyl acetate, and the combined organic layers washed twice with brine, dried over MgSO$_4$, filtered and evaporated to leave 58.5 mg of the title compound as white solid.

ESI-MS [M+H]$^+$=716.3

$^1$H NMR (600 MHz, DMSO) δ 8.13 (dd, 1H), 7.88 (d, 1H), 7.88 (m, 3H), 7.66 (s, 1H), 7.54 (s, 1H), 7.05 (dd, 1H), 6.70 (dd, 1H), 6.66 (d, 1H), 4.07 (q, 2H), 3.86 (s, 3H), 3.75 (m broad, 2H), 3.54 (m, 2H), 3.46 (s, 3H), 3.03 (m broad, 4H), 2.94 (m, 1H), 2.58 (m, overlapped with DMSO), 1.89 (m, 3H), 1.78 (m, 2H), 1.57 (m, 2H), 1.09 (m, 2H), 0.96 (t, 3H).

Example 8

(S)-3-([1,4'-bipiperidin]-1'-yl)-N-(5-chloro-1-((2,4-dimethoxyphenyl)sulfonyl)-3-(2-ethoxypyridin-3-yl)-2-oxoindolin-3-yl)azetidine-1-carboxamide (Compound of Formula I.1, Wherein $R^1$ is Methoxy, $R^2$ is Methoxy, $R^3$ is Hydrogen, $R^6$ is Chlorine, $R^7$ is Hydrogen, $R^8$ and $R^9$ Together with the Nitrogen Atom they are Bond to, Form piperidin-1-yl)

The title compound was prepared in analogy to the method described in example 7. Flash chromatography of the crude product (silica gel/gradient from 0 to 15% methanol in dichloromethane) afforded 42 mg of the title compound as white solid.

ESI-MS $[M+H]^+$=754.3

$^1$H NMR (600 MHz, DMSO) δ 8.13 (dd, 1H), 7.89 (d, 1H), 7.69 (dd, 1H), 7.66 (d, 2H), 7.49 (s, 1H), 7.38 (dd, 1H), 7.34-7.30 (m, 1H), 7.01 (dd, 1H), 6.70 (dd, 1H), 6.66 (d, 1H), 4.11 (q, 2H), 3.86 (s, 3H), 3.77 (m broad, 2H), 3.58 (m broad, 2H), 3.46 (s, 3H), 2.96 (m, 1H), 2.75 (m, 2H), 2.5-2.35 (m, overlapped with DMSO), 1.71 (m, 4H), 1.56-1.3 (m, 8H), 1.00 (t, 3H).

Example 9

(S)—N-(5-chloro-1-((2,4-dimethoxyphenyl)sulfonyl)-3-(2-ethoxypyridin-3-yl)-2-oxoindolin-3-yl)-3-(4-(pyrrolidin-1-yl)piperidin-1-yl)azetidine-1-carboxamide (Compound of Formula I.1, Wherein $R^1$ is Methoxy, $R^2$ is Methoxy, $R^3$ is Hydrogen, $R^6$ is Chlorine, $R^7$ is Hydrogen, $R^8$ and $R^9$ Together with the Nitrogen Atom they are Bond to, Form pyrrolidin-1-yl)

ESI-MS $[M+H]^+$=740.3

$^1$H NMR (600 MHz, DMSO) δ 8.12 (dd, 1H), 7.89 (d, 1H), 7.69 (dd, 1H), 7.66 (d, 1H), 7.49 (s, 1H), 7.38 (dd, 1H), 7.33 (d, 1H), 7.01 (dd, 1H), 6.70 (dd, 1H), 6.66 (d, 1H), 4.11 (q, 2H), 3.86 (s, 3H), 3.78 (m broad, 2H), 3.59 (m broad, 2H), 3.47 (s, 3H), 2.96 (m, 1H), 3, 2.69 (m, 2H), 2.45 (m, overlapped with DMSO), 2.49-2.34 (m, 6H), 1.95-1.54 (m, 9H), 1.37 (m, 1H), 1.02 (t, 3H).

III. Determination of the Biological Activity

1. Vasopressin V1b Receptor Binding Assay:
Substances:

The test substances were dissolved in a concentration of 5 mM in 100% DMSO and further diluted to $5\times10^{-4}$ M to $5\times10^{-9}$ M. These serial DMSO predilutions were diluted 1:10 with assay buffer. The substance concentration was further diluted 1:5 in the assay mixture resulting in 2% DMSO in the mixture. All dilutions were performed in a Biomek NX automation workstation (Beckman)

Membrane Preparation:

CHO-K1 cells with stably expressed human vasopressin V1b receptor (clone 3H2) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4.

In the assay mixture (200 µl), membranes (26 µg protein in incubation buffer) from CHO-K1 cells with stably expressed human V1b receptors (cell line hV1b_3H2_CHO) were incubated with 1.5 nM $^3$H-AVP (8-Arg-vasopressin, PerkinElmer, NET 800) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Fluka 94836). All determinations were carried out as duplicate determinations. After incubation (60 minutes at room temperature), the free radioligand was filtered off by vacuum filtration (Tomtec Mach III) through Wathman GF/B glass fiber filter plates (UniFilter, PerkinElmer 6005177). The liquid scintillation measurement took place in a Microbeta TriLux 12 (Wallac).

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant human V1b receptors is 0.4 nM and was used to determine the Ki.

2. Vasopressin V1a Receptor Binding Assay:
Substances:

The test substances were dissolved in a concentration of 5 mM M in DMSO. Further dilution of these DMSO solutions took place as described for V1b.

Membrane Preparation:

CHO-K1 cells with stably expressed human vasopressin V1a receptor (clone 5) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized in a High-Pressure-Homogenizer, Polytec 50K at 1500 PSI (Heinemann, Germany) and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4.

In the assay mixture (200 µl), membranes (40 µg protein in incubation buffer) from CHO-K1 cells with stably expressed human V1a receptors (cell line hV1a_5_CHO) were incubated with 0.04 nM $^{125}$I-AVP (8-Arg-vasopressin, PerkinElmer NEX 128) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Fluka 94836). Duplicate determinations were carried out. After incubation (60 minutes at room temperature), the samples were processed as described for V1b.

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^{125}$I-AVP for the recombinant hV1a receptors was determined in saturation experiments. A Kd of 1.33 nM was used to determine the Ki.

3. Oxytocin Receptor Binding Assay

Substances:

The substances were dissolved in a concentration of 5 mM in DMSO and diluted further as described for V1b.

Membrane Preparation:

Confluent HEK-293 cells with transiently expressing recombinant human oxytocin receptors were harvested and centrifuged at 750×g at room temperature for 5 minutes. The pellet was taken up in ice-cold lysis buffer (50 mM Tris-HCl, 10% glycerol, pH 7.4 and Roche complete protease inhibitor) and thereby subjected to an osmotic shock at 4° C. for 20 minutes. Lysed cells were then centrifuged at 750×g at 4° C. for 20 minutes, the pellet was taken up in incubation buffer (50 mM Tris, 10 mM $MgCl_2$, 0.1% BSA, pH 7.4), and aliquots corresponding to $10^7$ cells/ml were prepared. The aliquots were frozen at −80° C. until use.

Binding Assay:

On the day of the experiment, the cell lysate was thawed, homogenized, and diluted with incubation buffer (50 mM Tris, 10 mM $MgCl_2$, 0.1% BSA, pH 7.4) to the desired concentration. The reaction mixture of 0.200 ml was composed of cell lysate corresponding to 5×10$^4$ cells (HEK-293 cells expressing transiently human OT receptors) and 1 nM 3H-oxytocin (PerkinElmer NET858) in the presence of test substance (displacement experiment) or incubation buffer only (total binding). The nonspecific binding was determined in the presence of 1 µM oxytocin (Bachem AG, H2510). Determinations were carried out in duplicates. After 60 minutes incubation at room temperature, bound and free radioligand were separated by filtration under vacuum on GF/B UniFilter plates (Perkin Elmer #6005177) pre-incubated with 0.3% PEI. The bound radioactivity was determined by liquid scintillation measurement in a Microbeta (Perkin Elmer) plate counter.

Analysis:

The binding parameters were calculated by nonlinear regression analysis (SAS) in analogy to the LIGAND program of Munson and Rodbard (Analytical Biochem 1980; 107: 220-239). The Kd of $^3$H-oxytocin for the recombinant hOT receptors was 7.6 nM and was used to calculate the Ki from competition binding experiments.

4. Determination of the Microsomal Half-Life:

The metabolic stability of the compounds of the invention was determined in the following assay.

The test substances were incubated in a concentration of 0.5 µM as follows:

0.5 µM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 µl aliquots are removed, and the reaction is immediately stopped and cooled with the same volume of acetonitrile. The samples are frozen until analyzed. The remaining concentration of undegraded test substance is determined by MSMS. The half-life (T1/2) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln 2/T1/2/(content of microsomal protein in mg/ml)×1000 [ml/min/mg] (modified from references: Di, The Society for Biomoleculur Screening, 2003, 453-462; Obach, DMD, 1999 vol 27. N 11, 1350-1359).

5. Methods for In Vitro Determination of the Cytochrome P450 (CYP) Inhibition

Luminescent Substrates for 2C9 and 3A4:

0.4 mg/ml human liver microsomes are preincubated with the test substances to be investigated (0-20 µM), the CYP-specific substrates, in 0.05 M potassium phosphate buffer of pH 7.4 at 37° C. for 10 min. The Cyp-specific substrate for CYP 2C9 is luciferin H, and for CYP 3A4 is luciferin BE. The reaction is started by adding NADPH. After incubation at RT for 30 min, the luciferin detection reagent is added, and the resulting luminescence signal is measured (modified from reference: Promega, Technical Bulletin P450-GLO™ Assays).

Midazolam CYP 3A4 Time-Dependent Inhibition

The assay consists of 2 parts. Firstly, the test substance is preincubated with the liver microsomes (with NADPH=preincubation, then addition of the substrate; in the second part the substrate and the test substance are added simultaneously=coincubation.

Preincubation:

0.05 mg/ml microsomal protein (human liver microsomes) are preincubated with 0-10 µM (or 50 µM) test substance in 50 mM potassium phosphate buffer for 5 min. The reaction is started with NADPH. After 30 min 4 µM midazolam (final concentration) are added, and incubation is continued for 10 min. 75 µl of the reaction solution are removed after 10 min, and stopped with 150 µl of acetonitrile solution.

Coincubation:

0.05 mg/ml microsomal protein (human liver microsomes) are preincubated with 4 µm midazolam (final concentration) and 0-10 µM (or 50 µM) test substance in 50 mM potassium phosphate buffer for 5 min. The reaction is started with NADPH. 75 µl of the reaction solution are removed after 10 min and stopped with 150 µl of acetonitrile solution. The samples are frozen until the MSMS analysis (modified from references: Obdach, Journal of Pharmacology & Experimental Therapeutics, Vol 316, 1, 336-348, 2006; Walsky, Drug Metabolism and Disposition Vol 32, 6, 647-660, 2004).

6. Method for Determining the Solubility in Water (in mg/ml)

The solubility in water of the compounds of the invention can be determined for example by the so-called shake flask method (as specified in *ASTM International: E 1148-02, Standard test methods for measurement of aqueous solubility, Book of Standards Volume* 11.05.). This entails an excess of the solid compound being put into a buffer solution with a particular pH (for example phosphate buffer of pH 7.4), and the resulting mixture being shaken or stirred until equilibrium has been set up (typically 24 or 48 hours, sometimes even up to 7 days). The undissolved solid is then removed by filtration or centrifugation, and the concentration of the dissolved compound is determined by UV spectroscopy or high pressure liquid chromatography (HPLC) by means of an appropriate calibration plot.

7. Results

The results of the receptor binding investigations are expressed as receptor binding constants [$K_i$(V1b)] or selectivities [$K_i$(V1a)/$K_i$(V1b)]. The results of the investigation of the metabolic stability are indicated as microsomal clearance (mCl).

The compounds of the invention show very high affinities for the V1b receptor in these assays (maximally 100 nM, or maximally 10 nM, frequently <1 nM). The compounds also show high selectivities vis-à-vis the V1a receptor and a good metabolic stability, measured as microsomal clearance.

The results are listed in table C. The numbers of the compounds refer to the synthesis examples.

TABLE C

| Example | $K_i$(hV1b)* [nM] | $K_i$(hV1a)/$K_i$(hV1b) |
|---|---|---|
| 1 | +++ | +++ |
| 2 | ++ | +++ |
| 3 | ++ | +++ |
| 4 | ++ | +++ |
| 5 | +++ | +++ |
| 6 | ++ | +++ |
| 7 | ++ | +++ |
| 8 | +++ | + |
| 9 | +++ | +++ |

*h = human
Key:

| | $K_i$(hV1b) | $K_i$(hV1a)/$K_i$(hV1b) |
|---|---|---|
| + | >10-100 nM | 10-<25 |
| ++ | 1-10 nM | 25-75 |
| +++ | <1 nM | >75 |

The invention claimed is:
1. A compound of formula (I)

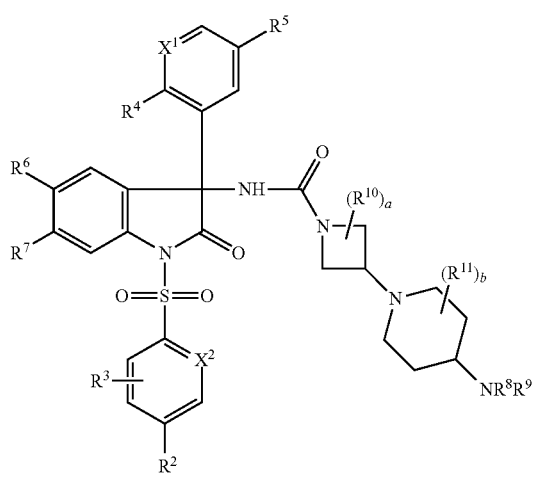

(I)

wherein
$X^1$ is N or CH;
$X^2$ is C—$R^1$ or N;
$R^1$ and $R^2$, independently of each other, are selected from the group consisting of hydrogen, halogen, cyano, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;
$R^3$ is selected from the group consisting of hydrogen, halogen, cyano, hydroxyl, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;
$R^4$ is $C_1$-$C_3$-alkoxy;
$R^5$ is hydrogen or $C_1$-$C_3$-alkoxy;
$R^6$ is cyano or halogen;
$R^7$ is selected from the group consisting of hydrogen, halogen and cyano;
$R^8$ and $R^9$, independently of each other, are selected from the group consisting of hydrogen, cyano, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_7$-cycloalkyl, $C_3$-$C_7$-halocycloalkyl and phenyl which may carry 1, 2 or 3 substituents selected from the group consisting of halogen, hydroxyl, cyano, $C_1$-$C_4$-alkoxy and $C_1$-$C_4$-haloalkoxy; or $R^8$ and $R^9$, together with the nitrogen atom they are bound to, form a 3-, 4-, 5-, 6- or 7-membered saturated, partially unsaturated or maximally unsaturated heterocyclic ring, where the heterocyclic ring may carry 1 or 2 substituents selected from the group consisting of cyano, $C_1$-$C_4$-alkyl and $C_1$-$C_4$-haloalkyl, where the nitrogen bound to $R^8$ and $R^9$ is the only heteroatom present in the 3-, 4-, 5-, 6- or 7-membered saturated, partially unsaturated or maximally unsaturated heterocyclic ring;

$R^{10}$ and $R^{11}$, independently of each other and independently of each occurrence, are selected from the group consisting of halogen, $C_1$-$C_4$-alkyl, $C_1$-$C_4$-haloalkyl, $C_1$-$C_4$-alkoxy and $C_1$-$C_4$-haloalkoxy, with the proviso that $R^{10}$ and $R^{11}$ are not halogen, $C_1$-$C_4$-alkoxy or $C_1$-$C_4$-haloalkoxy if they are bound to a carbon atom in α-position to a nitrogen ring atom; or two non-geminal radicals $R^{10}$ form together a group —(CH$_2$)$_n$—, where n is 1, 2, 3 or 4, where 1 or 2 hydrogen atoms in this group may be replaced a methyl group; or two non-geminal radicals $R^{11}$ form together a group —(CH$_2$)$_n$—, where n is 1, 2, 3 or 4, where 1 or 2 hydrogen atoms in this group may be replaced a methyl group;

a is 0, 1 or 2; and
b is 0, 1, 2, 3 or 4;

or a N-oxide, stereoisomer, or pharmaceutically acceptable salt thereof; or the above compound, wherein at least one of the atoms has been replaced by its stable, non-radioactive isotope.

2. The compound of claim 1, wherein at least one hydrogen atom has been replaced by a deuterium atom.

3. The compound of claim 1, wherein $X^2$ is C—$R^1$ and $R^1$, $R^2$ and $R^3$, independently of each other, are selected from the group consisting of hydrogen, halogen, $C_1$-$C_3$-alkyl, fluorinated $C_1$-$C_3$-alkyl, $C_1$-$C_3$-alkoxy and fluorinated $C_1$-$C_3$-alkoxy.

4. The compound of claim 3, wherein $R^1$, $R^2$ and $R^3$, independently of each other, are selected from the group consisting of hydrogen, fluorine and methoxy.

5. The compound of claim 4, wherein $R^1$ and $R^2$, independently of each other, are selected from the group consisting of hydrogen, fluorine and methoxy.

6. The compound of claim 4, wherein $R^3$ is hydrogen or fluorine.

7. The compound of claim 1, wherein $X^2$ is N and $R^2$ and $R^3$, independently of each other, are selected from the group consisting of hydrogen, halogen, $C_1$-$C_3$-alkyl, fluorinated $C_1$-$C_3$-alkyl, $C_1$-$C_3$-alkoxy and fluorinated $C_1$-$C_3$-alkoxy.

8. The compound of claim 7, wherein $R^2$ is selected from the group consisting of hydrogen, fluorine and methoxy.

9. The compound of claim 7, wherein $R^3$ is selected from the group consisting of hydrogen, fluorine and methoxy.

10. The compound of claim 1, wherein $R^4$ is methoxy or ethoxy.

11. The compound of claim 1, wherein $R^5$ is hydrogen or methoxy.

12. The compound of claim 1, wherein $R^6$ is selected from the group consisting of cyano, fluorine and chlorine.

13. The compound of claim 1, wherein $R^7$ is hydrogen or fluorine.

14. The compound of claim 1, wherein
$R^8$ and $R^9$, independently of each other, are selected from the group consisting of hydrogen, $C_1$-$C_4$-alkyl, $C_1$-$C_4$haloalkyl, $C_3$-$C_6$-cycloalkyl and $C_3$-$C_6$-halocycloalkyl; or $R^8$ and $R^9$, together with the nitrogen atom they are bound to, form a 3-, 4-, 5- or 6-membered saturated, partially unsaturated or maximally unsaturated heterocyclic ring, where the heterocyclic ring may carry 1 or 2 substituents selected from the group consisting of cyano, $C_1$-$C_4$-alkyl and $C_1$-$C_4$-haloalkyl.

15. The compound as claimed in claim 14, wherein
$R^8$ and $R^9$, independently of each other, are selected from the group consisting of $C_1$-$C_4$-alkyl, fluorinated $C_1$-$C_4$-alkyl, $C_3$-$C_6$-cycloalkyl and fluorinated $C_3$-$C_6$-cycloalkyl; or $R^8$ and $R^9$, together with the nitrogen atom they are bound to, form a 3-, 4-, 5- or 6-membered saturated heterocyclic ring, where the heterocyclic ring may carry 1 or 2 substituents selected from the group consisting of cyano, $C_1$-$C_4$-alkyl and $C_1$-$C_4$-haloalkyl.

16. The compound of claim 15, wherein
$R^8$ and $R^9$, independently of each other, are $C_1$-$C_4$-alkyl; or $R^8$ and $R^9$ form together a group —$(CH_2)_n$—, where n is 2, 3, 4, or 5, thus forming together with the nitrogen atom they are bound to a 3-, 4-, 5- or 6-membered saturated heterocyclic ring.

17. The compound of claim 1, wherein each $R^{10}$ is independently halogen or $C_1$-$C_4$-alkyl, with the proviso that $R^{10}$ is not halogen if it is bound to a carbon atom in α-position to a nitrogen ring atom.

18. The compound of claim 1, wherein each $R^{11}$ is independently halogen and/or $C_1$-$C_4$-alkyl, with the proviso that $R^{11}$ is not halogen if it is bound to a carbon atom in α-position to a nitrogen ring atom;
or two non-geminal radicals $R^{11}$ form together a group —$CH_2$—.

19. The compound of claim 1, wherein $X^1$ is N.
20. The compound of claim 1, wherein $X^1$ is CH.
21. The compound of claim 1, wherein $X^2$ is C—$R^1$.
22. The compound claim 1, wherein $X^2$ is N.
23. The compound of claim 1, wherein a is 0 or 1.
24. The compound of claim 1, wherein b is 0, 1 or 2.
25. A compound selected from the group consisting of
N-[(3S)-5-cyano-1-(2,4-dimethoxyphenyl)sulfonyl-3-(2-ethoxy-3-pyridyl)-2-oxo-indolin-3-yl]-3-[4-(1-piperidyl)-1-piperidyl]azetidine-1-carboxamide;
(S)—N-(5-cyano-1-((2,4-dimethoxyphenyl)sulfonyl)-3-(2-ethoxypyridin-3-yl)-2-oxoinodolin-3-yl)-3-(4-(dimethylamino)piperidin-1-yl)azetidine-1-carboxamide;
(S)—N-(5-cyano-1-((2,4-dimethoxyphenyl)sulfonyl)-3-(2-ethoxypyridin-3-yl)-2-oxoindolin-3-yl)-3-(4-(diethylamino)piperidin-1-yl)azetidine-1-carboxamide;
(S)—N-(5-cyano-1-((2,4-dimethoxyphenyl)sulfonyl)-3-(2-ethoxypyridin-3-yl)-2-oxoindolin-3-yl)-3-(4-(pyrrolidin-1-yl)piperidin-1-yl)azetidine-1-carboxamide;
(S)-3-([1,4'-bipiperidin]-1'-yl)-N-(5-cyano-1-((2,4-dimethoxyphenyl)sulfonyl)-3-(2-methoxypyridin-3-yl)-2-oxoindolin-3-yl)azetidine-1-carboxamide;
(S)—N-(5-cyano-((2,4-dimethoxyphenyl)sulfonyl)-3-(2-methoxypyridin-3-yl)-2-oxoindolin-3-yl)-3-(4-(pyrrolidin-1-yl)piperidin-1-yl)azetidine-1-carboxamide;
(S)-3-(4-(azetidin-1-yl)piperidin-1-yl)-N-(5-cyano-1-((2,4-dimethoxyphenyl)sulfonyl)-3-(2-ethoxypyridin-3-yl)-2-oxoindolin-3-yl)azetidine-1-carboxamide;
(S)-3-([1,4'-bipiperidin]-1'-yl)-N-(5-chloro-1-(2,4-dimethoxyphenyl)sulfonyl)-3-(2-ethoxypyridin-3-yl)-2-oxoindolin-3-yl)azetidine-1-carboxamide; and
(S)—N-(5-chloro-1-(2,4-dimethoxyphenyl)sulfonyl)-3-(2-ethoxypyridin-3-yl)-2-oxoindolin-3-yl)-3-(4-(pyrrolidin-1-yl)piperidin-1-yl)azetidine-1-carboxamide;
or a pharmaceutically acceptable salt thereof.

26. A pharmaceutical composition comprising a compound of claim 1 or an N-oxide, a stereoisomer, or a pharmaceutically acceptable salt thereof and at least one pharmaceutically acceptable carrier.

27. A method for the treatment of vasopressin-related diseases, comprising administering an effective amount of a compound of claim 1 or an N-oxide, stereoisomer or pharmaceutically acceptable salt thereof to a subject in need thereof,
wherein the vasopressin-related diseases are selected from the group consisting of hypertension; pulmonary hypertension; heart failure; myocardial infarction; coronary spasm; unstable angina; percutaneous transluminal coronary angioplasty; ischemias of the heart; impairments of the renal system; edemas; renal vasospasm; necrosis of the renal cortex; hyponatremia; hypokalemia; Schwartz-Bartter syndrome; impairments of the gastrointestinal tract; gastric vasospasm; hepatocirrhosis; gastric and intestinal ulcers; emesis; emesis related to chemotherapy; travel sickness; affective disorders; anxiety disorders; stress-dependent anxiety disorders; memory and cognitive impairments; psychoses and psychotic disorders; Cushing's syndrome; stress-dependent diseases; sleep disorders; depressive disorders; vasomotor symptoms; thermoregulatory dysfunctions; drug or pharmaceutical dependencies; stress caused by withdrawal of one or more factors mediating the dependence; stress-induced relapses into drug or pharmaceutical dependencies; drug-use disorders; schizophrenia; and delaying micturition.

28. The method of claim 27, wherein the vasopressin-related diseases are selected from the group consisting of depressive disorders; anxiety disorders; stress-dependent anxiety disorders; and drug or pharmaceutical dependencies, wherein the drug or pharmaceutical dependencies are selected from the group consisting of dependencies mediated by alcohol use disorder, alcohol intoxication, and alcohol withdrawal.

29. The method of claim 28, wherein the depressive disorders are selected from the group consisting of major depression, seasonal depression, bipolar disorders, treatment-resistant depression, dysthymic disorders and childhood onset mood disorders.

30. The method of claim 27, wherein the memory and cognitive impairments is Alzheimer's disease; mild cognitive impairment; or cognitive impairment associated with schizophrenia.

* * * * *